(12) United States Patent
Han et al.

(10) Patent No.: US 12,268,750 B2
(45) Date of Patent: *Apr. 8, 2025

(54) IMMUNOCONJUGATES AND METHODS

(71) Applicant: Immunome, Inc., Bothell, WA (US)

(72) Inventors: Xiaojun Han, San Diego, CA (US);
Suvi Tuula Marjukka Orr, San Diego, CA (US); Kevin Duane Bunker, Escondido, CA (US); Peter Qinhua Huang, San Diego, CA (US); Kimberlee Fischer, San Diego, CA (US)

(73) Assignee: Immunome, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/821,737

(22) Filed: Aug. 30, 2024

(65) Prior Publication Data

US 2024/0424124 A1 Dec. 26, 2024

Related U.S. Application Data

(63) Continuation of application No. 18/479,317, filed on Oct. 2, 2023, which is a continuation of application No. 17/936,346, filed on Sep. 28, 2022, now Pat. No. 11,806,405, which is a continuation-in-part of application No. 17/812,869, filed on Jul. 15, 2022.

(60) Provisional application No. 63/267,471, filed on Feb. 2, 2022, provisional application No. 63/203,347, filed on Jul. 19, 2021.

(51) Int. Cl.
| | | |
|---|---|---|
| *A61K 47/68* | (2017.01) |
| *A61K 31/4745* | (2006.01) |
| *A61K 39/00* | (2006.01) |
| *A61K 47/55* | (2017.01) |
| *C07K 16/18* | (2006.01) |

(52) U.S. Cl.
CPC ...... *A61K 47/6803* (2017.08); *A61K 31/4745* (2013.01); *A61K 47/55* (2017.08); *A61K 47/6851* (2017.08); *C07K 16/18* (2013.01); *A61K 2039/505* (2013.01)

(58) Field of Classification Search
CPC .... C07K 16/18; C07K 16/462; C07K 16/464; C07K 2317/56; C07K 2317/565; A61K 2039/505
See application file for complete search history.

(56) References Cited

U.S. PATENT DOCUMENTS

| | | | |
|---|---|---|---|
| 5,856,448 A | 1/1999 | Coughlin |
| 5,990,084 A | 11/1999 | Richter et al. |
| 6,197,541 B1 | 3/2001 | Coughlin |
| 6,291,671 B1 | 9/2001 | Inoue et al. |
| 6,436,912 B1 | 8/2002 | Inoue et al. |
| 6,590,061 B1 | 7/2003 | Rypacek et al. |
| 6,656,458 B1 | 12/2003 | Philippe et al. |
| 6,835,807 B1 | 12/2004 | Susaki et al. |
| 6,838,450 B2 | 1/2005 | Inoue et al. |
| 7,439,231 B2 | 10/2008 | Olson et al. |
| 7,601,796 B2 | 10/2009 | Breitenkamp et al. |
| 8,067,544 B2 | 11/2011 | Landes et al. |
| 8,217,005 B2 | 7/2012 | Jenkins et al. |
| 8,222,215 B2 | 7/2012 | Olson et al. |
| 8,268,936 B2 | 9/2012 | Breitenkamp et al. |
| 8,598,312 B2 | 12/2013 | Olson et al. |
| 8,747,904 B2 | 6/2014 | Mirosevich et al. |
| 8,921,418 B2 | 12/2014 | Jenkins et al. |
| 9,040,032 B2 | 5/2015 | Jenkins et al. |
| 9,095,557 B2 | 8/2015 | Stohr |
| 9,150,647 B2 | 10/2015 | Mellstedt et al. |
| 9,217,040 B2 | 12/2015 | Kipps et al. |
| 9,220,785 B2 | 12/2015 | Adami et al. |
| 9,228,023 B2 | 1/2016 | Rohlff et al. |
| 9,248,109 B2 | 2/2016 | Yu et al. |
| 9,376,381 B2 | 6/2016 | Yu |
| 9,446,011 B2 | 9/2016 | Stöhr |
| 9,585,963 B2 | 3/2017 | Jenkins et al. |
| 9,597,410 B2 | 3/2017 | Bachovchin et al. |
| 9,758,591 B2 | 9/2017 | Kipps et al. |
| 9,808,537 B2 | 11/2017 | Masuda et al. |
| 9,821,067 B2 | 11/2017 | Adami et al. |
| 9,872,924 B2 | 1/2018 | Naito et al. |
| 9,956,297 B2 | 5/2018 | Bachovchin et al. |
| 10,155,821 B2 | 12/2018 | Naito et al. |
| 10,195,288 B2 | 2/2019 | Masuda et al. |
| 10,287,317 B2 | 5/2019 | Muehlemann et al. |
| 10,335,496 B2 | 7/2019 | Lannutti et al. |
| 10,383,878 B2 | 8/2019 | Hettmann et al. |
| 10,398,783 B2 | 9/2019 | McDonald et al. |

(Continued)

FOREIGN PATENT DOCUMENTS

| | | |
|---|---|---|
| AU | 2021354823 A1 | 3/2023 |
| AU | 2022216696 A1 | 8/2023 |

(Continued)

OTHER PUBLICATIONS

Anonymous, Antibody-drug conjugates for cancer score with ROR1, Nat Biotechnol, 39(1): 10 (2021).

(Continued)

*Primary Examiner* — Karen A. Canella
(74) *Attorney, Agent, or Firm* — Goodwin Procter LLP

(57) ABSTRACT

Immunoconjugates of the Formula (I) include a linking group for linking an antibody targeting ligand (Ab) to a drug (D). Embodiments of such immunoconjugates are useful for delivering the drug to selected cells or tissues, e.g., for the treatment of cancer.

$$Ab-[S-L^1-L^2-L^3-L^4-L^5-L^6-L^7-D]_n \qquad (I)$$

3 Claims, 31 Drawing Sheets

Specification includes a Sequence Listing.

(56) References Cited

U.S. PATENT DOCUMENTS

| | | |
|---|---|---|
| 10,414,826 B2 | 9/2019 | Doronina et al. |
| 10,517,955 B2 | 12/2019 | Bachovchin et al. |
| 10,729,782 B2 | 8/2020 | Naito et al. |
| 10,808,039 B2 | 10/2020 | Doronina et al. |
| 10,869,934 B2 | 12/2020 | McDonald et al. |
| 10,906,974 B2 | 2/2021 | Iida et al. |
| 10,968,275 B2 | 4/2021 | Balakrishnan et al. |
| 10,973,924 B2 | 4/2021 | Masuda et al. |
| 11,155,615 B2 | 10/2021 | Wong et al. |
| 11,242,388 B2 | 2/2022 | Rader et al. |
| 11,806,405 B1 | 11/2023 | Han et al. |
| 2001/0043935 A1 | 11/2001 | Philippe et al. |
| 2002/0164360 A9 | 11/2002 | Philippe et al. |
| 2010/0273714 A1 | 10/2010 | Stoehr |
| 2011/0105381 A2 | 5/2011 | Jenkins et al. |
| 2013/0210854 A1 | 8/2013 | Jenkins et al. |
| 2015/0297748 A1 | 10/2015 | Masuda et al. |
| 2016/0333112 A1 | 11/2016 | Naito et al. |
| 2017/0035906 A1 | 2/2017 | Naito et al. |
| 2019/0077880 A1 | 3/2019 | Naito et al. |
| 2019/0151328 A1 | 5/2019 | Hettmann et al. |
| 2019/0153092 A1 | 5/2019 | Waldmeier et al. |
| 2019/0209702 A1 | 7/2019 | Han |
| 2019/0224330 A1 | 7/2019 | Wang et al. |
| 2019/0225686 A1 | 7/2019 | Iida et al. |
| 2019/0330368 A1 | 10/2019 | Jikoh et al. |
| 2019/0343828 A1 | 11/2019 | Jeffrey et al. |
| 2019/0367631 A1 | 12/2019 | Gromada et al. |
| 2020/0040048 A1 | 2/2020 | Aivado et al. |
| 2020/0061031 A1 | 2/2020 | Yonesaka et al. |
| 2020/0282073 A1 | 9/2020 | Masuda et al. |
| 2020/0323994 A1 | 10/2020 | Bachovchin et al. |
| 2020/0384121 A1 | 12/2020 | Nishi et al. |
| 2020/0385422 A1 | 12/2020 | Yamaguchi et al. |
| 2020/0385486 A1 | 12/2020 | Naito et al. |
| 2021/0069342 A1 | 3/2021 | Park et al. |
| 2021/0077482 A1 | 3/2021 | Chari et al. |
| 2022/0008549 A1 | 1/2022 | Tsuda et al. |
| 2022/0323598 A1 | 10/2022 | Takahashi |
| 2023/0054458 A1 | 2/2023 | Yang et al. |
| 2023/0123041 A1 | 4/2023 | Han et al. |
| 2023/0330242 A1 | 10/2023 | Han et al. |
| 2024/0075153 A1 | 3/2024 | Han et al. |

FOREIGN PATENT DOCUMENTS

| | | |
|---|---|---|
| CA | 2145473 A1 | 9/1995 |
| CA | 3107417 A1 | 1/2020 |
| CN | 110721559 A | 1/2020 |
| CN | 111001012 A | 4/2020 |
| CN | 211328833 U | 8/2020 |
| CN | 111686259 A | 9/2020 |
| CN | 111689980 A | 9/2020 |
| CN | 112138171 A | 12/2020 |
| CN | 113816969 A | 12/2021 |
| CN | 2021101599566 | 8/2022 |
| CN | 117715913 A | 3/2024 |
| EP | 0296597 A2 | 12/1988 |
| EP | 0673930 A1 | 9/1995 |
| EP | 0495432 B1 | 5/1996 |
| EP | 3632471 A1 | 4/2020 |
| EP | 3677589 A1 | 7/2020 |
| EP | 3831853 A1 | 6/2021 |
| EP | 3991754 A1 | 5/2022 |
| EP | 4183421 A1 | 5/2023 |
| EP | 4227309 A1 | 8/2023 |
| JP | H0687746 A | 3/1994 |
| JP | 2000044567 A | 2/2000 |
| JP | 2002060351 A | 2/2002 |
| JP | 2002146011 A | 5/2002 |
| WO | WO-1996027370 A1 | 9/1996 |
| WO | WO-1997040071 A1 | 10/1997 |
| WO | WO-1999049837 A1 | 10/1999 |
| WO | WO-1999064495 A1 | 12/1999 |
| WO | WO-2001076603 A1 | 10/2001 |
| WO | WO-2001098364 A2 | 12/2001 |
| WO | WO-2003033671 A2 | 4/2003 |
| WO | WO-2008000513 A2 | 1/2008 |
| WO | WO-2008101202 A1 | 8/2008 |
| WO | WO-2011133149 A1 | 10/2011 |
| WO | WO-2011133150 A1 | 10/2011 |
| WO | WO-2013173337 A2 | 11/2013 |
| WO | WO-2014096551 A1 | 6/2014 |
| WO | WO-2015057699 A2 | 4/2015 |
| WO | WO-2015095755 A1 | 6/2015 |
| WO | WO-2015123679 A1 | 8/2015 |
| WO | WO-2015155998 A1 | 10/2015 |
| WO | WO-2017165851 A1 | 9/2017 |
| WO | WO-2018175994 A1 | 9/2018 |
| WO | WO-2018237335 A1 | 12/2018 |
| WO | WO-2019005636 A2 | 1/2019 |
| WO | WO-2019034177 A1 | 2/2019 |
| WO | WO-2019044947 A1 | 3/2019 |
| WO | WO-2019136487 A2 | 7/2019 |
| WO | WO-2019195665 A1 | 10/2019 |
| WO | WO-2019219891 A1 | 11/2019 |
| WO | WO-2019236954 | 12/2019 |
| WO | WO-2020022363 A1 | 1/2020 |
| WO | WO-2020022475 A1 | 1/2020 |
| WO | WO-2020031936 A1 | 2/2020 |
| WO | WO-2020040245 A1 | 2/2020 |
| WO | WO-2020050406 A1 | 3/2020 |
| WO | WO-2020063673 A1 | 4/2020 |
| WO | WO-2020063676 A1 | 4/2020 |
| WO | WO-2020106780 A1 | 5/2020 |
| WO | WO-2020122034 A1 | 6/2020 |
| WO | WO-2020130125 A1 | 6/2020 |
| WO | WO-2020146541 A2 | 7/2020 |
| WO | WO-2020156513 A1 | 8/2020 |
| WO | WO-2020160527 A1 | 8/2020 |
| WO | WO-2020219287 A1 | 10/2020 |
| WO | WO-2020237173 A1 | 11/2020 |
| WO | WO-2020240467 A1 | 12/2020 |
| WO | WO-2020244657 A1 | 12/2020 |
| WO | WO-2020259258 A1 | 12/2020 |
| WO | WO-2021052402 A1 | 3/2021 |
| WO | WO-2021058027 A1 | 4/2021 |
| WO | WO-2021115426 A1 | 6/2021 |
| WO | WO-2021159029 A1 | 8/2021 |
| WO | WO-2022001864 A1 | 1/2022 |
| WO | WO-2022011075 A1 | 1/2022 |
| WO | WO-2022033578 A1 | 2/2022 |
| WO | WO-2022068878 A1 | 4/2022 |
| WO | WO-2022078259 A1 | 4/2022 |
| WO | WO-2022166762 A1 | 8/2022 |
| WO | WO-2022174103 A2 | 8/2022 |
| WO | WO-2022184082 A1 | 9/2022 |
| WO | WO-2022217054 A1 | 10/2022 |
| WO | WO-2023004266 A1 | 1/2023 |
| WO | WO-2023078273 A1 | 5/2023 |
| WO | WO-2023217064 A1 | 11/2023 |
| WO | WO-2024020536 A1 | 1/2024 |
| WO | WO-2024026323 A1 | 2/2024 |
| WO | WO-2024067811 A1 | 4/2024 |
| WO | WO-2024158996 A2 | 8/2024 |

OTHER PUBLICATIONS

Casi, G., et al., Antibody-drug conjugates: basic concepts, examples and future perspectives, J Control Release, 161(2): 422-428 (2012).

Conilh, L., et al., Exatecan Antibody Drug Conjugates Based on a Hydrophilic Polysarcosine Drug-Linker Platform, Pharmaceuticals (Basel), 14(3): 247 (2021).

Ding, H.X., et al., Synthetic approaches to the 2011 new drugs, Bioorg Med Chem, 21(11):2795-2825 (2013).

Maderna, A., et al., Discovery of cytotoxic dolastatin 10 analogues with N-terminal modifications, J Med Chem, 57(24): 10527-10543 (2014).

Nejadmoghaddam, M-R., et al., Antibody-Drug Conjugates: Possibilities and Challenges, Avicenna J Med Biotechnol, 11(1): 3-23 (2019).

Ogitani, Y., et al., Bystander killing effect of DS-8201a, a novel anti-human epidermal growth factor receptor 2 antibody-drug con-

(56) References Cited

OTHER PUBLICATIONS jugate, in tumors with human epidermal growth factor receptor 2 heterogeneity, Cancer Sci, 107(7): 1039-1046 (2016).
PCT/US2022/073780 International Search Report and Written Opinion mailed Nov. 4, 2022.
PCT/US2023/070971 International Search Report and Written Opinion mailed Oct. 30, 2023.
PCT/US2024/012923 International Search Report and Written Opinion mailed Aug. 22, 2024.
Renault, K., et al., Covalent Modification of Biomolecules through Maleimide-Based Labeling Strategies, Bioconjug Chem, 29(8): 2497-2513 (2018).
*Seagen Inc.* v *Daiichi Sankyo Co. Ltd.*, Complaint for Patent Infringement of U.S. Pat. No. 10,808,039 filed Oct. 19, 2020; US District Court Eastern District of Texas, pp. 1-13.
Shiose, Y., et al., Systematic research of peptide spacers controlling drug release from macromolecular prodrug system, carboxymethyldextran polyalcohol-peptide-drug conjugates, Bioconjug Chem, 20(1): 60-70 (2009).
Sugimori, M., et al., Synthesis and antitumor activity of ring A- and F-modified hexacyclic camptothecin analogues, J Med Chem, 41(13): 2308-2318 (1998).
U.S. Appl. No. 17/936,346 Office Action mailed Jun. 30, 2023.
U.S. Appl. No. 17/936,346 Office Action mailed Mar. 15, 2023.
U.S. Appl. No. 18/479,317 Office Action mailed Apr. 18, 2024.
U.S. Appl. No. 18/479,317 Office Action mailed Dec. 14, 2023.
Xu, Z., et al., Novel HER2-Targeting Antibody-Drug Conjugates of Trastuzumab Beyond T-DM1 in Breast Cancer: Trastuzumab Deruxtecan(DS-8201a) and (Vic-)Trastuzumab Duocarmazine (SYD985), Eur J Med Chem, 183: 111682 (2019).
Yang, J., et al., Therapeutic potential and challenges of targeting receptor tyrosine kinase ROR1 with monoclonal antibodies in B-cell malignancies, PloS One, 6(6): e21018 (2011).
U.S. Appl. No. 17/812,869, filed Jul. 15, 2022, Pending.
U.S. Appl. No. 17/936,346, filed Sep. 28, 2022, U.S. Pat. No. 11,806,405, Nov. 7, 2023, Issued.
U.S. Appl. No. 18/479,317, filed Oct. 2, 2023, Allowed.
U.S. Appl. No. 18/821,707, filed Aug. 30, 2024, Pending.
U.S. Appl. No. 18/821,718, filed Aug. 30, 2024, Pending.
U.S. Appl. No. 18/821,728, filed Aug. 30, 2024, Pending.
U.S. Appl. No. 18/821,730, filed Aug. 30, 2024, Pending.
U.S. Appl. No. 18/821,749, filed Aug. 30, 2024, Pending.

*Stereochemistry at this carbon is arbitrarily assigned.

*Stereochemistry at this carbon is arbitrarily assigned.*

| | | | | Analyte mAbs | | | | |
| --- | --- | --- | --- | --- | --- | --- | --- | --- |
| | | | | (Injected over chip surface at 10 µg/ml after Hu/Cy/Rh ROR1-His) | | | | |
| | | | Kinetics (KD) | 4.69E-09 | 1.09E-08 | 6.45E-09 | 8.40E-09 | 2.81E-09 |
| | | | Isotype | Human IgG1 | Human IgG1 | Human IgG1 | Human IgG1 | Mouse BALB/c IgG2b, κ |
| | Kinetics (KD) | Isotype | ID | ATX-P-453 | ATX-P-885 | ATX-P-875 | ATX-P-890 | 4A5 |
| Ligand mAbs (immobilized to Carterra chip Surface) | 4.69E-09 | Human IgG1 | ATX-P-453 | | | | | |
| | 1.09E-08 | Human IgG1 | ATX-P-885 | | | | | |
| | 6.45E-09 | Human IgG1 | ATX-P-875 | | | | | |
| | 8.40E-09 | Human IgG1 | ATX-P-890 | | | | | |
| | 2.81E-09 | Mouse BALB/c IgG2b, κ | 4A5 | | | | | |

| Seq ID No. | Description | Sequence |
|---|---|---|
| 1 | ATX-P-875 VH CDR1 (Kabat) | GFTFSNAW |
| 2 | ATX-P-875 VH CDR2 (Kabat) | IKSKTDGGTT |
| 3 | ATX-P-875 VH CDR3 (Kabat) | TTGPDDLDY |
| 4 | ATX-P-875 VH nt | GAGGTGCAGCTGGTGGAGTCCGGGGGAGGCCTGGTCAAGCCTGGGGGGTCCCTGAGACTCTCCTGTGCAGCCTCTGGATTCACTTTCAGTAACGCCTGGATGAGCTGGGTCCGCCAGGCTCCAGGGAAGGGGCTGGAGTGGGTTGGCCGTATTAAAAGCAAAACTGATGGTGGGACAACAGACTACGCTGCACCCGTGAAAGGCAGATTCACCATCTCAAGAGATGATTCAAAAAACACGCTCTATCTGCAAATGAACAGCCTGAAAACCGAGGACACAGCCGTGTATTACTGTACCACAGGCCCTGACGATCTTGACTACTGGGGCCAGGGAACCCCGGTCACCGTCTCCTCA |
| 5 | ATX-P-875 VH AA | EVQLVESGGGLVKPGGSLRLSCAASGFTFSNAWMSWVRQAPGKGLEWVGRIKSKTDGGTTDYAAPVKGRFTISRDDSKNTLYLQMNSLKTEDTAVYYCTTGPDDLDYWGQGTPVTVSS |
| 6 | ATX-P-875 HC IgG1-Fc nt | GAGGTGCAGCTGGTGGAGTCCGGGGGAGGCCTGGTCAAGCCTGGGGGGTCCCTGAGACTCTCCTGTGCAGCCTCTGGATTCACTTTCAGTAACGCCTGGATGAGCTGGGTCCGCCAGGCTCCAGGGAAGGGGCTGGAGTGGGTTGGCCGTATTAAAAGCAAAACTGATGGTGGGACAACAGACTACGCTGCACCCGTGAAAGGCAGATTCACCATCTCAAGAGATGATTCAAAAAACACGCTCTATCTGCAAATGAACAGCCTGAAAACCGAGGACACAGCCGTGTATTACTGTACCACAGGCCCTGACGATCTTGACTACTGGGGCCAGGGAACCCCGGTCACCGTCTCCTCAGCTAGCACTAAAGGGCCTTCTGTATTTCCCTTGGCCCCGTCCAGCAAATCGACCTCGGGAGGGACAGCCGCCCTGGGTTGCCTTGTGAAAGATTATTTCCCTGAGCCAGTTACCGTAAGTTGGAACAGTGGGGCGCTGACAAGTGGTGTGCACACGTTTCTGCCGTCCTGCAATCATCGGGCTTGTATAGCCTCAGCTCTGTGGTCACTGTCCCAAGTTCATCGCTGGGCACT |

FIG. 34 (continued)

| | | |
|---|---|---|
| | | CAGACGTATATTTGCAATGTGAACCACAAACCTTCAA<br>ATACAAAAGTGGATAAACGCGTAGAACCGAAATCGT<br>GTGATAAAACTCACACATGCCCGCCATGCCCGGCACC<br>TGAACTGCTTGGTGGTCCCAGCGTGTTCCTGTTCCCGC<br>CGAAGCCTAAAGATACTCTAATGATCAGCCGTACGCC<br>AGAGGTGACATGTGTCGTGGTTGACGTGTCCCACGAA<br>GATCCCGAAGTTAAGTTCAATTGGTATGTTGATGGTG<br>TAGAGGTACACAATGCTAAGACTAAACCTCGCGAGG<br>AGCAGTACAATTCGACCTATCGTGTCGTGAGCGTTCT<br>GACCGTCCTTCACCAAGATTGGCTTAACGGCAAAGAA<br>TATAAGTGCAAGGTAAGCAATAAAGCACTTCCGGCCC<br>CAATCGAGAAAACCATTTCCAAGGCCAAAGGTCAAC<br>CAAGAGAACCCCAGGTGTATACTCTTCCGCCTTCTCG<br>TGAGGAAATGACTAAAAATCAAGTATCCCTTACGTGT<br>CTGGTTAAAGGTTTTTATCCTAGCGATATTGCTGTTGA<br>ATGGGAATCGAACGGTCAGCCGGAGAATAATTATAA<br>AACAACGCCACCCGTCCTGGATAGCGACGGCTCATTT<br>TTTCTGTATAGCAAACTGACTGTAGATAAATCACGGT<br>GGCAGCAGGGCAATGTATTCAGTTGCTCCGTTATGCA<br>TGAAGCGTTACATAATCACTACACGCAGAAATCTCTT<br>AGTCTTTCACCCGGT |
| 7 | ATX-P-875 HC IgG1-Fc AA | EVQLVESGGGLVKPGGSLRLSCAASGFTFSNAWMSWV<br>RQAPGKGLEWVGRIKSKTDGGTTDYAAPVKGRFTISRD<br>DSKNTLYLQMNSLKTEDTAVYYCTTGPDDLDYWGQGT<br>PVTVSSASTKGPSVFPLAPSSKSTSGGTAALGCLVKDYF<br>PEPVTVSWNSGALTSGVHTFPAVLQSSGLYSLSSVVTVP<br>SSSLGTQTYICNVNHKPSNTKVDKRVEPKSCDKTHTCPP<br>CPAPELLGGPSVFLFPPKPKDTLMISRTPEVTCVVVDVS<br>HEDPEVKFNWYVDGVEVHNAKTKPREEQYNSTYRVVS<br>VLTVLHQDWLNGKEYKCKVSNKALPAPIEKTISKAKGQ<br>PREPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPG |
| 8 | ATX-P-875 VL CDR1 (Kabat) | QSISSY |
| | ATX-P-875 VL CDR2 (Kabat) | AAS |
| 10 | ATX-P-875 VL CDR3 (Kabat) | QQYDNLPIT |

FIG. 34 (continued)

| 11 | ATX-P-875 VL nt | GACATCCAGATGACCCAGTCTCCATCCTCCCTGTCTG CATCTGTAGGAGACAGAGTCACCATCACTTGCCGGGC AAGTCAGAGCATTAGCAGCTATTTAAATTGGTATCAG CAGAAACCAGGGAAAGCCCCTAAGCTCCTGATCTAT GCTGCATCCAGTTTGCAAAGTGGGGTCCCATCAAGGT TCAGCGGCAGTGGATCTGGGACAGATTTCACTCTCAC CATCAGCAGCCTGCAACCTGAAGATTTTGCAACTTAC TACTGTCAACAGTATGATAATCTCCCGATCACCTTCG GCCAAGGGACACGACTGGAGATTAAA |
|---|---|---|
| 12 | ATX-P-875 VL AA | DIQMTQSPSSLSASVGDRVTITCRASQSISSYLNWYQQK PGKAPKLLIYAASSLQSGVPSRFSGSGSGTDFTLTISSLQP EDFATYYCQQYDNLPITFGQGTRLEIK |
| 13 | ATX-P-875 Kappa LC nt | GACATCCAGATGACCCAGTCTCCATCCTCCCTGTCTG CATCTGTAGGAGACAGAGTCACCATCACTTGCCGGGC AAGTCAGAGCATTAGCAGCTATTTAAATTGGTATCAG CAGAAACCAGGGAAAGCCCCTAAGCTCCTGATCTAT GCTGCATCCAGTTTGCAAAGTGGGGTCCCATCAAGGT TCAGCGGCAGTGGATCTGGGACAGATTTCACTCTCAC CATCAGCAGCCTGCAACCTGAAGATTTTGCAACTTAC TACTGTCAACAGTATGATAATCTCCCGATCACCTTCG GCCAAGGGACACGACTGGAGATTAAACGTACGGTAG CTGCCCCTTCAGTTTTTATCTTTCCGCCGTCTGACGAG CAGTTAAAATCCGGGACCGCTTCTGTAGTTTGCCTGC TGAATAATTTTTATCCGCGTGAGGCTAAAGTACAATG GAAAGTCGACAATGCTTTGCAGTCGGGAAATTCACAG GAAAGTGTTACGGAGCAGGATTCTAAAGATTCCACAT ATTCACTCAGCTCCACCCTTACACTGAGCAAAGCCGA CTATGAAAAACATAAAGTTTACGCATGTGAGGTGACG CACCAAGGATTATCCAGTCCGGTCACAAAATCGTTTA ACCGCGGTGAGTGT |
| 14 | ATX-P-875 Kappa LC AA | DIQMTQSPSSLSASVGDRVTITCRASQSISSYLNWYQQK PGKAPKLLIYAASSLQSGVPSRFSGSGSGTDFTLTISSLQP EDFATYYCQQYDNLPITFGQGTRLEIKRTVAAPSVFIFPP SDEQLKSGTASVVCLLNNFYPREAKVQWKVDNALQSG NSQESVTEQDSKDSTYSLSSTLTLSKADYEKHKVYACE VTHQGLSSPVTKSFNRGEC |

FIG. 34 (continued)

| 15 | ATX-P-885 VH CDR1 (Kabat) | GGSFSGYY |
|---|---|---|
| 16 | ATX-P-885 VH CDR2 (Kabat) | INHSGST |
| 17 | ATX-P-885 VH CDR3 (Kabat) | AREGVYEDY |
| 18 | ATX-P-885 VH nt | CAGGTGCAGCTACAGCAGTGGGGCGCAGGACTGTTG AAGCCTTCGGAGACCCTGTCCCTCACCTGCGCTGTCT ATGGTGGGTCCTTCAGTGGTTACTACTGGAGCTGGAT CCGCCAGCCCCCAGGGAAGGGGCTGGAGTGGATTGG GGAAATCAATCATAGTGGAAGCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCTGTATATTACTGTGCGAGAGA GGGTGTCTACGAGGACTACTGGGGCCAGGGAACCCT GGTCACCGTCTCCTCA |
| 19 | ATX-P-885 VH AA | QVQLQQWGAGLLKPSETLSLTCAVYGGSFSGYYWSWI RQPPGKGLEWIGEINHSGSTNYNPSLKSRVTISVDTSKN QFSLKLSSVTAADTAVYYCAREGVYEDYWGQGTLVTV SS |
| 20 | ATX-P-885 HC IgG1-Fc nt | CAGGTGCAGCTACAGCAGTGGGGCGCAGGACTGTTG AAGCCTTCGGAGACCCTGTCCCTCACCTGCGCTGTCT ATGGTGGGTCCTTCAGTGGTTACTACTGGAGCTGGAT CCGCCAGCCCCCAGGGAAGGGGCTGGAGTGGATTGG GGAAATCAATCATAGTGGAAGCACCAACTACAACCC GTCCCTCAAGAGTCGAGTCACCATATCAGTAGACACG TCCAAGAACCAGTTCTCCCTGAAGCTGAGCTCTGTGA CCGCCGCGGACACGGCTGTATATTACTGTGCGAGAGA GGGTGTCTACGAGGACTACTGGGGCCAGGGAACCCT GGTCACCGTCTCCTCAGCTAGCACTAAAGGGCCTTCT GTATTTCCCTTGGCCCCGTCCAGCAAATCGACCTCGG GAGGGACAGCCGCCCTGGGTTGCCTTGTGAAAGATTA TTTCCCTGAGCCAGTTACCGTAAGTTGGAACAGTGGG GCGCTGACAAGTGGTGTGCACACGTTTCCTGCCGTCC TGCAATCATCGGGCTTGTATAGCCTCAGCTCTGTGGT CACTGTCCCAAGTTCATCGCTGGGCACTCAGACGTAT ATTTGCAATGTGAACCACAAACCTTCAAATACAAAAG TGGATAAACGCGTAGAACCGAAATCGTGTGATAAAA CTCACACATGCCCGCCATGCCCGGCACCTGAACTGCT |

FIG. 34 (continued)

| | | TGGTGGTCCCAGCGTGTTCCTGTTCCCGCCGAAGCCT AAAGATACTCTAATGATCAGCCGTACGCCAGAGGTG ACATGTGTCGTGGTTGACGTGTCCCACGAAGATCCCG AAGTTAAGTTCAATTGGTATGTTGATGGTGTAGAGGT ACACAATGCTAAGACTAAACCTCGCGAGGAGCAGTA CAATTCGACCTATCGTGTCGTGAGCGTTCTGACCGTC CTTCACCAAGATTGGCTTAACGGCAAGAATATAAGT GCAAGGTAAGCAATAAAGCACTTCCGGCCCCAATCG AGAAAACCATTTCCAAGGCCAAAGGTCAACCAAGAG AACCCCAGGTGTATACTCTTCCGCCTTCTCGTGAGGA AATGACTAAAAATCAAGTATCCCTTACGTGTCTGGTT AAAGGTTTTTATCCTAGCGATATTGCTGTTGAATGGG AATCGAACGGTCAGCCGGAGAATAATTATAAAACAA CGCCACCCGTCCTGGATAGCGACGGCTCATTTTTTCT GTATAGCAAACTGACTGTAGATAAATCACGGTGGCA GCAGGGCAATGTATTCAGTTGCTCCGTTATGCATGAA GCGTTACATAATCACTACACGCAGAAATCTCTTAGTC TTTCACCCGGT |
|---|---|---|
| 21 | ATX-P-885 HC IgG1-Fc AA | QVQLQQWGAGLLKPSETLSLTCAVYGGSFSGYYWSWI RQPPGKGLEWIGEINHSGSTNYNPSLKSRVTISVDTSKN QFSLKLSSVTAADTAVYYCAREGVYEDYWGQGTLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKRVEPKSCDKTHTCPPCPA PELLGGPSVFLFPPKPKDTLMISRTPEVTCVVVDVSHED PEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPG |
| 22 | ATX-P-885 VL CDR1 (Kabat) | QSVSNY |
| | ATX-P-885 VL CDR2 (Kabat) | DAY |
| 24 | ATX-P-885 VL CDR3 (Kabat) | QQRSNWPLT |
| 25 | ATX-P-885 VL nt | GAAATTGTGTTGACACAGTCTCCAGCCACCCTGTCTT TGTCTCCAGGGGAAAGAGCCACCCTCTCCTGCAGGGC CAGTCAGAGTGTTAGCAACTACTTAGCCTGGTACCAA |

FIG. 34 (continued)

| | | |
|---|---|---|
| | | CAGAAACCTGGCCAGGCTCCCAGGCTCCTCATCTATG ATGCCTACAACAGGGCCACTGGCATCCCAGCCAGGTT CAGTGGCAGTGGGTCTGGGACAGACTTCACTCTCACC ATCAGCAGCCTAGAGCCTGAAGATTTTGCAGTTTATT ACTGTCAGCAGCGTAGCAACTGGCCTCTCACCTTCGG CCAAGGGACACGACTGGAGATTAAA |
| 26 | ATX-P-885 VL AA | EIVLTQSPATLSLSPGERATLSCRASQSVSNYLAWYQQK PGQAPRLLIYDAYNRATGIPARFSGSGSGTDFTLTISSLE PEDFAVYYCQQRSNWPLTFGQGTRLEIK |
| 27 | ATX-P-885 Kappa LC nt | GAAATTGTGTTGACACAGTCTCCAGCCACCCTGTCTT TGTCTCCAGGGGAAAGAGCCACCCTCTCCTGCAGGGC CAGTCAGAGTGTTAGCAACTACTTAGCCTGGTACCAA CAGAAACCTGGCCAGGCTCCCAGGCTCCTCATCTATG ATGCCTACAACAGGGCCACTGGCATCCCAGCCAGGTT CAGTGGCAGTGGGTCTGGGACAGACTTCACTCTCACC ATCAGCAGCCTAGAGCCTGAAGATTTTGCAGTTTATT ACTGTCAGCAGCGTAGCAACTGGCCTCTCACCTTCGG CCAAGGGACACGACTGGAGATTAAACGTACGGTAGC TGCCCCTTCAGTTTTTATCTTTCCGCCGTCTGACGAGC AGTTAAAATCCGGGACCGCTTCTGTAGTTTGCCTGCT GAATAATTTTTATCCGCGTGAGGCTAAAGTACAATGG AAAGTCGACAATGCTTTGCAGTCGGGAAATTCACAGG AAAGTGTTACGGAGCAGGATTCTAAAGATTCCACATA TTCACTCAGCTCCACCCTTACACTGAGCAAAGCCGAC TATGAAAAACATAAAGTTTACGCATGTGAGGTGACGC ACCAAGGATTATCCAGTCCGGTCACAAAATCGTTTAA CCGCGGTGAGTGT |
| 28 | ATX-P-885 Kappa LC AA | EIVLTQSPATLSLSPGERATLSCRASQSVSNYLAWYQQK PGQAPRLLIYDAYNRATGIPARFSGSGSGTDFTLTISSLE PEDFAVYYCQQRSNWPLTFGQGTRLEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| 29 | ATX-P-890 VH CDR1 (Kabat) | GYTFTGYY |
| 30 | ATX-P-890 VH CDR2 (Kabat) | INPNSGGT |
| 31 | ATX-P-890 VH CDR3 (Kabat) | VRDQVQLERFDS |

FIG. 34 (continued)

| 32 | ATX-P-890 VH nt | CAGGTGCAGCTGGTGCAGTCTGGGGCTGAGGTGAAG AAGCCTGGGGCCTCAGTGAAGGTCTCCTGCAAGGCTT CTGGATACACCTTCACCGGCTACTATATGCACTGGGT GCGACAGGCCCCTGGACAAGGGCTTGAGTGGATGGG ATGGATCAACCCTAACAGTGGTGGCACAAACTATGCA CAGAAGTTTCAGGGCAGGGTCACCATGACCAGGGAC ACGTCCATCAGCACAGCCTACATGGAGCTGAGCAGG CTGAGATCTGACGACACGGCCGTGTATTACTGTGTGA GAGATCAGGTACAACTGGAACGGTTCGACTCCTGGG GCCAGGGAACCCTGGTCACCGTCTCCTCA |
| --- | --- | --- |
| 33 | ATX-P-890 VH AA | QVQLVQSGAEVKKPGASVKVSCKASGYTFTGYYMHW VRQAPGQGLEWMGWINPNSGGTNYAQKFQGRVTMTR DTSISTAYMELSRLRSDDTAVYYCVRDQVQLERFDSWG QGTLVTVSS |
| 34 | ATX-P-890 HC IgG1-Fc nt | CAGGTGCAGCTGGTGCAGTCTGGGGCTGAGGTGAAG AAGCCTGGGGCCTCAGTGAAGGTCTCCTGCAAGGCTT CTGGATACACCTTCACCGGCTACTATATGCACTGGGT GCGACAGGCCCCTGGACAAGGGCTTGAGTGGATGGG ATGGATCAACCCTAACAGTGGTGGCACAAACTATGCA CAGAAGTTTCAGGGCAGGGTCACCATGACCAGGGAC ACGTCCATCAGCACAGCCTACATGGAGCTGAGCAGG CTGAGATCTGACGACACGGCCGTGTATTACTGTGTGA GAGATCAGGTACAACTGGAACGGTTCGACTCCTGGG GCCAGGGAACCCTGGTCACCGTCTCCTCAGCTAGCAC TAAAGGGCCTTCTGTATTTCCCTTGGCCCCGTCCAGC AAATCGACCTCGGGAGGGACAGCCGCCCTGGGTTGC CTTGTGAAAGATTATTTCCCTGAGCCAGTTACCGTAA GTTGGAACAGTGGGGCGCTGACAAGTGGTGTGCACA CGTTTCCTGCCGTCCTGCAATCATCGGGCTTGTATAGC CTCAGCTCTGTGGTCACTGTCCCAAGTTCATCGCTGG GCACTCAGACGTATATTTGCAATGTGAACCACAAACC TTCAAATACAAAAGTGGATAAACGCGTAGAACCGAA ATCGTGTGATAAAACTCACACATGCCCGCCATGCCCG GCACCTGAACTGCTTGGTGGTCCCAGCGTGTTCCTGT TCCCGCCGAAGCCTAAAGATACTCTAATGATCAGCCG TACGCCAGAGGTGACATGTGTCGTGGTTGACGTGTCC |

FIG. 34 (continued)

| | | CACGAAGATCCCGAAGTTAAGTTCAATTGGTATGTTG
ATGGTGTAGAGGTACACAATGCTAAGACTAAACCTCG
CGAGGAGCAGTACAATTCGACCTATCGTGTCGTGAGC
GTTCTGACCGTCCTTCACCAAGATTGGCTTAACGGCA
AAGAATATAAGTGCAAGGTAAGCAATAAAGCACTTC
CGGCCCCAATCGAGAAACCATTTCCAAGGCCAAAG
GTCAACCAAGAGAACCCCAGGTGTATACTCTTCCGCC
TTCTCGTGAGGAAATGACTAAAAATCAAGTATCCCTT
ACGTGTCTGGTTAAAGGTTTTTATCCTAGCGATATTGC
TGTTGAATGGGAATCGAACGGTCAGCCGGAGAATAA
TTATAAAACAACGCCACCCGTCCTGGATAGCGACGGC
TCATTTTTTCTGTATAGCAAACTGACTGTAGATAAATC
ACGGTGGCAGCAGGGCAATGTATTCAGTTGCTCCGTT
ATGCATGAAGCGTTACATAATCACTACACGCAGAAAT
CTCTTAGTCTTTCACCCGGT |
| 35 | ATX-P-890 HC IgG1-Fc AA | QVQLVQSGAEVKKPGASVKVSCKASGYTFTGYYMHW
VRQAPGQGLEWMGWINPNSGGTNYAQKFQGRVTMTR
DTSISTAYMELSRLRSDDTAVYYCVRDQVQLERFDSWG
QGTLVTVSSASTKGPSVFPLAPSSKSTSGGTAALGCLVK
DYFPEPVTVSWNSGALTSGVHTFPAVLQSSGLYSLSSVV
TVPSSSLGTQTYICNVNHKPSNTKVDKRVEPKSCDKTHT
CPPCPAPELLGGPSVFLFPPKPKDTLMISRTPEVTCVVVD
VSHEDPEVKFNWYVDGVEVHNAKTKPREEQYNSTYRV
VSVLTVLHQDWLNGKEYKCKVSNKALPAPIEKTISKAK
GQPREPQVYTLPPSREEMTKNQVSLTCLVKGFYPSDIAV
EWESNGQPENNYKTTPPVLDSDGSFFLYSKLTVDKSRW
QQGNVFSCSVMHEALHNHYTQKSLSLSPG |
| 36 | ATX-P-890 VL CDR1 (Kabat) | QDISNY |
| | ATX-P-890 VL CDR2 (Kabat) | DAS |
| 38 | ATX-P-890 VL CDR3 (Kabat) | QQYDNLPPT |
| 39 | ATX-P-890 VL nt | GACATCCAGATGACCCAGTCTCCATCCTCCCTGTCTG
CATCTGTAGGAGACAGAGTCACCATCACTTGCCAGGC
GAGTCAGGACATTAGCAACTATTTAAATTGGTATCAG
CAGAAACCAGGGAAAGCCCCTAAGCTCCTGATCTAC
GATGCATCCAATTTGGAAACAGGGGTCCCATCAAGGT
TCAGTGGAAGTGGATCTGGGACAGATTTTACTTTCAC |

FIG. 34 (continued)

| | | |
|---|---|---|
| | | CATCAGCAGCCTGCAGCCTGAAGATATTGCAACATAT TACTGTCAACAGTATGATAATCTCCCTCCCACTTTCGG CCCTGGGACCAAGGTGGAAATCAAA |
| 40 | ATX-P-890 VL AA | DIQMTQSPSSLSASVGDRVTITCQASQDISNYLNWYQQK PGKAPKLLIYDASNLETGVPSRFSGSGSGTDFTFTISSLQ PEDIATYYCQQYDNLPPTFGPGTKVEIK |
| 41 | ATX-P-890 Kappa LC nt | GACATCCAGATGACCCAGTCTCCATCCTCCCTGTCTG CATCTGTAGGAGACAGAGTCACCATCACTTGCCAGGC GAGTCAGGACATTAGCAACTATTTAAATTGGTATCAG CAGAAACCAGGGAAAGCCCCTAAGCTCCTGATCTAC GATGCATCCAATTTGGAAACAGGGGTCCCATCAAGGT TCAGTGGAAGTGGATCTGGGACAGATTTTACTTTCAC CATCAGCAGCCTGCAGCCTGAAGATATTGCAACATAT TACTGTCAACAGTATGATAATCTCCCTCCCACTTTCGG CCCTGGGACCAAGGTGGAAATCAAACGTACGGTAGC TGCCCCTTCAGTTTTTATCTTTCCGCCGTCTGACGAGC AGTTAAAATCCGGGACCGCTTCTGTAGTTTGCCTGCT GAATAATTTTTATCCGCGTGAGGCTAAAGTACAATGG AAAGTCGACAATGCTTTGCAGTCGGGAAATTCACAGG AAAGTGTTACGGAGCAGGATTCTAAAGATTCCACATA TTCACTCAGCTCCACCCTTACACTGAGCAAAGCCGAC TATGAAAAACATAAAGTTTACGCATGTGAGGTGACGC ACCAAGGATTATCCAGTCCGGTCACAAAATCGTTTAA CCGCGGTGAGTGT |
| 42 | ATX-P-890 Kappa LC AA | DIQMTQSPSSLSASVGDRVTITCQASQDISNYLNWYQQK PGKAPKLLIYDASNLETGVPSRFSGSGSGTDFTFTISSLQ PEDIATYYCQQYDNLPPTFGPGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC |

FIG. 34 (continued)

IMMUNOCONJUGATES AND METHODS

INCORPORATION BY REFERENCE TO PRIORITY APPLICATIONS

This application is a continuation of U.S. application Ser. No. 18/479,317, filed Oct. 2, 2023, which is a continuation of U.S. application Ser. No. 17/936,346, filed Sep. 28, 2022, now issued as U.S. Pat. No. 11,806,405 on Nov. 7, 2023, which is a continuation-in-part of U.S. application Ser. No. 17/812,869, filed Jul. 15, 2022, which claims priority to U.S. Provisional Application No. 63/203,347, filed Jul. 19, 2021; and U.S. Provisional Application No. 63/267,471, filed Feb. 2, 2022. The disclosures of each of the aforementioned applications are hereby expressly incorporated herein by reference in their entireties.

SEQUENCE STATEMENT

The instant application contains a Sequence Listing, which has been submitted electronically and is hereby incorporated by reference in its entirety. The sequence listing was created on Sep. 28, 2023, is named IMNM-101USCIPC6_SL.xml, and is approximately 49,283 bytes in size.

BACKGROUND

Field

The application relates to conjugates that include a linking group for linking an antibody targeting ligand to a cell-killing moiety (such as a drug), methods of making such conjugates, and methods of using such conjugates to deliver the cell-killing moiety to selected cells or tissues, e.g., for the treatment or inhibition of a cancer.

Description

A number of antibody-drug conjugates (ADC) have been developed for medical uses. See, e.g., Nejadmoghaddam, M. et al., "Antibody-Drug Conjugates: Possibilities and Challenges", Avicenna J Med Biotech 11(1), 3-23 (2019). The antibody in the ADC functions as a targeting agent to deliver the drug to a selected cell or tissue such as a cancer cell or tumor. In the United States, the U.S. Food and Drug Administration (FDA) has approved several ADC formulations, including inotuzumab ozogamicin (tradename BESPONSA), gemtuzumab ozogamicin (tradename MYLOTARG), brentuximab vedotin (tradename ADCETRIS), and ado-trastuzumab emtansine (tradename KADCYLA).

U.S. Pat. No. 10,155,821 discloses ADCs in which an antitumor compound is conjugated to an anti-HER2 antibody via a linker. See also U.S. Patent Publication Nos. 2020/0385486 and 2019/0077880. Trastuzumab deruxtecan is an example of an ADC in which an anti-HER2 antibody (trastuzumab) is attached via a cleavable maleimide tetrapeptide linker to an antitumor compound (deruxtecan). The FDA has approved a formulation known as fam-trastuzumab deruxtecan-nxki (tradename ENHERTU) for the treatment of adult patients with unresectable or metastatic HER2-positive breast cancer who have received two or more prior anti-HER2-based regimens in the metastatic setting. FIG. 1 illustrates the manner in which it is believed the linker connects the antibody (mAb) to the drug moiety.

The FDA approvals represent milestones in the ongoing development of therapeutic ADCs. However, there remains a need for improved ADCs to help address the long-felt need for additional options to treat cancer and/or deliver therapeutic payloads to selected cells or tissues.

SUMMARY

Some embodiments provide an immunoconjugate of Formula (I) that comprises an antibody or antigen-binding fragment (Ab), and drug moiety (D) and a linker connecting Ab to D. In an embodiment, the immunoconjugate of Formula (I) comprises a drug moiety of the Formula (II).

An embodiment provides an immunoconjugate having Formula (I), $$Ab\text{-}[S\text{-}L^1\text{-}L^2\text{-}L^3\text{-}L^4\text{-}L^5\text{-}L^6\text{-}L^7\text{-}D]_n \qquad (I)$$

wherein:
Ab is an antibody or an antigen-binding fragment;
$L^1$ is

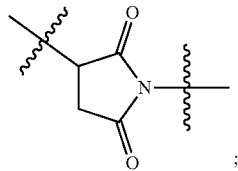 [SMILES: *C1CC(=O)N(*)C1=O]

$L^2$ is absent,

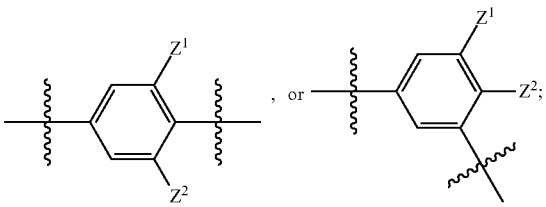

$Z^1$ and $Z^2$ are each individually hydrogen, halogen, $NO_2$, —O—($C_1$-$C_6$ alkyl), or $C_1$-$C_6$ alkyl;
$L^3$ is —$(CH_2)n^1$-C(=O)— or —$(CH_2CH_2O)n^1$-$(CH_2)n^1$C(=O)—;
$n^1$ are independently integers of 0 to 12;
$L^4$ is a tetrapeptide residue;
$L^5$ is absent or —[$NH(CH_2)n^2$]$n^3$-;
$n^2$ is an integer of 0 to 6;
$n^3$ is an integer of 0 to 2;
$L^6$ is absent or

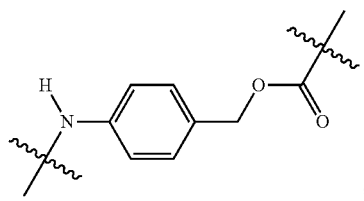

$L^7$ is absent,

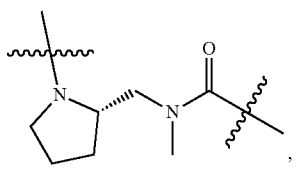

-continued

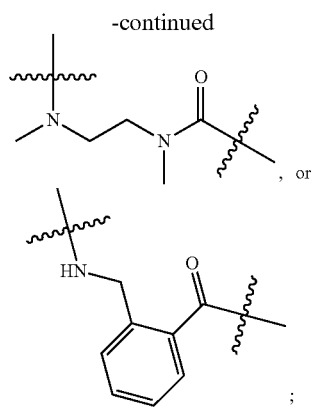

D is a drug moiety; and
n is an integer from 1 to 10.

In an embodiment, D in Formula (I) is a drug moiety of Formula (II) having the structure:

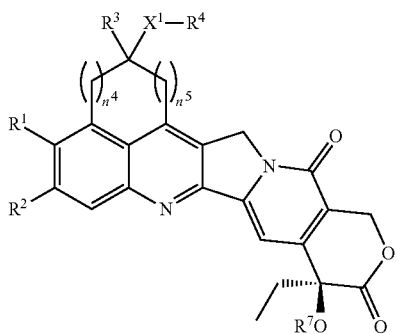

(II)

wherein:
$R^1$ and $R^2$ are each individually selected from the group consisting of hydrogen, halogen, —CN, —$OR^5$, —$NR^5R^6$, a substituted or an unsubstituted $C_1$-$C_6$ alkyl, a substituted or an unsubstituted $C_1$-$C_6$ haloalkyl, a substituted or an unsubstituted —O—($C_1$-$C_6$ alkyl), a substituted or an unsubstituted —O—($C_1$-$C_6$ haloalkyl), —$[(CY_2)_pO(CY_2)_q]_tCY_3$, or a substituted or an unsubstituted —O—$(CR^5R^6)_m$—O— such that $R^1$ and $R^2$ taken together form a ring;
$R^3$ is hydrogen or a substituted or an unsubstituted $C_1$-$C_6$ alkyl, a substituted or an unsubstituted $C_1$-$C_6$ haloalkyl, or —$[(CY_2)_pO(CY_2)_q]_tCY_3$;
$R^4$ is hydrogen, a substituted or an unsubstituted —($C_1$-$C_6$ alkyl)-$X^2$, a substituted or an unsubstituted —($C_1$-$C_6$ haloalkyl)-$X^2$, a substituted or an unsubstituted —($C_1$-$C_6$ alkenyl)-$X^2$, a substituted or an unsubstituted —($C_1$-$C_6$ haloalkenyl)-$X^2$, a substituted or an unsubstituted —($C_1$-$C_6$ alkynyl)-$X^2$, or a substituted or an unsubstituted —($C_1$-$C_6$ haloalkynyl)-$X^2$;
$X^1$ is —O—, —$S(O_{n6})$—, —NH—, —O—(C=O)—, —NH—(C=O)—, —NH—(C=O)—O—, —NH—(C=O)—NH—, or —NH—$S(O_{n6})$—;
$X^2$ is —$OR^9$, —$SR^9$, or —$NHR^9$;
$R^5$ and $R^6$ are each individually hydrogen, halogen, a substituted or an unsubstituted $C_1$-$C_6$ alkyl, a substituted or an unsubstituted $C_1$-$C_6$ haloalkyl, or —$[(CY_2)_pO(CY_2)_q]_tCY_3$;
m is 1 or 2;

$n^4$ and $n^5$ are each individually 0, 1 or 2, with the proviso that $n^4$ and $n^5$ are not both 0;
$n^6$ is 0, 1 or 2;
each Y is individually H or halogen;
each p is individually 1, 2, 3, 4, 5, or 6;
each q is individually 0, 1, 2, 3, 4, 5, or 6;
each t is individually 1, 2, 3, 4, 5, or 6;
$R^7$ is H, —$COR^8$, —$CO_2R^8$, —(CO)—$NHR^8$, $L^4$, $L^5$, $L^6$, or $L^7$;
$R^8$ is a substituted or an unsubstituted $C_1$-$C_6$ alkyl-$X^3$, a substituted or an unsubstituted $C_1$-$C_6$ haloalkyl-$X^3$, or —$[(CY_2)_pO(CY_2)_q]_tCY_2$—$X^3$;
$R^9$ is H, —$COR^8$, —$CO_2R^8$, —(CO)—$NHR^8$, $L^4$, $L^5$, $L^6$, or $L^7$, with the proviso that exactly one of $R^7$ and $R^9$ is $L^4$, $L^5$, $L^6$, or $L^7$; and
each $X^3$ is individually —H, —OH, —SH, or —$NH_2$.

An embodiment provides a compound of Formula (IV), or a pharmaceutically acceptable salt thereof, having the structure:

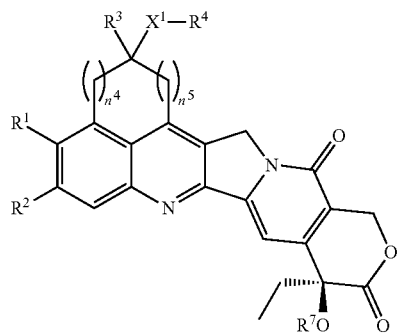

(IV)

wherein:
$R^1$ and $R^2$ are each individually selected from the group consisting of hydrogen, halogen, —CN, —$OR^5$, —$NR^5R^6$, a substituted or an unsubstituted $C_1$-$C_6$ alkyl, a substituted or an unsubstituted $C_1$-$C_6$ haloalkyl, a substituted or an unsubstituted —O—($C_1$-$C_6$ alkyl), a substituted or an unsubstituted —O—($C_1$-$C_6$ haloalkyl), —$[(CY_2)_pO(CY_2)_q]_tCY_3$, or a substituted or an unsubstituted —O—$(CR^5R^6)_m$—O— such that $R^1$ and $R^2$ taken together form a ring;
$R^3$ is hydrogen or a substituted or an unsubstituted $C_1$-$C_6$ alkyl, a substituted or an unsubstituted $C_1$-$C_6$ haloalkyl, or —$[(CY_2)_pO(CY_2)_q]_tCY_3$;
$R^4$ is hydrogen, a substituted or an unsubstituted —($C_1$-$C_6$ alkyl)-$X^2$, a substituted or an unsubstituted —($C_1$-$C_6$ haloalkyl)-$X^2$, a substituted or an unsubstituted —($C_1$-$C_6$ alkenyl)-$X^2$, a substituted or an unsubstituted —($C_1$-$C_6$ haloalkenyl)-$X^2$, a substituted or an unsubstituted —($C_1$-$C_6$ alkynyl)-$X^2$, or a substituted or an unsubstituted —($C_1$-$C_6$ haloalkynyl)-$X^2$;
$X^1$ is —O—, —$S(O_{n6})$—, —NH—, —O—(C=O)—, —NH—(C=O)—, —NH—(C=O)—O—, —NH—(C=O)—NH—, or —NH—$S(O_{n6})$—;
$X^2$ is —OH, —SH, or —$NR^5R^6$;
$R^5$ and $R^6$ are each individually hydrogen, halogen, a substituted or an unsubstituted $C_1$-$C_6$ alkyl, a substituted or an unsubstituted $C_1$-$C_6$ haloalkyl, or —$[(CY_2)_pO(CY_2)_q]_tCY_3$;
$R^7$ is H, —$COR^8$, —$CO_2R^8$, or —(CO)—$NHR^8$;
$R^8$ is a substituted or an unsubstituted $C_1$-$C_6$ alkyl, a substituted or an unsubstituted $C_1$-$C_6$ haloalkyl, or —$[(CY_2)_pO(CY_2)_q]_tCY_3$;

m is 1 or 2;

$n^4$ and $n^5$ are each individually 0, 1 or 2, with the proviso that $n^4$ and $n^5$ are not both 0;

$n^6$ is 0, 1 or 2; and each Y is individually H or halogen;

each p is individually 1, 2, 3, 4, 5, or 6;

each q is individually 0, 1, 2, 3, 4, 5, or 6; and each t is individually 1, 2, 3, 4, 5, or 6;

with the proviso that Formula (IV) does not represent deruxtecan or exatecan.

An embodiment provides a pharmaceutical composition comprising an immunoconjugate as described herein, a drug compound as described herein, or a pharmaceutically active salt thereof, and a pharmaceutically acceptable carrier, diluent, excipient or combination thereof.

An embodiment provides a method for treating a cancer or a tumor comprising administering an effective amount of an immunoconjugate as described herein, a drug compound as described herein, or a pharmaceutically active salt thereof, or a pharmaceutical composition as described herein, to a subject having the cancer or the tumor.

An embodiment provides a use of an effective amount of an immunoconjugate as described herein, a drug compound as described herein, or a pharmaceutically active salt thereof, or a pharmaceutical composition as described herein, in the manufacture of a medicament for treating a cancer or a tumor.

Some embodiments provide a conjugate of Formula (III) that comprises a functional group M1, a drug moiety (D) and a linker connecting Mi to D. In an embodiment, the conjugate of Formula (III) comprises a drug moiety of the Formula (II).

An embodiment provides a conjugate having Formula (III), $$Mi-L^2-L^3-L^4-L^5-L^6-L^7-D \quad (III)$$

wherein:

Mi is

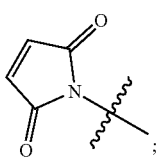

$L^2$ is absent,

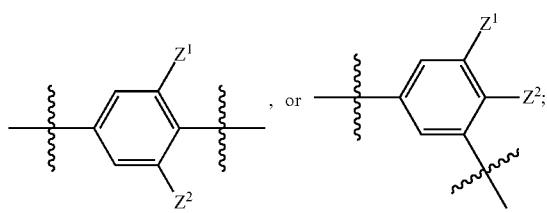

$Z^1$ and $Z^2$ are each individually hydrogen, halogen, $NO_2$, $-O-(C_1-C_6$ alkyl), or $C_1-C_6$ alkyl;

$L^3$ is $-(CH_2)n^1-C(=O)-$ or $-(CH_2CH_2O)n^1-(CH_2)n^1C(=O)-$;

$n^1$ are independently integers of 0 to 12;

$L^4$ is a tetrapeptide residue;

$L^5$ is absent or $-[NH(CH_2)n^2]n^3-$;

$n^2$ is an integer of 0 to 6;

$n^3$ is an integer of 0 to 2;

$L^6$ is absent or

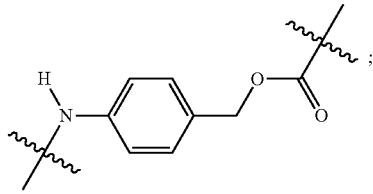

$L^7$ is absent,

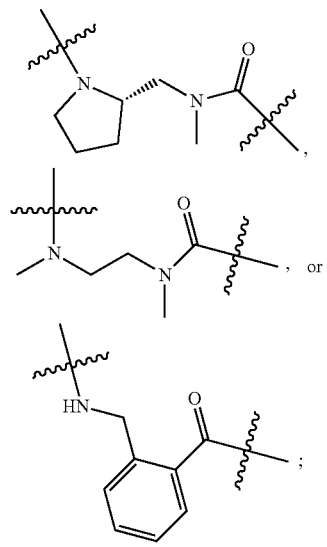

and

D is a drug moiety.

An embodiment provides a process of producing an immunoconjugate, comprising: reacting an effective amount of a thiol-functionalized antibody or antigen-binding fragment with a conjugate as described herein under reaction conditions effective to form an immunoconjugate as described herein.

Preferred alternatives include:

1. An antibody or antigen-binding fragment thereof, comprising:
   a) a heavy chain comprising:
   VHCDR 1 comprising an amino acid sequence having at least 95% sequence identity to the amino acid sequence of SEQ ID NO:1;
   VHCDR 2 comprising an amino acid sequence having at least 95% sequence identity to the amino acid sequence of SEQ ID NO:2; and
   VHCDR 3 comprising an amino acid sequence having at least 95% sequence identity to the amino acid sequence of SEQ ID NO:3; and
   b) a light chain comprising:
   VLCDR 1 comprising an amino acid sequence having at least 95% sequence identity to the amino acid sequence of SEQ ID NO:8;
   VLCDR 2 comprising an amino acid sequence having at least 95% sequence identity to the amino acid sequence of AAS; and
   VLCDR 3 comprising an amino acid sequence having at least 95% sequence identity to the amino acid sequence of SEQ ID NO:10;

wherein the antibody or antigen-binding fragment thereof specifically binds to the extracellular domain of human receptor tyrosine kinase like orphan receptor 1 (ROR1).

2. The antibody or antigen-binding fragment of alternative 1, comprising an amino acid sequence having at least 95% sequence identity to the amino acid sequence of any one of SEQ ID NOs: 5, 7, 12, or 14.

3. One or more nucleic acids encoding the antibody or antigen-binding fragment thereof of any one of alternatives 1 or 2, such as an antibody or antigen-binding fragment thereof encoded by one or more nucleic acids comprising a sequence having at least 95% sequence identity to the nucleic acid sequence set forth in any one of SEQ ID NOs: 4, 6, 11, or 13.

4. A host cell comprising the one or more nucleic acids of alternative 3.

5. The immunoconjugate of any one of the previous embodiments, wherein Ab is the antibody or antigen-binding fragment of claim alternatives 1 or 2.

6. An antibody or antigen-binding fragment thereof, comprising:
a) a heavy chain comprising:
VHCDR 1 comprising an amino acid sequence having at least 95% sequence identity to the amino acid sequence of SEQ ID NO:15;
VHCDR 2 comprising an amino acid sequence having at least 95% sequence identity to the amino acid sequence of SEQ ID NO:16; and
VHCDR 3 comprising an amino acid sequence having at least 95% sequence identity to the amino acid sequence of SEQ ID NO:17; and
b) a light chain comprising:
VLCDR 1 comprising an amino acid sequence having at least 95% sequence identity to the amino acid sequence of SEQ ID NO:22;
VLCDR 2 comprising an amino acid sequence having at least 95% sequence identity to the amino acid sequence of DAY; and
VLCDR 3 comprising an amino acid sequence having at least 95% sequence identity to the amino acid sequence of SEQ ID NO:24;
wherein the antibody or antigen-binding fragment thereof specifically binds to the extracellular domain of human receptor tyrosine kinase like orphan receptor 1 (ROR1).

7. The antibody or antigen-binding fragment of alternative 6, comprising an amino acid sequence having at least 95% sequence identity to the amino acid sequence of any one of SEQ ID NOs: 19, 21, 26 or 28.

8. One or more nucleic acids encoding the antibody or antigen-binding fragment thereof of any one of alternatives 6 or 7, such as an antibody or antigen-binding fragment thereof encoded by one or more nucleic acids comprising a sequence having at least 95% sequence identity to the nucleic acid sequence set forth in any one of SEQ ID NOs: 18, 20, 25, or 27.

9. A host cell comprising the one or more nucleic acids of alternative 8.

10. The immunoconjugate of any one of previous embodiments, wherein Ab is the antibody or antigen-binding fragment of alternatives 6 or 7.

11. An antibody or antigen-binding fragment thereof, comprising:
a) a heavy chain comprising:
VHCDR 1 comprising an amino acid sequence having at least 95% sequence identity to the amino acid sequence of SEQ ID NO:29;
VHCDR 2 comprising an amino acid sequence having at least 95% sequence identity to the amino acid sequence of SEQ ID NO:30; and
VHCDR 3 comprising an amino acid sequence having at least 95% sequence identity to the amino acid sequence of SEQ ID NO:31; and
b) a light chain comprising:
VLCDR 1 comprising an amino acid sequence having at least 95% sequence identity to the amino acid sequence of SEQ ID NO:36;
VLCDR 2 comprising an amino acid sequence having at least 95% sequence identity to the amino acid sequence of DAS; and
VLCDR 3 comprising an amino acid sequence having at least 95% sequence identity to the amino acid sequence of SEQ ID NO:38;
wherein the antibody or antigen-binding fragment specifically binds to the extracellular domain of human receptor tyrosine kinase like orphan receptor 1 (ROR1).

12. The antibody or antigen-binding fragment of alternative 11, comprising an amino acid sequence having at least 95% sequence identity to the amino acid sequence of any one of SEQ ID NOs: 33, 35, 40 or 42.

13. One or more nucleic acids encoding the antibody or antigen-binding fragment thereof of any one of alternatives 11 or 12, such as an antibody or antigen-binding fragment thereof encoded by one or more nucleic acids comprising a sequence having at least 95% sequence identity to the nucleic acid sequence set forth in any one of SEQ ID NOs: 32, 34, 39, or 41.

14. A host cell comprising the one or more nucleic acids of alternative 13.

15. The immunoconjugate of any one of the previous embodiments, wherein Ab is the antibody or antigen-binding fragment of alternatives 11 or 12.

16. An antibody or binding fragment thereof where the heavy chain is encoded by the nucleic acid sequence set forth in SEQ ID NO: 6 and the light chain is encoded by the nucleic acid sequence set forth in SEQ ID NO: 13 or a composition comprising said antibody or binding fragment thereof.

17. The antibody or binding fragment thereof of alternative 16 or a composition comprising said antibody or binding fragment thereof, wherein the heavy chain of the antibody comprises the polypeptide sequence of SEQ ID NO:7 and the light chain comprises the polypeptide sequence of SEQ ID NO: 14.

18. The antibody or binding fragment thereof of any one of alternatives 16 or 17 or a composition comprising said antibody or binding fragment thereof, wherein said antibody or binding fragment thereof is conjugated to a molecule.

19. The antibody or binding fragment thereof of alternative 18 or a composition comprising said antibody or binding fragment thereof, wherein the molecule is a drug, toxin, or cytokine.

20. The immunoconjugate of anyone of claims 1-25, wherein said antibody or binding fragment thereof is the antibody or binding fragment thereof of any one of alternatives 16 or 17.

21. A method of using the antibody or binding fragment thereof of any one of alternatives 16-19 or a composition comprising said antibody or binding fragment thereof, such as the immunoconjugate of alternative 20, for inhibiting or treating a disease such as a cancer comprising administering the antibody or binding fragment thereof of any one of alternatives 16-19 or said composition to a subject in need thereof, optionally selecting a subject to receive a therapy for said disease such as cancer and/or optionally determining the inhibition of said disease such as cancer after administration of said antibody or binding fragment thereof.

22 The antibody or binding fragment thereof of any one of alternatives 16-19 or a composition comprising said antibody or binding fragment thereof, such as the immunoconjugate of alternative 20, for use as a medicament, such as for the purpose of inhibiting or treating a disease such as a cancer.

23. An antibody or binding fragment thereof where the heavy chain is encoded by the nucleic acid sequence set forth in SEQ ID NO: 20 and the light chain is encoded by the nucleic acid sequence set forth in SEQ ID NO: 27 or a composition comprising said antibody or binding fragment thereof.

24. The antibody or binding fragment thereof of alternative 23 or a composition comprising said antibody or binding fragment thereof, wherein the heavy chain of the antibody comprises the polypeptide sequence of SEQ ID NO:21 and the light chain comprises the polypeptide sequence of SEQ ID NO: 28.

25. The antibody or binding fragment thereof of any one of alternatives 23 or 24 or a composition comprising said antibody or binding fragment thereof, wherein said antibody or binding fragment thereof is conjugated to a molecule.

26. The antibody or binding fragment thereof of alternative 25 or a composition comprising said antibody or binding fragment thereof, wherein the molecule is a drug, toxin, or cytokine.

27. The immunoconjugate of anyone of claims 1-25, wherein said antibody or binding fragment thereof is the antibody or binding fragment thereof of any one of alternatives 23 or 24.

28. A method of using the antibody or binding fragment thereof of any one of alternatives 23-26 or a composition comprising said antibody or binding fragment thereof, such as the immunoconjugate of alternative 27, for inhibiting or treating a disease such as a cancer comprising administering the antibody or binding fragment thereof of any one of claims alternatives 23-26 or said composition to a subject in need thereof, optionally selecting a subject to receive a therapy for said disease such as cancer and/or optionally determining the inhibition of said disease such as cancer after administration of said antibody or binding fragment thereof.

29. The antibody or binding fragment thereof of any one of alternatives 23-26 or a composition comprising said antibody or binding fragment thereof, such as the immunoconjugate of alternative 27, for use as a medicament, such as for the purpose of inhibiting or treating a disease such as a cancer.

30. An antibody or binding fragment thereof where the heavy chain is encoded by the nucleic acid sequence set forth in SEQ ID NO: 34 and the light chain is encoded by the nucleic acid sequence set forth in SEQ ID NO: 41 or a composition comprising said antibody or binding fragment thereof.

31. The antibody or binding fragment thereof of alternative 30 or a composition comprising said antibody or binding fragment thereof, wherein the heavy chain of the antibody comprises the polypeptide sequence of SEQ ID NO:35 and the light chain comprises the polypeptide sequence of SEQ ID NO: 42.

32. The antibody or binding fragment thereof of any one of alternatives 30 or 31 or a composition comprising said antibody or binding fragment thereof, wherein said antibody or binding fragment thereof is conjugated to a molecule.

33. The antibody or binding fragment thereof of alternative 32 or a composition comprising said antibody or binding fragment thereof, wherein the molecule is a drug, toxin, or cytokine.

34. The immunoconjugate of anyone of claims 1-25, wherein said antibody or binding fragment thereof is the antibody or binding fragment thereof of any one of alternatives 30 or 31.

35. A method of using the antibody or binding fragment thereof of any one of alternatives 30-33 or a composition comprising said antibody or binding fragment thereof, such as the immunoconjugate of alternative 34, for inhibiting or treating a disease such as a cancer comprising administering the antibody or binding fragment thereof of any one of alternatives 30-33 or said composition to a subject in need thereof, optionally selecting a subject to receive a therapy for said disease such as cancer and/or optionally determining the inhibition of said disease such as cancer after administration of said antibody or binding fragment thereof.

36. The antibody or binding fragment thereof of any one of alternative 30-33 or a composition comprising said antibody or binding fragment thereof, such as the immunoconjugate of alternative 34, for use as a medicament, such as for the purpose of inhibiting or treating a disease such as a cancer.

BRIEF DESCRIPTION OF THE DRAWINGS

FIG. 34 illustrates nucleotide and amino acid sequences for anti-ROR-1 antibodies ATX-P-875, ATX-P-885, and ATX-P-890.

DETAILED DESCRIPTION

Definitions

Figure 1:
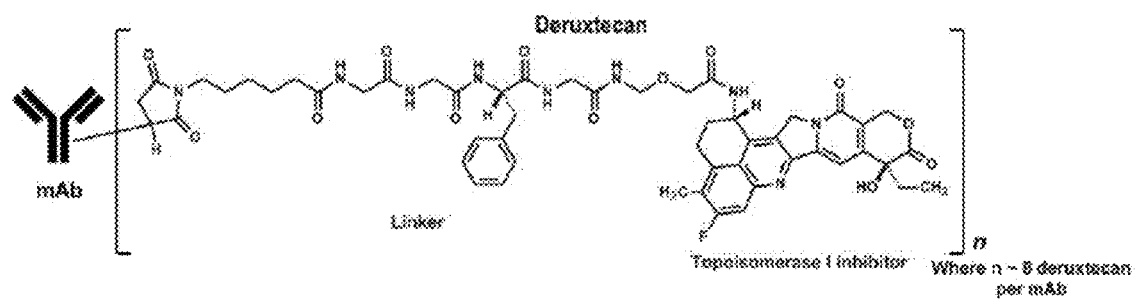
FIG. 1 illustrates a trastuzumab deruxtecan antibody-drug conjugate.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, a "conjugate" is a compound that comprises two or more substances (such as an antibody, a linker moiety and/or a drug moiety) joined together by chemical bonds. Examples of conjugates include antibody-drug conjugates (which may optionally include a linker moiety), drug-linker conjugates, and antibody-linker conjugates. An "immunoconjugate" is a conjugate that comprise an immunological substance such as an antibody.

As used herein, an "antibody" (Ab) is a protein made by the immune system, or a synthetic variant thereof, that binds to specific sites on cells or tissues. An "antigen-binding fragment" (Fab) is a portion of an antibody that binds to a specific antigen. Monoclonal antibodies are a type of synthetic antibody. In cancer treatment, monoclonal antibodies may kill cancer cells directly, they may block development of tumor blood vessels, or they may help the immune system kill cancer cells.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl) and a di-substituted amine(alkyl).

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if ortho $R^1$ and $R^2$ substituents on a phenyl ring are indicated to be $-O-(CR^5R^6)_m-O-$ such that $R^1$ and $R^2$ "taken together" form a ring, it means that the $-O-(CR^5R^6)_m-O-$ is covalently bonded to the phenyl ring at the $R^1$ and $R^2$ positions to form a heterocyclic ring:

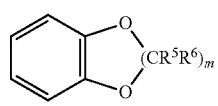

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted. An alkyl group is typically monovalent unless the context indicates otherwise. For example, those skilled in the art recognize that $C_1$-$C_6$ alkyl is bivalent in the following formula: $-(C_1$-$C_6$ alkyl)-$X^2$.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by ∿∿∿, followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 4 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g.,

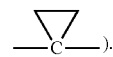

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

The term "halogen atom" or "halogen" as used herein, means any one of the radio-stable atoms of column 7 of the Periodic Table of the Elements, such as, fluorine, chlorine, bromine and iodine.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkenyl" refers to an alkenyl group in which one or more of the hydrogen atoms are replaced by a halogen (e.g., mono-haloalkenyl, di-haloalkenyl, tri-haloalkenyl and polyhaloalkenyl).

As used herein, "haloalkynyl" refers to an alkynyl group in which one or more of the hydrogen atoms are replaced by a halogen (e.g., mono-haloalkynyl, di-haloalkynyl, tri-haloalkynyl and polyhaloalkynyl).

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

Where the number of substituents is not specified (e.g. haloalkyl, haloalkenyl, haloalkynyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3+$) and the positive charge can be balanced by a negatively charged counterion (such as $Cl^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Various embodiments disclosed herein relate to a compound of Formula (IV), or a pharmaceutically acceptable salt thereof, having the structure:

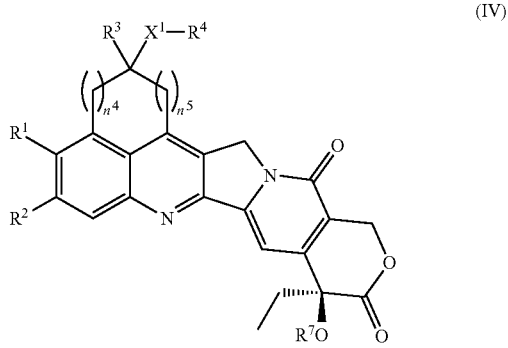

(IV)

In various embodiments, $R^1$ and $R^2$ in Formula (IV) are each individually selected from the group consisting of hydrogen, halogen, —CN, —OR$^5$, —NR$^5$R$^6$, a substituted or an unsubstituted $C_1$-$C_6$ alkyl, a substituted or an unsubstituted $C_1$-$C_6$ haloalkyl, a substituted or an unsubstituted —O—($C_1$-$C_6$ alkyl), a substituted or an unsubstituted —O—($C_1$-$C_6$ haloalkyl), —[(CY$_2$)$_p$O(CY$_2$)$_q$]$_t$CY$_3$, or a substituted or an unsubstituted —O—(CR$^5$R$^6$)$_m$—O— such that $R^1$ and $R^2$ taken together form a ring. In an embodiment, at least one of $R^1$ and $R^2$ is hydrogen. In an embodiment, at least one of $R^1$ and $R^2$ is halogen. For example, in an embodiment, at least one of $R^1$ and $R^2$ is fluoro. In an embodiment, at least one of $R^1$ and $R^2$ is —CN. In an embodiment, at least one of $R^1$ and $R^2$ is —OR$^5$, wherein $R^5$ is hydrogen, halogen, a substituted or an unsubstituted $C_1$-$C_6$ alkyl, a substituted or an unsubstituted $C_1$-$C_6$ haloalkyl, or —[(CY$_2$)$_p$O(CY$_2$)$_q$]$_t$CY$_3$. For example, in an embodiment, at least one of $R^1$ and $R^2$ is methoxy.

In an embodiment, at least one of $R^1$ and $R^2$ in Formula (IV) is —NR$^5$R$^6$, wherein $R^5$ and $R^6$ are each individually hydrogen, halogen, a substituted or an unsubstituted $C_1$-$C_6$ alkyl, a substituted or an unsubstituted $C_1$-$C_6$ haloalkyl, or —[(CY$_2$)$_p$O(CY$_2$)$_q$]$_t$CY$_3$. In an embodiment, at least one of $R^1$ and $R^2$ is a substituted or an unsubstituted $C_1$-$C_6$ alkyl. For example, in an embodiment, at least one of $R^1$ and $R^2$ is methyl. In an embodiment, at least one of $R^1$ and $R^2$ is a substituted or an unsubstituted $C_1$-$C_6$ haloalkyl. For example, in an embodiment, at least one of $R^1$ and $R^2$ is difluoromethyl. In an embodiment, at least one of $R^1$ and $R^2$ is a substituted or an unsubstituted —O—($C_1$-$C_6$ alkyl). For example, in an embodiment, at least one of $R^1$ and $R^2$ is methoxy. In an embodiment, at least one of $R^1$ and $R^2$ is —[(CY$_2$)$_p$O(CY$_2$)$_q$]$_t$CY$_3$. In an embodiment, $R^1$ and $R^2$ are a substituted or an unsubstituted —O—(CR$^5$R$^6$)$_m$—O— such that $R^1$ and $R^2$ taken together form a ring in which the ends of the —O—(CR$^5$R$^6$)$_m$—O— are covalently bonded to the phenyl ring at the $R^1$ and $R^2$ positions of Formula (IV) to form a heterocyclic ring.

In an embodiment, one of $R^1$ and $R^2$ in Formula (IV) is hydrogen and the other of $R^1$ and $R^2$ is halogen. In an embodiment, one of $R^1$ and $R^2$ is hydrogen and the other of $R^1$ and $R^2$ is a substituted or an unsubstituted $C_1$-$C_6$ alkyl. In an embodiment, one of $R^1$ and $R^2$ is hydrogen and the other of $R^1$ and $R^2$ is a substituted or an unsubstituted $C_1$-$C_6$ haloalkyl. In an embodiment, one of $R^1$ and $R^2$ is hydrogen and the other of $R^1$ and $R^2$ is a substituted or an unsubstituted —O—($C_1$-$C_6$ alkyl). In an embodiment, both $R^1$ and $R^2$ are hydrogen. In an embodiment, neither $R^1$ nor $R^2$ is hydrogen.

In an embodiment, one of $R^1$ and $R^2$ in Formula (IV) is halogen and the other of $R^1$ and $R^2$ is a substituted or an unsubstituted $C_1$-$C_6$ alkyl. In an embodiment, one of $R^1$ and $R^2$ is halogen and the other of $R^1$ and $R^2$ is a substituted or an unsubstituted $C_1$-$C_6$ haloalkyl. In an embodiment, one of $R^1$ and $R^2$ is halogen and the other of $R^1$ and $R^2$ is a substituted or an unsubstituted —O—($C_1$-$C_6$ alkyl). In an embodiment, both $R^1$ and $R^2$ are independently halogen. In an embodiment, neither $R^1$ nor $R^2$ is halogen.

In an embodiment, one of $R^1$ and $R^2$ in Formula (IV) is a substituted or an unsubstituted $C_1$-$C_6$ alkyl and the other of $R^1$ and $R^2$ is a substituted or an unsubstituted $C_1$-$C_6$ haloalkyl. In an embodiment, one of $R^1$ and $R^2$ is a substituted or an unsubstituted $C_1$-$C_6$ alkyl and the other of $R^1$ and $R^2$ is a substituted or an unsubstituted —O—($C_1$-$C_6$ alkyl). In an embodiment, both $R^1$ and $R^2$ are independently a substituted or an unsubstituted $C_1$-$C_6$ alkyl. In an embodiment, neither $R^1$ nor $R^2$ is a substituted or an unsubstituted $C_1$-$C_6$ alkyl.

In an embodiment, one of $R^1$ and $R^2$ in Formula (IV) is a substituted or an unsubstituted $C_1$-$C_6$ haloalkyl and the other of $R^1$ and $R^2$ is a substituted or an unsubstituted —O—($C_1$-$C_6$ alkyl). In an embodiment, both $R^1$ and $R^2$ are independently a substituted or an unsubstituted $C_1$-$C_6$ haloalkyl. In an embodiment, neither $R^1$ nor $R^2$ is a substituted or an unsubstituted $C_1$-$C_6$ haloalkyl.

In an embodiment, one of $R^1$ and $R^2$ in Formula (IV) is a substituted or an unsubstituted —O—($C_1$-$C_6$ alkyl). In an embodiment, both $R^1$ and $R^2$ are independently a substituted or an unsubstituted —O—($C_1$-$C_6$ alkyl). In an embodiment, neither $R^1$ nor $R^2$ is a substituted or an unsubstituted —O—($C_1$-$C_6$ alkyl). In an embodiment, $R^1$ and $R^2$ are a substituted or an unsubstituted —O—$(CR^5R^6)_m$—O— such that $R^1$ and $R^2$ taken together form a ring. In various embodiments, $R^1$ and $R^2$ are each individually selected from the group consisting of hydrogen, fluoro, methoxy, methyl, difluoromethyl, and —O—$(CH_2)$—O— such that $R^1$ and $R^2$ taken together form a ring.

In various embodiments, $R^3$ in Formula (IV) is hydrogen or a substituted or an unsubstituted $C_1$-$C_6$ alkyl, a substituted or an unsubstituted $C_1$-$C_6$ haloalkyl, or —$[(CY_2)_pO(CY_2)_q]_t$ $CY_3$, where each Y is individually H or halogen. In an embodiment, $R^3$ is hydrogen. In an embodiment, $R^3$ is a substituted or an unsubstituted $C_1$-$C_6$ alkyl. For example, in an embodiment, $R^3$ is methyl. In an embodiment, $R^3$ is a substituted or an unsubstituted $C_1$—$C_6$ haloalkyl. In an embodiment, $R^3$ is —$[(CY_2)_pO(CY_2)_q]_tCY_3$, where each Y is individually H or halogen.

In various embodiments, $R^4$ in Formula (IV) is hydrogen, a substituted or an unsubstituted —$(C_1$-$C_6$ alkyl)-$X^2$, a substituted or an unsubstituted —$(C_1$-$C_6$ haloalkyl)-$X^2$, a substituted or an unsubstituted —$(C_1$-$C_6$ alkenyl)-$X^2$, a substituted or an unsubstituted —$(C_1$-$C_6$ haloalkenyl)-$X^2$, a substituted or an unsubstituted —$(C_1$-$C_6$ alkynyl)-$X^2$, a substituted or an unsubstituted —$(C_1$-$C_6$ haloalkynyl)-$X^2$, where $X^2$ is —OH, —SH, or —$NR^5R^6$. In an embodiment, $R^4$ is hydrogen. In an embodiment, $R^4$ is a substituted or an unsubstituted —$(C_1$-$C_6$ alkyl)-$X^2$. In an embodiment, $R^4$ is a substituted or an unsubstituted —$(C_1$-$C_6$ haloalkyl)-$X^2$. In an embodiment, $R^4$ is a substituted or an unsubstituted —$(C_1$-$C_6$ alkenyl)-$X^2$. In an embodiment, $R^4$ is a substituted or an unsubstituted —$(C_1$-$C_6$ haloalkenyl)-$X^2$. In an embodiment, $R^4$ is a substituted or an unsubstituted —$(C_1$-$C_6$ alkynyl)-$X^2$. In an embodiment, $R^4$ is a substituted or an unsubstituted —$(C_1$-$C_6$ haloalkynyl)-$X^2$.

In various embodiments, $X^1$ in Formula (IV) is —O—, —$S(O_{n6})$—, —NH—, —O—(C=O)—, —NH—(C=O)—, —NH—(C=O)—O—, —NH—(C=O)—NH—, or —NH—$S(O_{n6})$—, where $n^6$ is 0, 1 or 2. In an embodiment, $X^1$ is —O—. In an embodiment, $X^1$ is —$S(O_{n6})$—. In an embodiment, $X^1$ is —NH—. In an embodiment, $X^1$ is —O—(C=O)—. In an embodiment, $X^1$ is —NH—(C=O)—. In an embodiment, $X^1$ is —NH—(C=O)—O—. In an embodiment, $X^1$ is —NH—(C=O)—NH—. In an embodiment, $X^1$ is —NH—$S(O_{n6})$—.

In various embodiments, $X^2$ in Formula (IV) is —OH, —SH, or —$NR^5R^6$, where $R^5$ and $R^6$ are each individually hydrogen, halogen or a substituted or an unsubstituted $C_1$-$C_6$ alkyl, $C_1$-$C_6$ haloalkyl, —$[(CY_2)_pO(CY_2)_q]_tCY_3$. In an embodiment, $X^2$ is —OH. In an embodiment, $X^2$ is —SH. In an embodiment, $X^2$ is —$NR^5R^6$.

In various embodiments, $R^5$ and $R^6$ in Formula (IV) are each individually hydrogen, halogen, a substituted or an unsubstituted $C_1$-$C_6$ alkyl, a substituted or an unsubstituted $C_1$-$C_6$ haloalkyl, or —$[(CY_2)_pO(CY_2)_q]_tCY_3$, where each Y is individually H or halogen and variables p, q and t are as described elsewhere herein. In an embodiment, $R^5$ and $R^6$ are each individually hydrogen or a substituted or an unsubstituted $C_1$-$C_6$ alkyl. In an embodiment, $R^5$ and $R^6$ are both hydrogen. In an embodiment, $R^5$ and $R^6$ are each individually a substituted or an unsubstituted $C_1$-$C_6$ alkyl.

In various embodiments, $R^7$ in Formula (IV) is H, —$COR^8$, —$CO_2R^8$, or —(CO)—$NHR^8$, wherein $R^8$ is described elsewhere herein. In an embodiment, $R^7$ is H. In an embodiment, $R^7$ is —$COR^8$. In an embodiment, $R^7$ is —$CO_2R^8$. In an embodiment, $R^7$ is —(CO)—$NHR^8$.

In various embodiments, $R^8$ in Formula (IV) is a substituted or an unsubstituted $C_1$-$C_6$ alkyl, a substituted or an unsubstituted $C_1$-$C_6$ haloalkyl, or —$[(CY_2)_pO(CY_2)_q]_tCY_3$, where the variables p, q, t and Y are described elsewhere herein. In an embodiment, $R^8$ is a substituted or an unsubstituted $C_1$-$C_6$ alkyl. In an embodiment, $R^8$ is a substituted or an unsubstituted $C_1$-$C_6$ haloalkyl. In an embodiment, $R^1$ is a —$[(CY_2)_pO(CY_2)_q]_tCY_3$.

In various embodiments, m in Formula (IV) is 1 or 2. In an embodiment, m is 1. In another embodiment, m is 2.

In various embodiments, $n^4$ and $n^5$ in Formula (IV) are each individually 0, 1 or 2, with the proviso that $n^4$ and $n^5$ are not both 0. In an embodiment, $n^4$ and $n^5$ are both 1. In an embodiment, $n^4$ is 0 and $n^5$ is 1. In an embodiment, $n^4$ is 0 and $n^5$ is 2. In an embodiment, $n^4$ is 1 and $n^5$ is 0. In an embodiment, $n^4$ is 2 and $n^5$ is 0.

In various embodiments, $n^6$ in Formula (IV) is 0, 1 or 2. In an embodiment, $n^6$ is 0, in which case $X^1$ is —S— or —NH—S—. In an embodiment, $n^6$ is 1, in which case $X^1$ is —S(=O)— or —NH—S(=O)—. In an embodiment, $n^6$ is 2, in which case $X^1$ is —$S(=O)_2$— or —NH—$S(=O)_2$—.

In various embodiments, each Y in Formula (IV) is individually H or halogen. In an embodiment, each Y is hydrogen. In an embodiment, —$CY_2$ is $CH_2$. In an embodiment, —$CY_3$ is $CH_3$. In an embodiment, —$CY_3$ is $CHF_2$. In an embodiment, —$CH_2F$ is $CH_3$. In an embodiment, —$CY_3$ is $CF_3$.

In various embodiments, each p in Formula (IV) is individually 1, 2, 3, 4, 5, or 6. In an embodiment, p is 1. In an embodiment, p is 2.

In various embodiments, each q in Formula (IV) is individually 0, 1, 2, 3, 4, 5, or 6. In an embodiment, q is 1. In an embodiment, q is 2.

In various embodiments, each t in Formula (IV) is individually 1, 2, 3, 4, 5, or 6. In an embodiment, t is 1. In an embodiment, p is t.

In various embodiments, Formula (IV) does not represent deruxtecan or exatecan.

In various embodiments, the compound of Formula (IV) is represented by Formula (IVa):

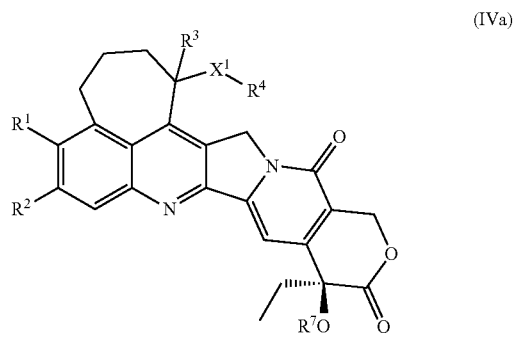

(IVa)

In Formula (IVa), the variables are the same as defined elsewhere herein for Formula (IV).

In various embodiments, the compound of Formula (IV) is represented by Formula (IVb):

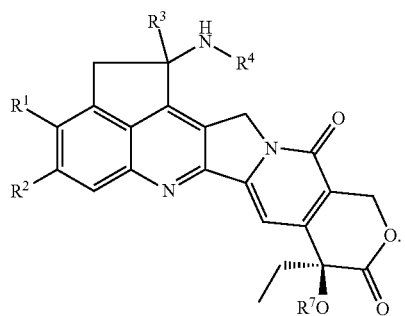

(IVb)

In Formula (IVb), the variables are the same as defined elsewhere herein for Formula (IV).

In various embodiments, the compound of Formula (IV) is represented by Formula (IVc):

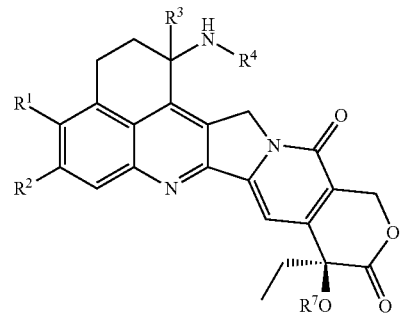

(IVc)

In Formula (IVc), the variables are the same as defined elsewhere herein for Formula (IV).

In various embodiments, the compound of Formula (IV) is represented by a structure selected from the following, or a pharmaceutically acceptable salt thereof:

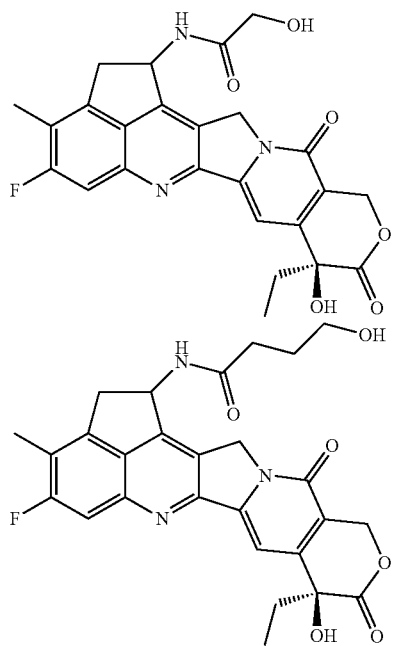

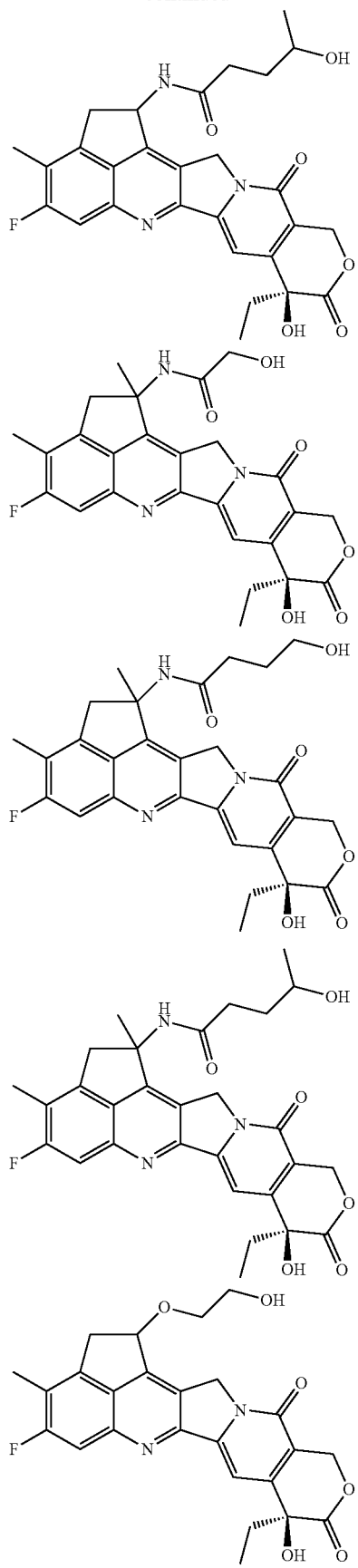

-continued
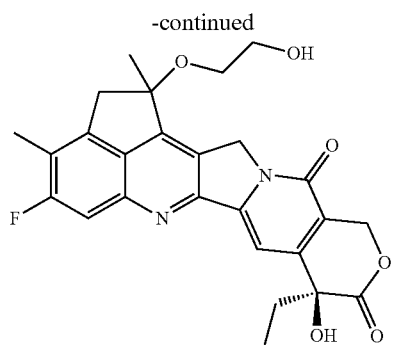
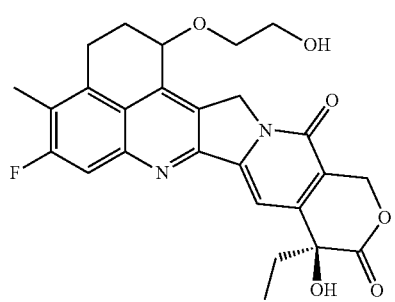
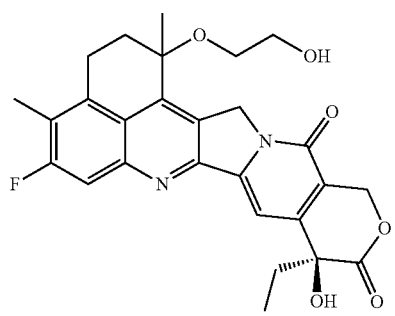
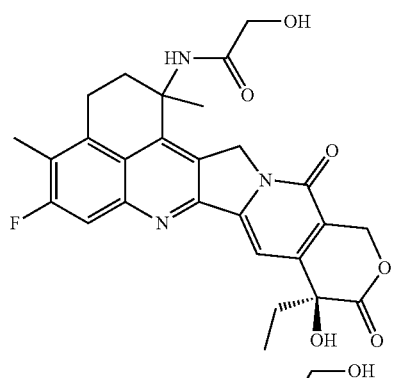
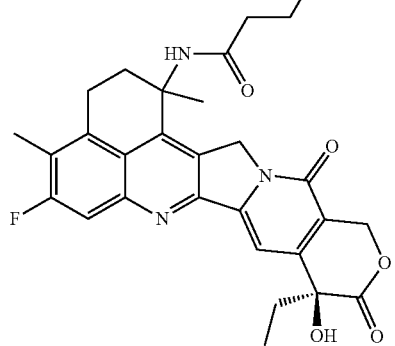
-continued
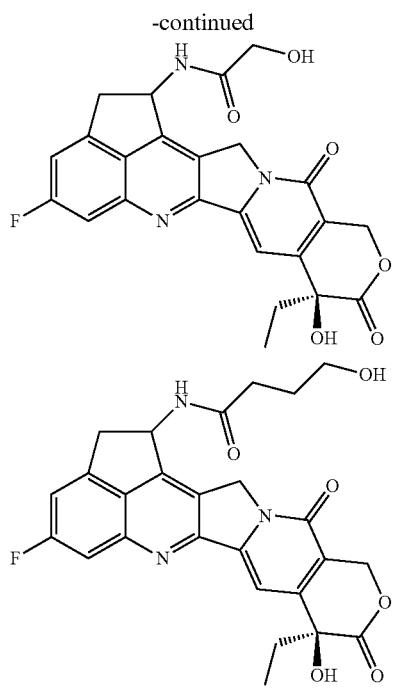
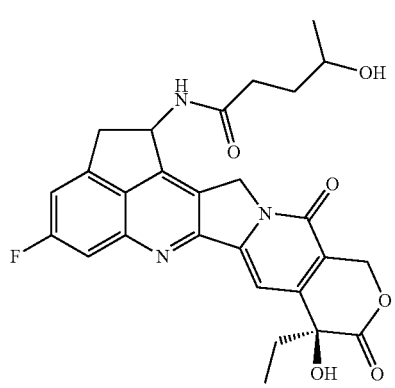
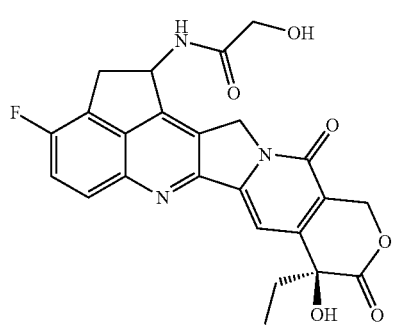
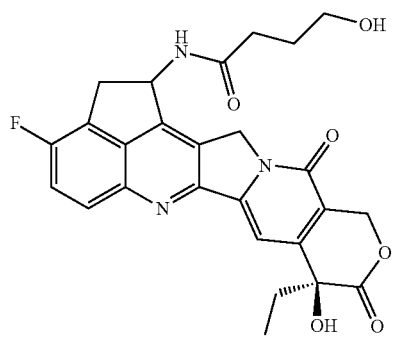

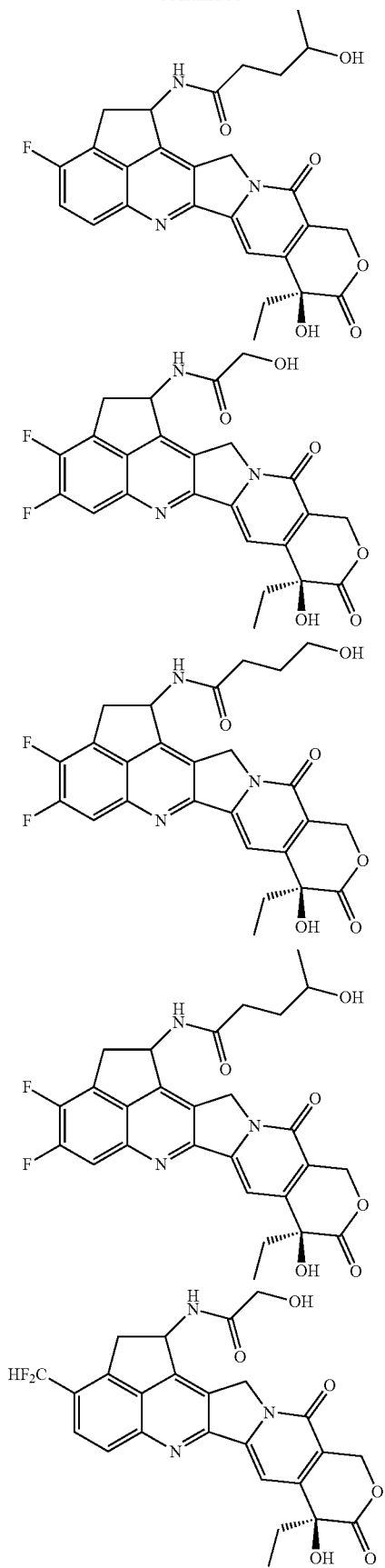
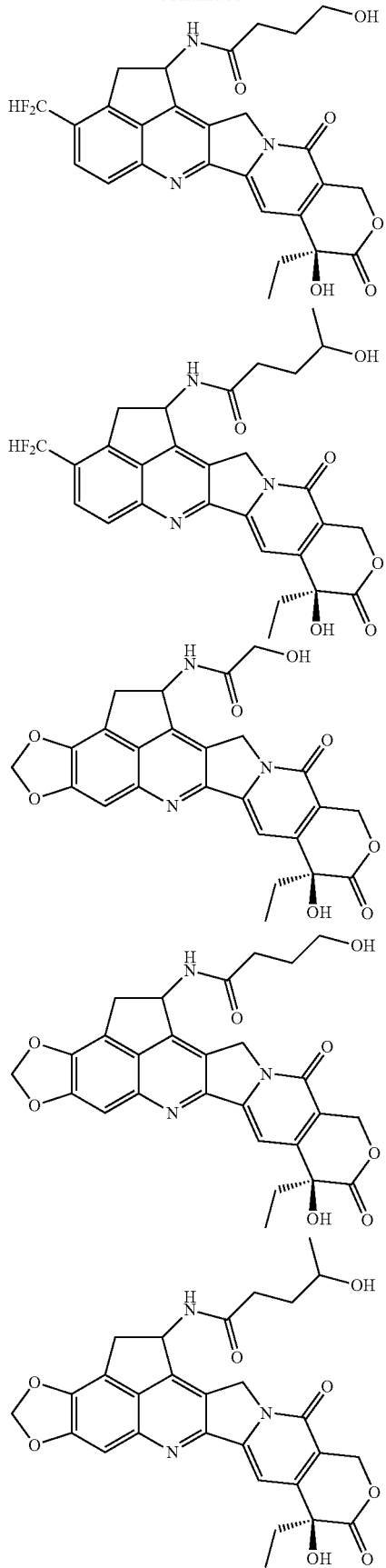

27
-continued
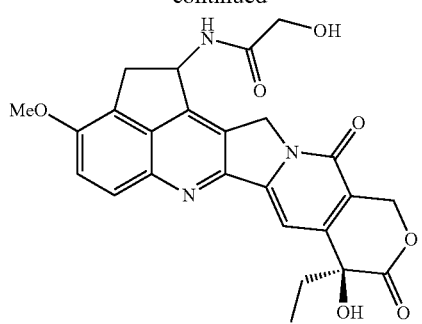
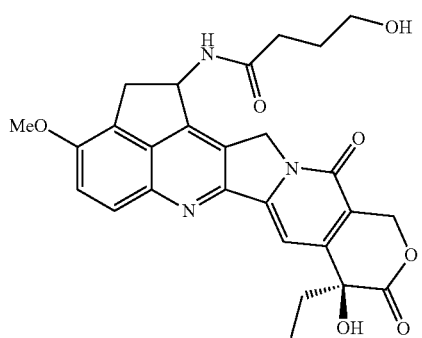
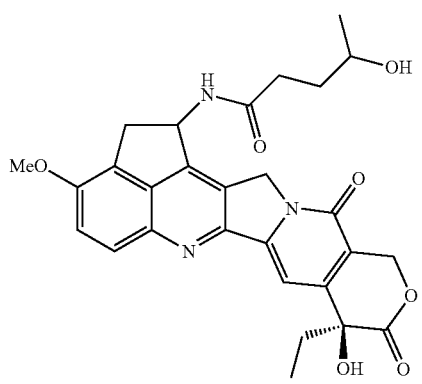
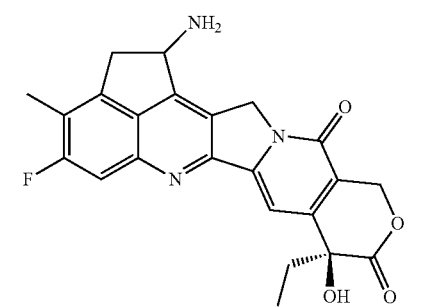
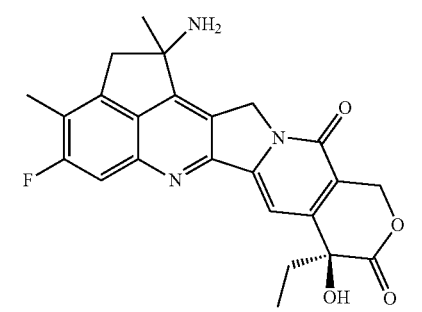
28
-continued
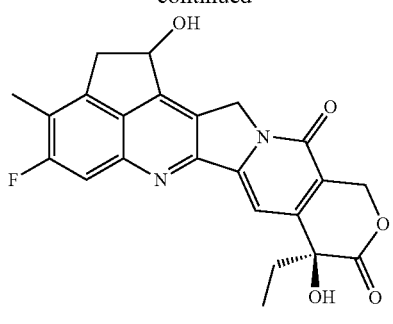
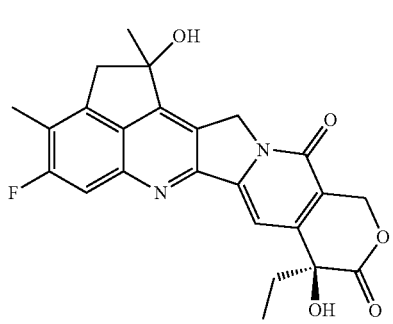
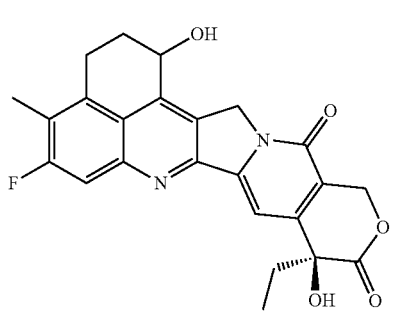
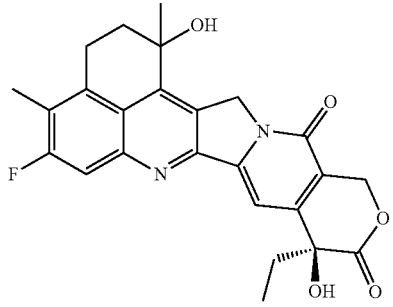
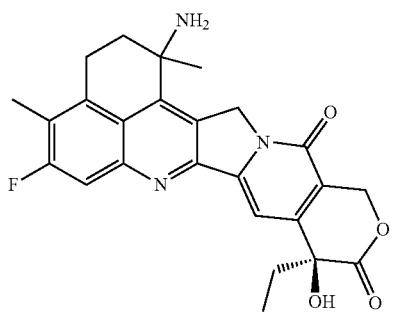

29
-continued
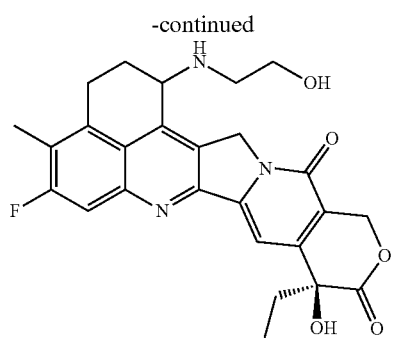
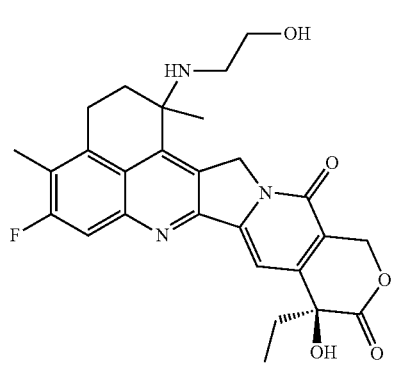
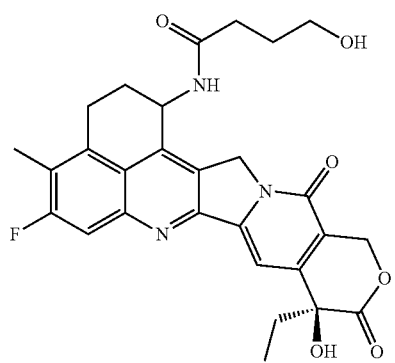
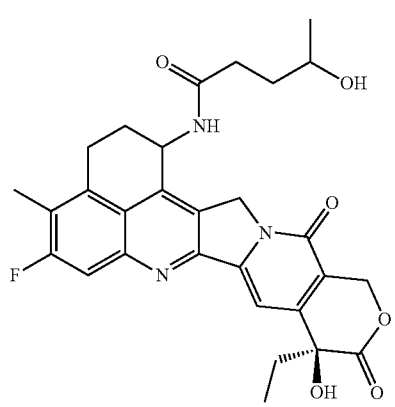
30
-continued
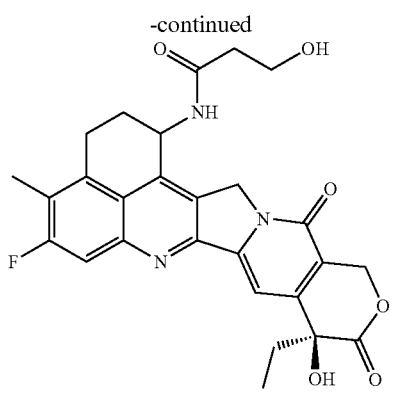
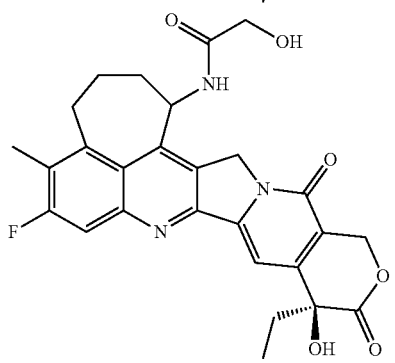
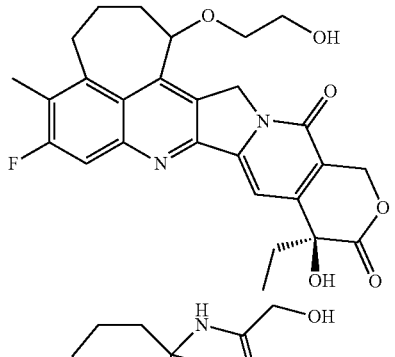
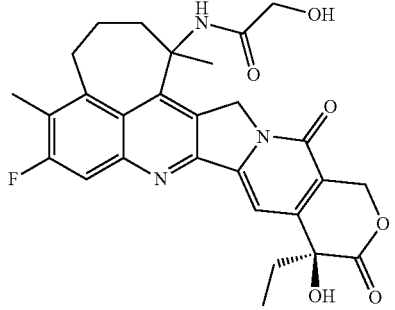
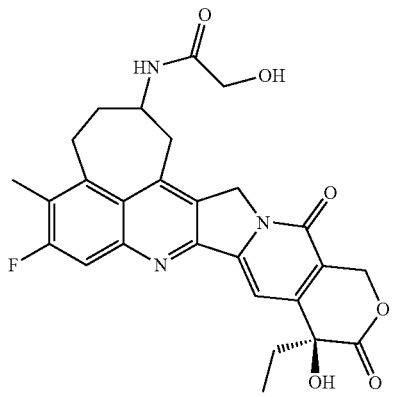

-continued

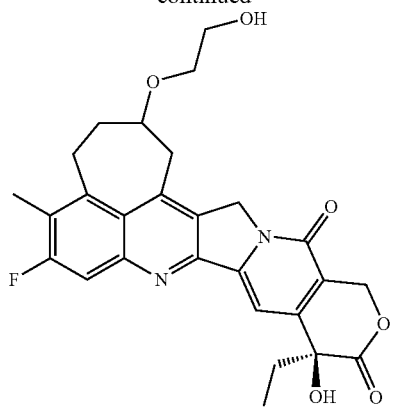

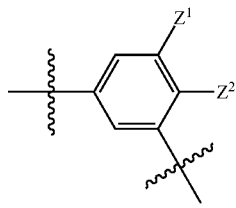

where $Z^1$ and $Z^2$ are each individually hydrogen, halogen, $NO_2$, —O—($C_1$-$C_6$ alkyl), or $C_1$-$C_6$ alkyl. In an embodiment, $L^2$ in Formula (III) is absent. In an embodiment, $L^2$ in Formula (III) is

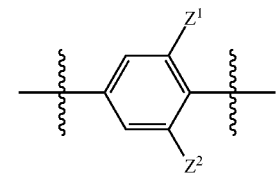

In an embodiment, $L^2$ in Formula (III) is

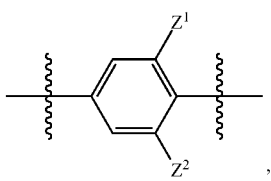

In various embodiments, $Z^1$ and $Z^2$ in Formula (III) are each individually hydrogen, halogen, $NO_2$, —O—($C_1$-$C_6$ alkyl), or $C_1$-$C_6$ alkyl. In an embodiment, at least one of $Z^1$ and $Z^2$ is hydrogen. In an embodiment, at least one of $Z^1$ and $Z^2$ is halogen. In an embodiment, at least one of $Z^1$ and $Z^2$ is $NO_2$. In an embodiment, at least one of $Z^1$ and $Z^2$ is —O—($C_1$-$C_6$ alkyl). For example, in an embodiment, at least one of $Z^1$ and $Z^2$ is methoxy. In an embodiment, at least one of $Z^1$ and $Z^2$ is $C_1$-$C_6$ alkyl. For example, in an embodiment, at least one of $Z^1$ and $Z^2$ is methyl.

In various embodiments, $L^3$ in Formula (III) is —($CH_2$)$n^1$-C(=O)— or —($CH_2CH_2O$)$n^1$-($CH_2$)$n^1$C(=O)—, where $n^1$ are independently integers of 0 to 12. In an embodiment, $L^3$ is —($CH_2$)$n^1$-C(=O)—. For example, in an embodiment, $L^3$ is —C(=O)—. In an embodiment, $L^3$ is —($CH_2CH_2O$)$n^1$-($CH_2$)$n^1$C(=O)—. For example, in an embodiment, $L^3$ is —$CH_2$C(=O)—. In embodiment, $n^1$ is an integer of 1 to 12, such as 1 to 6 or 1 to 3.

In various embodiments, $L^4$ in Formula (III) is a tetrapeptide residue. For example, in an embodiment, $L^4$ is a tetrapeptide residue selected from SEQ ID NO: 43 GGFG (gly-gly-phe-gly), SEQ ID NO: 44 EGGF (glu-gly-gly-phe), SEQ ID NO: 45 SGGF (ser-gly-gly-phe), and SEQ ID NO: 46 KGGF (lys-gly-gly-phe).

In various embodiments, $L^5$ in Formula (III) is absent or —[NH($CH_2$)$n^2$]$n^3$-, where $n^2$ is an integer of 0 to 6 and $n^3$ is an integer of 0 to 2. In an embodiment, $L^5$ is absent. In an embodiment, $L^5$ is —[NH($CH_2$)$n^2$]$n^3$-. For example, in an embodiment, $L^5$ is —NH—. In another embodiment, $L^5$ is —$NHCH_2$—.

Conjugates

Various embodiments disclosed herein relate to a conjugate of Formula (III), having the structure:

Mi-$L^2$-$L^3$-$L^4$-$L^5$-$L^6$-$L^7$-D)   (III)

In various embodiments, Mi in Formula (III) is

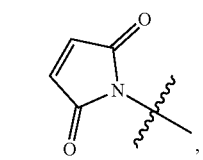 [SMILES: *N1C(=O)C=CC1=O]

D is a drug moiety and -$L^2$-$L^3$-$L^4$-$L^5$-$L^6$-$L^7$- is a linker that connects Mi to D.

In various embodiments, $L^2$ in Formula (III) is absent,

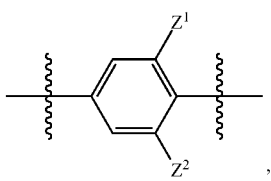

or

In various embodiments, $L^6$ in Formula (III) is absent or

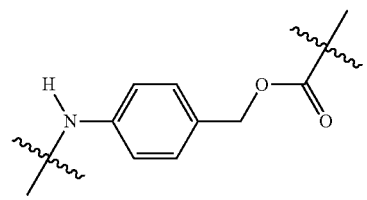

In an embodiment, $L^6$ is absent. In another embodiment, $L^6$ is

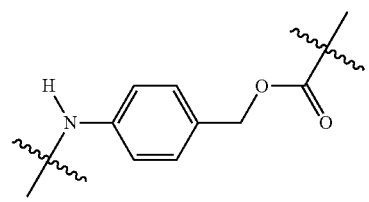

In various embodiments, $L^7$ in Formula (III) is absent,

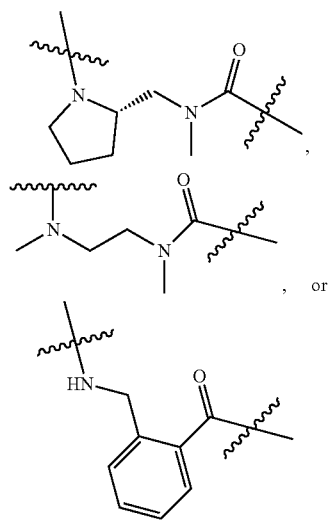

In an embodiment, $L^7$ is absent. In an embodiment, $L^7$ is

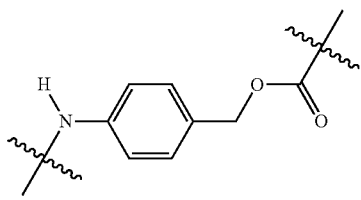

In an embodiment, $L^7$ is

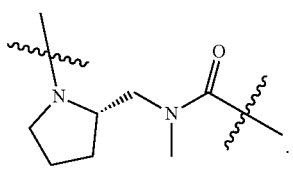 [SMILES: *C(=O)N(C)C[C@@H]1CCCN1*]

In an embodiment, $L^7$ is

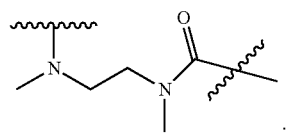 [SMILES: *C(=O)N(C)CCN(*)C]

In an embodiment, $L^7$ is

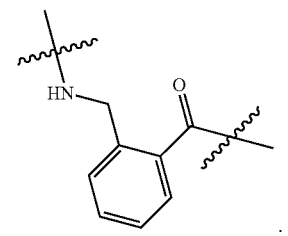 [SMILES: *NCc1ccccc1C(*)=O]

In various embodiments, D in the conjugate of Formula (III) is a drug moiety as described herein (e.g., under the heading "Drug Moieties" below). In an embodiment, D is a cytotoxic anti-cancer drug moiety.

In various embodiments, the conjugate of Formula (III) is represented by a structure selected from the following, for which $Z^1$ and $Z^2$ are each individually selected from hydrogen, fluoro, chloro, $-NO_2$, and $-OCH_3$:

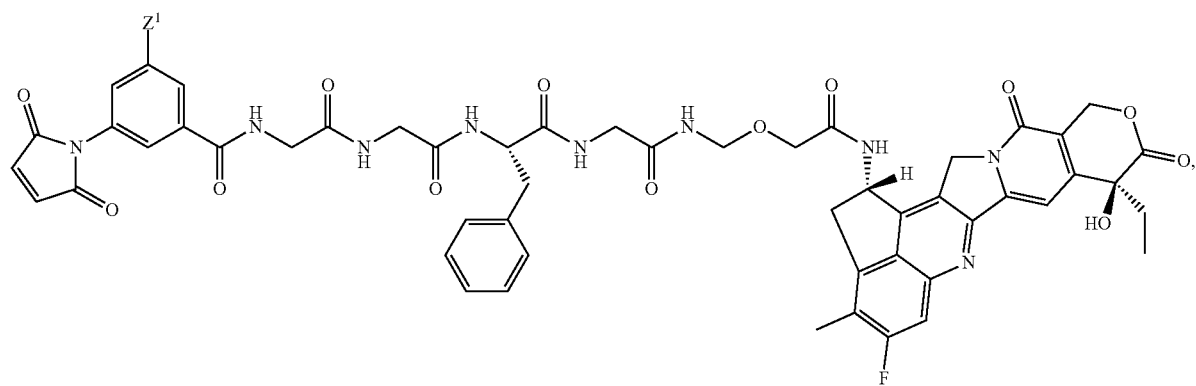

-continued
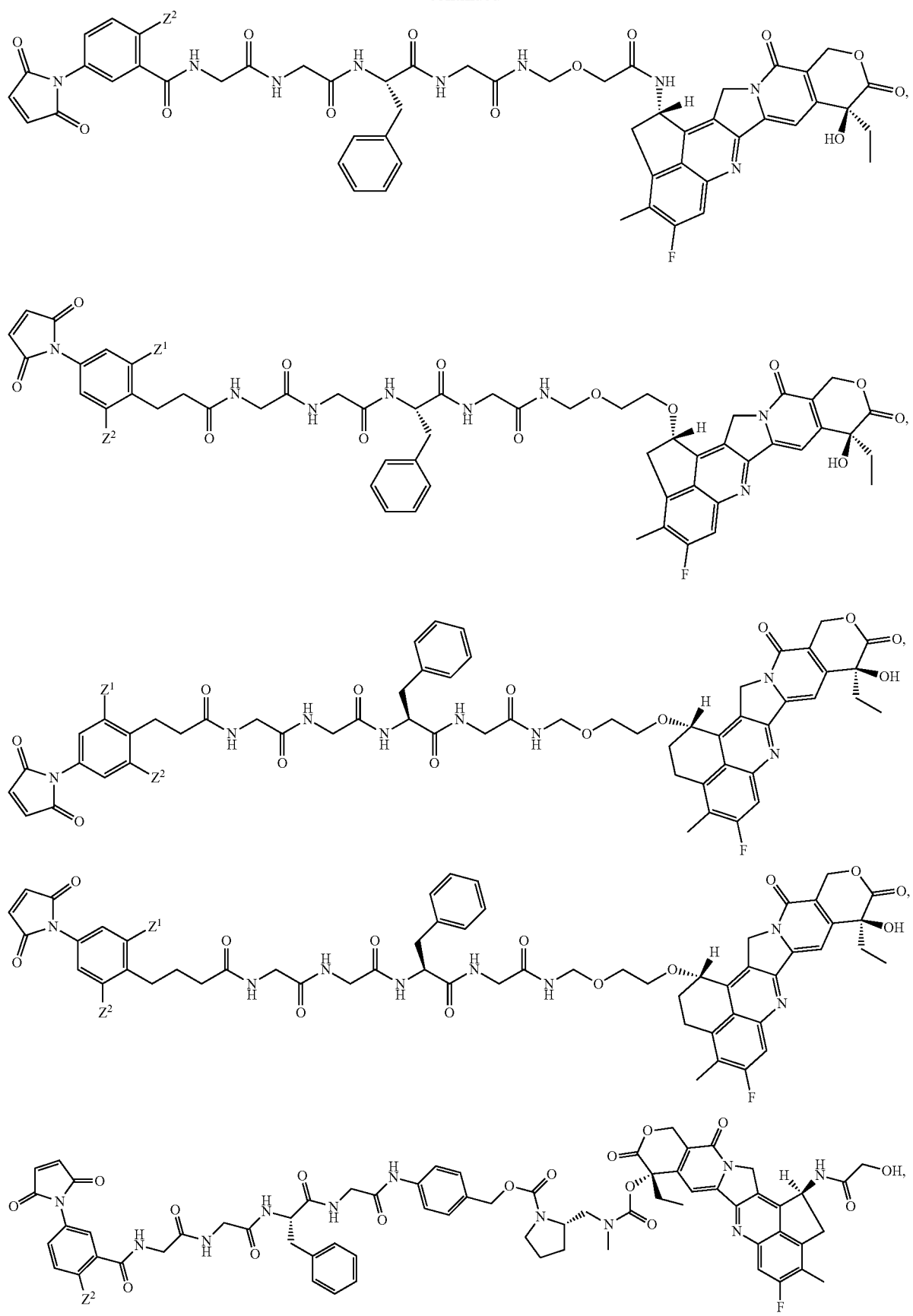

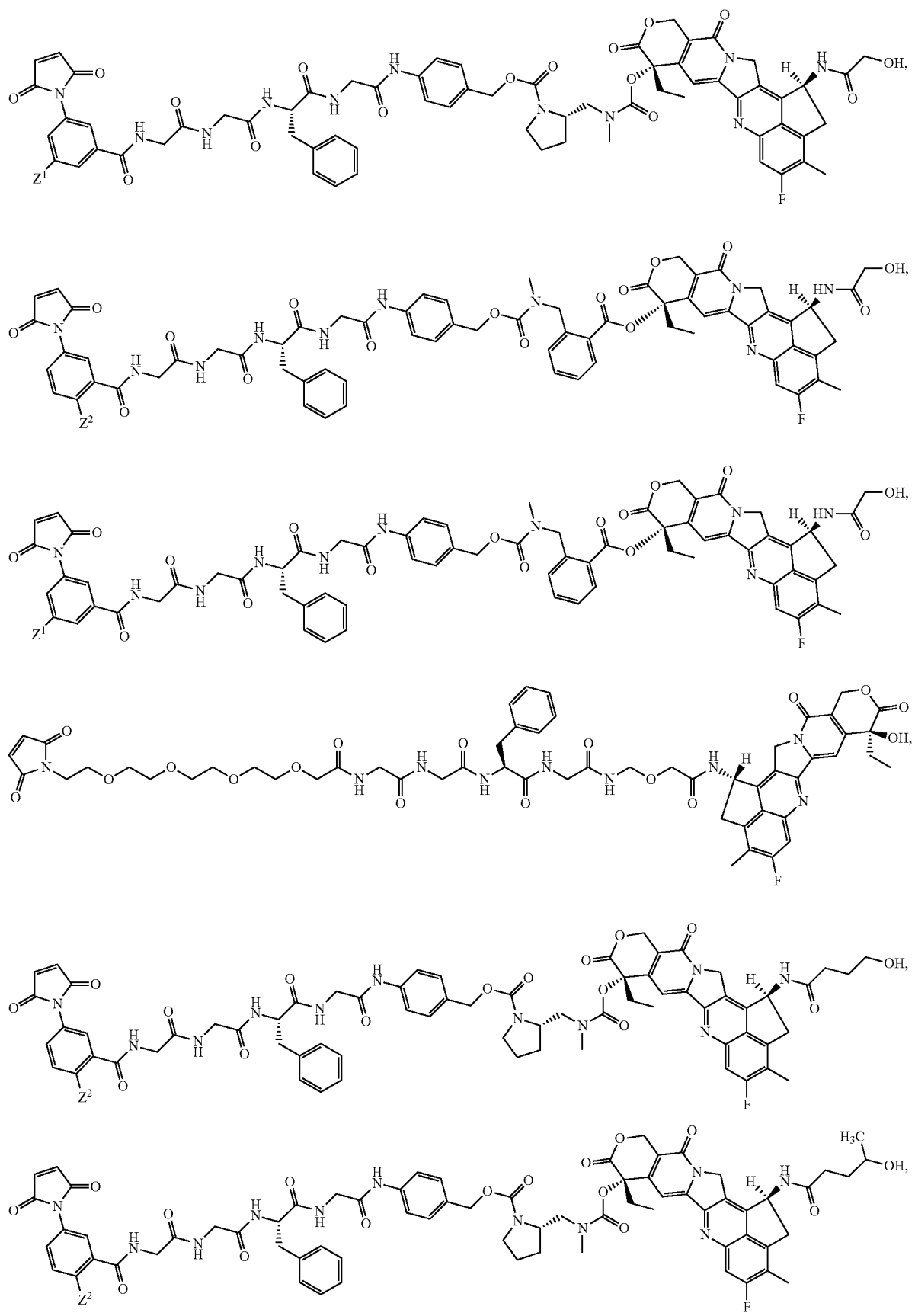

-continued
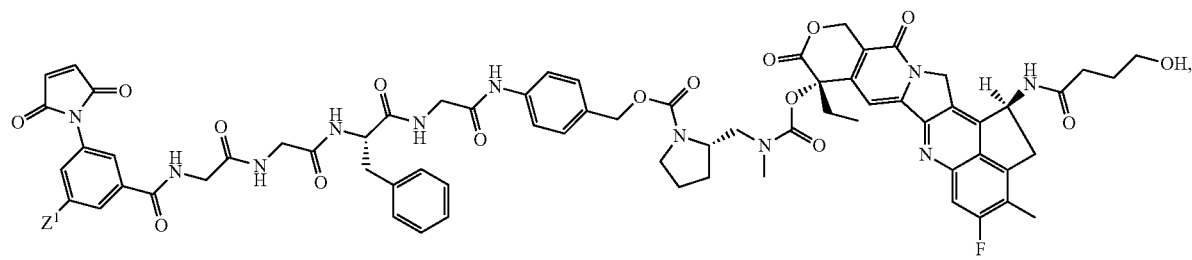
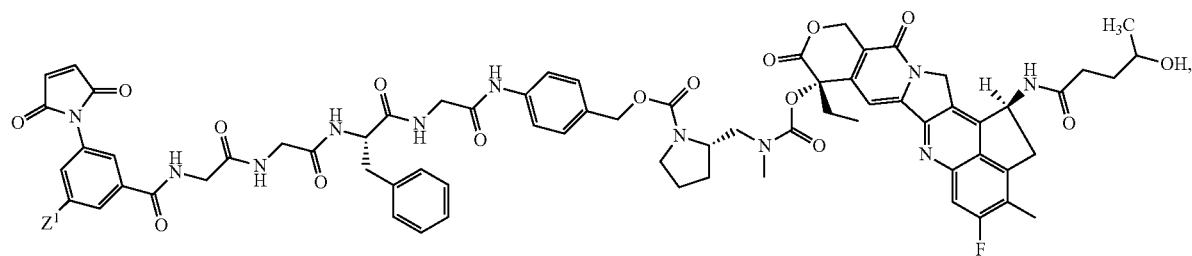
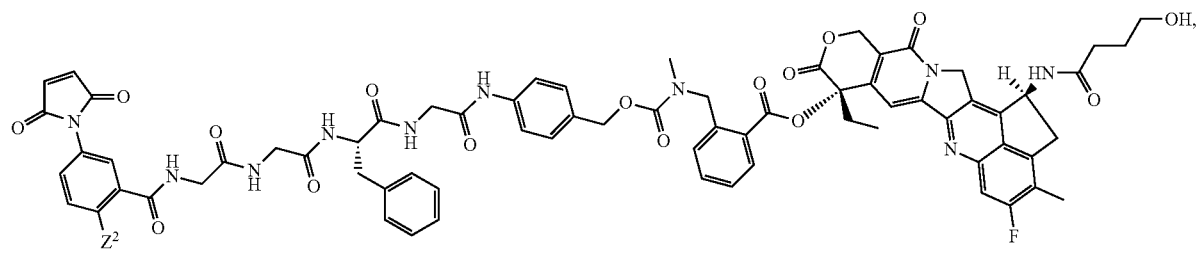
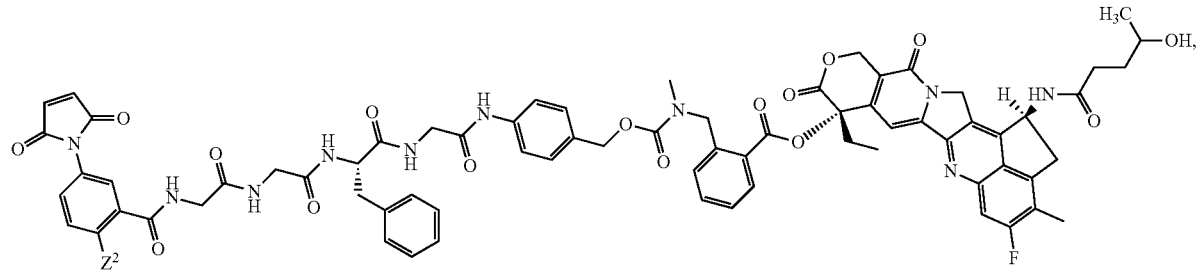
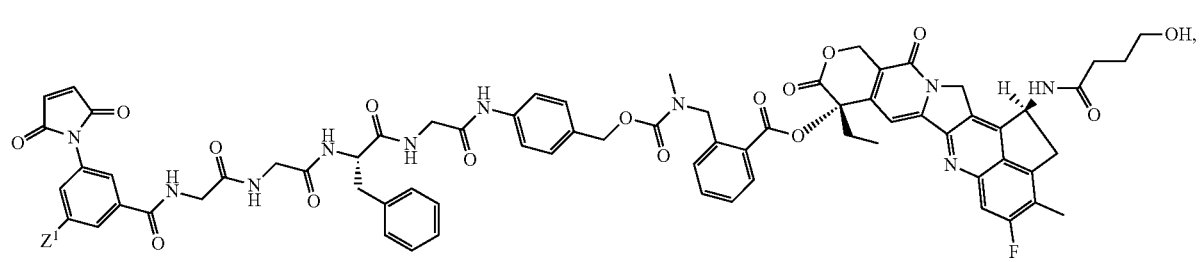
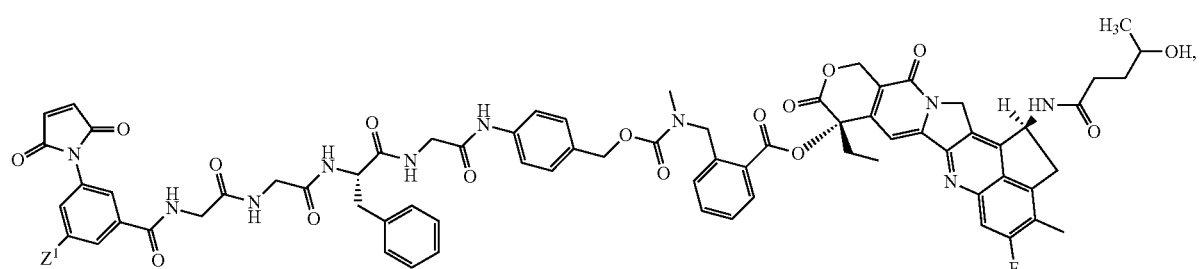

-continued
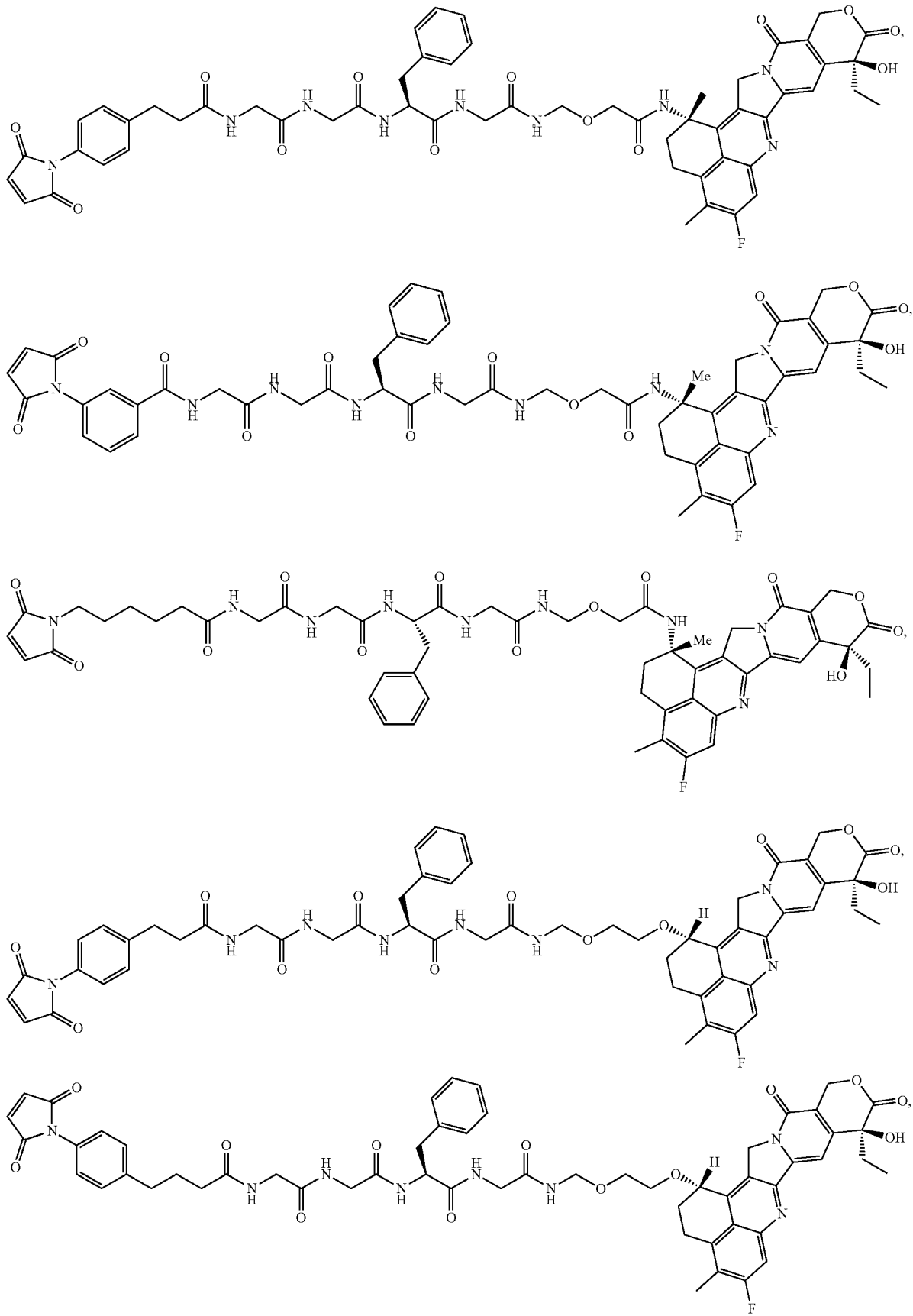

-continued

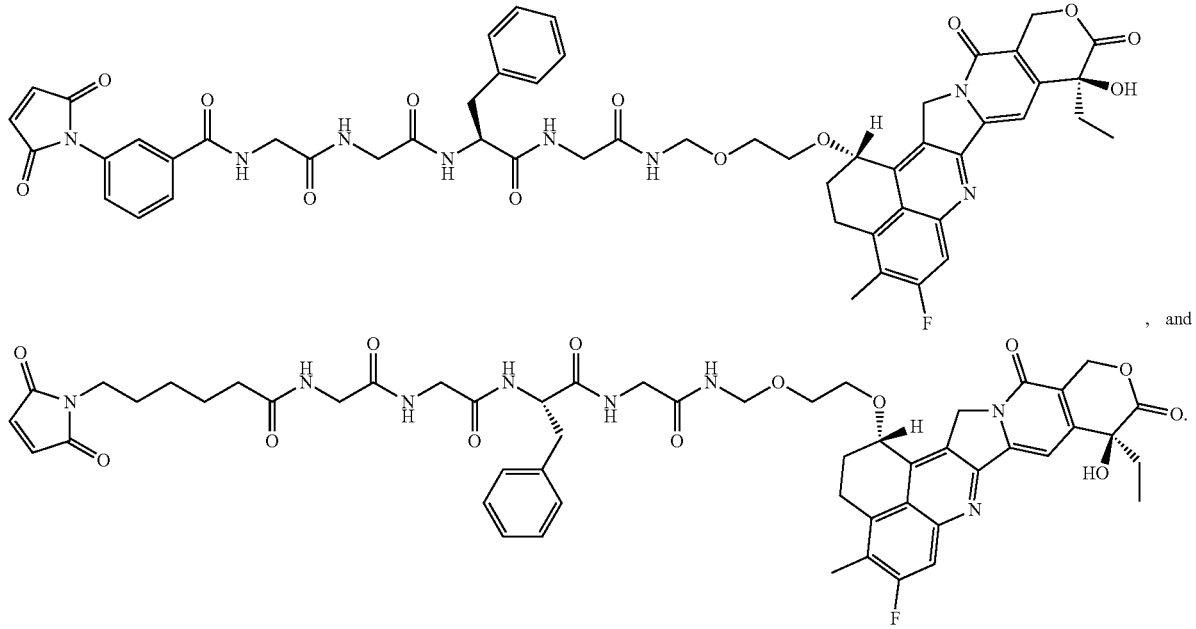

, and

Drug Moieties

In various embodiments, D in the immunoconjugate of Formula (I) or in the conjugate of Formula (III) is a drug moiety. The drug moiety may be any compound of the Formula (IV) as described herein (e.g., as described above under the heading "Compounds"), with appropriate modification so that the linker -$L^2$-$L^3$-$L^4$-$L^5$-$L^6$-$L^7$- connects to D. For example, in various embodiments the drug moiety D is a compound of Formula (II) having the structure:

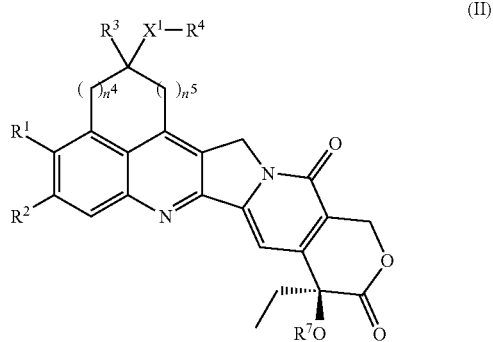

(II)

Those skilled in the art will appreciate that the compound of Formula (II) connects to the linker -$L^2$-$L^3$-$L^4$-$L^5$-$L^6$-$L^7$- via $R^4$ (when defined to include $X^2$ and thus $R^9$) or via $R^7$ as described below.

In various embodiments, $R^1$ and $R^2$ in Formula (II) are each individually selected from the group consisting of hydrogen, halogen, —CN, —$OR^5$, —$NR^5R^6$, a substituted or an unsubstituted $C_1$-$C_6$ alkyl, a substituted or an unsubstituted $C_1$-$C_6$ haloalkyl, a substituted or an unsubstituted —O—($C_1$-$C_6$ alkyl), a substituted or an unsubstituted —O—($C_1$-$C_6$ haloalkyl), —[(C$Y_2$)$_p$O(C$Y_2$)$_q$]$_t$C$Y_3$, or a substituted or an unsubstituted —O—(C$R^5R^6$)$_m$—O— such that $R^1$ and $R^2$ taken together form a ring. In an embodiment, at least one of $R^1$ and $R^2$ is hydrogen. In an embodiment, at least one of $R^1$ and $R^2$ is halogen. For example, in an embodiment, at least one of $R^1$ and $R^2$ is fluoro. In an embodiment, at least one of $R^1$ and $R^2$ is —CN. In an embodiment, at least one of $R^1$ and $R^2$ is —$OR^5$, wherein $R^5$ is hydrogen, halogen, a substituted or an unsubstituted $C_1$-$C_6$ alkyl, a substituted or an unsubstituted $C_1$-$C_6$ haloalkyl, or —[(C$Y_2$)$_p$O(C$Y_2$)$_q$]$_t$C$Y_3$. For example, in an embodiment, at least one of $R^1$ and $R^2$ is methoxy.

In an embodiment, at least one of $R^1$ and $R^2$ in Formula (II) is —$NR^5R^6$, wherein $R^5$ and $R^6$ are each individually hydrogen, halogen, a substituted or an unsubstituted $C_1$-$C_6$ alkyl, a substituted or an unsubstituted $C_1$-$C_6$ haloalkyl, or —[(C$Y_2$)$_p$O(C$Y_2$)$_q$]$_t$C$Y_3$. In an embodiment, at least one of $R^1$ and $R^2$ is a substituted or an unsubstituted $C_1$-$C_6$ alkyl. For example, in an embodiment, at least one of $R^1$ and $R^2$ is methyl. In an embodiment, at least one of $R^1$ and $R^2$ is a substituted or an unsubstituted $C_1$-$C_6$ haloalkyl. For example, in an embodiment, at least one of $R^1$ and $R^2$ is difluoromethyl. In an embodiment, at least one of $R^1$ and $R^2$ is a substituted or an unsubstituted —O—($C_1$-$C_6$ alkyl). For example, in an embodiment, at least one of $R^1$ and $R^2$ is methoxy. In an embodiment, at least one of $R^1$ and $R^2$ is —[(C$Y_2$)$_p$O(C$Y_2$)$_q$]$_t$C$Y_3$. In an embodiment, $R^1$ and $R^2$ are a substituted or an unsubstituted —O—(C$R^5R^6$)$_m$—O— such that $R^1$ and $R^2$ taken together form a ring in which the ends of the —O—(C$R^5R^6$)$_m$O— are covalently bonded to the phenyl ring at the $R^1$ and $R^2$ positions of Formula (IV) to form a heterocyclic ring.

In an embodiment, one of $R^1$ and $R^2$ in Formula (II) is hydrogen and the other of $R^1$ and $R^2$ is halogen. In an embodiment, one of $R^1$ and $R^2$ is hydrogen and the other of $R^1$ and $R^2$ is a substituted or an unsubstituted $C_1$-$C_6$ alkyl. In an embodiment, one of $R^1$ and $R^2$ is hydrogen and the other of $R^1$ and $R^2$ is a substituted or an unsubstituted $C_1$-$C_6$ haloalkyl. In an embodiment, one of $R^1$ and $R^2$ is hydrogen and the other of $R^1$ and $R^2$ is a substituted or an unsubstituted —O—($C_1$-$C_6$ alkyl). In an embodiment, both $R^1$ and $R^2$ are hydrogen. In an embodiment, neither $R^1$ nor $R^2$ is hydrogen.

In an embodiment, one of $R^1$ and $R^2$ in Formula (II) is halogen and the other of $R^1$ and $R^2$ is a substituted or an unsubstituted $C_1$-$C_6$ alkyl. In an embodiment, one of $R^1$ and $R^2$ is halogen and the other of $R^1$ and $R^2$ is a substituted or an unsubstituted $C_1$-$C_6$ haloalkyl. In an embodiment, one of $R^1$ and $R^2$ is halogen and the other of $R^1$ and $R^2$ is a substituted or an unsubstituted —O—($C_1$-$C_6$ alkyl). In an embodiment, both $R^1$ and $R^2$ are independently halogen. In an embodiment, neither $R^1$ nor $R^2$ is halogen.

In an embodiment, one of $R^1$ and $R^2$ in Formula (II) is a substituted or an unsubstituted $C_1$-$C_6$ alkyl and the other of $R^1$ and $R^2$ is a substituted or an unsubstituted $C_1$-$C_6$ haloalkyl. In an embodiment, one of $R^1$ and $R^2$ is a substituted or an unsubstituted $C_1$-$C_6$ alkyl and the other of $R^1$ and $R^2$ is a substituted or an unsubstituted —O—($C_1$-$C_6$ alkyl). In an embodiment, both $R^1$ and $R^2$ are independently a substituted or an unsubstituted $C_1$-$C_6$ alkyl. In an embodiment, neither $R^1$ nor $R^2$ is a substituted or an unsubstituted $C_1$-$C_6$ alkyl.

In an embodiment, one of $R^1$ and $R^2$ in Formula (II) is a substituted or an unsubstituted $C_1$-$C_6$ haloalkyl and the other of $R^1$ and $R^2$ is a substituted or an unsubstituted —O—($C_1$-$C_6$ alkyl). In an embodiment, both $R^1$ and $R^2$ are independently a substituted or an unsubstituted $C_1$-$C_6$ haloalkyl. In an embodiment, neither $R^1$ nor $R^2$ is a substituted or an unsubstituted $C_1$-$C_6$ haloalkyl.

In an embodiment, one of $R^1$ and $R^2$ in Formula (II) is a substituted or an unsubstituted —O—($C_1$-$C_6$ alkyl). In an embodiment, both $R^1$ and $R^2$ are independently a substituted or an unsubstituted —O—($C_1$-$C_6$ alkyl). In an embodiment, neither $R^1$ nor $R^2$ is a substituted or an unsubstituted —O—($C_1$-$C_6$ alkyl). In an embodiment, $R^1$ and $R^2$ are a substituted or an unsubstituted —O—$(CR^5R^6)_m$—O— such that $R^1$ and $R^2$ taken together form a ring. In various embodiments, $R^1$ and $R^2$ are each individually selected from the group consisting of hydrogen, fluoro, methoxy, methyl, difluoromethyl, and —O—($CH_2$)—O— such that $R^1$ and $R^2$ taken together form a ring.

In various embodiments, $R^3$ in Formula (II) is hydrogen or a substituted or an unsubstituted $C_1$-$C_6$ alkyl, a substituted or an unsubstituted $C_1$-$C_6$ haloalkyl, or —$[(CY_2)_pO(CY_2)_q]_t$$CY_3$, where each Y is individually H or halogen. In an embodiment, $R^3$ is hydrogen. In an embodiment, $R^3$ is a substituted or an unsubstituted $C_1$-$C_6$ alkyl. For example, in an embodiment, $R^3$ is methyl. In an embodiment, $R^3$ is a substituted or an unsubstituted $C_1$-$C_6$haloalkyl. In an embodiment, $R^3$ is —$[(CY_2)_pO(CY_2)_q]_t$$CY_3$, where each Y is individually H or halogen.

In various embodiments, $R^4$ in Formula (II) is hydrogen, a substituted or an unsubstituted —($C_1$-$C_6$ alkyl)-$X^2$, a substituted or an unsubstituted —($C_1$-$C_6$ haloalkyl)-$X^2$, a substituted or an unsubstituted —($C_1$-$C_6$ alkenyl)-$X^2$, a substituted or an unsubstituted —($C_1$-$C_6$ haloalkenyl)-$X^2$, a substituted or an unsubstituted —($C_1$-$C_6$ alkynyl)-$X^2$, a substituted or an unsubstituted —($C_1$-$C_6$ haloalkynyl)-$X^2$, where $X^2$ is —$OR^9$, —$SR^9$, or —$NHR^9$ and $R^9$ is H, absent, —$COR^8$, —$CO_2R^8$, —(CO)—$NHR^8$, $L^4$, $L^5$, $L^6$, or $L^7$. In an embodiment, $R^4$ is hydrogen, in which case $X^2$ is not present and the compound of Formula (II) connects to the linker -$L^2$-$L^3$-$L^4$-$L^5$-$L^6$-$L^7$- via $R^7$ as described in greater detail below.

In other embodiments, the compound of Formula (II) connects to the linker -$L^2$-$L^3$-$L^4$-$L^5$-$L^6$-$L^7$- via $R^4$ when $R^4$ includes $X^2$ and $R^9$ is $L^4$, $L^5$, $L^6$, or $L^7$. In an embodiment $R^4$ is a substituted or an unsubstituted —($C_1$-$C_6$ alkyl)-$X^2$. In an embodiment, $R^4$ is a substituted or an unsubstituted —($C_1$-$C_6$ haloalkyl)-$X^2$. In an embodiment, $R^4$ is a substituted or an unsubstituted —($C_1$-$C_6$ alkenyl)-$X^2$. In an embodiment, $R^4$ is a substituted or an unsubstituted —($C_1$-$C_6$ haloalkenyl)-$X^2$. In an embodiment, $R^4$ is a substituted or an unsubstituted —($C_1$-$C_6$ alkynyl)-$X^2$. In an embodiment, $R^4$ is a substituted or an unsubstituted —($C_1$-$C_6$ haloalkynyl)-$X^2$. In each such embodiment in which $R^4$ includes $X^2$, the option for $R^9$ to be $L^4$, $L^5$, $L^6$, or $L^7$ is provided, thus providing the option to thereby connect the compound of Formula (II) to the linker -$L^2$-$L^3$-$L^4$-$L^5$-$L^6$-$L^7$- via $R^4$.

In various embodiments, $X^1$ in Formula (II) is —O—, —$S(O_{n6})$—, —NH—, —O—(C=O)—, —NH—(C=O)—, —NH—(C=O)—O—, —NH—(C=O)—NH—, or —NH—$S(O_{n6})$—, where $n^6$ is 0, 1 or 2. In an embodiment, $X^1$ is —O—. In an embodiment, $X^1$ is —$S(O_{n6})$—. In an embodiment, $X^1$ is —NH—. In an embodiment, $X^1$ is —O—(C=O)—. In an embodiment, $X^1$ is —NH—(C=O)—. In an embodiment, $X^1$ is —NH—(C=O)—O—. In an embodiment, $X^1$ is —NH—(C=O)—NH—. In an embodiment, $X^1$ is —NH—$S(O_{n6})$—.

In various embodiments, $R^5$ and $R^6$ in Formula (II) are each individually hydrogen, halogen, a substituted or an unsubstituted $C_1$-$C_6$ alkyl, $C_1$-$C_6$ haloalkyl, or —$[(CY_2)_pO(CY_2)_q]_t$$CY_3$, where each Y is individually H or halogen and variables p, q and t are as described elsewhere herein. In an embodiment, $R^5$ and $R^6$ are each individually hydrogen or a substituted or an unsubstituted $C_1$-$C_6$ alkyl. In an embodiment, $R^5$ and $R^6$ are both hydrogen. In an embodiment, $R^5$ and $R^6$ are each individually a substituted or an unsubstituted $C_1$-$C_6$ alkyl.

In various embodiments, $R^7$ in Formula (II) is H, —$COR^8$, —$CO_2R^8$, —(CO)—$NHR^8$, $L^4$, $L^5$, $L^6$, or $L^7$, where each $R^8$ is individually a substituted or an unsubstituted $C_1$-$C_6$ alkyl-$X^3$, a substituted or an unsubstituted $C_1$-$C_6$ haloalkyl-$X^3$, or —$[(CY_2)_pO(CY_2)_q]_t$$CY_2$—$X^3$. In an embodiment, $R^7$ is H. In an embodiment, $R^7$ is —$COR^8$. In an embodiment, $R^7$ is —$CO_2R^8$. In an embodiment, $R^7$ is —(CO)—$NHR^8$. Those skilled in the art will appreciate that when $R^7$ is H, —$COR^8$, —$CO_2R^8$, or —(CO)—$NHR^8$, connection of the compound of Formula (II) to the linker -$L^2$-$L^3$-$L^4$-$L^5$-$L^6$-$L^7$- is via $R^4$ as described elsewhere herein.

In various embodiments, each $R^8$ in Formula (II) is individually a substituted or an unsubstituted $C_1$-$C_6$ alkyl-$X^3$, a substituted or an unsubstituted $C_1$-$C_6$ haloalkyl-$X^3$, or —$[(CY_2)_pO(CY_2)_q]_t$$CY_2$—$X^3$, where $X^3$ is —H, —OH, —SH, or —$NH_2$. In an embodiment, each $R^8$ is individually a substituted or an unsubstituted $C_1$-$C_6$ alkyl-$X^3$. In an embodiment, each $R^8$ is individually a substituted or an unsubstituted $C_1$-$C_6$ haloalkyl-$X^3$. In an embodiment, each $R^8$ is individually —$[(CY_2)_pO(CY_2)_q]_t$$CY_2$—$X^3$.

In various embodiments, $X^2$ in Formula (II) is —$OR^9$, —$SR^9$, or —$NHR^9$, where $R^9$ is H, —$COR^8$, —$CO_2R^8$, —(CO)—$NHR^8$, $L^4$, $L^5$, $L^6$, or $L^7$. In an embodiment, $X^2$ is —$OR^9$. In an embodiment, $X^2$ is —$SR^9$. In an embodiment, $X^2$ is —$NHR^9$.

In various embodiments, $R^9$ in Formula (II) is H, —$COR^8$, —$CO_2R^8$, —(CO)— $NHR^8$, $L^4$, $L^5$, $L^6$, or $L^7$, where $R^8$ is a substituted or an unsubstituted $C_1$-$C_6$ alkyl-$X^3$, a substituted or an unsubstituted $C_1$-$C_6$ haloalkyl-$X^3$, or —$[(CY_2)_pO(CY_2)_q]_t$$CY_2$—$X^3$. In an embodiment, $R^9$ is H. In an embodiment, $R^9$ is —$COR^8$. In an embodiment, $R^9$ is —$CO_2R^8$. In an embodiment, $R^9$ is —(CO)—$NHR^8$. Those skilled in the art will appreciate that when $R^9$ is H, —$COR^8$, —$CO_2R^8$, or —(CO)—$NHR^8$, connection of the compound of Formula (II) to the linker -$L^2$-$L^3$-$L^4$-$L^5$-$L^6$-$L^7$- is via $R^7$ as described elsewhere herein.

In various embodiments, $R^9$ in Formula (II) is $L^4$, $L^5$, $L^6$, or $L^7$. In an embodiment, $R^9$ is $L^4$. In an embodiment, $R^9$ is L. In an embodiment, $R^9$ is $L^6$. In an embodiment, $R^9$ is $L^7$. Those skilled in the art will appreciate that when $R^9$ is $L^4$, $L^5$, $L^6$, or $L^7$, connection of the compound of Formula (II) to the linker $-L^2-L^3-L^4-L^5-L^6-L^7-$ is via $R^4$ as described elsewhere herein. In an embodiment, exactly one of $R^7$ and $R^9$ is $L^4$, $L^5$, $L^6$, or $L^7$, in which case a single covalent bond links the drug D to the linker $-L^2-L^3-L^4-L^5-L^6-L^7-$ and thereby to Mi.

In various embodiments, each $X^3$ in Formula (II) is individually —H, —OH, —SH, or —NH$_2$. In an embodiment, $X^3$ is —H. In an embodiment, $X^3$ is —OH. In an embodiment, $X^3$ is —SH. In an embodiment, $X^3$ is-NH$_2$.

In various embodiments, m in Formula (II) is 1 or 2. In an embodiment, m is 1. In another embodiment, m is 2.

In various embodiments, $n^4$ and $n^5$ in Formula (II) are each individually 0, 1 or 2, with the proviso that $n^4$ and $n^5$ are not both 0. In an embodiment, $n^4$ and $n^5$ are both 1. In an embodiment, $n^4$ is 0 and $n^5$ is 1. In an embodiment, $n^4$ is 0 and $n^5$ is 2. In an embodiment, $n^4$ is 1 and $n^5$ is 0. In an embodiment, $n^4$ is 2 and $n^5$ is 0.

In various embodiments, $n^6$ in Formula (II) is 0, 1 or 2. In an embodiment, $n^6$ is 0, in which case $X^1$ is —S— or —NH—S—. In an embodiment, $n^6$ is 1, in which case $X^1$ is —S(═O)— or —NH—S(═O)—. In an embodiment, $n^6$ is 2, in which case $X^1$ is —S(═O)$_2$— or —NH—S(═O)$_2$—.

In various embodiments, each Y in Formula (II) is individually H or halogen. In an embodiment, each Y is hydrogen. In an embodiment, —CY$_2$ is CH$_2$. In an embodiment, —CY$_3$ is CH$_3$. In an embodiment, —CY$_3$ is CHF$_2$. In an embodiment, —CH$_2$F is CH$_3$. In an embodiment, —CY$_3$ is CF$_3$.

In various embodiments, each p in Formula (II) is individually 1, 2, 3, 4, 5, or 6. In an embodiment, p is 1. In an embodiment, p is 2.

In various embodiments, each q in Formula (II) is individually 0, 1, 2, 3, 4, 5, or 6. In an embodiment, q is 1. In an embodiment, q is 2.

In various embodiments, each t in Formula (II) is individually 1, 2, 3, 4, 5, or 6. In an embodiment, t is 1. In an embodiment, p is t.

In various embodiments, Formula (II) does not represent deruxtecan or exatecan.

Immunoconjugates

Various embodiments disclosed herein relate to an immunoconjugate of Formula (I), having the structure:

$$Ab-[S-L^1-L^2-L^3-L^4-L^5-L^6-L^7-D]_n \quad (I)$$

In various embodiments, $L^1$ in Formula (III) is $L^1$ is

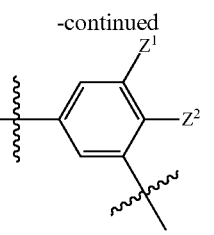

In various embodiments, $L^2$ in Formula (III) is absent,

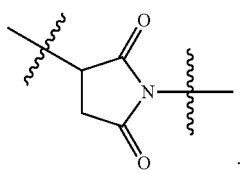 [SMILES: *C1CC(=O)N(*)C1=O ; "."], or

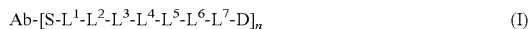

where $Z^1$ and $Z^2$ are each individually hydrogen, halogen, NO$_2$, —O—(C$_1$-C$_6$ alkyl), or C$_1$-C$_6$ alkyl. In an embodiment, $L^2$ in Formula (III) is absent. In an embodiment, $L^2$ in Formula (III) is

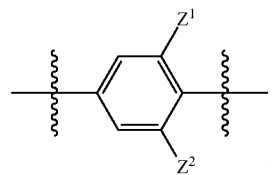

In an embodiment, $L^2$ in Formula (III) is

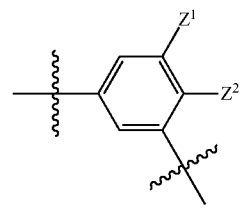

In various embodiments, $Z^1$ and $Z^2$ in Formula (III) are each individually hydrogen, halogen, NO$_2$, —O—(C$_1$-C$_6$ alkyl), or C$_1$-C$_6$ alkyl. In an embodiment, at least one of $Z^1$ and $Z^2$ is hydrogen. In an embodiment, at least one of $Z^1$ and $Z^2$ is halogen. In an embodiment, at least one of $Z^1$ and $Z^2$ is NO$_2$. In an embodiment, at least one of $Z^1$ and $Z^2$ is —O—(C$_1$-C$_6$ alkyl). For example, in an embodiment, at least one of $Z^1$ and $Z^2$ is methoxy. In an embodiment, at least one of $Z^1$ and $Z^2$ is C$_1$-C$_6$ alkyl. For example, in an embodiment, at least one of $Z^1$ and $Z^2$ is methyl.

In various embodiments, $L^3$ in Formula (III) is —(CH$_2$)$n^1$-C(═O)— or —(CH$_2$CH$_2$O)$n^1$-(CH$_2$)$n^1$C(═O)—, where $n^1$ are independently integers of 0 to 12. In an embodiment, $L^3$ is —(CH$_2$)$n^1$-C(═O)—. For example, in an embodiment, $L^3$ is —C(═O)—. In an embodiment, $L^3$ is —(CH$_2$CH$_2$O)$n^1$-(CH$_2$)$n^1$C(═O)—. For example, in an embodiment, $L^3$ is —CH$_2$C(═O)—. In embodiment, $n^1$ is an integer of 1 to 12, such as 1 to 6 or 1 to 3.

In various embodiments, $L^4$ in Formula (III) is a tetrapeptide residue. For example, in an embodiment, $L^4$ is a tetrapeptide residue selected from SEQ ID NO: 43 GGFG (gly-gly-phe-gly), SEQ ID NO: 44 EGGF (glu-gly-gly-phe), SEQ ID NO: 45 SGGF (ser-gly-gly-phe), and SEQ ID NO: 46 KGGF (lys-gly-gly-phe).

In various embodiments, $L^5$ in Formula (III) is absent or —[NH(CH$_2$)$n^2$]$n^3$-, where $n^2$ is an integer of 0 to 6 and $n^3$ is an integer of 0 to 2. In an embodiment, $L^5$ is absent. In an embodiment, $L^5$ is —[NH(CH$_2$)$n^2$]$n^3$-. For example, in an embodiment, $L^5$ is —NH—. In another embodiment, $L^5$ is —NHCH$_2$—.

In various embodiments, $L^6$ in Formula (III) is absent or

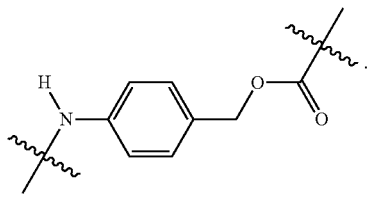 [SMILES: *Nc1ccc(COC(*)=O)cc1]

In an embodiment, $L^6$ is absent. In another embodiment, $L^6$ is

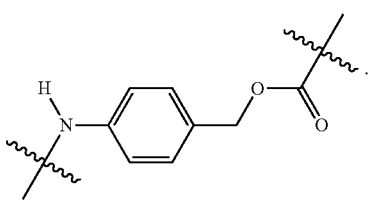 [SMILES: *Nc1ccc(COC(*)=O)cc1]

In various embodiments, $L^7$ in Formula (III) is absent,

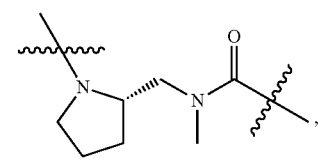 [SMILES: *C(=O)N(C)C[C@@H]1CCCN1*]

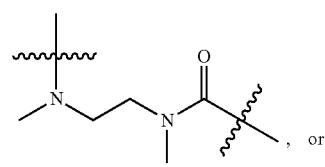, or

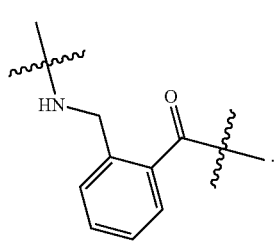 [SMILES: *NCc1ccccc1C(*)=O]

In an embodiment, $L^7$ is absent. In an embodiment, $L^7$ is

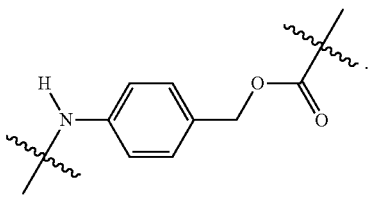

In an embodiment, $L^7$ is

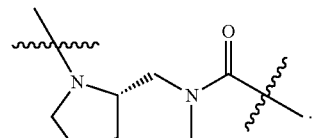

In an embodiment, $L^7$ is

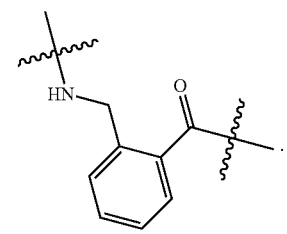

In an embodiment, $L^7$ is

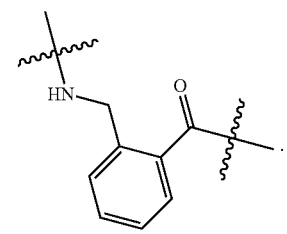

In various embodiments, D in the immunoconjugate of Formula (I) is a drug moiety as described herein (e.g., under the heading "Drug Moieties" above). In an embodiment, D is a cytotoxic anti-cancer drug moiety. In an embodiment, the drug moiety is exatecan.

In various embodiments, Ab in Formula (III) is an antibody or an antigen-binding fragment. In an embodiment, Ab specifically binds to human receptor tyrosine kinase like orphan receptor 1 (ROR1). In an embodiment, Ab binds to a cancer cell surface. In an embodiment, Ab is an anti-HER2 antibody.

In various embodiments, the immunoconjugate of Formula (I) is represented by a structure selected from the following, for which $Z^1$ and $Z^2$ are each individually selected from hydrogen, fluoro, chloro, —NO$_2$, and —OCH$_3$:

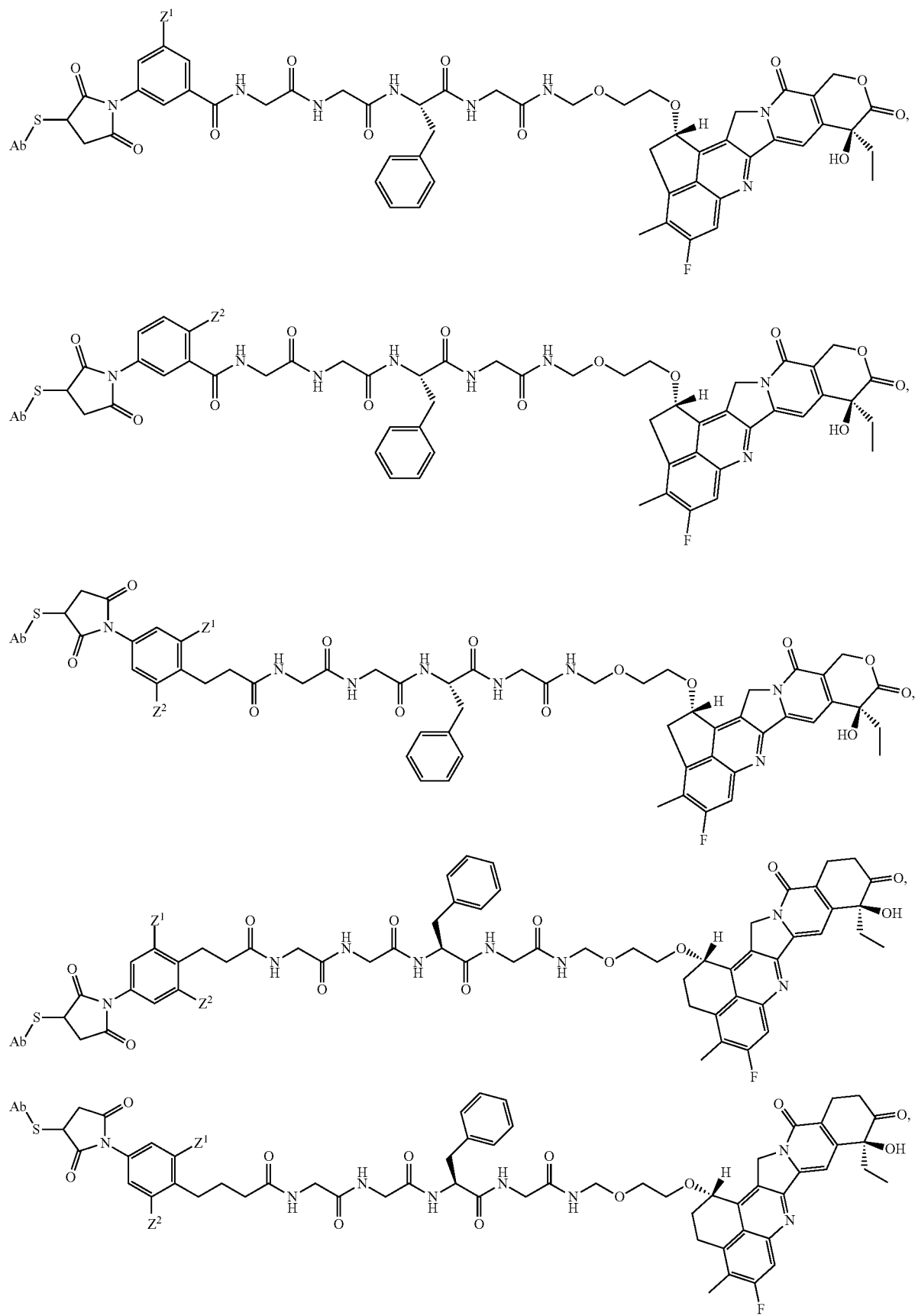

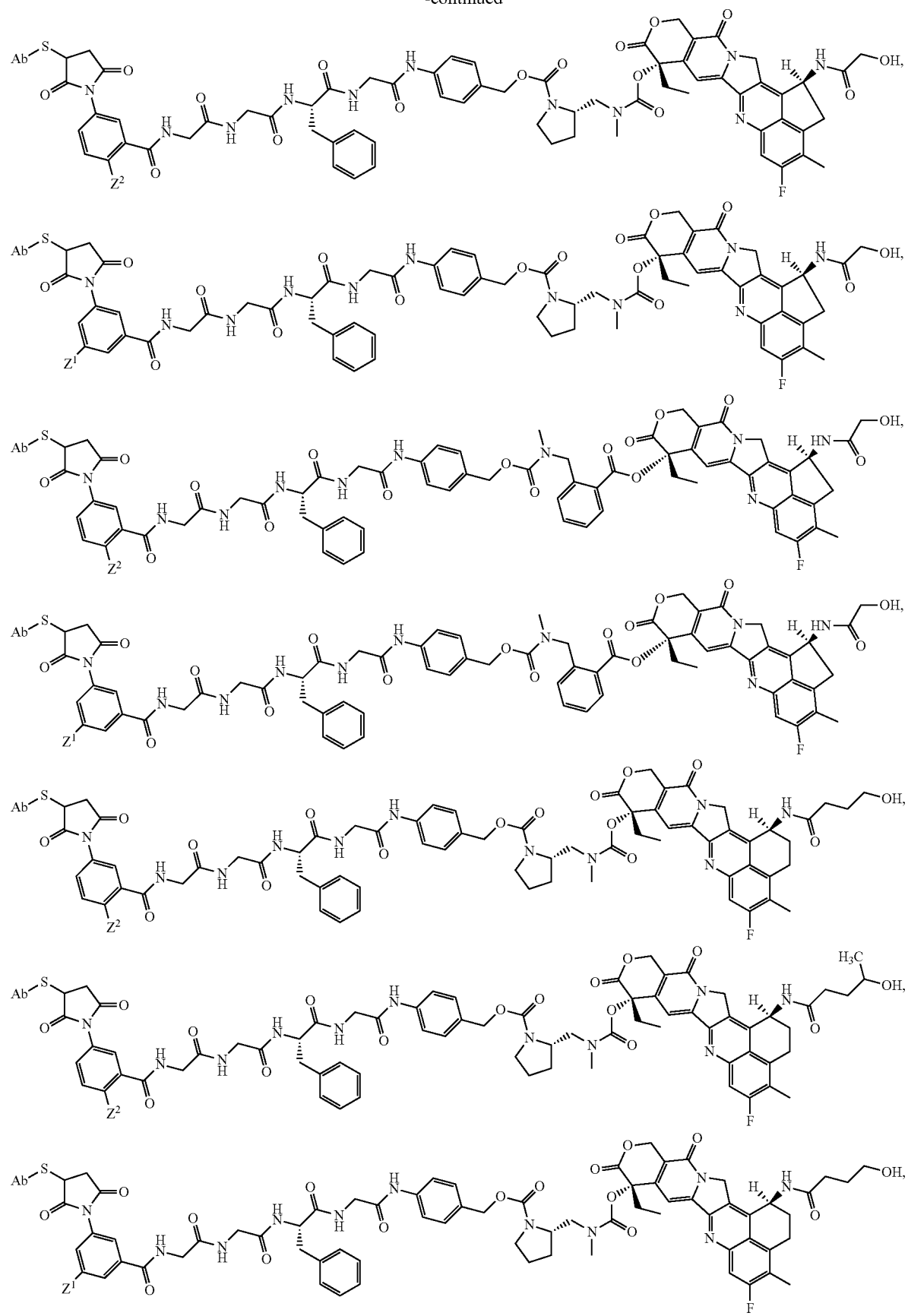

-continued

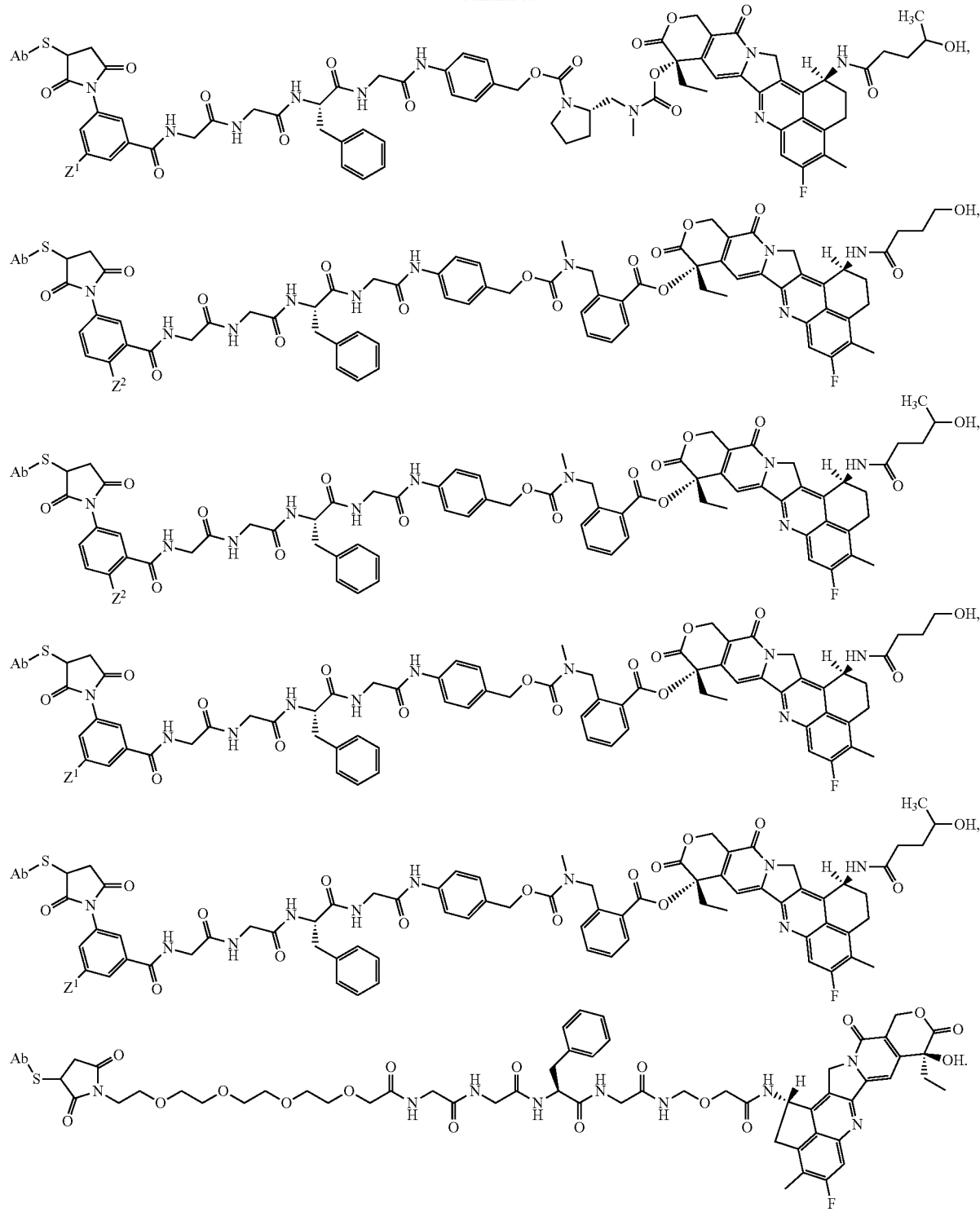

Pharmaceutical Compositions

Some embodiments described herein relate to a pharmaceutical composition, that can include an effective amount of one or more compounds described herein (for example, an immunoconjugate compound of Formula (I), a drug compound of the Formula (IV), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as anti-oxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a targeting ligand to a specific cell or tissue type. The liposomes will be targeted to and taken up selectively by the targeted cell or tissue.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container and labeled for treatment of an indicated condition.

Uses and Methods of Treatment

Some embodiments described herein relate to a method for treating a cancer or a tumor described herein that can include administering an effective amount of a compound described herein (for example, an immunoconjugate compound of Formula (I), a drug compound of the Formula (IV), or a pharmaceutically acceptable salt thereof) or a pharmaceutical composition that includes a compound described herein (for example, an immunoconjugate compound of Formula (I), a drug compound of the Formula (IV), or a pharmaceutically acceptable salt thereof) to a subject having the cancer or tumor. Other embodiments described herein relate to the use of an effective amount of a compound described herein (for example, an immunoconjugate compound of Formula (I), a drug compound of the Formula (IV), or a pharmaceutically acceptable salt thereof) or a pharmaceutical composition that includes a compound described herein (for example, an immunoconjugate compound of Formula (I), a drug compound of the Formula (IV), or a pharmaceutically acceptable salt thereof) in the manufacture of a medicament for treating a cancer or a tumor described herein. Still other embodiments described herein relate to an effective amount of a compound described herein (for example, an immunoconjugate compound of Formula (I), a drug compound of the Formula (IV), or a pharmaceutically acceptable salt thereof) or a pharmaceutical composition that includes a compound described herein (for example, an immunoconjugate compound of Formula (I), a drug compound of the Formula (IV), or a pharmaceutically acceptable salt thereof) for treating a cancer or a tumor described herein.

Examples of cancers and tumors include but are not limited to: lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer), a therapeutically effective amount is that amount that alleviates or eliminates cough, shortness of breath and/or pain.

The amount of the immunoconjugate compound of Formula (I), drug compound of the Formula (IV), or pharmaceutically acceptable salt thereof, required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day, or any amount in between. The compound may be administered in unit dosage form; for example, containing 1 to 500 mg, 10 to 100 mg, 5 to 50 mg or any amount in between, of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of an immunoconjugate compound of Formula (I), a drug compound of the Formula (IV), or a pharmaceutically acceptable salt thereof, can be determined by comparing their in vitro activity and in vivo activity in animal models. Such comparison can be done by comparison against an established drug, such as cisplatin and/or gemcitabine.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Synthesis

Figure 2:
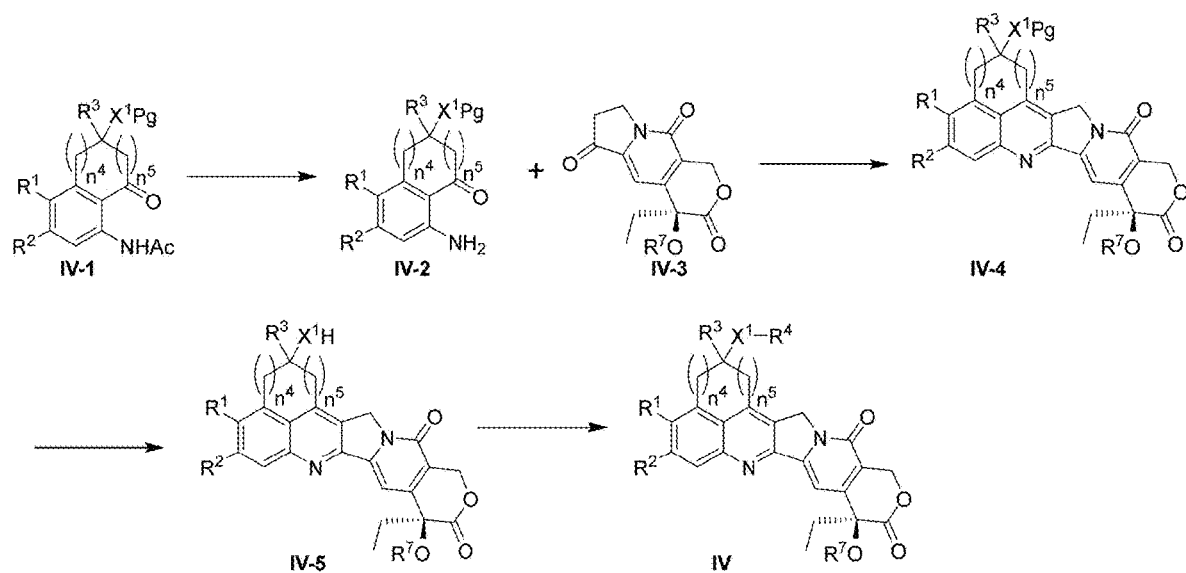
FIG. 2 illustrates a reaction scheme for making a compound of the Formula (IV). Under acidic or basic hydrolysis conditions, IV-2 is formed from IV-1. The Friedlander reaction of IV-2 and IV-3 affords IV-4. Removal of the protecting group (Pg) in IV-4 affords IV-5. IV-5 undergoes alkylation, esterification, or amidation to afford IV.
Figure 3:
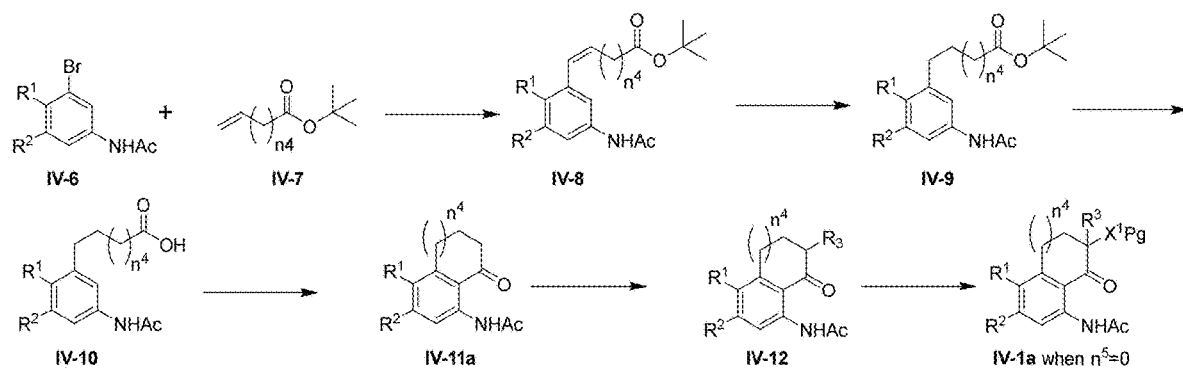
FIG. 3 illustrates a reaction scheme for making a compound of the Formula (IV-la). The Heck reaction between IV-6 and IV-7 affords IV-8. IV-8 undergoes hydrogenation to afford IV-9, that is hydrolyzed to afford IV-10. Intramolecular Friedel-Crafts reaction of IV-10 affords IV-11a. IV-11a undergoes alpha alkylation to afford IV-12 that is treated either with alpha-hydroxylation, or alpha-amination conditions to afford IV-la (when $n^5=0$).
Figure 4:
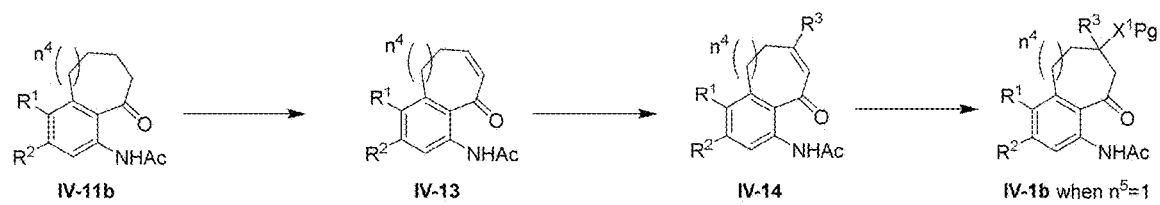
FIG. 4 illustrates a reaction scheme for making a compound of the Formula (IV-1b). Dehydrogenation of IV-11b affords IV-13. IV-13 undergoes Michael reaction followed by dehydrogenation to afford IV-14. IV-14 undergoes Michael reaction using oxygen or nitrogen containing nucleophile to afford IV-1b (when $n^5=1$).
Figure 5:
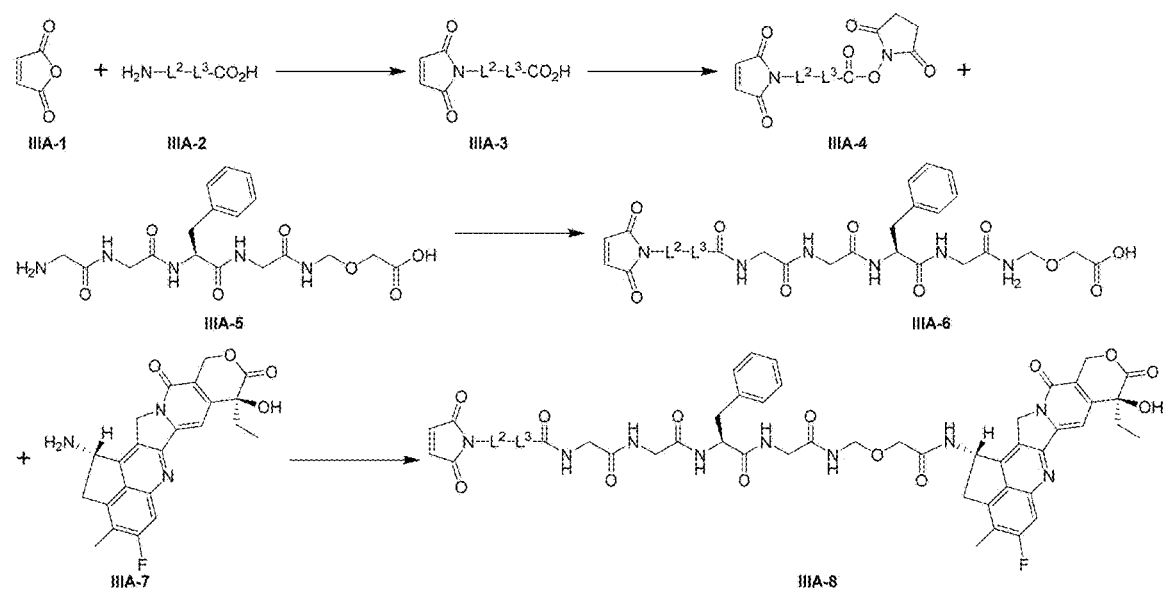
FIG. 5 illustrates a reaction scheme for making a conjugate of the Formula (III) that comprises attaching a linking moiety to a compound of the Formula (IV). The reaction of IIIA-1 and IIIA-2 under heating conditions affords IIIA-3. IIIA-3 reacts with N-hydroxysuccinimide to afford IIIA-4. The reaction of IIIA-4 and IIIA-5 affords IIIA-6. IIIA-6 reacts with IIIA-7 under amide coupling conditions affording IIIA-8.
Figure 6:
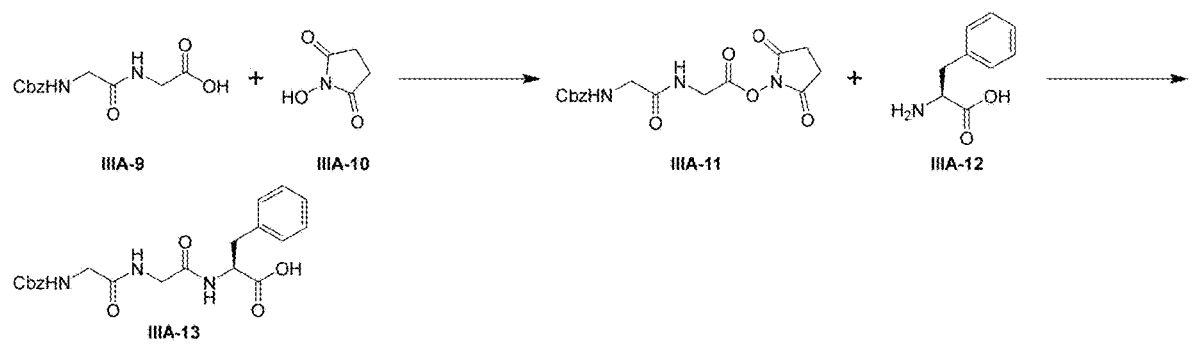
FIG. 6 illustrates a reaction scheme for making IIIA-13. The reaction of IIIA-9 and N-hydroxysuccinimide (IIIA-10) affords IIIA-11, which reacts with IIIA-12 to afford IIIA-13.
Figures 7, 8:
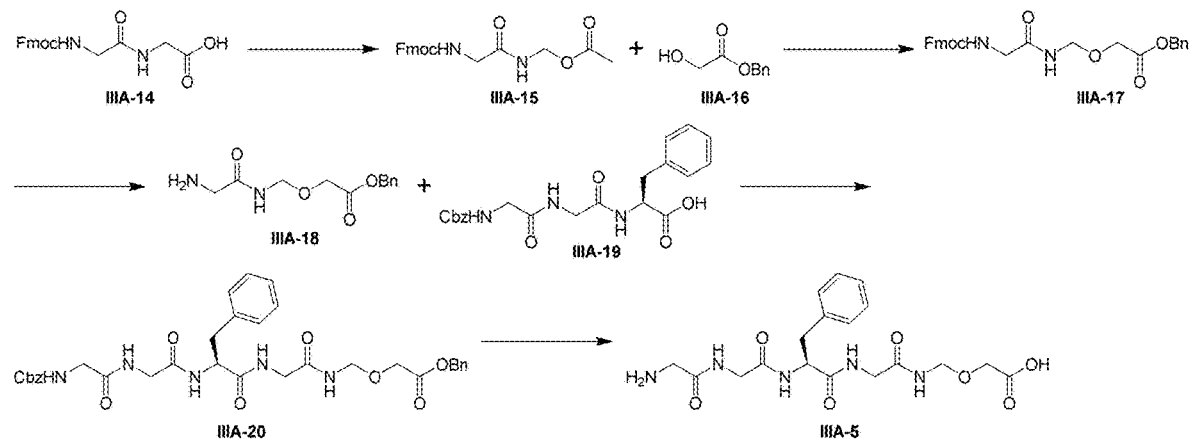
FIG. 7 illustrates a reaction scheme for making IIIA-5. The reaction of IIIA-14 with Pb(OAc)$_4$ affords IIIA-15. Treatment of IIIA-15 and IIIA-16 in the presence of NaOH affords IIIA-17. IIIA-17 is treated with DBU to afford IIIA-1, which couples with IIIA-19 to afford IIIA-20. Hydrogenation of IIIA-20 affords IIIA-5.
FIG. 8 illustrates a reaction scheme for making IIIB-4. The reaction of IIIA-4 and IIIB-1 in the presence of a base affords IIIB-2, which reacts with 4-amino benzyl alcohol and EEDQ to produce IIIB-3. The treatment of IIIB-3 with 4-nitro phenyl chloroformate gives IIIB-4.
Figure 9:
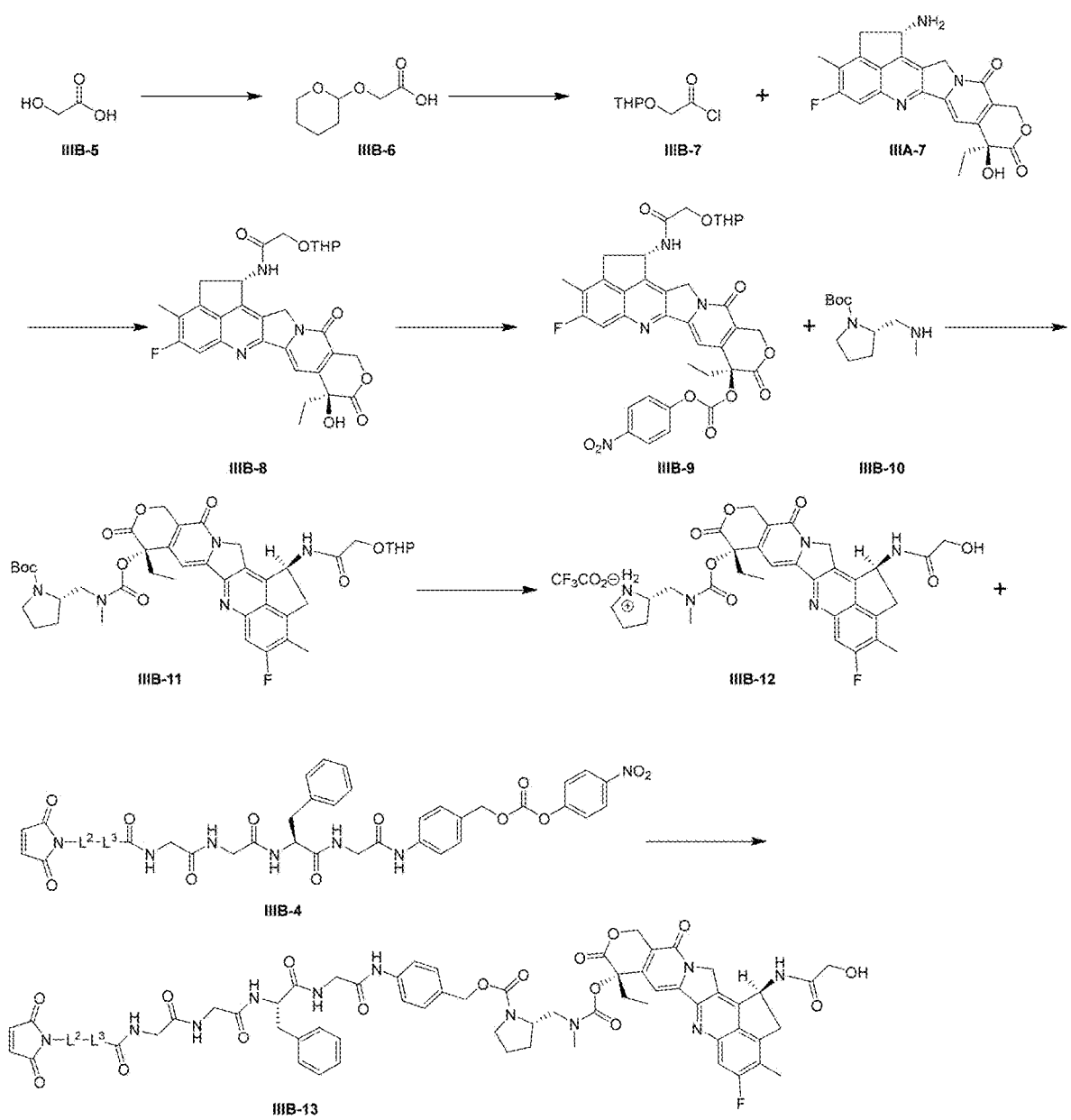
FIG. 9 illustrates a reaction scheme for making IIIB-13. The reaction of IIIB-5 with DHP produces IIIB-6. IIIB-6 reacts with oxalyl chloride and catalytic DMF to produce IIIB-7. The reaction of IIIB-7 and IIIA-7 gives IIIB-8, which reacts with 4-nitro phenyl chloroformate to afford IIIB-9. The reaction IIIB-9 and IIIB-10 in the presence of a base affords IIIB-11. IIIB-11 is treated with TFA to afford IIIB-12. The combination of IIB-12 and IIIB-4 in the presence of a base affords IIIB-13.
Figure 10:
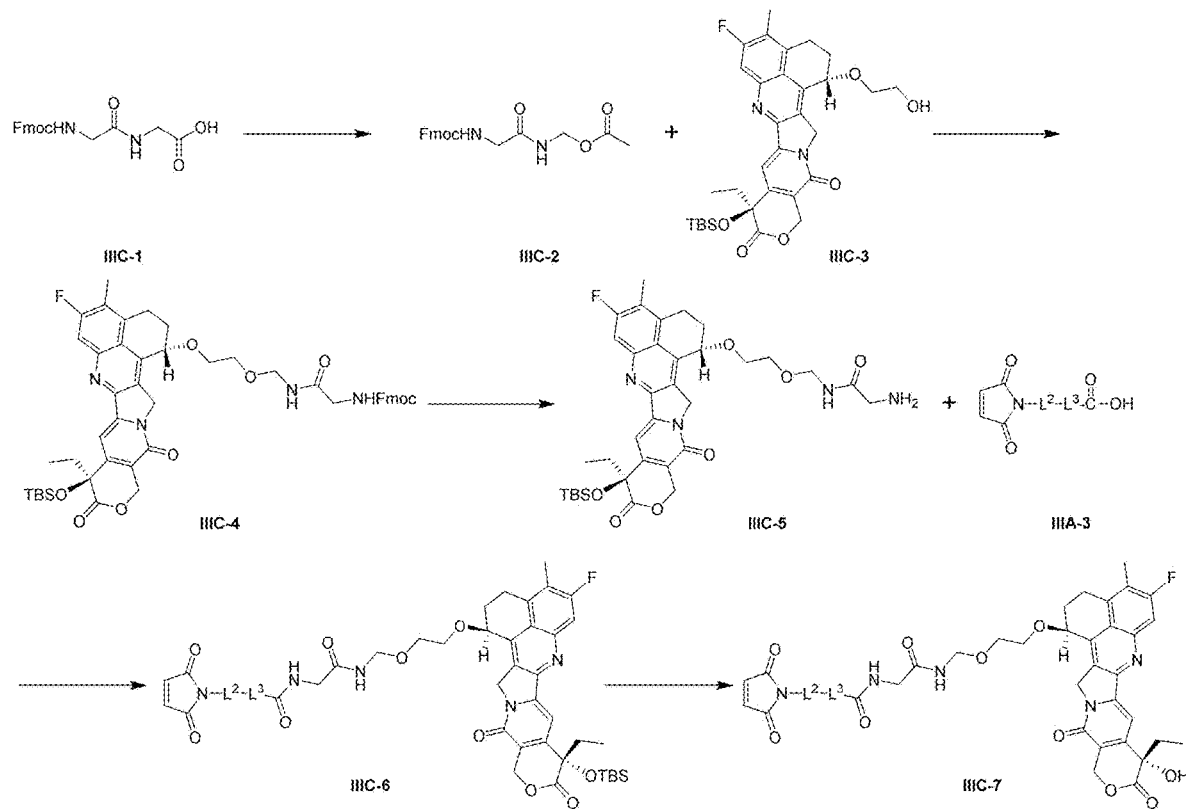
FIG. 10 illustrates a reaction scheme for making IIIC-7. The reaction of IIIC-1 with Pb(OAc)$_4$ produces IIIC-2, which reacts with IIIC-3 in the presence of ZnCl$_2$ to afford IIIC-4. Treating IIIC-4 with DBU affords IIIC-5. The amide coupling of IIIC-5 and IIIA-3 affords IIIC-6, which reacts with HF-pyridine to afford IIIC-7.

Drug compounds of the Formula (IV), or pharmaceutically acceptable salts thereof, can be made in various ways by those skilled using known techniques as guided by the detailed teachings provided herein. For example, in an embodiment, drug compounds of the Formula (IV) are prepared in accordance with the general schemes illustrated in FIGS. 2-4.

Conjugates of the Formula (III) can be made in various ways by those skilled using known techniques as guided by the detailed teachings provided herein. For example, in an embodiment, conjugates of the Formula (II) are prepared in accordance with the general schemes illustrated in FIGS. 5-10. Although illustrated with specific linkers and payloads, those skilled in the art will appreciate that other linkers and/or payloads may be used in similar manners.

Figure 11:
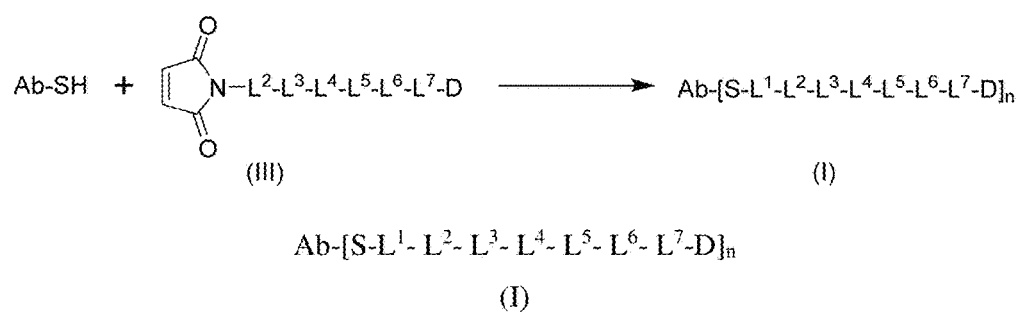
FIG. 11 illustrates a reaction scheme for making an immunoconjugate of the Formula (I) that comprises attaching Ab to a conjugate of the Formula (III). The Michael reaction of the thiol group of cysteines from the antibody with the maleimide in Formula III produces Formula I.

Immunoconjugates of the Formula (I) can be made in various ways by those skilled using known techniques as guided by the detailed teachings provided herein. For example, in an embodiment, immunoconjugates of the Formula (I) are prepared in accordance with the general scheme illustrated in FIG. 11. In an embodiment, a process of producing an immunoconjugate as described herein comprises reacting an effective amount of a thiol-functionalized antibody or antigen-binding fragment with a conjugate as described herein under reaction conditions effective to form the immunoconjugate. In an embodiment, the process further comprises reducing an antibody or an antigen-binding fragment under reducing conditions effective to form the thiol-functionalized antibody or antigen-binding fragment.

EXAMPLES

Additional embodiments are disclosed in further detail in the following examples, which are not in any way intended to limit the scope of the claims.

Example 1

Figure 12:
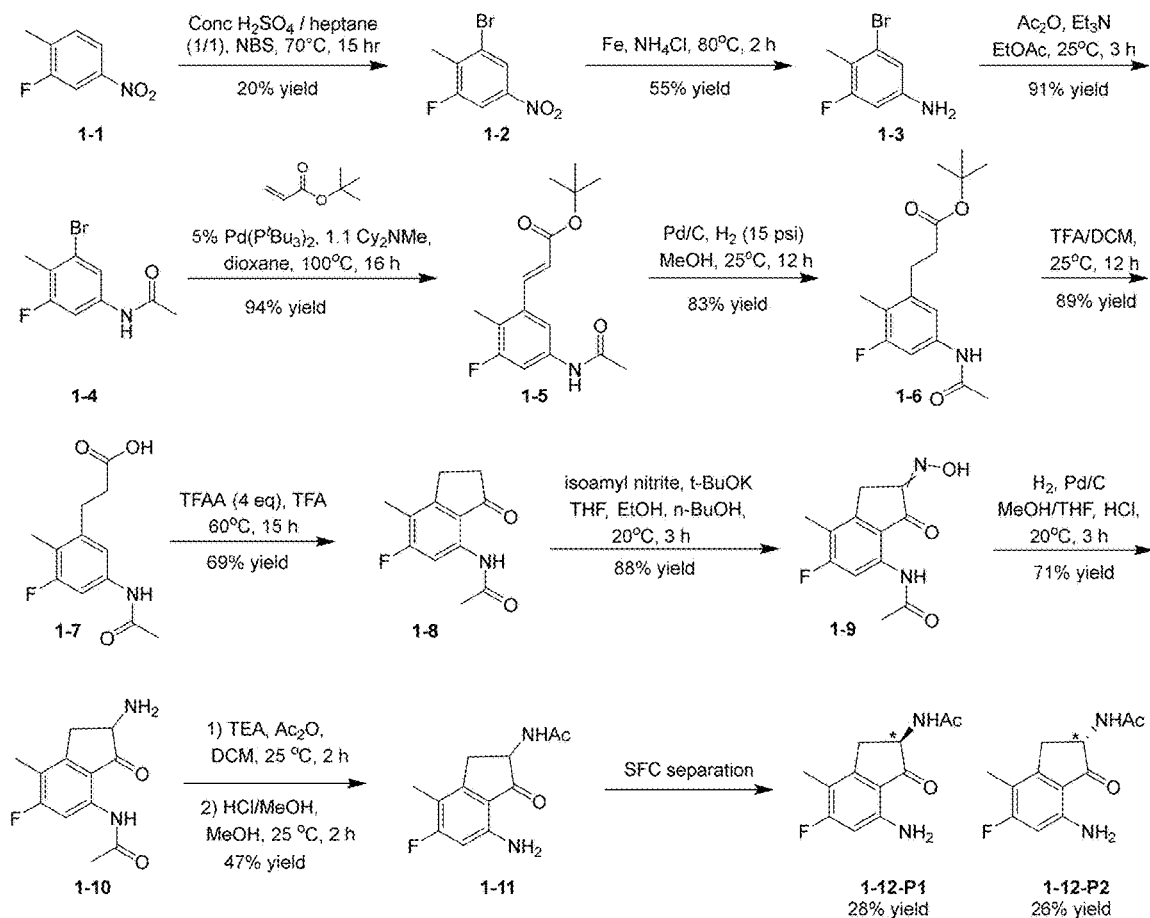
FIG. 12 illustrates a reaction scheme for making compound 1-14.
Figure 12:
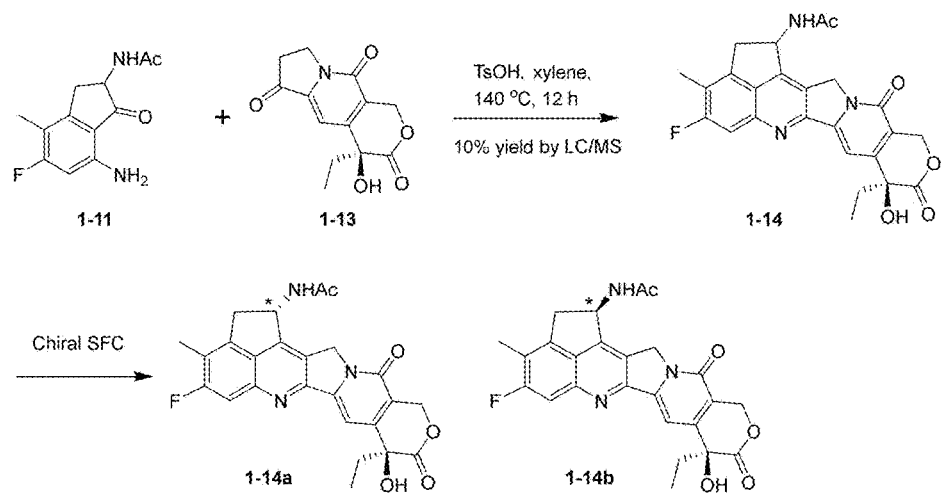

N-((1S,8S)-8-ethyl-4-fluoro-8-hydroxy-3-methyl-9, 12-dioxo-1,2,8,9,12,14-hexahydro-11H-cyclopenta [de]pyrano[3',4':6,7]indolizino[1,2-b]quinolin-1-yl) acetamide (1-14) (FIG. 12)

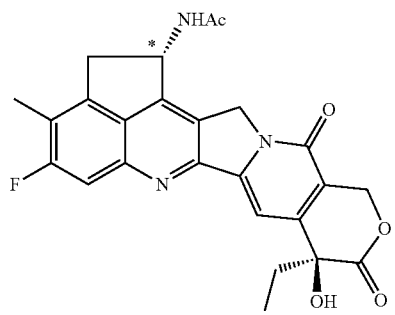 [SMILES: CC[C@@]1(O)C(=O)OCc2c1cc1n(c2=O)Cc2c-1nc1cc(F)c(C)c3c1c2[C@@H](NC(C)=O)C3]

1-14 (stereochemistry at * carbon arbitrarily assigned)

1-Bromo-3-fluoro-2-methyl-5-nitrobenzene (1-2)

A mixture of 2-fluoro-1-methyl-4-nitrobenzene (1-1) (25.0 g, 322 mmol, 1.0 equiv) in heptane (250 mL) and $H_2SO_4$ (250 mL) was heated at 70° C. Then N-bromosuccinimide (68.84 g, 386.78 mmol, 1.2 eq) was added portionwise to the above mixture at 70° C. The resulting red suspension was stirred at 70° C. for 15 h. TLC (petroleum ether/ethyl acetate=10/1, $R_f$=0.6) showed that a new main spot was formed. The reaction mixture was poured into ice water (1 L) and extracted with ethyl acetate (3×500 mL). The combined organic phases were washed with brine (500 mL), dried over $Na_2SO_4$, filtered, and concentrated under reduced pressure. The residue was purified by column chromatography on silica gel eluting with petroleum ether to give 1-bromo-3-fluoro-2-methyl-5-nitrobenzene (1-2) (17.0 g, 20% yield). $^1$H NMR (400 MHz, $CDCl_3$) δ ppm 8.27 (t, J=1.79 Hz, 1H), 7.89 (dd, J=8.76, 2.21 Hz, 1H), 2.44 (d, J=2.50 Hz, 3H).

3-Bromo-5-fluoro-4-methylaniline (1-3)

To a solution of bromo-3-fluoro-2-methyl-5-nitrobenzene (1-2) (15.0 g, 64.1 mmol, 1.0 equiv) in ethanol (750 mL) and water (150 mL) were added iron powder (10.7 g, 192 mmol, 3.0 equiv) and $NH_4Cl$ (6.86 g, 128 mmol, 2.0 equiv). The suspension was stirred at 80° C. for 2 h. TLC (petroleum ether/ethyl acetate=10/1, $R_f$=0.3) showed that a new main spot was formed. After cooling to 25° C., the reaction mixture was filtered through Celite pad, washing with ethanol (500 mL). The combined filtrates were concentrated to dryness and the residue was purified by column chromatography on silica gel eluting with 9% ethyl acetate in petroleum ether to give 3-bromo-5-fluoro-4-methylaniline (1-3) (8.0 g, 55% yield). $^1$H NMR (400 MHz, $CDCl_3$) δ ppm 6.67-6.73 (m, 1H), 6.34 (dd, J=10.97, 2.27 Hz, 1H), 3.65 (br s, 2H), 2.20 (d, J=2.15 Hz, 3H). $^{19}$F NMR (400 MHz, $CDCl_3$) δ ppm −111.86.

N-(3-Bromo-5-fluoro-4-methylphenyl)acetamide (1-4)

To a mixture of 3-bromo-5-fluoro-4-methylaniline (1-3) (8.00 g, 39.2 mmol, 1.0 equiv) in ethyl acetate (100 mL) were added triethylamine (8.13 g, 80.4 mmol, 11.2 mL, 2.05 equiv) and acetic anhydride (5.20 g, 51.0 mmol, 4.77 mL, 1.3 equiv). The reaction mixture was stirred at 25° C. for 3 h. TLC (petroleum ether/ethyl acetate=3/1, $R_f$=0.25) showed that a new main spot was formed. The reaction mixture was quenched with water and extracted with ethyl acetate (3×50 mL). The combined organic phases were washed with brine (100 mL), dried over $Na_2SO_4$, filtered, and concentrated under reduced pressure to give N-(3-bromo-5-fluoro-4-methyl-phenyl)acetamide (1-4) (8.8 g, 91% yield). $^1$H NMR (400 MHz, $CD_3OD$) δ ppm 7.59 (d, J=1.53 Hz, 1H), 7.41 (dd, J=11.55, 2.02 Hz, 1H), 2.26 (d, J=2.20 Hz, 3H), 2.11 (s, 3H).

tert-Butyl (E)-3-(5-acetamido-3-fluoro-2-methylphenyl)acylate (1-5)

To an orange solution of N-(3-bromo-5-fluoro-4-methyl-phenyl)acetamide (1-4) (8.00 g, 32.5 mmol, 1.0 equiv) and tert-butyl acrylate (4.58 g, 35.8 mmol, 5.19 mL, 1.1 equiv) in dioxane (100 mL) were added N-cyclohexyl-N-methylcyclohexanamine (6.99 g, 35.8 mmol, 7.58 mL, 1.1 equiv) and Pd(t-Bu$_3$P)$_2$ (831 mg, 1.63 mmol, 0.05 equiv). The reaction mixture was stirred at 100° C. for 16 h under nitrogen atmosphere. LCMS (retention time=0.797 min) showed the formation of desired product. The reaction mixture was quenched with water (100 mL) and extracted with ethyl acetate (3×100 mL). The combined organic layers were washed with brine (200 mL), dried over Na$_2$SO$_4$, filtered and concentrated under reduced pressure to dryness. The residue was purified by column chromatography on silica gel, eluting with 16% of ethyl acetate in petroleum ether to give tert-butyl (E)-3-(5-acetamido-3-fluoro-2-methylphenyl)acylate (1-5) (10.0 g, 94% yield). $^1$H NMR (400 MHz, DMSO-D$_6$) δ ppm 10.06 (s, 1H), 7.72 (d, J=15.77 Hz, 1H), 7.61 (s, 1H), 7.51 (dd, J=11.98, 1.47 Hz, 1H), 6.22 (d, J=15.77 Hz, 1H), 2.20 (d, J=1.59 Hz, 3H), 2.04 (s, 3H) 1.49 (s, 9H). $^{19}$F NMR (400 MHz, CDCl$_3$) δ ppm −115.02. LCMS (ESI+) m/z: [MH]$^+$ calcd for C$_{16}$H$_{21}$FNO$_3^+$: 294.1, found: 294.0.

tert-Butyl 3-(5-acetamido-3-fluoro-2-methylphenyl)propanoate (1-6)

To a solution of tert-butyl (E)-3-(5-acetamido-3-fluoro-2-methylphenyl)acrylate (1-5) (2.80 g, 9.55 mmol, 1.0 equiv) in dichloromethane (20 mL) and methanol (20 mL) was added Pd/C (10 wt % (1.01 g, 0.1 equiv) under argon atmosphere. The suspension was degassed under vacuum and purged with H$_2$ three times. The mixture was stirred under H$_2$ (15 psi) at 25° C. for 12 h. TLC (petroleum ether/ethyl acetate=3/1, R$_f$=0.2) showed that a new major spot was formed. After the H$_2$ atmosphere was exchanged with argon, it was filtered through a pad of celite and the filter cake was washed with methanol (100 mL). The combined filtrates were concentrated under reduced pressure to give tert-butyl 3-(5-acetamido-3-fluoro-2-methylphenyl)propanoate (1-6) (2.6 g, 83% yield). $^1$H NMR (400 MHz, CD$_3$OD) δ ppm 7.33 (dd, J=11.80, 2.02 Hz, 1H), 7.06 (s, 1H), 2.88 (t, J=7.64 Hz, 2H), 2.49 (t, J=7.70 Hz, 2H), 2.17 (d, J=1.96 Hz, 3H), 2.10 (s, 3H), 1.41 (s, 9H).

3-(5-Acetamido-3-fluoro-2-methylphenyl)propanoic acid (1-7)

To a solution of tert-butyl 3-(5-acetamido-3-fluoro-2-methylphenyl)propanoate (1-6) (2.60 g, 8.80 mmol, 1.0 equiv) in dichloromethane (30 mL) was added trifluoroacetic acid (10 mL) at 25° C. The reaction mixture was stirred at 25° C. for 12 h. TLC (petroleum ether/ethyl acetate=3/1, R$_f$=0.01) showed that a new major spot was formed. The reaction mixture was concentrated to give 3-(5-acetamido-3-fluoro-2-methylphenyl)propanoic acid (1-7) (2.1 g, 89% yield). $^1$H NMR (400 MHz, CD$_3$OD) δ ppm 7.35 (dd, J=11.86, 1.83 Hz, 1H), 7.04 (s, 1H), 2.91 (t, J=7.76 Hz, 2H), 2.55 (t, J=7.83 Hz, 2H), 2.17 (d, J=1.83 Hz, 3H), 2.10 (s, 3H). $^{19}$F NMR (400 MHz, CDCl$_3$) δ ppm −117.33, −77.77.

N-(6-Fluoro-7-methyl-3-oxo-2,3-dihydro-1H-inden-4-yl)acetamide (1-8)

To a solution of 3-(5-acetamido-3-fluoro-2-methyl-phenyl)propanoic acid (1-7) (2.10 g, 8.78 mmol, 1.0 equiv) in trifluoroacetic acid (7 mL) was added trifluoroacetic anhydride (7.37 g, 35.1 mmol, 4.88 mL, 4.0 equiv). The reaction mixture was stirred at 60° C. for 15 h. LCMS showed the formation of desired product. The reaction mixture was diluted with 50% acetonitrile/H$_2$O solution (100 mL), and the pH was adjusted to ~7 by addition of 25% aqueous NaOH solution at 0° C. The mixture was extracted with ethyl acetate (3×100 mL). The combined organic layers were washed with brine (100 mL), dried over Na$_2$SO$_4$, filtered and the concentrated under reduced pressure to give N-(6-fluoro-7-methyl-3-oxo-2,3-dihydro-1H-inden-4-yl)acetamide (1-8) (1.5 g, 69% yield). $^1$H NMR (400 MHz, CD$_3$OD) δ ppm 8.02 (d, J=12.57 Hz, 1H), 3.01-3.08 (m, 2H), 2.72-2.79 (m, 2H), 2.18-2.23 (m, 6H). LCMS (ESI+) m/z: [MH]$^+$ calcd for C$_{12}$H$_{13}$FNO$_2^+$: 222.1, found: 222.0.

N-(6-Fluoro-2-hydroxyimino-7-methyl-3-oxo-2,3-dihydro-1H-inden-4-yl) acetamide (1-9)

A solution of potassium tert-butoxide (1.19 g, 10.58 mmol, 1.3 equiv) in tetrahydrofuran (12 mL), ethanol (2.4 mL) and butanol (2.4 mL) were stirred at 0° C. for 0.5 h. Isoamyl nitrite (1.43 g, 12.2 mmol, 1.64 mL, 1.5 equiv) and N-(6-fluoro-7-methyl-3-oxo-2,3-dihydro-1H-inden-4-yl)acetamide (1-8) (1.80 g, 8.14 mmol, 1.0 equiv) were added to the above mixture. The reaction mixture was stirred at 20° C. for 3 h. TLC (petroleum ether/ethyl acetate=1/1, R$_f$=0.4) showed that a new major spot was formed. The resulting red suspension was cooled to 0° C. and quenched with 1 N hydrochloric acid solution (50 mL) and extracted with ethyl acetate (3×50 mL). The combined organic layers were washed with brine (50 mL), dried over Na$_2$SO$_4$, filtered and concentrated under reduced pressure to give N-(6-fluoro-2-hydroxyimino-7-methyl-3-oxo-2,3-dihydro-1H-inden-4-yl) acetamide (1-9) (2.0 g, 88% yield). $^1$H NMR (400 MHz, DMSO-D$_6$) δ ppm 12.81 (s, 1H), 10.33 (s, 1H), 8.03 (d, J=12.57 Hz, 1H), 3.71 (s, 2H), 2.20 (s, 3H), 2.16 (s, 3H).

N-(2-Amino-6-fluoro-7-methyl-3-oxo-2,3-dihydro-1H-inden-4-yl)acetamide hydrochloric acid salt (1-10)

To a solution of N-(6-fluoro-2-hydroxyimino-7-methyl-3-oxo-2,3-dihydro-1H-inden-4-yl)acetamide (1-9) (2.00 g, 6.98 mmol, 1 equiv) in methanol (100 mL) were added Pd/C (10 wt %) (1.48 g, 0.2 equiv) and hydrochloric acid (12 M, 1.74 mL, 3 equiv) under nitrogen atmosphere. The suspension was degassed under vacuum and purged with H$_2$ three times. The mixture was stirred under H$_2$ (15 psi) at 20° C. for 3 h. TLC (petroleum ether/ethyl acetate=1/1, R$_f$=0) showed that a new major spot was formed. After the H$_2$ atmosphere was exchanged with nitrogen, it was filtered through a pad of Celite and washed with methanol (200 mL). The combined filtrates were concentrated to dryness to give N-(2-amino-6-fluoro-7-methyl-3-oxo-2,3-dihydro-1H-inden-4-yl)acetamide hydrochloric acid salt (1-10) (1.5 g, 71% yield). This material was used in the next step directly without further purification. $^1$H NMR (400 MHz, DMSO-D$_6$) δ ppm 9.99 (s, 1H), 8.02 (d, J=12.59 Hz, 1H), 4.33 (br s, 1H), 3.98 (br s, 2H), 3.50 (dd, J=16.99, 8.19 Hz, 1H), 3.00 (dd, J=17.18, 4.46 Hz, 1H), 2.21 (s, 3H), 2.18 (s, 3H). $^{19}$F NMR (400 MHz, CDCl$_3$) δ ppm −102.81.

N-(7-Amino-5-fluoro-4-methyl-1-oxo-2,3-dihydro-1H-inden-2-yl)acetamide (1-11)

To a mixture of N-(2-amino-6-fluoro-7-methyl-3-oxo-2,3-dihydro-1H-inden-4-yl)acetamide hydrochloric acid salt (1-10) (1.50 g, 6.35 mmol, 1.0 equiv) in dichloromethane (45 mL) were added triethylamine (1.93 g, 19.0 mmol, 2.65 mL, 3.0 equiv) and acetic anhydride (778 mg, 7.62 mmol, 0.714 mL, 1.2 equiv). The reaction mixture was stirred at 25° C. for 2 h. TLC (petroleum ether/ethyl acetate=1/1, $R_f$=0.1) showed that a new major spot was formed. The reaction mixture was quenched with water (50 mL) and extracted with dichloromethane (3×50 mL). The combined organic layers were washed with brine (50 mL), dried over $Na_2SO_4$, filtered and concentrated under reduced pressure to give a red gum.

The gum was dissolved in HCl/MeOH (20 mL, 4 M) and stirred at 25° C. for 2 h. LCMS showed formation of the desired product. The resulting red suspension was concentrated to give a red residue. The residue was diluted with methanol (2 mL) and purified by prep-HPLC (column: Phenomenex luna C18 80*40 mm*3 um; mobile phase: [water (HCl)-ACN]; B %: 28%-48%, 7 min) to afford N-(7-amino-5-fluoro-4-methyl-1-oxo-2,3-dihydro-1H-inden-2-yl)acetamide (1-11) (0.70 g, 47% yield). $^1$H NMR (400 MHz, $CD_3OD$) δ ppm 6.52 (d, J=11.56 Hz, 1H), 4.48 (dd, J=8.23, 5.01 Hz, 1H), 3.44 (dd, J=17.05, 8.23 Hz, 1H), 2.83 (dd, J=17.11, 4.95 Hz, 1H), 2.11 (d, J=1.07 Hz, 3H), 2.02 (s, 3H). $^{19}$F NMR (400 MHz, $CDCl_3$) δ ppm −107.29. $^{13}$CNMR (100 MHz, $CD_3OD$): 201.9, 172.1, 167.9, 165.4, 153.8, 153.7, 143.1, 143.0, 117.0, 112.6, 112.4, 101.6, 101.3, 55.5, 31.8, 20.8, 8.0. LCMS (ESI+) m/z: [MH]$^+$ calcd for $C_{12}H_{14}FN_2O_2^+$: 237.1, found: 237.0.

(R)—N-(7-Amino-5-fluoro-4-methyl-1-oxo-2,3-dihydro-1H-inden-2-yl]acetamide (1-12-P1) and (S)—N-7-amino-5-fluoro-4-methyl-1-oxo-2,3-didro-1H-inden-2-yl]acetamide (1-12-P2)

N-(7-amino-5-fluoro-4-methyl-1-oxo-2,3-dihydro-1H-inden-2-yl) acetamide (1-11) (0.70 g, 2.96 mmol) was dissolved in MeOH, neutralized with $NH_4OH$ and separated by chiral SFC to afford (R)—N-7-amino-5-fluoro-4-methyl-1-oxo-2,3-dihydro-1H-inden-2-yl]acetamide (1-12-P1) (compound 1-12-P1 may be the opposite enantiomer of that depicted) (200 mg, 28% yield) and (S)—N-7-amino-5-fluoro-4-methyl-1-oxo-2,3-dihydro-1H-inden-2-yl]acetamide (1-12-P2) (compound 1-12-P2 may be the opposite enantiomer of that depicted) (180 mg, 26% yield). Note: the stereochemistry is arbitrarily assigned. SFC separation method: column: DAICEL CHIRALPAK AD (250 mm*30 mm, 10 um); mobile phase: [0.1% $NH_3H_2O$ IPA]; B %: 30%-30%, 12 min, SFC (1-12-P1, RT=3.012 min) and SFC (1-12-P2, RT=3.270 min).

Spectra for 1-12-P1: $^1$H NMR (400 MHz, $CD_3OD$) δ ppm 2.01 (s, 3H) 2.05 (s, 3H) 2.74 (dd, J=16.81, 5.01 Hz, 1H) 3.40 (br d, J=8.70 Hz, 1H) 4.50 (dd, J=8.23, 5.01 Hz, 1H) 6.26 (d, J=12.40 Hz, 1H). $^{19}$F NMR (400 MHz, $CDCl_3$) δ ppm −108.05. LCMS (ESI+) m/z: [MH]$^+$ calcd for $C_{12}H_{14}FN_2O_2$: 237.10, found: 237.0.

Spectra for 12-P2: $^1$H NMR (400 MHz, $CD_3OD$) δ ppm 2.01 (s, 3H) 2.05 (s, 3H) 2.74 (dd, J=17.11, 4.95 Hz, 1H) 3.40 (br d, J=8.82 Hz, 1H) 4.50 (dd, J=8.29, 5.07 Hz, 1H) 6.26 (d, J=12.40 Hz, 1H). $^{19}$F NMR (400 MHz, $CDCl_3$) δ ppm −108.03. LCMS (ESI+) m/z: [MH]$^+$ calcd for $C_{12}H_{14}FN_2O_2$: 237.10, found: 237.1.

N-((1S,8S)-8-ethyl-4-fluoro-8-hydroxy-3-methyl-9,12-dioxo-1,2,8,9,12,14-hexahydro-11H-cyclopenta[de]pyrano[3',4':6,7]indolizino[1,2-b]quinolin-1-yl) acetamide (1-14)

The mixture of N-(7-amino-5-fluoro-4-methyl-1-oxo-2,3-dihydro-1H-inden-2-yl)acetamide (1-11) (50 mg, 0.21 mmol), (S)-4-ethyl-4-hydroxy-7,8-dihydro-1H-pyrano[3,4-f]indolizine-3,6,10(4H)-trione (1-13) (111.4 mg, 0.42 mmol), TsOH (36.2 mg, 0.21 mmol) in xylene (2 mL) was heated at 140° C. for 12 h. All volatiles were removed under high vacuum, and the residue subjected to chromatography first, then chiral SFC separation to afford 1-14a and 1-14b. LCMS (ESI+) m/z: [MH]$^+$ calcd for $C_{25}H_{23}FN_3O_5$: 464.2, found: 464.3.

Example 2

Figure 13:
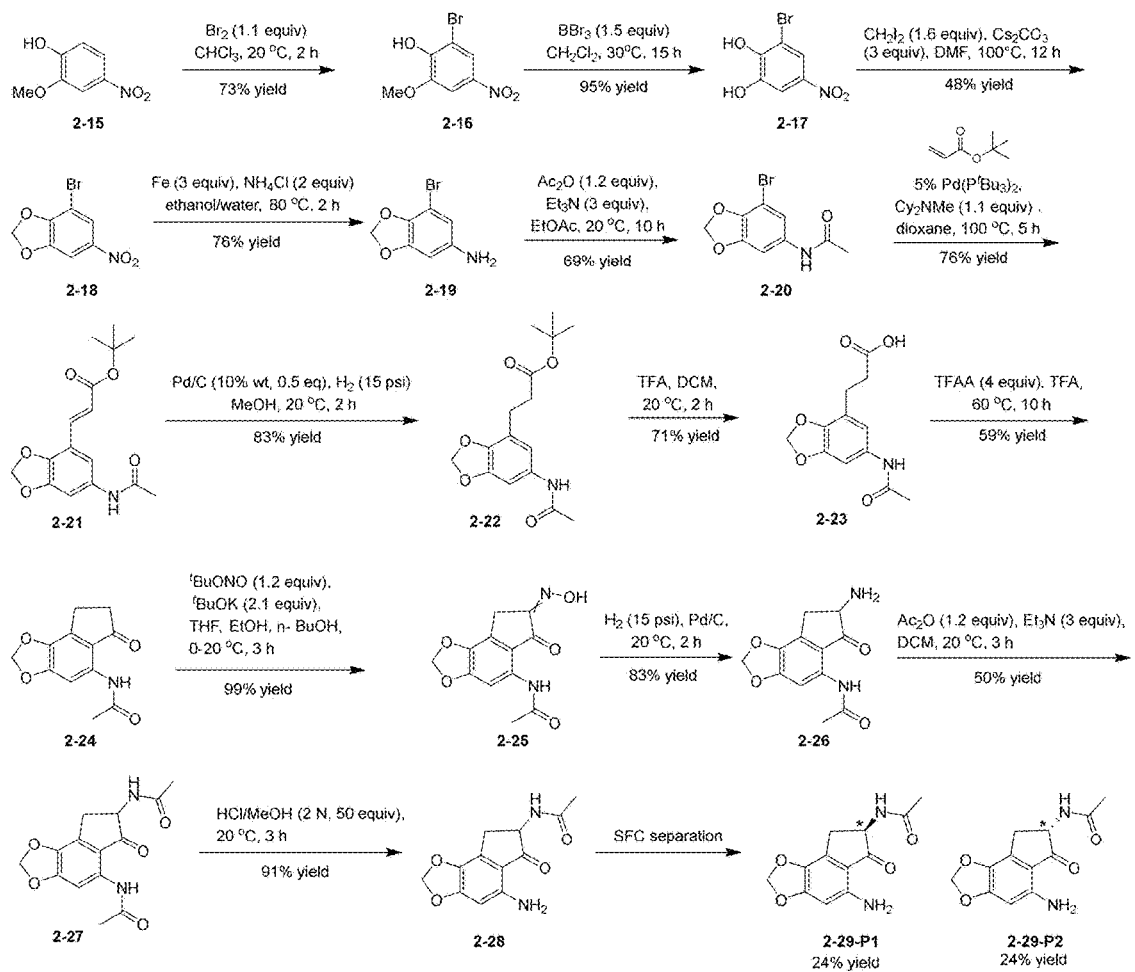
FIG. 13 illustrates a reaction scheme for making compound 2-30.
Figure 13:
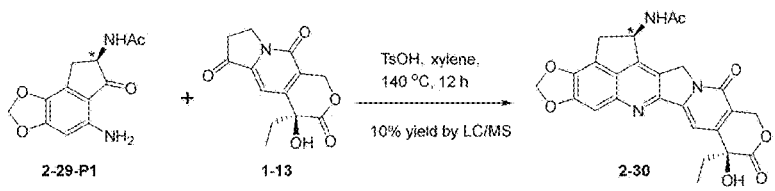

N-((1S,9S)-9-ethyl-9-hydroxy-10,13-dioxo-1,2,9,10,13,15-hexahydro-12H-cyclopenta[de][1,3]dioxolo[4,5-g]pyrano[3',4':6,7]indolizino[1,2-b]quinolin-1-yl) acetamide (2-30) (FIG. 13)

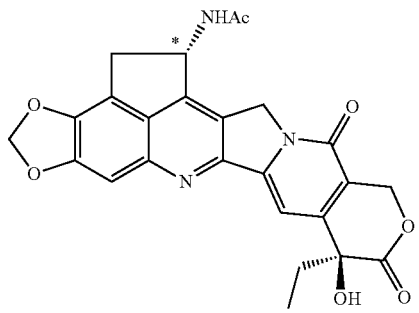 [SMILES: CC[C@@]1(O)C(=O)OCc2c1cc1n(c2=O)Cc2c-1nc1cc3c(c4c1c2[C@@H](NC(C)=O)C4)OCO3]

2-30 (stereochemistry at * carbon arbitrarily assigned)

2-Bromo-6-methoxy-4-nitrophenol (2-16)

To a solution of 2-methoxy-4-nitrophenol (2-15) (50.0 g, 296 mmol, 1.0 equiv) in glacial acetic acid (500 mL) was added bromine (52.0 g, 325 mmol, 16.8 mL, 1.1 equiv) slowly using a dropping funnel at 20° C. The resulting mixture was stirred at 20° C. for 2 h. TLC (petroleum ether:ethyl acetate=2:1) indicated the starting material was consumed and a major spot with lower polarity was formed. The reaction mixture was slowly poured into water (1.5 L) while stirring, and the resulting mixture was stirred at 20° C. for additional 10 min. The mixture was filtered, and concentrated under reduced pressure to dryness. The residue was triturated with water (2×500 mL), the resulting product was collected by filtration and dried in a vacuum oven to afford 2-bromo-6-methoxy-4-nitrophenol (2-16) (60.0 g, 73% yield). $^1$H NMR (400 MHz, $CDCl_3$): δ ppm 8.13 (d, J=2.4 Hz, 1H), 7.74 (d, J=2.4 Hz, 1H), 6.61 (s, 1H), 4.03 (s, 3H). LCMS (ESI−) m/z: [MH]$^-$ calcd for $C_7H_5BrNO_4^-$: 245.9, found: 245.9.

3-Bromo-5-nitrobenzene-1,2-diol (2-17)

To a solution of 2-bromo-6-methoxy-4-nitrophenol (2-16) (30.0 g, 121 mmol, 1 eq) in $CH_2Cl_2$ (1.5 L) was added boron tribromide (45.4 g, 181 mmol, 17.5 mL, 1.5 equiv) at 0° C. The reaction mixture was allowed to warm to 30° C. and stirred for 15 h. TLC (petroleum ether:ethyl acetate=1:1) indicated the starting material was consumed and a new major spot with higher polarity was formed. The reaction mixture was quenched with methanol (200 mL) and concentrated under reduced pressure to afford 3-bromo-5-nitrobenzene-1,2-diol (2-17) (26.9 g, 95% yield). $^1$H NMR (400 MHz, DMSO-$D_6$): δ ppm 10.94 (s, 2H), 7.87 (d, J=2.8 Hz, 1H), 7.62 (d, J=2.8 Hz, 1H).

4-Bromo-6-nitro-1,3-benzodioxole (2-18)

To a solution of 3-bromo-5-nitrobenzene-1,2-diol (2-17) (30.0 g, 128 mmol, 1.0 equiv) in N,N-dimethylformamide (1 L) was added $Cs_2CO_3$ (125 g, 385 mmol, 3 equiv) and diiodomethane (54.9 g, 205 mmol, 16.6 mL, 1.6 equiv) at 20° C. The reaction mixture was stirred at 100° C. for 12 h. TLC (petroleum ether:ethyl acetate=3:1) indicated the starting material was consumed and a new major spot with lower polarity was formed. The reaction mixture was cooled to 20° C., poured into ice-water (1.5 L), and extracted with ethyl acetate (2×1.5 L). The combined organic layers were washed with brine (2×1 L), dried over anhydrous $Na_2SO_4$, filtered and concentrated under reduced pressure to give a brown oil. The oil was triturated with toluene (20 mL), and the resulting product was collected by filtration, dried in a vacuum oven to afford 4-bromo-6-nitro-1,3-benzodioxole (2-18) (17 g, 48% yield). $^1$H NMR (400 MHz, $CDCl_3$): δ ppm 8.06 (d, J=2.0 Hz, 1H), 7.63 (d, J=2.4 Hz, 1H), 6.23 (s, 2H).

7-Bromobenzo[d][1,3]dioxol-5-amine (2-19)

To a solution of 4-bromo-6-nitro-1,3-benzodioxole (2-18) (10.0 g, 40.6 mmol, 1.0 equiv) in ethanol (500 mL) and water (100 mL) was added iron (6.81 g, 122 mmol, 3.0 equiv) and $NH_4Cl$ (4.35 g, 81.3 mmol, 2.0 equiv) at 20° C. The mixture was stirred at 80° C. for 2 h. TLC (petroleum ether:ethyl acetate=1:1) indicated the starting material was consumed and a new major spot with lower polarity was formed. After the reaction mixture was cooled to 20° C., it was filtered through a pad of Celite, washed with ethanol (500 mL). The filtrate was concentrated under reduced pressure and crushed ice was added. The resulting product was collected by filtration, washed with water, and dried in a vacuum oven to afford 7-bromobenzo[d] [1,3]dioxol-5-amine (2-19) (7.5 g, 76% yield). $^1$H NMR (400 MHz, $CDCl_3$): δ ppm 6.29 (s, 1H), 6.21 (s, 1H), 5.94 (s, 2H), 3.51 (s, 2H).

N-(7-Bromobenzo[d][1,3]dioxol-5-yl)acetamide (2-20)

To a solution of 7-bromo-1,3-benzodioxol-5-amine (2-19) (6.00 g, 27.78 mmol, 1.0 equiv) in ethyl acetate (50 mL) was added acetic anhydride (3.40 g, 33.33 mmol, 3.12 mL, 1.2 equiv) and triethylamine (8.43 g, 83.3 mmol, 11.6 mL, 3.0 equiv) at 20° C. and the resulting mixture was stirred for 10 h. TLC (ethyl acetate:methanol=4:1) indicated the starting material was consumed and a new major spot with higher polarity was formed. The reaction mixture was quenched by the addition of saturated $NaHCO_3$ (50 mL) at 0° C. and extracted with ethyl acetate (2×50 mL). The combined organic layers were dried over $Na_2SO_4$, filtered, and concentrated under reduced pressure. The residue was purified by column chromatography (eluting with petroleum ether/ethyl acetate=1/3 to 1/4) to afford N-(7-bromobenzo[d][1,3]dioxol-5-yl)acetamide (2-20) (5.5 g, 69% yield). $^1$H NMR (400 MHz, $CDCl_3$): δ ppm 7.19 (s, 1H), 7.13 (d, J=1.6 Hz, 1H), 7.02 (d, J=2.0 Hz, 1H), 6.02 (s, 2H), 2.15 (s, 3H). LCMS (ESI+) m/z: [MH]$^+$ calcd for $C_9H_9BrNO_3^+$: 258.0, found: 257.9.

tert-Butyl (E)-3-(6-acetamido-1,3-benzodioxol-4-yl)acrylate (2-21)

To a solution of N-(7-bromo-1,3-benzodioxol-5-yl)acetamide (2-20) (2.00 g, 7.75 mmol, 1.0 equiv) and tert-butyl acrylate (1.09 g, 8.52 mmol, 1.24 mL, 1.1 equiv) in dioxane (20 mL) were added N-cyclohexyl-N-methyl-cyclohexanamine (1.67 g, 8.52 mmol, 1.81 mL, 1.1 equiv) and bis(tri-tert-butylphosphine)palladium(0) (198 mg, 0.387 mmol, 0.05 equiv) under nitrogen atmosphere. The mixture was stirred at 100° C. for 5 h. TLC (petroleum ether:ethyl acetate=2:1, $R_f$=0.4) and LCMS showed the starting material was consumed and the desired product was formed. After cooling down to RT, the reaction mixture was filtered, and the filtrate was concentrated to give a product that was then triturated with ethyl acetate (40 mL) at 20° C. for 10 min, then filtered and the filtrate was concentrated under reduced pressure to give tert-butyl (E)-3-(6-acetamido-1,3-benzodioxol-4-yl)acrylate (2-21) (2.0 g, 76% yield). $^1$H NMR (400 MHz, $CDCl_3$) δ ppm 7.44 (d, J=16.09 Hz, 1H) 7.23 (d, J=1.91 Hz, 1H) 7.05 (br s, 1H) 6.86 (d, J=1.91 Hz, 1H) 6.55 (d, J=15.97 Hz, 1H) 6.06 (s, 2H) 2.17 (s, 3H) 1.53 (s, 9H). LCMS (ESI+) m/z: [M-56]$^+$ calcd for $C_{16}H_{20}NO_5$—$C_4H_9$ ($^t$Bu)+H]$^+$: 249.1, found: 249.9.

tert-Butyl 3-(6-acetamido-1,3-benzodioxol-4-yl)propanoate (2-22)

To a suspension of Pd/C (2.90 g, 2.46 mmol, 10% purity, 0.5 equiv) in MeOH (20 mL) was added a solution of tert-butyl (E)-3-(6-acetamido-1,3-benzodioxol-4-yl)acrylate (2-21) (1.50 g, 4.91 mmol, 1.0 equiv) in MeOH (20 mL) at 20° C. The mixture was hydrogenated at 20° C. for 2 h under 15 psi of hydrogen atmosphere. TLC (petroleum ether/ethyl acetate=1/1, $R_f$=0.48) showed the starting material was consumed and a new spot was formed. After the $H_2$ atmosphere was exchanged with nitrogen, the reaction mixture was filtered, and filtrate was concentrated to give tert-butyl 3-(6-acetamido-1,3-benzodioxol-4-yl) propanoate (2-22) (1.4 g, 83% yield). It was used for the next step without further purification. $^1$H NMR (400 MHz, $CDCl_3$) δ ppm 7.09 (d, J=1.96 Hz, 1H), 6.98 (br s, 1H), 6.64 (s, 1H), 5.94 (s, 2H), 2.83 (t, J=7.76 Hz, 2H), 2.51-2.59 (m, 2H), 2.14 (s, 3H), 1.43 (s, 9H). LCMS (ESI+) m/z: [M+Na]$^+$ calcd for $C_{16}H_{21}NO_5Na^+$: 330.1, found: 330.1.

3-(6-Acetamido-1,3-benzodioxol-4-yl)propanoic acid (2-23)

To a solution of tert-butyl 3-(6-acetamido-1,3-benzodioxol-4-yl)propanoate (2-22) (1.40 g, 4.56 mmol, 1.0 equiv) in $CH_2Cl_2$ (15 mL) was added TFA (3 mL) at 20° C. and the mixture was stirred for 2 h. TLC (petroleum ether:ethyl acetate=0:1, Rr-0.48) showed the starting material was consumed and a new spot was formed. The reaction mixture was concentrated under reduced pressure, and the residue was purified by column chromatography (eluting with petroleum ether/ethyl acetate=1/0 to 1/9) to give 3-(6-acetamido-1,3-benzodioxol-4-yl)propanoic acid (2-23) (0.85 g, 71% yield). $^1$H NMR (400 MHz, $CD_3OD$) δ ppm 7.08 (d, J=1.91 Hz, 1H), 6.76 (d, J=1.79 Hz, 1H), 5.93 (s, 2H), 2.80-2.88 (m, 2H), 2.57-2.65 (m, 2H), 2.07 (s, 3H). LCMS (ESI+) m/z: [MH]$^+$ calcd for $C_{12}H_{14}NO_5^+$: 252.1, found: 251.9.

N-(6-Oxo-7,8-dihydrocyclopenta[g][1,3]benzodioxol-5-yl) acetamide (2-24)

To a solution of 3-(6-acetamido-1,3-benzodioxol-4-yl)propanoic acid (2-23) (16.0 g, 63.7 mmol, 1.0 equiv) in TFA (64 mL) was added TFAA (53.5 g, 255 mmol, 35.4 mL, 4 equiv) dropwise at 20° C. The resulting solution was heated to 60° C. for 10 h. TLC (petroleum ether:ethyl acetate=2:1, $R_f$=0.40) and LCMS indicated the reaction was completed. After cooling down to RT, the reaction mixture was poured into a solution of acetonitrile (100 mL) and water (100 mL). After cooling to 0° C., the pH of the mixture was adjusted to 7 with 25% aqueous sodium hydroxide (150 mL), and water (100 mL) was added. The resulting mixture was extracted with ethyl acetate (500 mL×3). The combined organic layers were washed with brine (800 mL), dried over anhydrous $Na_2SO_4$, filtered and concentrated under reduced pressure. The residue was triturated with ethyl acetate (100 mL), filtered and the filter cake was collected to give N-(6-oxo-7,8-dihydrocyclopenta[g][1,3]benzodioxol-5-yl)acetamide (2-24) (10.4 g, 59% yield). $^1$H NMR (400 MHz, DMSO-$D_6$) δ ppm 10.47 (s, 1H), 7.85 (s, 1H), 6.15 (s, 2H), 2.84-3.04 (m, 2H), 2.60-2.74 (m, 2H), 2.17 (s, 3H). LCMS (ESI+) m/z: [MH]$^+$ calcd for $C_{12}H_{12}NO_4^+$: 234.1, found: 234.0.

N-(7-Hydroxyimino-6-oxo-8H-cyclopenta[g][1,3]benzodioxol-5-yl)acetamide (2-25)

A solution of potassium tert-butoxide (1.0 M, 45.0 mL, 2.1 equiv) in THF (41.6 mL), EtOH (6.7 mL) and n-BuOH (6.7 mL) was stirred at 0° C. for 30 min. Isopentyl nitrite (3.01 g, 25.7 mmol, 3.46 mL, 1.2 equiv) and N-(6-oxo-7,8-dihydrocyclopenta[g][1,3]benzodioxol-5-yl)acetamide (2-24) (5.00 g, 21.4 mmol, 1.0 equiv) were added to the above solution at 0° C. The resulting mixture was stirred at 20° C. for 3 h. LCMS showed the formation of the desired product. The reaction mixture was quenched by 1.0 N hydrochloric acid (200 mL), and ethyl acetate (200 mL) was added. The resulting precipitation was collected by filtration. The filtrate was extracted with ethyl acetate (3×500 mL), the combined organic layers were washed with brine, dried over sodium sulfate, filtered and concentrated under reduced pressure. The resulting product was combined with the filter cake to give N-(7-hydroxyimino-6-oxo-8H-cyclopenta[g][1,3]benzodioxol-5-yl)acetamide (2-25) (5.6 g, 99% yield). $^1$H NMR (400 MHz, DMSO-$D_6$) δ ppm 12.71 (s, 1H), 10.53 (s, 1H), 7.89 (s, 1H), 6.19 (s, 2H), 3.63 (s, 2H), 2.17 (s, 3H). LCMS (ESI+) m/z: [MH]$^+$ calcd for $C_{12}H_{11}N_2O_5^+$: 263.1, found: 263.0.

N-(7-Amino-6-oxo-7,8-dihydrocyclopenta[g][1,3]benzodioxol-5-yl)acetamide hydrochloride (2-26)

To a mixture of N-(7-hydroxyimino-6-oxo-8H-cyclopenta[g][1,3]benzodioxol-5-yl)acetamide (2-25) (550 mg, 2.10 mmol, 1.0 equiv) and HCl (12 M, 0.26 mL, 1.5 equiv) in MeOH (50 mL) was added Pd/C (10 wt. %) (300 mg). The reaction mixture was purged with hydrogen gas three times, and stirred at 20° C. for 2 h under 15 psi of hydrogen atmosphere. LCMS indicated the reaction was completed. After the $H_2$ atmosphere was exchanged with nitrogen, the reaction mixture was filtered through a pad of Celite, and the filtrate was concentrated under reduced pressure to give N-(7-amino-6-oxo-7,8-dihydrocyclopenta[g] [1,3]benzodioxol-5-yl)acetamide hydrochloride (2-26) (500 mg, 83% yield). It was used in the next step without further purification. $^1$H NMR (400 MHz, DMSO-$D_6$) δ ppm 10.09 (br s, 1H), 9.05 (br s, 2H), 8.82 (br s, 2H), 7.85 (s, 1H), 6.23-6.70 (m, 2H), 3.98-4.39 (m, 2H), 3.35-3.48 (m, 1H), 2.16 (s, 3H). LCMS (ESI+) m/z: [MH]$^+$ calcd for $C_{12}H_{13}N_2O_4^+$: 249.1, found: 249.0.

N-(7-Acetamido-6-oxo-7,8-dihydrocyclopenta[g][1,3]benzodioxol-5-yl)acetamide (2-27)

To a solution of N-(7-amino-6-oxo-7,8-dihydrocyclopenta[g][1,3]benzodioxol-5-yl)acetamide hydrochloride (2-26) (4.50 g, 15.8 mmol, 1.0 equiv) in DCM (150 mL) was added TEA (4.80 g, 47.4 mmol, 6.60 mL, 3.0 equiv), acetic anhydride (1.94 g, 19.0 mmol, 1.78 mL, 1.2 equiv) at 20° C. and the mixture was stirred for 3 h. TLC (ethyl acetate, $R_f$=0.40) and LCMS indicated the reaction was completed. The mixture was diluted with DCM (500 mL) and washed with water (100 mL). The organic layer was dried over anhydrous $Na_2SO_4$, filtered and concentrated under reduced pressure. The residue was purified by column chromatography (eluting with petroleum ether/ethyl acetate=2/1 to 0/1, 5% THF) to give N-(7-acetamido-6-oxo-7,8-dihydrocyclopenta[g][1,3]benzodioxol-5-yl)acetamide (2-27) (2.55 g, 50% yield). $^1$H NMR (400 MHz, DMSO-$D_6$) δ ppm 10.35 (s, 1H), 8.53 (d, J=7.51 Hz, 1H), 7.87 (s, 1H), 6.13-6.19 (m, 2H), 4.30-4.37 (m, 1H), 3.17-3.32 (m, 1H), 2.79 (dd, J=16.75, 5.07 Hz, 1H), 2.14 (s, 3H), 1.85 (s, 3H). LCMS (ESI+) m/z: [MH]$^+$ calcd for $C_{14}H_{15}N_2O_5^+$: 291.1, found: 291.0.

N-(5-Amino-6-oxo-7,8-dihydrocyclopenta[g][1,3]benzodioxol-7-yl)acetamide (2-28)

To a solution of N-(7-acetamido-6-oxo-7,8-dihydrocyclopenta[g][1,3]benzodioxol-5-yl) acetamide (2-27) (2.55 g, 8.78 mmol, 1.0 equiv) in MeOH (110 mL) was added HCl/MeOH (4 M, 110 mL, 50 equiv) at 20° C. and the solution was stirred for 3 h. LCMS indicated the reaction was completed. The reaction mixture was concentrated under reduced pressure, the residue was dissolved in MeOH (10 mL) and pH was adjusted to 7 with saturated $NaHCO_3$, and then extracted with ethyl acetate (20 mL×3). The combined organic phases were dried over anhydrous $Na_2SO_4$, filtered and concentrated under reduced pressure to give N-(5-amino-6-oxo-7,8-dihydrocyclopenta[g][1,3] benzodioxol-7-yl)acetamide (2-28) (2.0 g, 91% yield). $^1$H NMR (400 MHz, DMSO-$D_6$) δ ppm 8.40 (d, J=7.89 Hz, 1H), 6.21 (s, 1H), 5.97 (d, J=15.79 Hz, 2H), 4.35 (td, J=8.17, 5.37 Hz, 1H), 3.20 (dt, J=16.55, 8.17 Hz, 1H), 2.62 (dd, J=16.66, 5.26 Hz, 1H), 1.84 (s, 3H). $^{13}$CNMR (100 MHz, DMSO-$D_6$): δ 199.6, 169.1, 154.3, 145.6, 133.4, 127.7, 111.3, 101.3, 93.5, 54.5, 28.7, 22.3. LCMS (ESI+) m/z: [MH]$^+$ calcd for $C_{12}H_{13}N_2O_4^+$: 249.1, found: 249.0.

N-[(7R)-5-Amino-6-oxo-7,8-dihydrocyclopenta[g][1,3] benzodioxol-7-yl]acetamide (2-29-P1) and N-[(7S)-5-amino-6-oxo-7,8-dihydrocyclopenta[g][1,3]benzodioxol-7-yl]acetamide (2-29-P2)

N-(5-Amino-6-oxo-7,8-dihydrocyclopenta[g][1,3] benzodioxol-7-yl)acetamide (2-28) (1.0 g) was dissolved in MeOH and separated by chiral SFC to afford N-[(7R)-5-amino-6-oxo-7,8-dihydrocyclopenta[g][1,3] benzodioxol-7-yl]acetamide (2-29-P1) (compound 22-9-P1 may be the opposite enantiomer of that depicted) (250 mg, 24% yield), and N-[(7S)-5-amino-6-oxo-7,8-dihydrocyclopenta[g][1,3]benzodioxol-7-yl]acetamide (2-29-P2) (compound 2-29-P2 may be the opposite enantiomer of that depicted) (250 mg, 24% yield).

SFC separation method: column (column: Phenomenex-Cellulose-2 (250 mm×30 mm, 10 um); mobile phase: [Neu-ETOH]; B %: 40%-40%, 5 min). Compounds (2-29-P1, RT=2.719 min) and (2-29-P2, RT=2.942 min) were separated by chiral SFC. Note: The stereochemistry is arbitrarily assigned for 2-29-P1 and 2-29-P2.

Spectra for 2-29-P1: $^1$H NMR (400 MHz, DMSO-$D_6$) δ ppm 8.30 (br d, J=7.95 Hz, 1H), 6.59 (s, 2H), 6.17 (s, 1H), 5.96 (d, J=15.89 Hz, 2H), 4.36 (td, J=8.16, 5.32 Hz, 1H), 3.16-3.25 (m, 1H), 2.61 (dd, J=16.69, 5.20 Hz, 1H), 1.84 (s, 3H). LCMS (ESI+) m/z: [MH]+ calcd for $C_{12}H_{13}N_2O_4^+$: 249.1, found: 248.9.

Spectra for 2-29-P2: $^1$H NMR (400 MHz, DMSO-D$_6$) δ ppm 8.30 (br d, J=7.95 Hz, 1H), 6.59 (s, 2H), 6.17 (s, 1H), 5.96 (d, J=15.89 Hz, 2H), 4.36 (td, J=8.19, 5.26 Hz, 1H), 3.21 (dd, J=16.69, 8.50 Hz, 1H), 2.61 (dd, J=16.69, 5.20 Hz, 1H), 1.85 (s, 3H). LCMS (ESI+) m/z: [MH]+ calcd for $C_{12}H_{13}N_2O_4^+$: 249.1, found: 248.9.

The mixture of N-[(7R)-5-amino-6-oxo-7,8-dihydrocyclopenta[g][1,3]benzodioxol-7-yl]acetamide (2-29-P1) (30 mg, 0.12 mmol), (S)-4-ethyl-4-hydroxy-7,8-dihydro-1H-pyrano[3,4-f]indolizine-3,6,10(4H)-trione (1-13) (63.6 mg, 0.24 mmol), TsOH (20.7 mg, 0.12 mmol) in xylene (2 mL) was heated at 140° C. for 12 h. All volatiles were removed under high vacuum, and the residue subjected to chromatography to afford 2-30. LCMS (ESI+) m/z: [MH]+ calcd for $C_{25}H_{22}N_3O_7$: 476.5, found: 476.4.

Example 3

Figure 14:
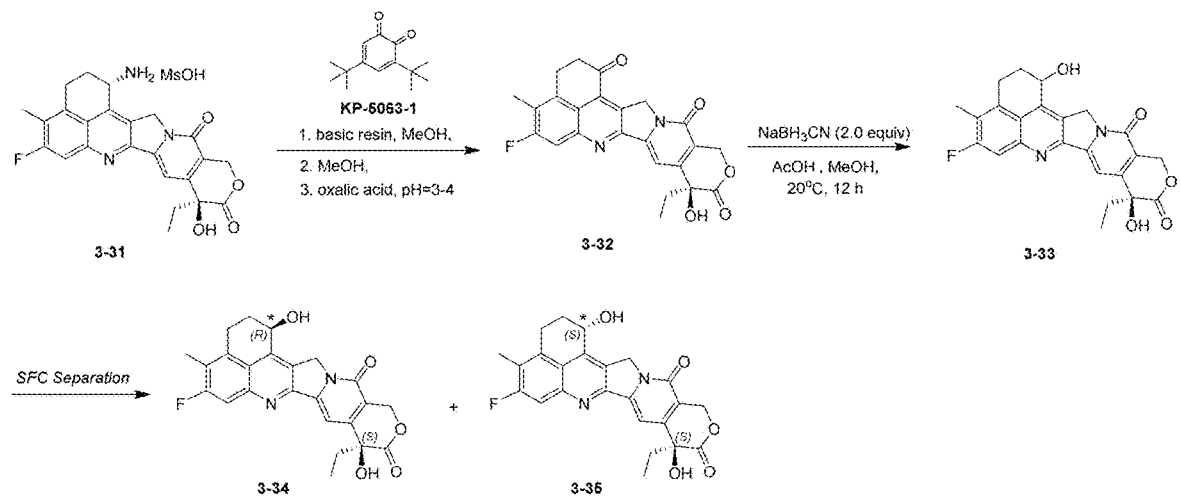
FIG. 14 illustrates a reaction scheme for making compounds 3-34 and 3-35.

(1R,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-34) and (1S,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-35)
(FIG. 14)

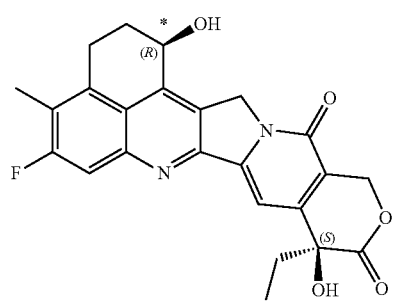

3-34

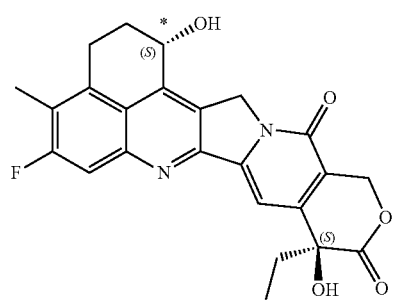

3-33

(stereochemistry at * carbon arbitrarily assigned)

(S)-9-ethyl-5-fluoro-9-hydroxy-4-methyl-2,3-dihydrobenzo[de] pyrano[3',4':6,7]indolizino[1,2-b]quinoline-1,10,13(9H,12H,15H)-trione (3-32)

To a solution of (1S,9S)-1-amino-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione methanesulfonate (100 mg, 0.230 mmol, 1 equiv) in methanol (20 mL) was added basic resin (300 mg) at 25° C. and the mixture was stirred for 30 min under ultrasonic wave. The mixture was filtered, and the filtrate was concentrated to give a free base.

To a solution of the above obtained free base in methanol (2 mL) was added 3,5-ditert-butyl-1,2-benzoquinone (101 mg, 0.459 mmol, 2 equiv). The reaction mixture was stirred at 60° C. for 10 min. The color of the reaction mixture turned from red to dark yellow. The reaction mixture was stirred at 25° C. for additional 3 h. TLC (ethyl acetate:methanol=8:1) indicated about 10% of unreacted starting material was remaining and a new spot was formed. The reaction mixture was quenched by the addition of oxalic acid (2 M in tetrahydrofuran/H$_2$O=3:1 solution, 0.5 mL) at 25° C. and the mixture was stirred for 3 h. The reaction mixture was diluted with tetrahydrofuran (5 mL), filtered and the filtrate was concentrated under reduced pressure. The residue was purified by preparative-HPLC (under HCl condition) to give (S)-9-ethyl-5-fluoro-9-hydroxy-4-methyl-2,3-dihydrobenzo[de]pyrano[3',4':6,7]indolizino[1,2-b]quinoline-1,10,13(9H,12H,15H)-trione (3-32) (70 mg, 25% yield). $^1$H NMR (400 MHz, DMSO-D$_6$) δ ppm 7.94 (d, J=10.6 Hz, 1H), 7.35 (s, 1H), 5.44 (s, 2H), 5.39 (s, 2H), 3.55-3.47 (m, 2H), 3.09 (t, J=7.0 Hz, 2H), 2.46 (s, 3H), 1.92-1.79 (m, 2H), 0.91-0.85 (m, 3H). LCMS (ESI) m/z: [M+H+] calcd for $C_{24}H_{20}FN_2O_5^+$: 435.1, found: 435.2.

Preparative-HPLC Method:
  Instrument: Gilson 281 semi-preparative HPLC system
  Mobile phase: A: HCl/H$_2$O=0.040% v/v; B: CH$_3$CN
  Column: Phenomenex Luna 80*30 mm*3 um
  Flow rate: 25 mL/min
  Monitor wavelength: 220 & 254 nm

| Time | B % |
| --- | --- |
| 0.0 | 30 |
| 8.0 | 60 |
| 8.1 | 60 |
| 8.2 | 100 |
| 10.2 | 100 |
| 10.3 | 30 |
| 11.5 | 30 |

(9S)-9-ethyl-5-fluoro-1,9-dihydroxy-4-methyl-2,3,12,15-tetrahydrobenzo[de]pyrano-[3',4':6,7]indolizino[1,2-b]quinoline-10,13(1H,9H)-dione (3-33)

To a solution of give (S)-9-ethyl-5-fluoro-9-hydroxy-4-methyl-2,3-dihydrobenzo[de] pyrano[3',4':6,7]indolizino[1,2-b]quinoline-1,10,13(9H,12H,15H)-trione (3-32) (70 mg, 0.16 mmol, 1.0 equiv) in methanol (2 mL) was added AcOH (27.6 mg, 0.460 mmol, 26.3 μL, 10 equiv) and NaBH$_3$CN (20.1 mg, 0.322 mmol, 2.0 equiv). The mixture was stirred at 0° C. for 10 min, and then at 20° C. for 12 h. TLC (ethyl acetate:methanol=8:1) indicated the starting material was consumed, and a new major spot was formed. The reaction mixture was quenched by H$_2$O (0.5 mL) at 25° C. and concentrated under reduced pressure. The residue was purified by preparative-HPLC to give (9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (33) (20 mg, 29% yield).

The chiral SFC separation of compound 3-33 afforded (1R,9S)-9-ethyl-5-fluoro-1,9-dihydroxy-4-methyl-1,2,3,9,12,15-hexahydro-10H,13H-benzo[de]pyrano[3',4':6,7]indolizino[1,2-b]quinoline-10,13-dione (3-34) (compound 3-34 may be the opposite diastereomer of that depicted) (2.9 mg, 4% yield) (Peak 1 in SFC at 1.429 min) and (1S,9S)-9-ethyl-5-fluoro-1,9-dihydroxy-4-methyl-1,2,3,9,12,15-hexahydro-10H,13H-benzo[de]pyrano[3',4':6,7]indolizino[1,2-b]quinoline-10,13-dione (3-35) (compound 3-35 may be the opposite diastereomer of that depicted) (4.7 mg, 7% yield) (Peak 2 in SFC at 1.534 min). Note: The stereochemistry is arbitrarily assigned.

Spectra of (1R,9S)-9-ethyl-5-fluoro-1,9-dihydroxy-4-methyl-1,2,3,9,12,15-hexahydro-10H,13H-benzo[de]pyrano[3',4':6,7]indolizino[1,2-b]quinoline-10,13-dione (3-34): $^1$H NMR (400 MHz, DMSO-D$_6$) δ ppm 7.73 (dd, J=10.8, 1.8 Hz, 7.31 (s, 1H), 6.50 (s, 1H), 5.97 (d, J=16.0 Hz, 1H), 5.42 (s, 2H), 5.41 (d, J=19.2 Hz, 1H), 5.28 (d, J=18.6 Hz, 1H), 5.12-5.17 (m, 1H), 3.20-3.26 (m, 1H), 2.98-3.05 (m, 1H), 2.31-2.35 (m, 1H), 2.33 (s, 3H), 1.95-2.00 (m, 1H), 1.84-1.90 (m, 2H), 0.88 (t, J=7.2 Hz, 3H). $^{19}$F NMR (400 MHz, DMSO-D$_6$): δ ppm −111.8 (s, 1F). LCMS (ESI) m/z: [MH$^+$] calcd for $C_{24}H_{22}FN_2O_5^+$: 437.1, found: 437.1.

Spectra of (1S,9S)-9-ethyl-5-fluoro-1,9-dihydroxy-4-methyl-1,2,3,9,12,15-hexahydro-10H,13H-benzo[de]pyrano[3',4':6,7]indolizino[1,2-b]quinoline-10,13-dione (3-35): $^1$H NMR (400 MHz, DMSO-D$_6$) δ ppm 7.73 (dd, J=10.8, 1.8 Hz, 7.31 (s, 1H), 6.50 (s, 1H), 5.97 (d, J=16.0 Hz, 1H), 5.42 (s, 2H), 5.41 (d, J=19.2 Hz, 1H), 5.28 (d, J=18.6 Hz, 1H), 5.12-5.17 (m, 1H), 3.20-3.26 (m, 1H), 2.98-3.05 (m, 1H), 2.31-2.35 (m, 1H), 2.33 (s, 3H), 1.95-2.00 (m, 1H), 1.84-1.90 (m, 2H), 0.88 (t, J=7.2 Hz, 3H). $^{19}$F NMR (400 MHz, DMSO-D$_6$): δ ppm −111.8 (s, 1F). LCMS (ESI) m/z: [MH$^+$] calcd for $C_{24}H_{22}FN_2O_5^+$: 437.1, found: 437.1.

Preparative-HPLC Method:
  Instrument: Gilson 281 semi-preparative HPLC system
  Mobile phase: A: HCl/H$_2$O=0.040% v/v; B: CH$_3$CN
  Column: Phenomenex Luna 80*30 mm*3 um
  Flow rate: 25 mL/min
  Monitor wavelength: 220 & 254 nm

| Time | B % |
|---|---|
| 0.0 | 20 |
| 8.0 | 50 |
| 8.1 | 50 |
| 8.2 | 100 |
| 10.2 | 100 |
| 10.3 | 20 |
| 11.5 | 20 |

SFC Separation Method:
  Instrument: Waters SFC150AP preparative SFC
  Column: DAICEL CHIRALCEL OD (250 mm*30 mm, 10 um)
  Mobile phase: A for CO2 and B for EtOH
  Gradient: B %=45% isocratic elution mode
  Flow rate: 70 g/min
  Wavelength: 220 nm
  Column temperature: 35 degrees centigrade
  System back pressure: 120 bar Example 4

Figure 15:
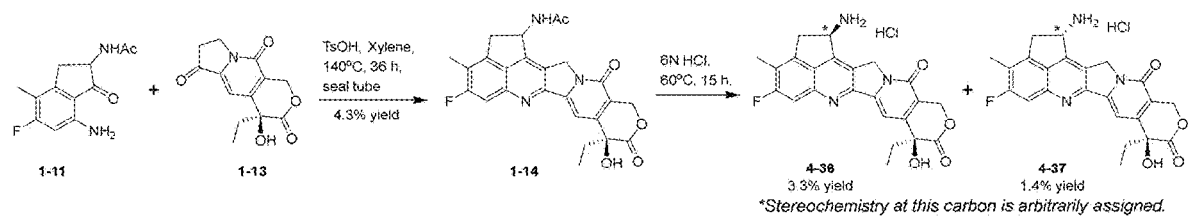
FIG. 15 illustrates a reaction scheme for making compounds 4-36 and 4-37.

(1R,8S)-1-amino-8-ethyl-4-fluoro-8-hydroxy-3-methyl-11,14-dihydro-1H-cyclopenta[de]pyrano[3',4':6,7]indolizino[1,2-b]quinoline-9,12(2H,8H)-dione hydrochloride (4-36) and (1S,8S)-1-amino-8-ethyl-4-fluoro-8-hydroxy-3-methyl-11,14-dihydro-1H-cyclopenta[de]pyrano[3',4':6,7]indolizino[1,2-b]quinoline-9,12(2H,8H)-dione hydrochloride (4-37) (FIG. 15)

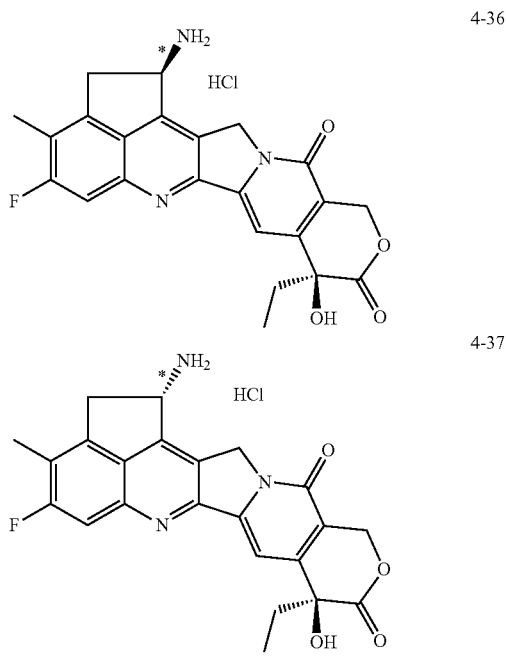

*Stereochemistry at this carbon is arbitrarily assigned.

N-((8S)-8-Ethyl-4-fluoro-8-hydroxy-3-methyl-9,12-dioxo-2,8,9,11,12,14-hexahydro-1H-cyclopenta[de]pyrano[3',4':6,7]indolizino[1,2-b]quinolin-1-yl)acetamide (1-14)

To a mixture of N-(7-amino-5-fluoro-4-methyl-1-oxo-2,3-dihydro-1H-inden-2-yl)acetamide (100 mg, 0.423 mmol, 1.0 equiv) (1-11) and (S)-4-ethyl-4-hydroxy-7,8-dihydro-1H-pyrano[3,4-f]indolizine-3,6,10(4H)-trione (1-13) (223 mg, 0.847 mmol, 2.0 equiv) in xylene (10 mL) at 140° C., was added 4-methylbenzenesulfonic acid (29.1 mg, 0.169 mmol, 0.4 equiv), and the mixture was stirred at 140° C. for 36 h in a 40 mL seal tube. It was cooled to room temperature and concentrated under reduced pressure, and the residue purified by column chromatography on silica gel eluting with 9% of MeOH in dichloromethane to give N-((8S)-8-ethyl-4-fluoro-8-hydroxy-3-methyl-9,12-dioxo-2,8,9,11,12,14-hexahydro-1H-cyclopenta[de]pyrano[3',4':6,7]indolizino[1,2-b]quinolin-1-yl)acetamide (1-14) (8.50 mg, 4.3% yield). $^1$H NMR (400 MHz, DMSO-D$_6$) δ ppm 8.65 (d, J=8.11 Hz, 1H), 7.72 (d, J=11.56 Hz, 1H), 7.34 (s, 1H), 6.51 (d, J=2.27 Hz, 1H), 5.95 (br d, J=5.01 Hz, 1H), 5.43 (s, 2H), 5.09-5.13 (m, 2H), 3.82-3.93 (m, 1H), 3.30 (br s, 1H), 2.38 (s, 3H), 1.94 (d, J=2.86 Hz, 3H), 1.87 (br d, J=7.39 Hz, 2H), 0.87 (br d, J=4.41 Hz, 3H). LCMS (ESI+) m/z: [MH]$^+$ calcd for $C_{25}H_{23}FN_3O_5{}^+$: 464.1, found: 464.2.

(1R,8S)-1-amino-8-ethyl-4-fluoro-8-hydroxy-3-methyl-11,14-dihydro-1H-cyclopenta[de]-pyrano[3',4':6,7]indolizino[1,2-b]quinoline-9,12(2H,8H)-dione hydrochloride (4-36) and (1S,8S)-1-amino-8-ethyl-4-fluoro-8-hydroxy-3-methyl-11,14-dihydro-1H-cyclopenta[de]pyrano[3',4':6,7]indolizino[1,2-b]quinoline-9,12(2H,8H)-dione hydrochloride (4-37)

A solution of N-((8S)-8-ethyl-4-fluoro-8-hydroxy-3-methyl-9,12-dioxo-2,8,9,11,12,14-hexahydro-1H-cyclopenta[de]pyrano[3',4':6,7]indolizino[1,2-b]quinolin-1-yl)acetamide (1-14) (150 mg, 0.323 mmol, 1.0 equiv) in 6 N aqueous HCl solution (15 mL) was stirred at 60° C. for 15 h in a sealed tube. After cooled down to 25° C., the reaction mixture was concentrated under reduced pressure, the residue diluted with methanol (5 mL) and purified by prep-HPLC to give (1R,8S)-1-amino-8-ethyl-4-fluoro-8-hydroxy-3-methyl-11,14-dihydro-1H-cyclopenta[de]-pyrano[3',4':6,7]indolizino[1,2-b]quinoline-9,12(2H,8H)-dione hydrochloride (4-36) (5.0 mg, 3.3% yield) (compound 4-36 may be the opposite enantiomer of that depicted) and (1S,8S)-1-amino-8-ethyl-4-fluoro-8-hydroxy-3-methyl-11,14-dihydro-1H-cyclopenta[de]pyrano[3',4':6,7]indolizino[1,2-b]quinoline-9,12(2H,8H)-dione hydrochloride (4-37) (3.0 mg, 1.4% yield) (compound 4-37 may be the opposite enantiomer of that depicted). Note: the stereochemistry is arbitrarily assigned.

Prep-HPLC Method:
Instrument: Gilson 281 semi-preparative HPLC system
Mobile phase: A: HCl/H$_2$O=0.040% v/v; B: CH$_3$CN
Column: Phenomenex luna C18 80*40 mm*3 um
Flow rate: 40 mL/min
Monitor wavelength: 220 & 254 nm

| Time | B % |
|---|---|
| 0.0 | 13 |
| 7.0 | 38 |
| 7.1 | 38 |
| 7.2 | 100 |
| 9.2 | 100 |
| 9.3 | 13 |
| 10.5 | 13 |

Spectra of 4-36: $^1$H NMR (400 MHz, D$_2$O) δ ppm 7.33-7.40 (m, 2H), 5.65 (br d, J=5.72 Hz, 1H), 5.44-5.52 (m, 1H), 5.33 (br d, J=17.17 Hz, 2H), 5.18-5.26 (m, 1H), 4.00 (br dd, J=18.06, 7.81 Hz, 1H), 3.45 (br d, J=18.84 Hz, 1H), 2.30 (s, 3H), 1.90 (q, J=7.27 Hz, 2H), 0.87 (t, J=7.27 Hz, 3H). $^{19}$F NMR (376 MHz, D$_2$O) δ ppm −106.41. LCMS (ESI+) m/z: [MH]$^+$ calcd for $C_{23}H_{21}FN_3O_4{}^+$: 422.1, found: 422.0. SFC (RT=1.208 min).

Spectra of 4-37: $^1$H NMR (400 MHz, D$_2$O) δ ppm 7.43 (s, 1H), 7.24 (br d, J=11.26 Hz, 1H), 5.58 (br dd, J=8.00, 3.25 Hz, 1H), 5.54 (d, J=16.26 Hz, 1H), 5.37-5.45 (m, 2H), 5.22 (br d, J=19.01 Hz, 1H), 4.05 (br dd, J=18.01, 8.13 Hz, 1H), 3.52-3.61 (m, 1H), 2.36 (s, 3H), 1.95 (q, J=7.30 Hz, 2H), 0.93 (t, J=7.38 Hz, 3H). $^{19}$F NMR (376 MHz, D$_2$O) δ ppm −106.53. LCMS (ESI+) m/z: [MH]$^+$ calcd for $C_{23}H_{21}FN_3O_4{}^+$: 422.1, found: 422.0. SFC (RT=1.252 min).

Example 5

Figure 16:
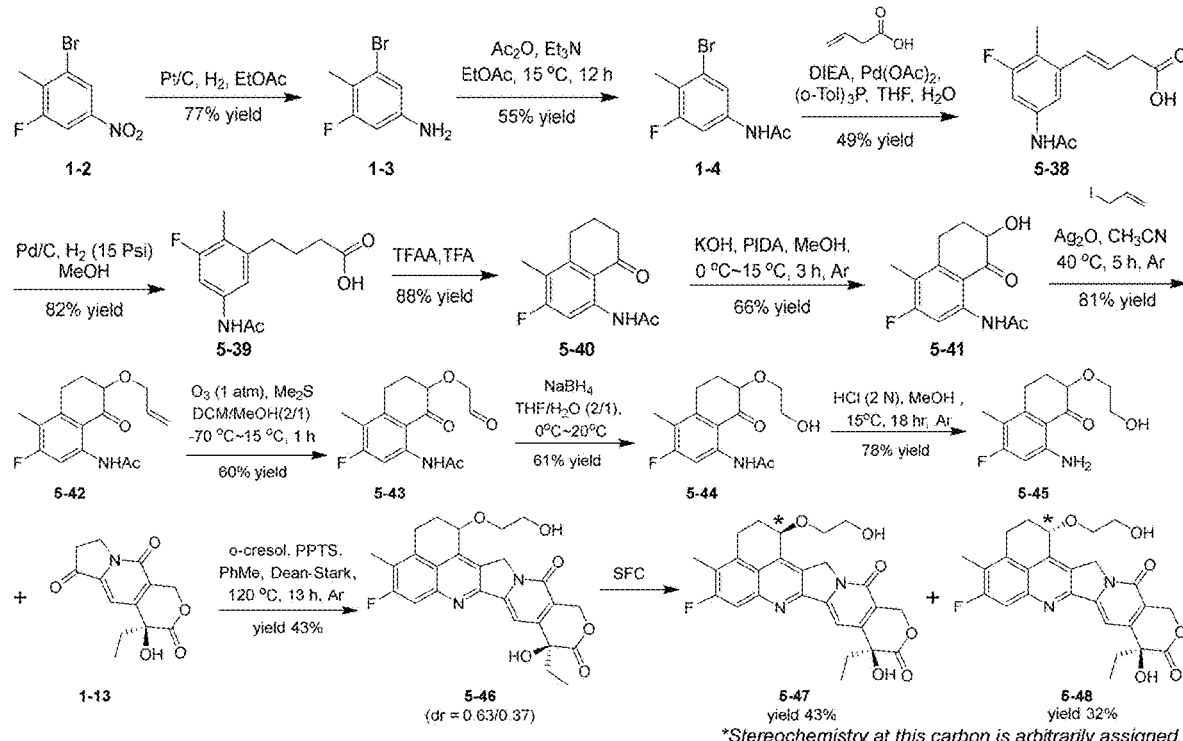
FIG. 16 illustrates a reaction scheme for making compounds 5-47 and 5-48.

Synthesis of (1R,9S)-9-ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-47) and (1S,9S)-9-ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-48) (FIG. 16)

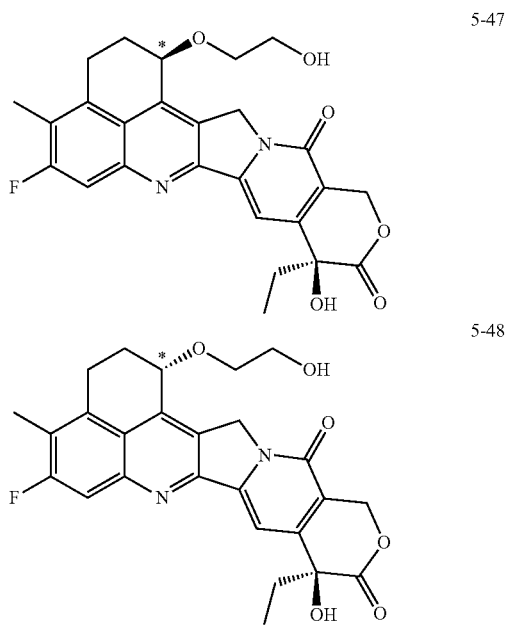

*Stereochemistry at this carbon is arbitrarily assigned.

3-Bromo-5-fluoro-4-methyl-aniline (1-3)

To a solution of 1-bromo-3-fluoro-2-methyl-5-nitro-benzene (1-2) (100 g, 427 mmol, 1.0 equiv) in ethyl acetate (1.50 L) was added Pt/C (10 wt %, 10.0 g) under argon atmosphere. After the resulting suspension was degassed under vacuum and purged with H$_2$ three times, it was stirred under H$_2$ (15 psi) at 60° C. for 4 h. Then, the H$_2$ atmosphere was exchanged with argon, the combined reaction mixtures were filtered through a pad of celite, and the filter cake washed with ethyl acetate (10.0 L). (Eighteen additional reactions were set up as described above and all nineteen reaction mixtures were combined). The combined filtrates were concentrated under reduced pressure to give 3-bromo-5-fluoro-4-methyl-aniline (1-3) (1.8 kg, purity 71%, 77% yield). $^1$H NMR (400 MHz, DMSO-d$_6$) δ ppm 6.79 (s, 1H), 6.50 (dd, J=11.74, 2.08 Hz, 1H), 2.10 (d, J=2.08 Hz, 3H). $^{19}$F NMR (376 MHz, CD$_3$OD) δ=−112.13. LCMS (ESI+) m/z: [MH]$^+$ calcd for $C_7H_8BrFN^+$: 205.0, found: 205.8.

N-(3-Bromo-5-fluoro-4-methyl-phenyl)acetamide (1-4)

To a solution of 3-bromo-5-fluoro-4-methyl-aniline (1-3) (300 g, 1.47 mol, 1.0 equiv) in ethyl acetate (4.50 L) was added triethylamine (420 mL, 3.02 mol, 2.1 equiv) and acetic anhydride (179 mL, 1.91 mol, 1.3 equiv), and the mixture was stirred at 15° C. for 12 h. (Five additional vials were set up as described above and all six reaction mixtures were combined). The combined mixtures were quenched with saturated NH$_4$Cl solution (15.0 L) and extracted with ethyl acetate (3×5.0 L). The combined organic layers were washed with brine (8.0 L), dried over Na$_2$SO$_4$, concentrated, the residue dissolved in dichloromethane (2.00 L) and purified by column chromatography on silica gel eluting with 15% of ethyl acetate in petroleum ether to give N-(3-bromo-5-fluoro-4-methyl-phenyl)acetamide (1-4) (1.2 kg, 55% yield). $^1$H NMR (400 MHz, CD$_3$OD) δ=7.59 (t, J=1.5 Hz, 1H), 7.41 (dd, J=2.0, 11.6 Hz, 1H), 2.26 (d, J=2.2 Hz, 3H), 2.11 (s, 3H). $^{19}$F NMR (376 MHz, CD$_3$OD) δ=−112.95. LCMS (ESI+) m/z: [MH]$^+$ calcd for C$_9$H$_{10}$BrFNO$^+$: 247.0, found: 247.8.

(E)-4-(5-Acetamido-3-fluoro-2-methyl-phenyl)but-3-enoic acid (5-38)

To a mixture of N-(3-bromo-5-fluoro-4-methyl-phenyl)acetamide (1-4) (200 g, 813 mmol, 1.0 equiv) in tetrahydrofuran (1.00 L) and water (200 mL) were added diisopropylethyl amine (566 mL, 3.25 mol, 4.0 equiv), tris-o-tolylphosphane (49.5 g, 163 mmol, 0.20 equiv), but-3-enoic acid (168 g, 1.95 mol, 2.4 equiv) and Pd(OAc)$_2$ (18.2 g, 81.3 mmol, 0.10 equiv) under N$_2$, and the reaction mixture was stirred at 75° C. for 16 h. (Five additional reactions were set up as described above and all six reaction mixtures were combined). The combined reaction mixtures were diluted with water (2.0 L), adjusted to pH=2 by addition of 3 N HCl, the mixture filtered through a pad of Celite, and the filtrate cake washed with ethyl acetate (4.0 L). The mixture was extracted with water (4.0 L), the aqueous phase was extracted with ethyl acetate (3×1.80 L). The combined organic layers were washed with brine (4.0 L), dried over anhydrous Na$_2$SO$_4$, filtered, concentrated, and the residue purified by column chromatography on silica gel eluting with 70% ethyl acetate in petroleum ether to give (E)-4-(5-acetamido-3-fluoro-2-methyl-phenyl)but-3-enoic acid (5-38) (400 g, 49% yield). $^1$H NMR (400 MHz, DMSO-d$_6$) δ=12.32 (br s, 1H), 10.02 (s, 1H), 7.48 (ddd, J=1.6, 8.3, 12.0 Hz, 1H), 7.39 (s, 1H), 7.08-6.98 (m, 1H), 6.94-6.83 (m, 1H), 6.75-6.50 (m, 1H), 6.13 (td, J=7.2, 15.7 Hz, 1H), 5.69 (d, J=15.5 Hz, 1H), 3.59 (ddd, J=2.5, 4.1, 6.5 Hz, 1H), 3.56-3.46 (m, 1H), 3.31-3.21 (m, 1H), 2.16-2.06 (m, 3H), 2.05-1.99 (m, 3 H). $^{19}$F NMR (376 MHz, DMSO-d$_6$) δ=−115.3. LCMS (ESI+) m/z: [MH]$^+$ calcd for C$_{13}$H$_{15}$FNO$_3^+$: 252.1, found: 252.0.

4-(5-Acetamido-3-fluoro-2-methyl-phenyl)butanoic acid (5-39)

To a solution of (E)-4-(5-acetamido-3-fluoro-2-methyl-phenyl)but-3-enoic acid (5-38) (100 g, 398 mmol, 1.0 equiv) in methanol (1.50 L) was added Pd/C (30.0 g, 39.8 mmol, 10 wt %, 0.10 equiv) under argon atmosphere. The resulting suspension was degassed under vacuum and purged with H$_2$ three times and stirred under H$_2$ (15 psi) at 35° C. for 12 h. (Three additional reactions were set up as described above and all four reaction mixtures were combined). After the H$_2$ atmosphere was replaced with argon, the combined mixtures filtered through a pad of celite, and the filter cake washed with methanol (8 L). The combined filtrates were concentrated under reduced pressure to give 4-(5-acetamido-3-fluoro-2-methyl-phenyl)butanoic acid (5-39) (330 g, 82% yield), which was used directly in next step without purification. $^1$H NMR (400 MHz, DMSO-d$_6$) δ=12.77-11.04 (m, 1H), 9.98 (s, 1H), 7.42 (dd, J=1.7, 12.2 Hz, 1H), 7.04 (s, 1H), 2.59-2.53 (m, 2H), 2.27 (t, J=7.2 Hz, 2H), 2.09 (d, J=1.8 Hz, 3H), 2.01 (s, 3H), 1.71 (quin, J=7.5 Hz, 2H). $^{19}$F NMR (376 MHz, DMSO-d$_6$) δ=−115.64. LCMS (ESI+) m/z: [MH]$^+$ calcd for C$_{13}$H$_{17}$FNO$_3^+$: 254.1, found: 254.0.

N-(7-Fluoro-8-methyl-4-oxo-tetralin-5-yl)acetamide (5-40)

To a solution of 4-(5-acetamido-3-fluoro-2-methyl-phenyl)butanoic acid (5-39) (110 g, 434 mmol, 1.0 equiv) in trifluoroacetic acid (330 mL) was added trifluoroacetic anhydride (121 mL, 869 mmol, 2.0 equiv) at 0° C. under N$_2$, and the mixture stirred at 15° C. for 15 h. (Two additional reactions were set up as described above and all three reaction mixtures were combined). The combined reaction mixtures were poured into 50% acetonitrile aqueous solution (6.0 L) at 0° C. and stirred at 0° C. for 0.5 h. The resulting suspension was adjusted to pH=7 with 25% NaOH aqueous solution at 0° C. The mixture was filtered, and the reside washed with water (1.00 L), methyl tert-butyl ester (2.00 L) and then dried under high vacuum. This residue was triturated with methyl methyl tert-butyl ester (600 mL) and filtered to give N-(7-fluoro-8-methyl-4-oxo-tetralin-5-yl)acetamide (5-40) (300 g, 88% yield). $^1$H NMR (400 MHz, DMSO-d$_6$) δ=12.18 (s, 1H), 8.28 (d, J=13.2 Hz, 1H), 2.89 (t, J=6.1 Hz, 2H), 2.68-2.60 (m, 2H), 2.18-2.08 (m, 6H), 1.99 (quin, J=6.4 Hz, 2H). $^{19}$F NMR (376 MHz, DMSO-d$_6$) δ=−103.89. LCMS (ESI+) m/z: [MH]$^+$ calcd for C$_{13}$H$_{15}$FNO$_2^+$: 236.1, found: 236.0.

N-(7-Fluoro-3-hydroxy-8-methyl-4-oxo-tetralin-5-yl)acetamide (5-41)

To a solution of N-(7-fluoro-8-methyl-4-oxo-tetralin-5-yl)acetamide (5-40) (75.0 g, 319 mmol, 1.0 equiv) in methanol (1.20 L) was added a solution of KOH (53.7 g, 956 mmol, 3 equiv) in methanol (600 mL) and (diacetoxyiodo)benzene (113 g, 351 mmol, 1.1 equiv) at 0° C. under argon, and the mixture stirred at 15° C. for 3 h. (Three additional reactions were set up as described above and all four reaction mixtures were combined). The combined mixtures were adjusted to pH~4 by addition of 1 N HCl, concentrated to remove most of methanol at 35° C., and the mixture extracted with dichloromethane (3×1.0 L). The combined organic layers were washed with brine, dried over Na$_2$SO$_4$, filtered, and the residue purified by silica gel chromatography (petroleum ether/ethyl acetate=5/1 to 4/1) to give N-(7-fluoro-3-hydroxy-8-methyl-4-oxo-tetralin-5-yl)acetamide (5-41) (210 g, 66% yield). $^1$H NMR (400 MHz, DMSO-d$_6$) δ=11.92 (s, 1H), 8.26 (d, J=13.1 Hz, 1H), 5.90-4.94 (m, 1H), 4.28 (dd, J=5.0, 12.7 Hz, 1H), 3.07-2.97 (m, 1H), 2.96-2.84 (m, 1H), 2.29-2.20 (m, 1H), 2.16 (s, 3H), 2.10 (d, J=1.2 Hz, 3H), 1.95-1.82 (m, 1H). $^{19}$F NMR (377 MHz, DMSO-d$_6$) δ=−104.3. LCMS (ESI+) m/z: [MH]$^+$ calcd for C$_{13}$H$_{15}$FNO$_3^+$: 252.1, found: 252.0.

N-(3-Allyloxy-7-fluoro-8-methyl-4-oxo-tetralin-5-yl)acetamide (5-42)

To a solution of N-(7-fluoro-3-hydroxy-8-methyl-4-oxo-tetralin-5-yl)acetamide (5-41) (70.0 g, 279 mmol, 1.0 equiv) in acetonitrile (1.40 L) was added Ag$_2$O (129 g, 557 mmol, 2.0 equiv) and a solution of 3-iodoprop-1-ene (140 g, 836 mmol, 76.3 mL, 3.0 equiv) in acetonitrile (280 mL) at 15° C., and the mixture stirred at 40° C. for 5 h. (Two additional reactions were set up as described above and all three reaction mixtures were combined). The combined mixtures were filtered through a pad of Celite, and the filter cake washed with dichloromethane (5.00 L). The combined filtrates were concentrated, and the residue purified by silica gel chromatography (petroleum ether/ethyl acetate=9/1-4/1) to give a material. This material was triturated with methyl tert-butyl ester (500 mL) and filtered to afford N-(3-allyloxy-7-fluoro-8-methyl-4-oxo-tetralin-5-yl)acetamide (5-42) (198 g, 81% yield). $^1$H NMR (400 MHz, DMSO-d$_6$) δ=11.81 (s, 1H), 8.27 (d, J=13.1 Hz, 1H), 5.93 (tdd, J=5.3, 10.5, 17.2 Hz, 1H), 5.29 (qd, J=1.8, 17.2 Hz, 1H), 5.16 (dd, J=1.7, 10.5 Hz, 1H), 4.32-4.06 (m, 3H), 3.12-2.83 (m, 2H), 2.32-2.23 (m, 1H), 2.17 (s, 3H), 2.11 (d, J=1.5 Hz, 3H), 2.09-1.98 (m, 1H). $^{19}$F NMR (376 MHz, DMSO-d$_6$) δ=−104.2. LCMS (ESI+) m/z: [MH]$^+$ calcd for $C_{16}H_{19}FNO_3^+$: 292.1, found: 291.9.

N-[7-Fluoro-8-methyl-4-oxo-3-(2-oxoethoxy)tetralin-5-yl]acetamide (5-43)

A mixture of N-(3-allyloxy-7-fluoro-8-methyl-4-oxo-tetralin-5-yl)acetamide (5-42) (42.0 g, 144 mmol, 1.0 equiv) in dichloromethane (840 mL) and methanol (420 mL) was cooled down to −70° C., ozone (6.92 g, 144 mmol, 1.0 equiv) was bubbled into the mixture for 60 min, followed by bubbled with O$_2$ for 30 min. Then, methylsulfanylmethane (26.5 mL, 360 mmol, 2.5 equiv) was added to the mixture at −70° C. and it was warmed up to 15° C. and stirred at 15° C. for 1 h. (Three additional reactions were set up as described above and all four reaction mixtures were combined). The combined reaction mixtures were quenched with water (5.0 L) and extracted with dichloromethane (3×1.0 L). The combined organic layers were washed with brine, dried over Na$_2$SO$_4$, filtered and concentrated to give N-[7-fluoro-8-methyl-4-oxo-3-(2-oxoethoxy)tetralin-5-yl]acetamide (5-43) (168 g, 59% yield), which was used directly for the next step without further purification. $^1$H NMR (400 MHz, CDCl$_3$) δ=11.94 (br s, 1H), 9.80 (s, 1H), 8.44 (d, J=12.7 Hz, 1H), 4.55-4.30 (m, 1H), 3.85-3.69 (m, 2H), 3.51-3.48 (m, 1H), 3.18-3.03 (m, 1H), 2.96-2.78 (m, 1H), 2.52-2.34 (m, 1H), 2.26-2.21 (m, 3H), 2.14 (br dd, J=1.7, 3.9 Hz, 3H). $^{19}$F NMR (376 MHz, CDCl$_3$) δ=−100.7. LCMS (ESI+) m/z: [MH]$^+$ calcd for $C_{15}H_{17}FNO_4^+$: 294.1, found: 293.9.

N-[7-Fluoro-3-(2-hydroxyethoxy)-8-methyl-4-oxo-tetralin-5-yl]acetamide (5-44)

To a solution of N-[7-fluoro-8-methyl-4-oxo-3-(2-oxoethoxy)tetralin-5-yl]acetamide (5-43) (42 g, 85.9 mmol, 60% purity, 1.0 equiv) in THF (850 mL) and H$_2$O (425 mL) was added NaBH$_4$ (975 mg, 25.8 mmol, 0.30 equiv) portion wise at 0° C., the mixture was stirred at 0° C. for 10 min, and quenched with cold water (2.0 L). (Three additional reactions were set up as described above and all four reaction mixtures were combined). The combined reaction mixtures were extracted with dichloromethane (3×1.0 L), organic layers washed with brine, dried over Na$_2$SO$_4$, filtered, concentrated and the residue purified by silica gel chromatography (petroleum ether/ethyl acetate=1/1-1/3) to give N-[7-fluoro-3-(2-hydroxyethoxy)-8-methyl-4-oxo-tetralin-5-yl]acetamide (5-44) (70 g, 61% yield). $^1$H NMR (400 MHz, CDCl$_3$) δ=11.96 (br s, 1H), 8.45 (d, J=12.7 Hz, 1H), 4.06 (dd, J=12.0 Hz, 1H), 4.01-3.62 (m, 4H), 3.11 (td, J=4.6, 17.6 Hz, 1H), 3.03-2.79 (m, 2H), 2.45-2.36 (m, 1H), 2.24 (s, 3H), 2.15 (d, J=1.5 Hz, 4H). $^{19}$F NMR (376 MHz, CDCl$_3$) δ=−100.9. LCMS (ESI+) m/z: [MH]$^+$ calcd for $C_{15}H_{19}FNO_4^+$: 296.1, found: 296.1.

8-Amino-6-fluoro-2-(2-hydroxyethoxy)-5-methyl-tetralin-1-one (5-45)

To a solution of N-[7-fluoro-3-(2-hydroxyethoxy)-8-methyl-4-oxo-tetralin-5-yl]acetamide (5-44) (21.0 g, 71.0 mmol, 1.0 equiv) in methanol (400 mL) was added HCl (2 N, 630 mL, 18 equiv) under argon, the mixture was stirred at 15° C. for 18 h and adjusted to pH=7-8 by addition of saturated NaHCO$_3$. (Three additional reactions were set up as described above and all four reaction mixtures were combined). The combined reaction mixtures were extracted with ethyl acetate (3×2.0 L), organic layers washed with brine, dried over Na$_2$SO$_4$, filtered and concentrated. The residue was triturated with methyl tert-butyl ester/dichloromethane (1:2, 300 mL) and filtered to give 8-amino-6-fluoro-2-(2-hydroxyethoxy)-5-methyl-tetralin-1-one (5-45) (42 g, 81% yield). $^1$H NMR (400 MHz, CD$_3$OD) δ=6.30 (d, J=12.3 Hz, 1H), 4.06 (dd, J=4.4, 11.2 Hz, 1H), 3.83-3.67 (m, 4H), 3.04 (td, J=4.9, 17.5 Hz, 1H), 2.85-2.73 (m, 1H), 2.40-2.30 (m, 1H), 2.09-1.93 (m, 4H). $^{19}$F NMR (376 MHz, CD$_3$OD) δ=−108.7. LCMS (ESI+) m/z: [MH]$^+$ calcd for $C_{13}H_{17}FNO_3^+$: 254.1, found: 254.1.

(9S)-9-Ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13 (1H,9H)-dione (5-46)

To a mixture of 8-amino-6-fluoro-2-(2-hydroxyethoxy)-5-methyl-3,4-dihydronaphthalen-1(2H)-one (5-45) (10.5 g, 41.4 mmol, 1.0 equiv) and (S)-4-ethyl-4-hydroxy-7,8-dihydro-1H-pyrano[3,4-f]indolizine-3,6,10(4H)-trione (1-13) (12.0 g, 45.6 mmol, 1.1 equiv) in toluene (525 mL) was added o-cresol (31.5 mL, 303 mmol, 7.3 equiv) and pyridin-1-ium 4-methylbenzenesulfonate (1.56 g, 6.23 mmol, 0.15 equiv) at 120° C. under argon, and the mixture was stirred at 120° C. for 13 h. (Three additional reactions were set up as described above and four reaction mixtures were combined). The combined reaction mixtures were concentrated under reduced pressure, and the residue purified by column chromatography on silica gel, eluting with 13% of methanol in ethyl acetate to give (9S)-9-ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-46) (34.2 g, 43% yield). $^1$H NMR (400 MHz, DMSO-D$_6$) δ ppm 7.58 (dd, J=10.8, 1.91 Hz, 1H), 7.23 (d, J=6.8 Hz, 1H), 6.49 (s, 1H), 5.40 (s, 2H), 4.95-5.24 (m, 2H), 4.88 (dt, J=8.4, 4.4 Hz, 1H), 4.69-4.81 (m, 1H), 3.78-3.91 (m, 1H), 3.56-3.76 (m, 3H), 3.10 (d, J=16.4 Hz, 1H), 2.77-2.92 (m, 1H), 2.33-2.45 (m, 1H), 2.21 (s, 3H), 1.83-2.04 (m, 3H), 0.77-1.00 (m, 3H). $^{19}$F NMR (376 MHz, DMSO-D$_6$) δ ppm −111.57. LCMS (ESI+) m/z: [M+H]$^+$ calcd for $C_{26}H_{26}FN_2O_6^+$: 481.2, found: 481.0.

(1R,9S)-9-Ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13 (1H,9H)-dione (5-47) and (1S,9S)-9-Ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-48)

(9S)-9-ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-46) (31.0 g, 64.3 mmol, 1.0 equiv) was separated by chiral SFC (Instrument: Waters SFC350 preparative SFC; Column: DAICEL CHIRALCEL OD (250 mm*50 mm, 10 um); Mobile phase: A for CO₂ and B for MeOH; Gradient: B %=60% isocratic elution mode; Flow rate: 200 g/min; Wavelength: 220 nm; Column temperature: 40 degrees centigrade; System back pressure: 100 bar) to afford (1R, 9S)-9-Ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-47) (13.5 g, 43% yield) (compound 5-47 may be the opposite enantiomer of that depicted) and (1S,9S)-9-Ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-48) (10.0 g, 32% yield) (compound 5-48 may be the opposite enantiomer of that depicted). Note: the stereochemistry is arbitrarily assigned.

Spectra of 5-47: ¹H NMR (400 MHz, DMSO-D₆) δ ppm 7.64 (d, J=10.88 Hz, 1H), 7.25 (s, 1H), 6.50 (s, 1H), 5.13-5.52 (m, 4H), 4.95 (br dd, J=8.25, 3.75 Hz, 1H), 4.74 (br t, J=5.00 Hz, 1H), 3.84 (dt, J=9.72, 4.96 Hz, 1H), 3.59-3.76 (m, 3H), 3.10-3.21 (m, 1H), 2.84-2.99 (m, 1H), 2.23-2.46 (m, 4H), 2.04 (m, 1H), 1.87 (m, 2H), 0.88 (t, J=7.32 Hz, 3H). ¹⁹F NMR (376 MHz, DMSO-D₆) δ ppm −111.59. LCMS (ESI+) m/z: [M+H]⁺ calcd for $C_{26}H_{26}FN_2O_6^+$: 481.2, found: 481.0. Chiral SFC: RT=1.48 min.

Spectra of 5-48: ¹H NMR (400 MHz, DMSO-D₆) δ ppm 7.74 (d, J=10.97 Hz, 1H), 7.30 (s, 1H), 6.51 (s, 1H), 5.31-5.46 (m, 4H), 5.03 (dd, J=8.11, 3.70 Hz, 1H), 4.74 (t, J=5.36 Hz, 1H), 3.81-3.89 (m, 1H), 3.59-3.75 (m, 3H), 3.21 (dt, J=17.02, 5.38 Hz, 1H), 2.94-3.07 (m, 1H), 2.31-2.45 (m, 4H), 2.08 (m, 1H), 1.88 (dt, J=13.23, 6.62 Hz, 2H), 0.89 (t, J=7.33 Hz, 3H). ¹⁹F NMR (376 MHz, DMSO-D₆) δ ppm −111.53. LCMS (ESI+) m/z: [M+H]⁺ calcd for $C_{26}H_{26}FN_2O_6^+$: 481.2, found: 481.0. Chiral SFC: RT=1.61 min.

Example 6

Figure 17:
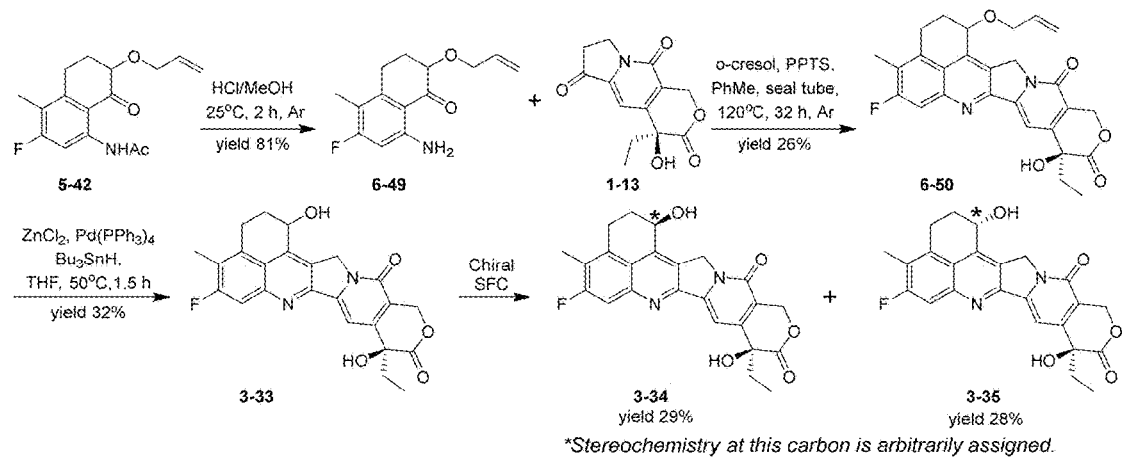
FIG. 17 illustrates a reaction scheme for making compounds 3-34 and 3-35.

Synthesis of (1R,9S)-9-ethyl-5-fluoro-1,9-dihydroxy-4-methyl-2,3,12,15-tetrahydrobenzo[de]pyrano[3',4':6,7]indolizino[1,2-b]quinoline-10,13 (1H,9H)-dione (3-34) and (1S,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-35) (FIG. 17)

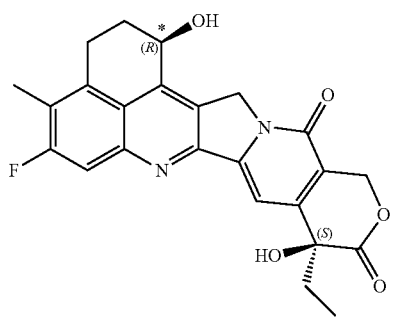

3-34

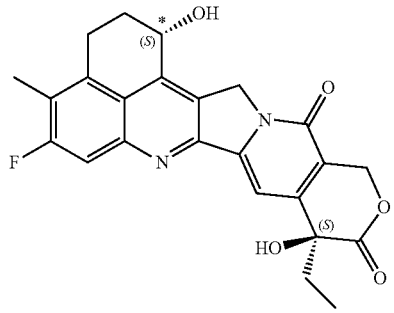

3-35

*Stereochemistry at this carbon is arbitrarily assigned.

2-(Allyloxy)-8-amino-6-fluoro-5-methyl-3,4-dihydronaphthalen-1(2H)-one (6-49)

To a mixture of N-(7-(allyloxy)-3-fluoro-4-methyl-8-oxo-5,6,7,8-tetrahydronaphthalen-1-yl)acetamide (5-42) (600 mg, 2.06 mmol, 1.0 equiv) in methanol (6.0 mL) was added HCl/Methanol (6.0 mL, 4 M, 11.65 equiv) at 0° C. under argon, the mixture was stirred at 25° C. for 2 h, cooled to 0° C. and the pH adjusted to 8 by addition of saturated NaHCO₃. It was extracted with dichloromethane (3×40 mL), combined organic layers washed with brine, dried over Na₂SO₄, filtered, concentrated under reduced pressure, and the residue purified by column chromatography on silica gel eluting with 10% of ethyl acetate in petroleum ether to give 2-(allyloxy)-8-amino-6-fluoro-5-methyl-3,4-dihydronaphthalen-1(2H)-one (6-49) (415 mg, 81% yield). ¹H NMR (400 MHz, CDCl₃) δ ppm 6.24-6.68 (m, 2H), 6.20 (d, J=11.62 Hz, 1H), 5.91-6.03 (m, 1H), 5.33 (dq, J=17.24, 1.63 Hz, 1H), 5.20 (dq, J=10.38, 1.35 Hz, 1H), 4.36 (m, 1H), 4.17 (m, 1H), 3.97 (dd, J=10.15, 4.16 Hz, 1H), 3.01 (dt, J=17.45, 5.33 Hz, 1H), 2.75 (m, 1H), 2.27 (dq, J=13.17, 5.02 Hz, 1H), 2.09-2.19 (m, 1H), 2.04 (d, J=1.71 Hz, 3H). ¹⁹F NMR (376 MHz, CDCl₃) δ ppm −106.28. LCMS (ESI+) m/z: [MH]⁺ calcd for $C_{14}H_{17}FNO_2^+$: 250.1, found: 250.1.

(9S)-1-(Allyloxy)-9-ethyl-5-fluoro-9-hydroxy-4-methyl-2,3,12,15-tetrahydrobenzo[de]pyrano[3',4':6,7]indolizino[1,2-b]quinoline-10,13(1H,9H)-dione (6-50)

To a mixture of 2-(allyloxy)-8-amino-6-fluoro-5-methyl-3,4-dihydronaphthalen-1(2H)-one (6-49) (200 mg, 0.802 mmol, 1.0 equiv), and (S)-4-ethyl-4-hydroxy-7,8-dihydro-1H-pyrano[3,4-f]indolizine-3,6,10(4H)-trione (1-13) (232 mg, 0.883 mmol, 1.1 equiv) in toluene (10 mL) at 120° C. were added o-cresol (0.609 mL, 5.86 mmol, 7.3 equiv) and pyridin-1-ium 4-methylbenzenesulfonate (30.2 mg, 0.120 mmol, 0.15 equiv) under argon, the mixture was stirred at 120° C. for 32 h, concentrated under reduced pressure, and the residue purified by column chromatography on silica gel eluting with 55% of ethyl acetate in petroleum ether to give (9S)-1-(allyloxy)-9-ethyl-5-fluoro-9-hydroxy-4-methyl-2,3,12,15-tetrahydrobenzo[de]pyrano[3',4':6,7]indolizino[1,2-b]quinoline-10,13(1H,9H)-dione (6-50) (100 mg, 26% yield). ¹H NMR (400 MHz, CDCl₃) δ ppm 7.58-7.67 (m, 2H), 6.03-6.16 (m, 1H), 5.74 (dd, J=16.26, 1.83 Hz, 1H), 5.39-5.52 (m, 2H), 5.21-5.36 (m, 3H), 4.94 (m, 1H), 4.38-4.47 (m, 1H), 4.26 (m, 1H), 3.87 (d, J=19.32 Hz, 1H), 3.23-3.36 (m, 1H), 2.99 (br t, J=13.02 Hz, 1H), 2.45-2.57

(m, 1H), 2.40 (br s, 3H) 2.11-2.25 (m, 1H), 1.82-1.98 (m, 2H), 1.04 (td, J=7.37, 2.87 Hz, 3H). $^{19}$F NMR (376 MHz, CDCl$_3$) δ ppm −110.35. LCMS (ESI+) m/z: [MH]$^+$ calcd for C$_{27}$H$_{26}$FN$_2$O$_5$$^+$: 477.2, found: 477.2.

(9S)-9-Ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-33)

To a mixture of (9S)-1-(allyloxy)-9-ethyl-5-fluoro-9-hydroxy-4-methyl-2,3,12,15-tetrahydro-benzo[de]pyrano[3',4':6,7]indolizino[1,2-b]quinoline-10,13(1H,9H)-dione (6-50) (300 mg, 0.63 mmol, 1.0 equiv) in tetrahydrofuran (15 mL) was added ZnCl$_2$ (110 mg, 0.82 mmol, 1.3 equiv) at 25° C. under argon, and 0.25 h later Pd(PPh$_3$)$_4$ (58.0 mg, 0.157 mmol, 0.25 equiv), and another 0.25 h later Bu$_3$SnH (3.33 mL, 12.6 mmol, 20 equiv), and the mixture was stirred at 50° C. for 1.5 h. It was concentrated under reduced pressure, and the residue purified by column chromatography on silica gel eluting with 5% of methanol in ethyl acetate to give a residue, which was further purified by prep-HPLC to afford (9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-33) (90.0 mg, 32% yield). $^1$H NMR (400 MHz, DMSO-D$_6$) δ ppm 7.72 (d, J=10.97 Hz, 1H), 7.30 (d, J=2.27 Hz, 1H), 6.50 (d, J=0.72 Hz, 1H), 5.98 (dd, J=5.90, 2.92 Hz, 1H), 5.36-5.46 (m, 3H), 5.23-5.32 (m, 1H), 5.14 (dt, J=9.60, 4.86 Hz, 1H), 3.23 (dt, J=16.90, 4.60 Hz, 2H), 2.96-3.06 (m, 1H), 2.35 (s, 3H), 1.94-2.06 (m, 1H), 1.80-1.93 (m, 2H), 0.88 (td, J=7.30, 1.49 Hz, 3H). $^{19}$F NMR (376 MHz, DMSO-D$_6$) δ ppm −111.78. LCMS (ESI+) m/z: [MH]$^+$ calcd for C$_{24}$H$_{22}$FN$_2$O$_5$$^+$: 437.2, found: 437.0.

Prep-HPLC Method:
Instrument: Gilson 281 semi-preparative HPLC system
Mobile phase: A: H2O; B: MeOH
Column: Phenomenex Luna 80*30 mm*3 um
Flow rate: 25 mL/min
Monitor wavelength: 220 & 254 nm

| Time | B % |
|---|---|
| 0.0 | 45 |
| 8.0 | 70 |
| 8.1 | 70 |
| 8.2 | 100 |
| 10.2 | 100 |
| 10.3 | 45 |
| 11.5 | 45 |

(1R,9S)-9-Ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-34) and (1S,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-35)

(9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-33) (90.0 mg, 0.206 mmol, 1.0 equiv) was separated by chiral SFC (Instrument: Waters SFC80 preparative SFC; Column: DAICEL CHIRALCEL OD (250 mm*30 mm, 10 um); Mobile phase: A for CO$_2$ and B for EtOH; Gradient: B %=55% isocratic elution mode; Flow rate: 60 g/min; Wavelength: 220 nm; Column temperature: 40° C.; System back pressure: 100 bar.) to afford (1R,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-34) (26.1 mg, 29% yield) (compound 3-34 may be the opposite enantiomer of that depicted) and (1S,9S)-9-ethyl-5-fluoro-1,9-dihydroxy-4-methyl-2,3,12,15-tetrahydrobenzo[de]pyrano[3',4':6,7]indolizino[1,2-b]quinoline-10,13(1H,9H)-dione (3-35) (25.1 mg, 28% yield) (compound 3-35 may be the opposite enantiomer of that depicted). Note: The stereochemistry for two products are arbitrarily assigned.

Spectra of 3-34: $^1$H NMR (400 MHz, DMSO-D$_6$) δ ppm 7.73 (d, J=10.97 Hz, 1H), 7.30 (s, 1H), 6.50 (s, 1H), 5.98 (d, J=5.84 Hz, 1H), 5.37-5.47 (m, 3H), 5.26-5.35 (m, 1H), 5.10-5.20 (m, 1H), 3.20-3.30 (m, 2H), 2.97-3.07 (m, 1H), 2.35 (s, 3H), 1.95-2.05 (m, 1H), 1.78-1.94 (m, 2H), 0.88 (t, J=7.33 Hz, 3H). $^{19}$F NMR (376 MHz, DMSO-D$_6$) δ ppm −111.78. LCMS (ESI+) m/z: [MH]$^+$ calcd for C$_{24}$H$_{22}$FN$_2$O$_5$$^+$: 437.2, found: 437.0. Chiral SFC: RT=1.43 min.

Spectra of 3-35: $^1$H NMR (400 MHz, DMSO-D$_6$) δ ppm 7.73 (d, J=11.09 Hz, 1H), 7.30 (s, 1H), 6.50 (s, 1H), 5.97 (d, J=5.84 Hz, 1H), 5.34-5.48 (m, 3H), 5.21-5.32 (m, 1H), 5.09-5.20 (m, 1H), 3.20-3.24 (m, 2H), 2.96-3.08 (m, 1H), 2.35 (s, 3H), 1.99 (d, J=9.54 Hz, 1H), 1.80-1.93 (m, 2H), 0.89 (t, J=7.09 Hz, 3H). $^{19}$F NMR (376 MHz, DMSO-D$_6$) δ ppm −111.80. LCMS (ESI+) m/z: [MH]$^+$ calcd for C$_{24}$H$_{22}$FN$_2$O$_5$$^+$: 437.2, found: 437.0. Chiral SFC: RT=1.54 min.

Example 7

Figure 18:
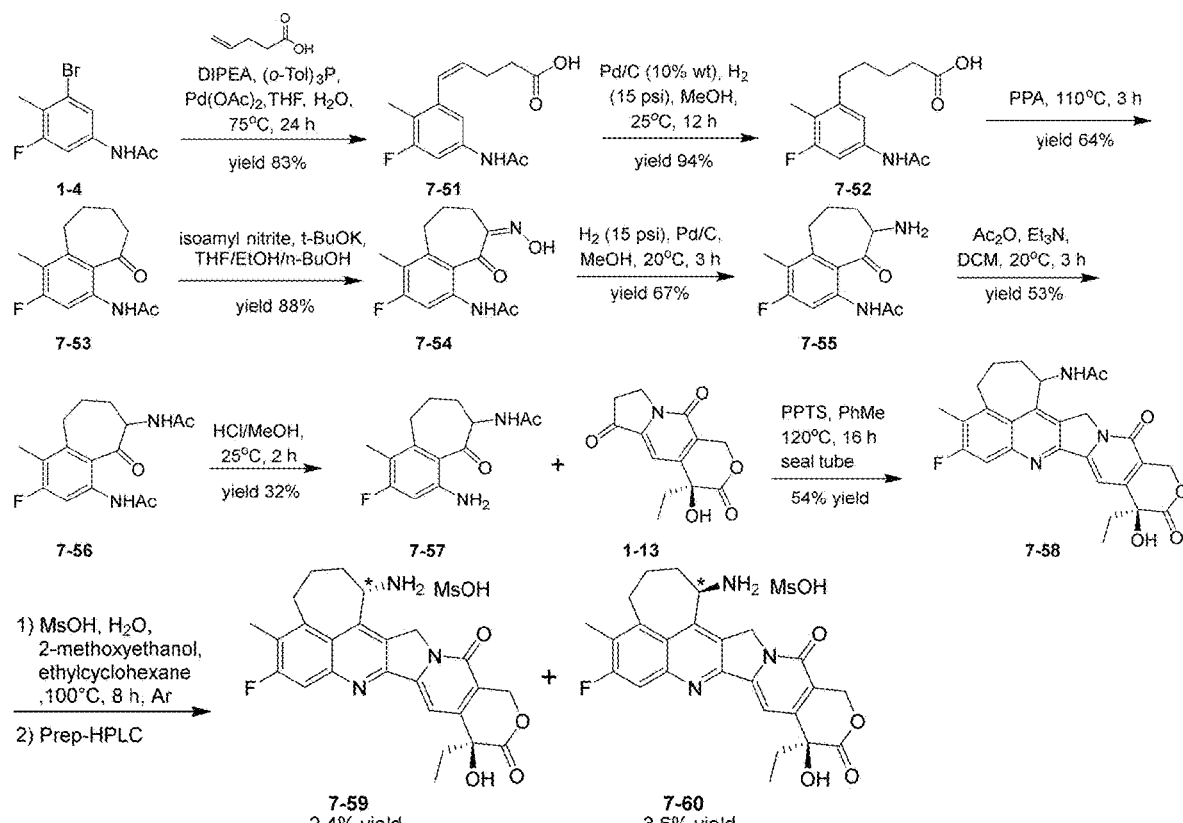
FIG. 18 illustrates a reaction scheme for making compounds 7-59 and 7-60.

(1S,10S)-1-amino-10-ethyl-6-fluoro-10-hydroxy-5-methyl-3,4,13,16-tetrahydro-1H-cyclohepta[de]pyrano[3',4':6,7]indolizino[1,2-b]quinoline-11,14(2H,10H)-dione methanesulfonate (7-59) and (1R,10S)-1-amino-10-ethyl-6-fluoro-10-hydroxy-5-methyl-3,4,13,16-tetrahydro-1H-cyclohepta[de]pyrano[3',4':6,7]indolizino[1,2-b]quinoline-11,14(2H,10H)-dione methanesulfonate (7-60) (FIG. 18)

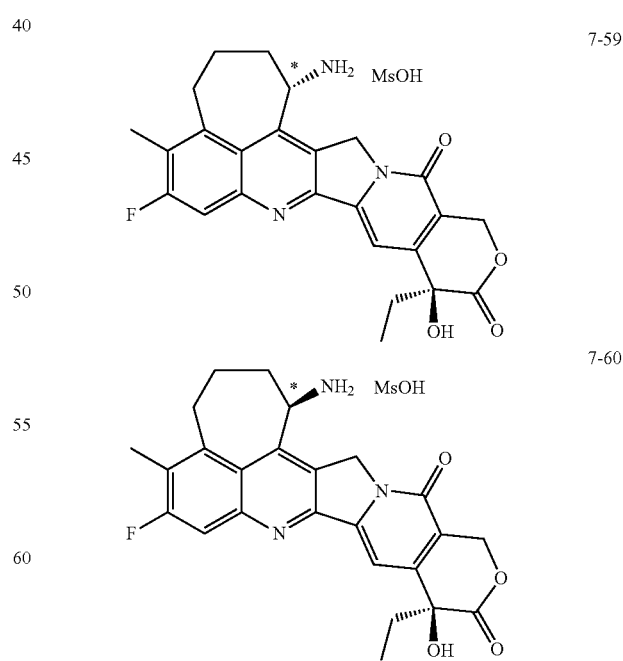

*Stereochemistry at this carbon is arbitrarily assigned.

5-(5-Acetamido-3-fluoro-2-methylphenyl)pent-4-enoic acid (7-51)

To a solution of N-(3-bromo-5-fluoro-4-methyl-phenyl)acetamide (1-4) (50.0 g, 203 mmol, 1.0 equiv) in THF (250 mL) and $H_2O$ (50.0 mL) was added pent-4-enoic acid (49.9 mL, 487 mmol, 2.4 equiv), diisopropylethyl amine (155 mL, 894 mmol, 4.4 equiv), tris-o-tolylphosphane (12.4 g, 40.6 mmol, 0.20 equiv) and palladium (II) diacetate (4.56 g, 20.3 mmol, 0.10 equiv) under $N_2$ atmosphere, the mixture was stirred at 75° C. for 24 h and cooled down to 30° C. (Three additional reactions were set up as described above and all four reaction mixtures were combined). The combined mixtures were filtered through a pad of celite, and the filter cake washed with water (2.0 L) and ethyl acetate (3.0 L). The mixture was adjusted to pH 4-5 with HCl solution (5 N), extracted with ethyl acetate (3×800 mL), organic layers dried over $Na_2SO_4$, concentrated, and the residue purified by silica gel flash column chromatography eluting with 30% of ethyl acetate in petroleum ether to give 5-(5-acetamido-3-fluoro-2-methylphenyl) pent-4-enoic acid (7-51) (0.20 kg, 83% yield). $^1$H NMR (400 MHz, DMSO-$d_6$) δ=12.19 (br s, 1H), 9.99 (s, 1H), 7.51-7.28 (m, 1H), 7.00 (s, 1H), 6.17-5.36 (m, 2H), 3.35-3.24 (m, 2H), 3.19-2.93 (m, 2H), 2.07 (s, 3H), 2.01 (s, 3H) $^{19}$F NMR (376 MHz, DMSO-$d_6$) δ ppm −115.96.

5-(5-Acetamido-3-fluoro-2-methylphenyl) pentanoic acid (7-52)

To a mixture of 5-(5-acetamido-3-fluoro-2-methylphenyl)pent-4-enoic acid (7-51) (50.0 g, 170 mmol, 90% purity, 1.0 equiv) in methanol (500 mL) was added Pd/C (25.0 g, 170 mmol, 10 wt %, 1.0 equiv) under argon atmosphere. After the mixture was vacuumed and filled with $H_2$ three times, it stirred at 25° C. for 12 h under $H_2$ (15 Psi). (Three additional reactions were set up as described above and all four reaction mixtures were combined). After the $H_2$ atmosphere was replaced with argon, it was filtered through a pad of celite, filter cake washed with methanol (6.00 L), filtrates concentrated to give 5-(5-acetamido-3-fluoro-2-methylphenyl) pentanoic acid (7-52) (190 g, 94% yield), which was used directly in the next step directly without further purification. $^1$H NMR (400 MHz, DMSO-$d_6$) δ=9.97 (s, 1H), 7.41 (dd, J=1.7, 12.2 Hz, 1H), 7.03 (s, 1H), 2.54 (br t, J=7.4 Hz, 2H), 2.23 (t, J=7.0 Hz, 2H), 2.08 (d, J=1.7 Hz, 3H), 2.01 (s, 3H), 1.59-1.43 (m, 4H). $^{19}$F NMR (376 MHz, CDCl$_3$) δ ppm −115.806. LCMS (ESI+) m/z: [MH]$^+$ calcd for $C_{14}H_{19}FNO_3^+$: 268.1, found: 268.0.

N-(3-fluoro-4-methyl-9-oxo-6,7,8,9-tetrahydro-5H-benzo[7]annulen-1-yl)acetamide (7-53)

A mixture of 5-(5-acetamido-3-fluoro-2-methylphenyl)pentanoic acid (7-52) (38.0 g, 142 mmol, 1.0 equiv) in polyphosphoric acid (500 mL) was stirred at 110° C. for 3 h. (Four additional reactions were set up as described above and all five reaction mixtures were combined). The combined reaction mixtures were slowly poured into stirred ice water (10.0 L), the pH adjusted to 7 with saturated NaHCO$_3$ solution, the mixture extracted with ethyl acetate (3×1.00 L). The combined organic layers were washed with brine, dried over anhydrous $Na_2SO_4$, filtered, concentrated under reduced pressure, and the residue purified by silica gel flash column chromatography eluting with 15% of ethyl acetate in petroleum ether to give N-(3-fluoro-4-methyl-9-oxo-6,7,8,9-tetrahydro-5H-benzo[7]annulen-1-yl)acetamide (7-53) (91 g, 64% yield). $^1$H NMR (400 MHz, DMSO-$d_6$) δ=9.83 (s, 1H), 7.19 (d, J=11.6 Hz, 1H), 2.69 (t, J=6.3 Hz, 2H), 2.58-2.52 (m, 2H), 2.16 (d, J=2.0 Hz, 3H), 1.95 (s, 3H), 1.74-1.58 (m, 4H). $^{19}$F NMR (376 MHz, DMSO-$d_6$) δ ppm −111.49. LCMS (ESI+) m/z: [MH]$^+$ calcd for $C_{14}H_{17}FNO_2^+$: 250.12, found: 250.0.

(Z)—N-(3-fluoro-8-(hydroxyimino)-4-methyl-9-oxo-6,7,8,9-tetrahydro-5H-benzo[7]annulen-1-yl)acetamide (7-54)

To a mixture of potassium tert-butoxide (1 M in tetrahydrofuran, 191 mL, 2.1 equiv) in tetrahydrofuran (194 mL), ethanol (31.4 mL), and n-butanol (31.4 mL), were added N-(2-fluoro-1-methyl-5-oxo-6,7,8,9-tetrahydrobenzo[7]annulen-4-yl)acetamide (7-53) (22.7 g, 90.9 mmol, 1.0 equiv) and isopentyl nitrite (14.8 mL, 109 mmol, 1.2 equiv) at 0° C., and the mixture was stirred at 20° C. for 3 h. (Three additional reactions were set up as described above and all four reaction mixtures were combined). The combined reaction mixtures were cooled to 0° C., quenched with 0.5 N hydrochloric acid (1.00 L) and extracted with ethyl acetate (3×300 mL), organic layers washed with brine, dried over sodium sulfate, filtered, concentrated under reduced pressure. The residue was triturated with methyl tert-butyl ester (500 mL), and filtered to give (Z)—N-(3-fluoro-8-(hydroxyimino)-4-methyl-9-oxo-6,7,8,9-tetrahydro-5H-benzo[7]annulen-1-yl)acetamide (7-54) (80.0 g, 88% yield). $^1$H NMR (400 MHz, DMSO-$d_6$) δ=12.69-11.95 (m, 1H), 10.10 (s, 1H), 7.28 (d, J=11.6 Hz, 1H), 2.68 (br t, J=6.6 Hz, 2H), 2.57 (t, J=6.8 Hz, 2H), 2.17 (d, J=1.8 Hz, 3H), 1.96 (s, 3H), 1.78-1.75 (m, 2H) $^{19}$F NMR (376 MHz, DMSO-$d_6$) δ ppm −107.85, −109.67, −110.39. LCMS (ESI+) m/z: [MH]$^+$ calcd for $C_{14}H_{16}FN_2O_3^+$: 279.1, found: 279.1.

N-(8-amino-3-fluoro-4-methyl-9-oxo-6,7,8,9-tetrahydro-5H-benzo[7]annule-1-yl)acetamide hydrochloric acid salt (7-55)

To a mixture of N-[(5E)-2-fluoro-5-hydroxyimino-1-methyl-6,7,8,9-tetrahydrobenzo[7]annulen-4-yl]acetamide (7-54) (20.0 g, 75.7 mmol, 1.0 equiv) in methanol (240 mL) were added hydrochloric acid (12 M, 18.9 mL, 3.0 equiv) and Pd/C (4.00 g, 75.7 mmol, 10 wt %, 1.0 equiv) under $N_2$ atmosphere, the mixture was vacuumed and filled with $H_2$ three times, and stirred at 20° C. for 3 h under $H_2$ (15 Psi). (Three additional reactions were set up as described above and all four reaction mixtures were combined). After the $H_2$ atmosphere was replaced with argon, the reaction mixtures were combined, diluted with methanol (800 mL), filtered through a pad of celite, filter cake washed with methanol (10.0 L), combined filtrates concentrated under reduced pressure to dryness. The residue was triturated with methyl tert-buty ether (800 mL) and filtered to give N-(8-amino-3-fluoro-4-methyl-9-oxo-6,7,8,9-tetrahydro-5H-benzo[7]annulen-1-yl)acetamide hydrochloric acid salt (7-55) (75 g, 98% yield). $^1$H NMR showed this material contained about 25% de-Ac byproduct. $^1$H NMR (400 MHz, DMSO-$d_6$) δ=10.34 (s, 1H), 8.75-8.40 (m, 3H), 7.31-7.20 (m, 1H), 4.44-4.21 (m, 1H), 2.98 (dt, J=6.1, 7.9 Hz, 1H), 2.85-2.75 (m, 1H), 2.47 (br s, 1H), 2.27-2.11 (m, 3H), 2.10-1.94 (m, 3H), 1.94-1.50 (m, 3H). $^{19}$F NMR (376 MHz, DMSO-$d_6$) δ ppm −107.88, −110.63. LCMS (ESI+) m/z: [MH]$^+$ calcd for $C_{14}H_{16}FN_2O_3^+$: 265.1, found: 265.0.

N,N'-(3-fluoro-4-methyl-9-oxo-6,7,8,9-tetrahydro-5H-benzo[7]annulene-1,8-iyl)diacetamide (7-56)

To a suspension of N-(5-amino-2-fluoro-1-methyl-6,7,8,9-tetrahydro-5H-benzo[7]annulen-4-yl)acetamide hydrochloric acid salt (7-55) (25.0 g, 87.2 mmol, 1.0 equiv) in dichloromethane (225 mL) were added triethylamine (36.4 mL, 262 mmol, 3.0 equiv) and acetic anhydride (9.80 mL, 105 mmol, 1.2 equiv), and the mixture was stirred at 20° C. for 3 h. (Three additional reactions were set up as described above and all four reaction mixtures were combined). The combined reaction mixtures were extracted with saturated NH$_4$Cl solution (2.00 L), the aqueous phase extracted with ethyl acetate (3×500 mL), combined organic layers dried over Na$_2$SO$_4$, filtered, concentrated under reduced pressure, and the residue purified by silica gel flash column chromatography eluting with 30% of ethyl acetate in petroleum ether to give N,N'-(3-fluoro-4-methyl-9-oxo-6,7,8,9-tetrahydro-5H-benzo[7]annulene-1,8-diyl)diacetamide (7-56) (54.0 g, 53% yield) and N-(4-amino-2-fluoro-1-methyl-6, 7, 8, 9-tetrahydro-5H-benzo[7] annulen-5-yl) acetamide (7-57) (9.00 g, 10% yield).

Spectra of 7-56: $^1$H NMR (400 MHz, DMSO-d$_6$) δ=9.61 (br s, 1H), 8.69 (br d, J=4.5 Hz, 1H), 7.69 (d, J=12.2 Hz, 1H), 4.56-4.39 (m, 1H), 2.93 (br dd, J=7.0, 12.3 Hz, 1H), 2.43 (br dd, J=10.3, 14.7 Hz, 1H), 2.14 (d, J=1.2 Hz, 3H), 2.01 (s, 4H), 1.93 (s, 4H), 1.81-1.61 (m, 2H). $^{19}$F NMR (376 MHz, DMSO-d$_6$) δ ppm −111.86. LCMS (ESI+) m/z: [M+H]$^+$ calcd for C$_{16}$H$_{20}$FN$_2$O$_3^+$: 307.1, found: 307.1.

Spectra of 7-57: $^1$H NMR (400 MHz, DMSO-d$_6$) δ=8.25 (br d, J=7.1 Hz, 1H), 6.45-6.33 (m, 3H), 4.57 (td, J=6.7, 11.5 Hz, 1H), 2.97-2.86 (m, 1H), 2.81-2.70 (m, 1H), 2.07-1.97 (m, 4H), 1.95-1.88 (m, 1H), 1.84 (s, 3H), 1.70-1.59 (m, 1H), 1.57-1.42 (m, 1H). $^{19}$F NMR (376 MHz, DMSO) δ ppm −110.23. LCMS (ESI+) m/z: [M+H]$^+$ calcd for C$_{14}$H$_{18}$FN$_2$O$_3^+$: 265.1, found: 265.1.

N-(4-amino-2-fluoro-1-methyl-5-oxo-6,7,8,9-tetrahydro-5H-benzo[7]annulen-6-yl) acetamide (7-57)

To a mixture of N,N'-(3-fluoro-4-methyl-9-oxo-6,7,8,9-tetrahydro-5H-benzo[7]annulene-1,8-diyl)diacetamide (7-56) (18.0 g, 61.6 mmol, 1.0 equiv) in methanol (180 mL) was added hydrochloric acid/methanol (4 M, 180 mL, 11.7 equiv), and the mixture was stirred at 25° C. for 2 h. (Three additional reactions were set up as described above and all four reaction mixtures were combined). The combined reaction mixtures were concentrated under reduced pressure, and the residue extracted with saturated NaHCO$_3$ solution (2.00 L) and ethyl acetate/methanol (10/1, 3×800 mL). The combined organic phases were washed with brine, dried over anhydrous Na$_2$SO$_4$, filtered, concentrated under reduced pressure, and the residue purified by silica gel flash column chromatography eluting with 30% of ethyl acetate in petroleum ether to give N-(4-amino-2-fluoro-1-methyl-6, 7, 8, 9-tetrahydro-5H-benzo[7]annulen-5-yl) acetamide (7-57) (25 g, 54% yield). $^1$H NMR (400 MHz, DMSO-d$_6$) δ=8.25 (br d, J=7.1 Hz, 1H), 6.45-6.33 (m, 3H), 4.57 (td, J=6.7, 11.5 Hz, 1H), 2.97-2.86 (m, 1H), 2.81-2.70 (m, 1H), 2.07-1.97 (m, 4H), 1.95-1.88 (m, 1H), 1.84 (s, 3H), 1.70-1.59 (m, 1H), 1.57-1.42 (m, 1H). $^{19}$F NMR (376 MHz, CDCl$_3$) δ ppm −111.22. LCMS (ESI+) m/z: [M+H]$^+$ calcd for C$_{14}$H$_{18}$FN$_2$O$_3^+$: 265.1, found: 265.1.

N-((10S)-10-Ethyl-6-fluoro-10-hydroxy-5-methyl-11,14-dioxo-2,3,4,10,11,13,14,16-octa-hydro-1H-cyclohepta[de]pyrano[3',4':6,7]indolizino[1,2-b]quinolin-1-yl)acetamide (7-58)

To a mixture of N-(4-amino-2-fluoro-1-methyl-5-oxo-6, 7,8,9-tetrahydro-5H-benzo[7]annulen-6-yl)acetamide (7-57) (230 mg, 0.870 mmol, 1.0 equiv) and (S)-4-ethyl-4-hydroxy-7,8-dihydro-1H-pyrano[3,4-f]indolizine-3,6,10(4H)-trione (1-13) (458 mg, 1.74 mmol, 2.0 equiv) in toluene (23 mL) was added pyridin-1-ium 4-methylbenzenesulfonate (87.4 mg, 0.348 mmol, 0.4 equiv), and the mixture was stirred at 120° C. for 16 h in a sealed tube. The reaction mixture was concentrated under reduced pressure, and the residue purified by silica gel flash column chromatography eluting with 50% ethyl acetate in petroleum ether to afford N-((10S)-10-ethyl-6-fluoro-10-hydroxy-5-methyl-11,14-dioxo-2,3,4,10,11,13,14,16-octahydro-1H-cyclohepta[de]pyrano[3',4':6,7]indole-zino[1,2-b]quinolin-1-yl)acetamide (7-58) (240 mg, 54% yield). $^1$H NMR (400 MHz, DMSO-D$_6$) δ=8.71 (br d, J=6.2 Hz, 1H), 7.73 (d, J=10.5 Hz, 1H), 7.29 (s, 1H), 6.52 (d, J=7.4 Hz, 1H), 5.62-5.50 (m, 1H), 5.46-5.31 (m, 3H), 5.22-5.11 (m, 1H), 3.27-3.20 (m, 2H), 3.17 (d, J=4.8 Hz, 1H), 2.42 (s, 3H), 2.31-2.20 (m, 1H), 2.14-2.02 (m, 2H), 1.97 (s, 3H), 1.84-1.60 (m, 2H), 0.87 (q, J=7.4 Hz, 3H). LCMS (ESI+) m/z: [MH]$^+$ calcd for C$_{27}$H$_{27}$FN$_3$O$_5^+$: 492.2, found: 492.1.

(1S,10S)-1-Amino-10-ethyl-6-fluoro-10-hydroxy-5-methyl-3,4,13,16-tetrahydro-1H-cyclohepta[de]pyrano[3',4':6,7]indolizino[1,2-b]quinoline-11,14(2H,10H)-dione methanesulfonate (7-59) and (1R,10S)-1-amino-10-ethyl-6-fluoro-10-hydroxy-5-methyl-3,4,13,16-tetrahydro-1H-cyclohepta[de]pyrano[3',4':6,7]indolizino[1,2-b]quinoline-11,14(2H,10H)-dione methanesulfonate (7-60)

A mixture of N-((10S)-10-ethyl-6-fluoro-10-hydroxy-5-methyl-11,14-dioxo-2,3,4,10,11,13,14, 16-octahydro-1H-cyclohepta[de]pyrano[3',4':6,7]indolizino[1,2-b]quinolin-1-yl)acetamide (7-58) (160 mg, 0.101 mmol, 1.0 equiv) in 2-methoxyethanol (0.8 mL) were added methylcyclohexane (0.8 mL), H$_2$O (0.75 mL) and methanesulfonic acid (0.25 mL) under argon, the mixture was stirred at 100° C. for 8 h, concentrated, and the residue purified by prep-HPLC to afford (1S,10S)-1-amino-10-ethyl-6-fluoro-10-hydroxy-5-methyl-3,4,13,16-tetrahydro-1H-cyclohepta[de]pyrano[3', 4':6,7]indolizino[1,2-b]quinoline-11,14(2H,10H)-dione methanesulfonate (7-59) (5.5 mg, 2.4% yield) (compound 7-59 may be the opposite enantiomer of that depicted) and (1R,10S)-1-amino-10-ethyl-6-fluoro-10-hydroxy-5-methyl-3,4,13,16-tetrahydro-1H-cyclohepta[de]pyrano[3',4':6,7]indolezino[1,2-b]quinoline-11,14(2H,10H)-dione methanesulfonate (7-60) (6.4 mg, 3.6% yield) (compound 7-60 may be the opposite enantiomer of that depicted). Note: the stereochemistry is arbitrarily assigned.

Prep-HPLC Method:
Instrument: Gilson 281 semi-preparative HPLC system
Mobile phase: A: H$_2$O; B: MeOH
Column: Phenomenex Luna 80*30 mm*3 um
Flow rate: 25 mL/min
Monitor wavelength: 220 & 254 nm

| Time | B % |
| --- | --- |
| 0.0 | 40 |
| 6.0 | 75 |
| 6.1 | 75 |
| 8.2 | 100 |
| 10.2 | 100 |
| 10.3 | 40 |
| 11.5 | 40 |

Spectra of 7-59: $^1$H NMR (400 MHz, D$_2$O) δ ppm 7.38-7.49 (m, 2H), 5.52-5.62 (m, 1H), 5.35-5.46 (m, 3H), 5.16 (t, J=4.4 Hz, 1H), 3.40-3.51 (m, 1H), 2.99-3.13 (m, 1H), 2.77 (s, 6H), 2.48-2.57 (m, 2H), 2.38 (d, J=1.6 Hz, 3H), 2.22-2.33 (m, 1H), 2.06-2.20 (m, 1H), 1.94 (q, J=7.5 Hz, 2H), 0.90 (t, J=7.2 Hz, 3H). $^{19}$F NMR (376 MHz, D$_2$O) δ ppm −111.53. LCMS (ESI+) m/z: [MH]$^+$ calcd for C$_{25}$H$_{25}$FN$_3$O$_4^+$: 450.2, found: 450.0.

Spectra of 7-60: $^1$H NMR (400 MHz, D$_2$O) δ ppm 7.40-7.51 (m, 2H), 5.44-5.60 (m, 2H), 5.33-5.43 (m, 2H), 5.09-5.14 (m, 1H), 3.37-3.48 (m, 1H), 3.01-3.14 (m, 1H), 2.77 (s, 3H), 2.43-2.54 (m, 1H), 2.39 (s, 3H), 2.27-2.35 (m, 1H), 2.06-2.23 (m, 2H), 1.95 (q, J=7.6 Hz, 2H), 0.92 (t, J=7.2 Hz, 3H). $^{19}$F NMR (376 MHz, D$_2$O) δ ppm −109.21. LCMS (ESI+) m/z: [MH]$^+$ calcd for C$_{25}$H$_{25}$FN$_3$O$_4^+$: 450.2, found: 450.0.

Example 8

Figure 19:
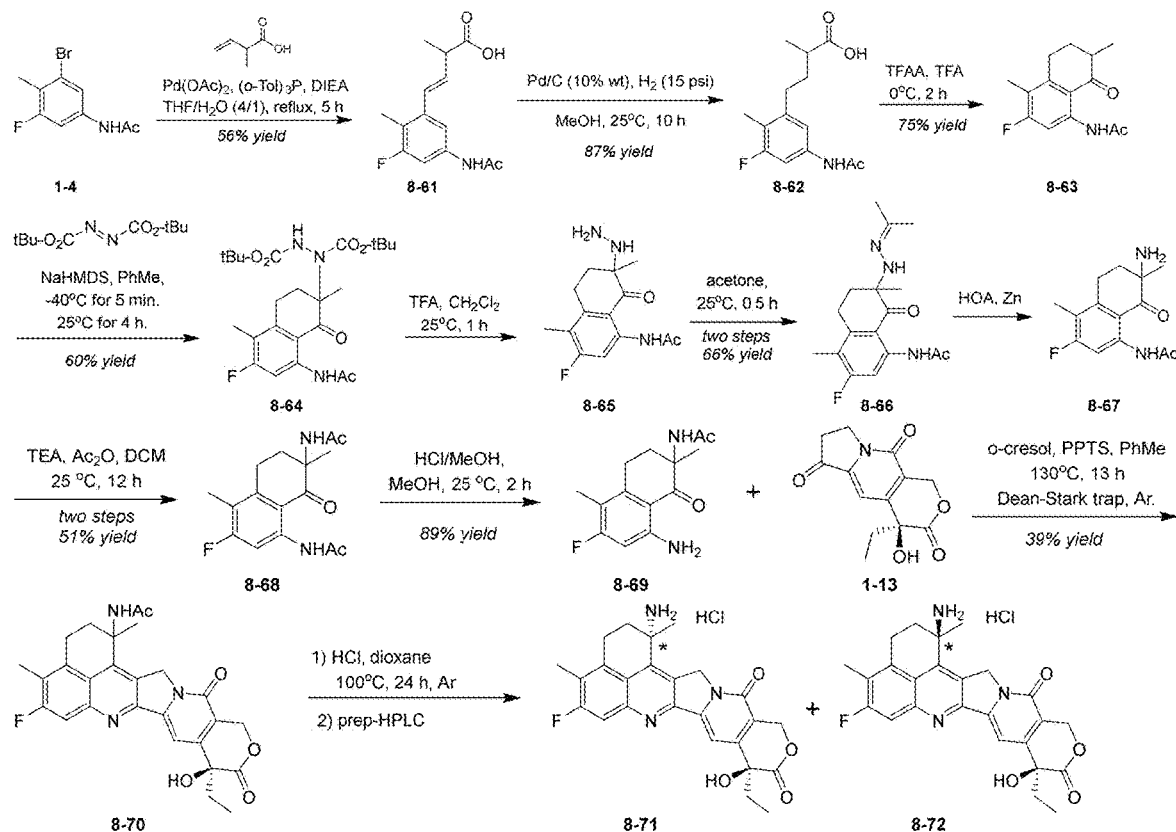
FIG. 19 illustrates a reaction scheme for making compounds 8-71 and 8-72.

(1S,9S)-1-amino-9-ethyl-5-fluoro-9-hydroxy-1,4-dimethyl-2,3,12,15-tetrahydrobenzo[de]pyrano[3',4':6,7]indolizino[1,2-b]quinoline-10,13(1H,9H)-dione hydrochloride (8-71) and (1R,9S)-1-amino-9-ethyl-5-fluoro-9-hydroxy-1,4-dimethyl-2,3,12,15-tetrahydrobenzo[de]pyrano[3',4':6,7]indolizino[1,2-b]quinoline-10,13(1H,9H)-dione hydrochloride (8-72) (FIG. 19)

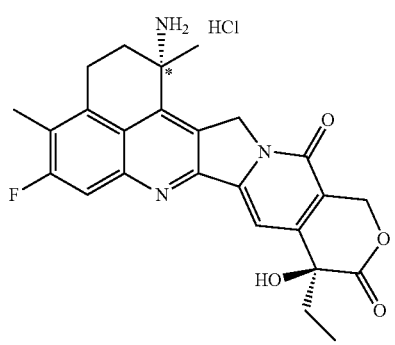

8-71

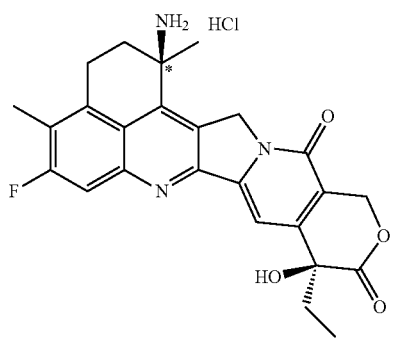

8-72

*Stereochemistry at this carbon is arbitrarily assigned.

4-(5-Acetamido-3-fluoro-2-methylphenyl)-2-methylbut-3-enoic acid (8-61)

To a mixture of N-(3-bromo-5-fluoro-4-methyl-phenyl)acetamide (1-4) (10.0 g, 40.6 mmol, 1.0 equiv) and 2-methylbut-3-enoic acid (13.0 g, 130 mmol, 3.2 equiv) in tetrahydrofuran (40 mL) and water (10 mL) were added N-ethyl-N,N-diisopropylamine (38.2 mL, 219 mmol, 5.4 equiv), tris-o-tolylphosphane (2.47 g, 8.13 mmol, 0.2 equiv) and diacetoxypalladium (912 mg, 4.06 mmol, 0.1 equiv) under nitrogen, and the mixture was stirred at 75° C. for 5 h., quenched with water (50 mL) and the pH adjusted to around 3 by addition of 3 N hydrochloric acid at 0° C. It was filtered through a pad of Celite, and the filtrate extracted with ethyl acetate (3×150 mL), organic layers washed with brine, dried over Na$_2$SO$_4$, filtered, concentrated, and the residue purified by silica gel flash column chromatography eluting with 50% ethyl acetate in petroleum ether to give 4-(5-acetamido-3-fluoro-2-methylphenyl)-2-methylbut-3-enoic acid (8-61) (6.00 g, 56% yield). $^1$H NMR (400 MHz, DMSO-D$_6$) δ ppm 12.38 (s, 1H), 10.02 (d, J=4.0 Hz, 1H), 7.46-7.52 (m, 1H), 6.99-7.38 (m, 1H), 6.65-6.69 (m, 1H), 6.17 (dd, J=15.6, 8.0 Hz, 1H), 3.49 (d, J=7.2 Hz, 1H), 2.11 (dd, J=13.2, 1.6 Hz, 3H), 2.02 (d, J=4.8 Hz, 3H), 1.24-1.88 (m, 3H). $^{19}$F NMR (376 MHz, DMSO-D$_6$) δ ppm −115.68. LCMS (ESI+) m/z: [MH]$^+$ calcd for C$_{14}$H$_{17}$FNO$_3^+$: 266.1, found: 266.1.

4-(5-Acetamido-3-fluoro-2-methylphenyl)-2-methylbutanoic acid (8-62)

To a mixture of 4-(5-acetamido-3-fluoro-2-methylphenyl)-2-methylbut-3-enoic acid (1) (5.00 g, 18.8 mmol, 1.0 equiv) in methanol (20 mL) was added Pd/C (10 wt %) (2.40 g, 0.12 equiv) under nitrogen, the suspension was degassed under vacuum and purged with H$_2$ three times, and stirred under H$_2$ (15 psi) at 25° C. for 10 h. After the H$_2$ atmosphere was replaced with argon, it was filtered through a pad of Celite and filter cake washed with methanol (300 mL). The combined filtrates were concentrated under reduced pressure to give 4-(5-acetamido-3-fluoro-2-methylphenyl)-2-methylbutanoic acid (8-62) (4.4 g, 87% yield). $^1$H NMR (400 MHz, DMSO-D$_6$) δ ppm 10.0 (s, 1H), 7.42 (dd, J=12.4, 1.6 Hz, 1H), 7.04 (s, 1H), 2.52-2.58 (m, 2H), 2.24 (t, J=6.8 Hz, 2H), 2.08 (d, J=1.6 Hz, 3H), 2.01 (s, 3H), 1.40-1.65 (m, 4H). $^{19}$F NMR (376 MHz, DMSO-D$_6$) δ ppm −125.77. LCMS (ESI+) m/z: [MH]$^+$ calcd for C$_{14}$H$_{19}$FNO$_3^+$: 268.1, found: 268.1.

N-(7-Fluoro-3,8-dimethyl-4-oxotetralin-5-yl)acetamide (8-63)

To a mixture of 4-(5-acetamido-3-fluoro-2-methylphenyl)-2-methylbutanoic acid (8-62) (5.00 g, 18.7 mmol, 1.0 equiv) in trifluoroacetic acid (10 mL) was added trifluoroacetic anhydride (5.20 mL, 37.4 mmol, 2.0 equiv) at 0° C., the mixture was stirred at 0° C. for 2 h, quenched with ice water (100 mL), and the pH adjusted to around 7 by addition of 25% aqueous NaOH at 0° C. It was extracted with ethyl acetate (3×200 mL), the combined organic layers washed with brine, dried over Na$_2$SO$_4$, filtered, concentrated under reduced pressure, and the residue purified by silica gel flash column chromatography eluting with 8% ethyl acetate in petroleum ether to give N-(7-fluoro-3,8-dimethyl-4-oxotetralin-5-yl)acetamide (8-63) (3.50 g, 75% yield). $^1$H NMR (400 MHz, DMSO-D$_6$) δ ppm 12.13 (s, 1H), 8.28 (d, J=13.2 Hz, 1H), 2.93-3.04 (m, 1H), 2.81-2.92 (m, 1H), 2.63-2.75 (m, 1H), 2.07-2.18 (m, 7H), 1.74 (qd, J=12.0, 4.8 Hz, 1H), 1.15 (d, J=6.4 Hz, 3H). $^{19}$F NMR (376 MHz, DMSO-D$_6$) δ ppm −104.64. LCMS (ESI+) m/z: [MH]$^+$ calcd for C$_{14}$H$_{17}$FNO$_2^+$: 250.1, found: 250.1.

Di-tert-Butyl 1-(8-acetamido-6-fluoro-2,5-dimethyl-1-oxo-1,2,3,4-tetrahydronaphthalen-2-yl)hydrazine-1,2-dicarboxylate (8-64)

To a mixture of N-(7-fluoro-3,8-dimethyl-4-oxotetralin-5-yl)acetamide (8-63) (35.1 g, 140 mmol, 1.0 equiv) in toluene (700 mL) was added sodium bis(trimethylsilyl) amide (309 mL, 1 M, 2.2 equiv) dropwise at 0° C. under nitrogen, the mixture was cooled down to −40° C., a solution of di-tert-butyl diazene-1,2-dicarboxylate (42.1 g, 183 mmol, 1.3 equiv) in toluene (350 mL) was added dropwise. The reaction mixture was warmed up to 25° C., stirred at 25° C. for 4 h, cooled to 0° C., diluted with water (1 L) and extracted with ethyl acetate (3×500 mL). The combined organic layers were washed with brine, dried over $Na_2SO_4$, filtered, concentrated under reduced pressure, and the residue purified by silica gel flash column chromatography eluting with 20% of ethyl acetate in petroleum ether to give di-tert-butyl 1-(8-acetamido-6-fluoro-2,5-dimethyl-1-oxo-1,2,3,4-tetrahydronaphthalen-2-yl) hydrazine-1,2-dicarboxylate (8-64) (41.0 g, 60% yield). $^1$H NMR (400 MHz, DMSO-$D_6$) δ ppm 11.61-11.84 (m, 1H), 8.26 (d, J=12.8 Hz, 1H), 7.96-8.15 (m, 1H), 2.96-3.16 (m, 2H), 2.68-2.84 (m, 1H), 2.12 (s, 4H), 2.08 (s, 3H), 1.35-1.46 (m, 21H). $^{19}$F NMR (376 MHz, DMSO-$D_6$) δ ppm −105.29. LCMS (ESI+) m/z: [MH]$^+$ calcd for $C_{24}H_{35}FN_3O_6^+$: 480.2, found: 502 (MS+Na).

N-(3-Fluoro-4,7-dimethyl-8-oxo-7-(2-(propan-2-ylidene)hydrazinyl)-5,6,7,8-tetrahydronaphthalen-1-yl)acetamide (8-66)

To a solution of di-tert-butyl 1-(8-acetamido-6-fluoro-2,5-dimethyl-1-oxo-1,2,3,4-tetrahydronaphthalen-2-yl)hydrazine-1,2-dicarboxylate (8-64) (41.0 g, 85.5 mmol, 1.0 equiv) in dichloromethane (820 mL) was added trifluoroacetic acid (410 mL) at 25° C., the mixture was stirred at 25° C. for 1 h, acetone (480 mL) added and the mixture stirred at 25° C. for another 0.5 h. It was concentrated to give N-(3-fluoro-4,7-dimethyl-8-oxo-7-(2-(propan-2-ylidene)hydrazinyl)-5,6,7,8-tetrahydronaphthalen-1-yl)acetamide (8-66) (18.1 g, 66% yield). $^1$H NMR (400 MHz, DMSO-$D_6$) δ ppm 11.90 (s, 1H), 8.31 (d, J=12.8 Hz, 1H), 3.05-3.14 (m, 1H), 2.90-3.02 (m, 1H), 2.11-2.19 (m, 7H), 2.05-2.08 (m, 2H), 1.98 (d, J=2.0 Hz, 6H), 1.34 (s, 3H). $^{19}$F NMR (376 MHz, DMSO-$D_6$) δ ppm −75.04. LCMS (ESI+) m/z: [MH]$^+$ calcd for $C_{17}H_{23}FN_3O_2^+$: 320.1, found: 320.1.

N-(7-Amino-3-fluoro-4,7-dimethyl-8-oxo-5,6,7,8-tetrahydronaphthalen-1-yl)acetamide (8-67)

To a mixture of N-(3-fluoro-4,7-dimethyl-8-oxo-7-(2-(propan-2-ylidene)hydrazinyl)-5,6,7,8-tetrahydronaphthalen-1-yl)acetamide (8-66) (15.1 g, 47.3 mmol, 1.0 equiv) in acetic acid (302 mL) was added zinc powder (40.8 g, 624 mmol, 13.2 equiv) portion wise, the mixture was stirred at 20° C. for 2 h, filtered and the filtrate concentrated under reduced pressure to give N-(7-amino-3-fluoro-4,7-dimethyl-8-oxo-5,6,7,8-tetrahydronaphthalen-1-yl)acetamide (8-67) (23.8 g, crude), which was used directly in the next step without further purification. $^1$H NMR (400 MHz, DMSO-$D_6$) δ ppm 11.56 (s, 1H), 8.26-8.30 (m, 1H), 3.01-3.09 (m, 2H), 2.12-2.19 (m, 10H), 1.43 (s, 3H). $^{19}$F NMR (376 MHz, DMSO-$D_6$) δ ppm −73.57. LCMS (ESI+) m/z: [MH]$^+$ calcd for $C_{14}H_{18}FN_2O_2^+$: 265.1, found: 265.1.

N,N'-(3-Fluoro-4,7-dimethyl-8-oxo-5,6,7,8-tetrahydronaphthalene-1,7-diyl)diacetamide (8-68)

To a mixture of N-(7-amino-3-fluoro-4,7-dimethyl-8-oxo-5,6,7,8-tetrahydronaphthalen-1-yl)acetamide (8-67) (23.8 g, 73.3 mmol, 1.0 equiv) in dichloromethane (414 mL) were added acetic anhydride (8.28 mL, 88.0 mmol, 1.2 equiv) and triethylamine (30.6 mL, 220 mmol, 3.0 equiv), the mixture was stirred at 25° C. for 12 h, quenched with water (500 mL) and extracted with dichloromethane (3×200 mL). The combined organic layers were washed with brine, dried over $Na_2SO_4$, filtered, concentrated under reduced pressure, and the residue purified by silica gel flash column chromatography eluting with 70% ethyl acetate in petroleum ether to give N,N'-(3-fluoro-4,7-dimethyl-8-oxo-5,6,7,8-tetrahydronaphthalene-1,7-diyl)diacetamide (8-68) (7.5 g, 51% yield). $^1$H NMR (400 MHz, DMSO-$D_6$) δ ppm 11.81 (s, 1H), 8.20-8.37 (m, 2H), 2.94-3.03 (m, 1H), 2.77-2.88 (m, 1H), 2.65 (m, 1H), 2.06-2.18 (m, 6H), 1.85 (m, 1H), 1.79 (s, 3H), 1.32 (s, 3H). $^{19}$F NMR (376 MHz, DMSO-$D_6$) δ ppm −105.03.

N-(8-Amino-6-fluoro-2,5-dimethyl-1-oxo-1,2,3,4-tetrahydronaphthalen-2-yl)acetamide (8-69)

To a mixture of N,N'-(3-fluoro-4,7-dimethyl-8-oxo-5,6,7,8-tetrahydronaphthalene-1,7-diyl)diacetamide (8-68) (7.50 g, 24.4 mmol, 1.0 equiv) in methanol (105 mL) was added HCl/MeOH (105 mL, 4 M), the mixture was stirred at 25° C. for 2 h, concentrated under reduced pressure, the residue diluted with dichloromethane (300 mL) and extracted with saturated aqueous $NaHCO_3$ (2×200 mL). The organic layer was washed with brine, dried over $Na_2SO_4$, filtered, and concentrated under reduced pressure to give N-(8-amino-6-fluoro-2,5-dimethyl-1-oxo-1,2,3,4-tetrahydronaphthalen-2-yl)acetamide (8-69) (5.50 g, 89% yield). $^1$H NMR (400 MHz, DMSO-$D_6$) δ ppm 7.91 (s, 1H), 7.39 (s, 2H), 6.36 (d, J=12.4 Hz, 1H), 2.78-2.89 (m, 1H), 2.67-2.75 (m, 2H), 1.97 (d, J=1.20 Hz, 3H), 1.83-1.88 (m, 1H), 1.80 (s, 3H), 1.27 (s, 3H). $^{19}$F NMR (376 MHz, DMSO-$D_6$) δ ppm −108.38. LCMS (ESI+) m/z: [MH]$^+$ calcd for $C_{14}H_{18}FN_2O_2^+$: 265.1, found: 265.1.

N-((9S)-9-Ethyl-5-fluoro-9-hydroxy-1,4-dimethyl-10,13-dioxo-1,2,3,9,10,12,13,15-octahydro-benzo[de]pyrano[3',4':6,7]indolizino[1,2-b]quinolin-1-yl)acetamide (8-70)

To a mixture of N-(8-amino-6-fluoro-2,5-dimethyl-1-oxo-1,2,3,4-tetrahydronaphthalen-2-yl)acetamide (500 mg, 1.89 mmol, 1.0 equiv) (8-69) and (S)-4-ethyl-4-hydroxy-7,8-dihydro-1H-pyrano[3,4-f]indolizine-3,6,10(4H)-trione (1-13) (547 mg, 2.08 mmol, 1.1 equiv) in toluene (25 mL) at 120° C. were added pyridine 4-methylbenzenesulfonate (71.3 mg, 0.283 mmol, 0.15 equiv) and o-cresol (1.44 mL, 13.8 mmol, 7.3 equiv) under argon, and the mixture was stirred at 130° C. for 13 h with Dean-Stark trap to remove the water formed. It was concentrated under reduced pressure, and the residue purified by silica gel flash column chromatography eluting with 7% methanol in dichloromethane to afford N-((9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)acetamide (8-70) (362 mg, 39% yield). $^1$H NMR (400 MHz, DMSO-$D_6$) δ ppm 7.78 (d, J=11.2 Hz, 1H), 7.30 (s, 1H), 6.53 (d, J=10.0 Hz, 1H), 5.25-5.54 (m, 4H), 4.81-4.90 (m, 1H), 3.24-3.29 (m, 1H), 2.86-3.11 (m, 3H), 2.39 (s, 3H), 1.95 (d, J=3.6 Hz, 3H), 1.84-1.89 (m, 2H), 1.50 (d, J=4.8 Hz, 3H), 0.87 (d, J=5.2 Hz, 3H). $^{19}$F NMR (376 MHz, DMSO-D$_6$) δ ppm −111.94. LCMS (ESI+) m/z: [MH]$^+$ calcd for C$_{27}$H$_{27}$FN$_3$O$_5{}^+$: 492.1, found: 492.2 (1S,9S)-1-Amino-9-ethyl-5-fluoro-9-hydroxy-1,4-dimethyl-2,3,12,15-tetrahydrobenzo[de]pyrano[3',4':6,7]indolizino[1,2-b]quinoline-10,13(1H,9H)-dione hydrochloride (8-71) and (1R,9S)-1-amino-9-ethyl-5-fluoro-9-hydroxy-1,4-dimethyl-2,3,12,15-tetrahydrobenzo[de] pyrano[3',4':6,7]indolizino[1,2-b]quinoline-10,13(1H,9H)-dione hydrochloride (8-72):

A mixture of N-((9S)-9-ethyl-5-fluoro-9-hydroxy-1,4-dimethyl-10,13-dioxo-1,2,3,9,10, 12,13,15-octahydrobenzo [de]pyrano[3',4':6,7]indolizino[1,2-b]quinolin-1-yl)acetamide (8-70) (600 mg, 1.22 mmol, 1.0 equiv) in dioxane (6 mL) and concentrated hydrochloric acid (6 mL, 12 M) was stirred at 100° C. for 24 h in a sealed tube under argon. It was concentrated under reduced pressure, and the residue purified by prep-HPLC to afford (1S,9S)-1-amino-9-ethyl-5-fluoro-9-hydroxy-1,4-dimethyl-2,3,12,15-tetrahydrobenzo [de]pyrano[3',4':6,7]indolizino[1,2-b]quinoline-10,13(1H, 9H)-dione hydrochloride (8-71) (61.0 mg, 10% yield) and (1R,9S)-1-amino-9-ethyl-5-fluoro-9-hydroxy-1,4-dimethyl-2,3,12,15-tetrahydrobenzo[de]pyrano[3',4':6,7]indoli-zino [1,2-b]quinoline-10,13(1H,9H)-dione hydrochloride (8-72) (85.0 mg, 14% yield). Note: the stereochemistry is arbitrarily assigned.

Prep-HPLC Conditions:

Instrument: Gilson 281 semi-preparative HPLC system

Mobile phase: A: HCl/H2O=0.040% v/v; B: ACN

Column: Phenomenex Luna 80*30 mm*3 um

Flow rate: 25 mL/min

Monitor wavelength: 220 & 254 nm

| Time | B % |
| --- | --- |
| 0.0 | 5 |
| 8.0 | 30 |
| 8.1 | 30 |
| 8.2 | 100 |
| 10.2 | 100 |
| 10.3 | 5 |
| 11.5 | 5 |

Spectra of 8-71: $^1$H NMR (400 MHz, DMSO-D$_6$) δ ppm 8.97 (s, 3H), 7.89 (d, J=10.8 Hz, 1H), 7.36 (s, 1H), 5.73-5.81 (m, 1H), 5.56-5.65 (m, 1H), 5.41-5.49 (m, 2H), 3.22 (d, J=4.4 Hz, 2H), 2.34-2.44 (m, 5H), 1.82-1.94 (m, 5H), 0.88 (t, J=7.2 Hz, 3H). $^{19}$F NMR (376 MHz, DMSO-D$_6$) δ ppm −111.24. LCMS (ESI+) m/z: [MH]$^+$ calcd for C$_{25}$H$_{25}$FN$_3$O$_4{}^+$: 450.1, found: 450.1.

Spectra of 8-72: $^1$H NMR (400 MHz, DMSO-D$_6$) δ ppm 8.98 (s, 3H), 7.89 (d, J=10.8 Hz, 1H), 7.36 (s, 1H), 5.71-5.79 (m, 1H), 5.57-5.64 (m, 1H), 5.46 (s, 2H), 3.18-3.26 (m, 2H), 2.36-2.44 (m, 5H), 1.81-1.94 (m, 5H), 0.87 (t, J=7.2 Hz, 3H). $^{19}$F NMR (376 MHz, DMSO-D$_6$) δ ppm −111.22. LCMS (ESI+) m/z: [MH]$^+$ calcd for C$_{25}$H$_{25}$FN$_3$O$_4{}^+$: 450.1, found: 450.1.

Figure 20:
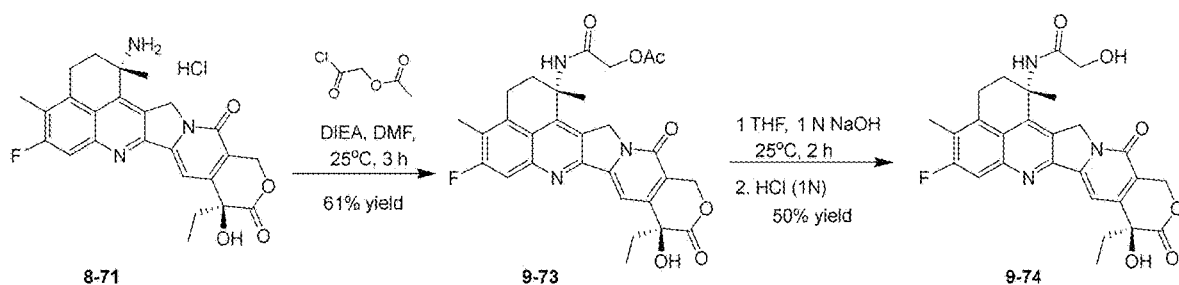
FIG. 20 illustrates a reaction scheme for making compound 9-74.

Example 9 N-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b] quinolin-1-yl)-2-hydroxyacetamide (9-74) (FIG. 20)

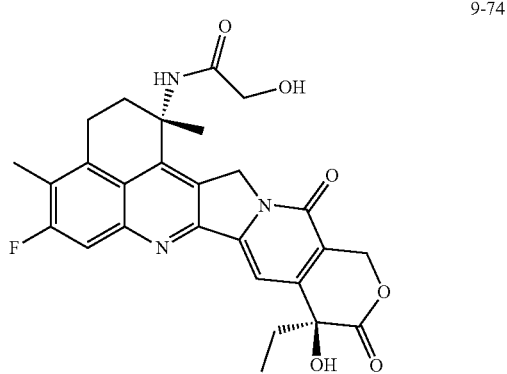 [SMILES: CC[C@@]1(O)C(=O)OCc2c1cc1n(c2=O)Cc2c-1nc1cc(F)c(C)c3c1c2[C@@](C)(NC(=O)CO)CC3]

9-74

2-(((1S,9S)-9-Ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)amino)-2-oxoethyl acetate (9-73)

The mixture of (1S,9S)-1-amino-9-ethyl-5-fluoro-9-hydroxy-1,4-dimethyl-2,3,12,15-tetra-hydrobenzo[de]pyrano [3',4':6,7]indolizino[1,2-b]quinoline-10,13(1H,9H)-dione hydrochloride (8-71) (40.0 mg, 0.089 mmol, 1.0 equiv)), N-ethyl-N-isopropylpropan-2-amine (46.5 μL, 0.266 mmol, 3.0 equiv) in N,N-dimethylformamide (2 mL) was stirred at 25° C. for 0.5 h, cooled to 0° C., 2-Chloro-2-oxoethyl acetate (14.6 mg, 11.5 μL, 0.106 mmol, 1.2 equiv) added dropwise over 5 min. It was warmed up to 25° C. and stirred at 25° C. for 3 h, concentrated under reduced pressure and the residue purified by silica gel flash column chromatography eluting with chloroform/methanol/water=7/3/1 to give 2-(((1S,9S)-9-ethyl-5-fluoro-9-hydroxy-1,4-dimethyl-10, 13-dioxo-1,2,3,9,10,12,13,15-octahydrobenzo[de]pyrano [3',4':6,7]indolizino[1,2-b]quinolin-1-yl)amino)-2-oxoethyl acetate (9-73) (30.0 mg, 61% yield). $^1$H NMR (400 MHz, DMSO-D$_6$) δ ppm 8.84 (s, 1H), 7.78 (d, J=10.85 Hz, 1H), 7.30 (s, 1H), 6.51 (s, 1H), 5.35-5.49 (m, 3H), 5.13 (d, J=19.07 Hz, 1H), 4.66 (d, J=14.66 Hz, 1H), 4.50 (d, J=14.66 Hz, 1H), 2.93-3.09 (m, 3H), 2.39 (s, 3H), 1.99 (s, 3H), 1.83-1.95 (m, 3H), 1.55 (s, 3H), 0.88 (t, J=7.33 Hz, 3H). $^{19}$F NMR (376 MHz, DMSO-D$_6$) δ ppm −111.87. LCMS (ESI+) m/z: [MH]$^+$ calcd for C$_{29}$H$_{29}$FN$_3$O$_7{}^+$: 550.2, found: 550.2.

N-((1S,9S)-9-Ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-2-hydroxyacetamide (9-74)

To a mixture of 2-(((1S,9S)-9-ethyl-5-fluoro-9-hydroxy-1,4-dimethyl-10,13-dioxo-1,2,3,9,10, 12,13,15-octahydrobenzo[de]pyrano[3',4':6,7]indolizino[1,2-b]quinolin-1-yl) amino)-2-oxoethyl acetate (9-73) (30.0 mg, 0.055 mmol, 1.0 equiv) in tetrahydrofuran (1 mL) was added 1 N aqueous NaOH (0.235 mL, 4.3 equiv) at 25° C. under argon. The mixture was stirred at 25° C. for 2 h, quenched with 1 N aqueous hydrochloric acid (0.273 mL, 5.0 equiv), concentrated under reduced pressure, and the residue purified by silica gel flash column chromatography eluting with chloroform/methanol/water-7/3/1) to give N-((1S,9S)-9-ethyl-5-fluoro-9-hydroxy-1,4-dimethyl-10,13-dioxo-1,2,3,9,10,12,13,15-octahydro-benzo[de]pyrano[3',4':6,7]indolizino[1,2-b]quinolin-1-yl)-2-hydroxyacetamide (9-74) (13.5 mg, 50% yield). $^1$H NMR (400 MHz, DMSO-D$_6$) δ ppm 8.31 (s, 1H), 7.77 (d, J=10.85 Hz, 1H), 7.29 (s, 1H), 6.50 (s, 1H), 5.34-5.54 (m, 4H), 4.91 (d, J=19.07 Hz, 1H), 3.77-4.01 (m, 2H), 3.22-3.31 (m, 1H), 2.87-3.13 (m, 2H), 2.39 (s, 3H), 1.77-2.01 (m, 3 H), 1.58 (s, 3H), 0.87 (t, J=7.33 Hz, 3H). $^{19}$F NMR (376 MHz, DMSO-D$_6$) δ ppm −111.92. LCMS (ESI+) m/z: [MH]$^+$ calcd for C$_{27}$H$_{27}$FN$_3$O$_6{}^+$: 508.2, found: 508.1.

Example 10

N-((1R,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-2-hydroxyacetamide (10-75)

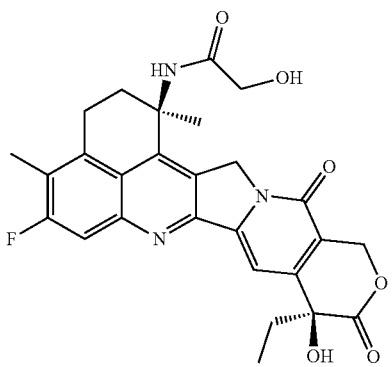

Example 10 (10-75) was made in a similar fashion to Example 9 using 8-72 instead of 8-71.

$^1$H NMR (400 MHz, DMSO-D$_6$) δ ppm 8.31 (s, 1H), 7.77 (d, J=10.85 Hz, 1H), 7.29 (s, 1H), 6.50 (s, 1H), 5.34-5.54 (m, 4H), 4.91 (d, J=19.07 Hz, 1H), 3.77-4.01 (m, 2H), 3.22-3.31 (m, 1H), 2.87-3.13 (m, 2H), 2.39 (s, 3H), 1.77-2.01 (m, 3H), 1.58 (s, 3H), 0.87 (t, J=7.33 Hz, 3H). $^{19}$F NMR (376 MHz, DMSO-D$_6$) δ ppm −111.88. LCMS (ESI+) m/z: [MH]$^+$ calcd for C$_{27}$H$_{27}$FN$_3$O$_6{}^+$: 508.2, found: 508.1.

Example 11

Figure 21:
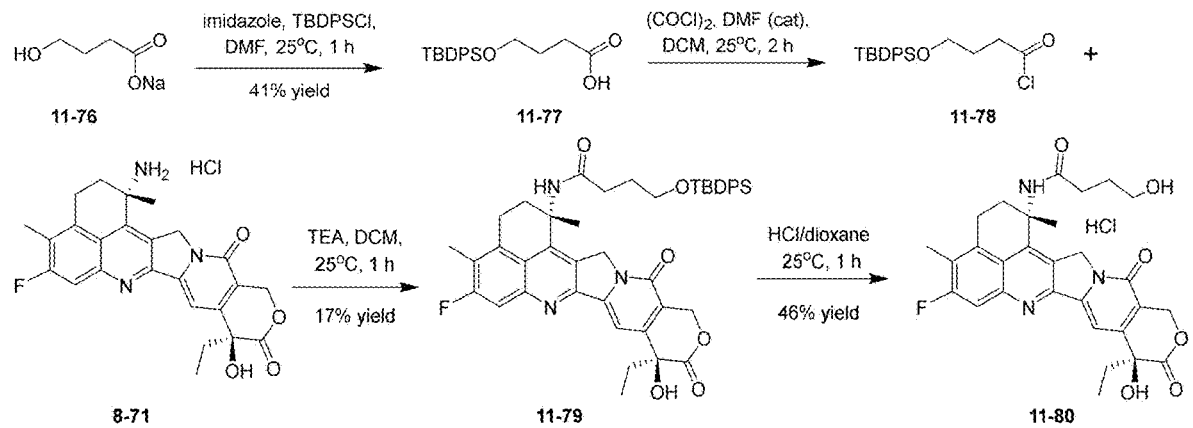
FIG. 21 illustrates a reaction scheme for making compound 11-80.

N-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-4-hydroxybutanamide hydrochloride (11-80) (FIG. 21)

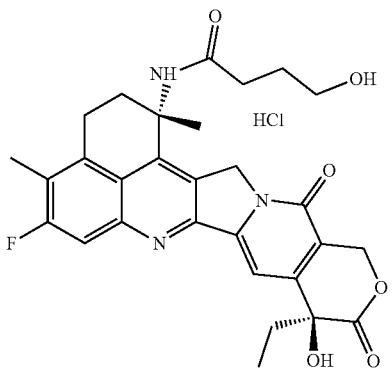

4-((tert-butyldiphenylsilyl)oxy)butanoic acid (11-77)

To a mixture of sodium 4-hydroxybutanoate (11-76) (2.10 g, 16.6 mmol, 1.0 equiv) and imidazole (1.70 g, 25.0 mmol, 1.5 equiv) in N, N-dimethylformamide (31.5 mL) was added tert-butylchlorodiphenylsilane (5.49 g, 19.9 mmol, 1.2 equiv) under argon, the mixture was stirred at 25° C. for 1 h, poured into ice water (60 mL) and extracted with ethyl acetate (3×50 mL). The combined organic layers were washed with brine, dried over Na$_2$SO$_4$, filtered, concentrated under reduced pressure, and the residue purified by silica gel flash column chromatography eluting with 30% ethyl acetate in petroleum ether to give 4-((tert-butyldiphenylsilyl)oxy)butanoic acid (11-77) (2.60 g, 41% yield). $^1$H NMR (400 MHz, DMSO-D$_6$) δ ppm 7.61-7.63 (m, 6H), 7.46 (dd, J=7.2, 4.4 Hz, 4H), 3.72 (t, J=6.4 Hz, 2H), 2.65 (t, J=7.2 Hz, 2H), 1.87 (t, J=6.8 Hz, 2H), 1.00 (s, 9H). LCMS (ESI−) m/z: [MH]$^−$ calcd for C$_{20}$H$_{25}$O$_3$Si$^−$: 341.2, found: 341.2.

4-((tert-Butyldiphenylsilyl)oxy)butanoyl chloride (11-78)

To a mixture of 4-((tert-butyldiphenylsilyl)oxy)butanoic acid (11-77) (1.50 g, 4.10 mmol, 1.0 equiv) in dichloromethane (75 mL) were added oxalyl dichloride (1.05 g, 8.24 mmol, 2.0 equiv) and N, N-dimethylformamide (9.02 mg, 0.03 equiv) under nitrogen at 0° C., the mixture was warmed up to 25° C., stirred at 25° C. for 2 h, and concentrated under reduced pressure to give 4-((tert-butyldiphenylsilyl)oxy)butanoyl chloride (11-78) (1.50 g, crude), which was used directly in the next step without purification. $^1$H NMR (400 MHz, CDCl$_3$) δ ppm 7.63-7.71 (m, 6H), 7.42-7.48 (m, 4H), 3.72 (dt, J=11.6, 6.0 Hz, 2H), 2.96-3.13 (m, 1H), 2.63 (t, J=7.6 Hz, 1H), 1.91-2.01 (m, 2H), 1.07 (s, 9H).

4-((tert-Butyldiphenylsilyl)oxy)-N-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)butanamide (11-79)

To a mixture of (1S,9S)-1-amino-9-ethyl-5-fluoro-9-hydroxy-1,4-dimethyl-2,3,12,15-tetra-hydrobenzo[de]pyrano[3',4':6,7]indolizino[1,2-b]quinoline-10,13(1H,9H)-dione hydrochloride (8-71) (100 mg, 0.206 mmol, 1.0 equiv) and trimethylamine (166 mg, 229 μL 1.65 mmol, 8.0 equiv) in dichloromethane (5 mL) was added 4-((tert-butyldiphenylsilyl) oxy)butanoyl chloride (11-78) (303 mg, 0.839 mmol, 2.4 equiv), the mixture was stirred at 25° C. for 1 h, filtered, the filtrate concentrated and the residue purified by silica gel flash column chromatography eluting with 60% dichloromethane in ethyl acetate to give 4-((tert-butyldiphenylsilyl)oxy) —N-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)butanamide (11-79) (30.0 mg, 17% yield). LCMS (ESI+) m/z: [MH]$^+$ calcd for C$_{45}$H$_{49}$FN$_3$O$_6$Si$^+$: 774.3, found: 774.2.

N-((1S,9S)-9-Ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-4-hydroxybutanamide hydrochloride (11-80)

To a stirring mixture of 4-((tert-butyldiphenylsilyl)oxy)-N-((1S,9S)-9-ethyl-5-fluoro-9-hydroxy-1,4-dimethyl-10,13-dioxo-1,2,3,9,10,12,13,15-octahydrobenzo[de]pyrano

[3',4':6,7]indolizino[1,2-b]quinolin-1-yl)butanamide (11-79) (30.0 mg, 0.039 mmol, 1.0 equiv) in dioxane (0.15 mL) was added HCl/dioxane (0.5 mL, 8 M) dropwise at 25° C. under nitrogen, the mixture was stirred at 25° C. for 1 h, filtered, and the filter cake collected. The material was triturated with methyl tert-butyl ether (2 mL) at 25° C. for 30 min, collected by filtration, and dried under vacuum to give N-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-4-hydroxybutanamide hydrochloride (11-80) (10.2 mg, 46% yield). $^1$H NMR (400 MHz, DMSO-D$_6$) δ ppm 8.61 (s, 1H), 7.78 (d, J=10.8 Hz, 1H), 7.31 (s, 1H), 5.35-5.48 (m, 3H), 4.87 (d, J=18.8 Hz, 1H), 3.37 (t, J=6.4 Hz, 3H), 3.22-3.32 (m, 1H), 2.86-3.11 (m, 3H), 2.39 (s, 3H), 2.25-2.33 (m, 2H), 1.79-1.95 (m, 3H), 1.56-1.66 (m, 2H), 1.51 (s, 3H), 0.88 (t, J=7.2 Hz, 3H). $^{19}$F NMR (376 MHz, DMSO-D$_6$) δ ppm -111.98. LCMS (ESI+) m/z: [MH]$^+$ calcd for C$_{29}$H$_{31}$FN$_3$O$_6^+$: 536.2, found: 536.2.

Example 12

N-((1R,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)-4-hydroxybutanamide hydrochloride (12-81)

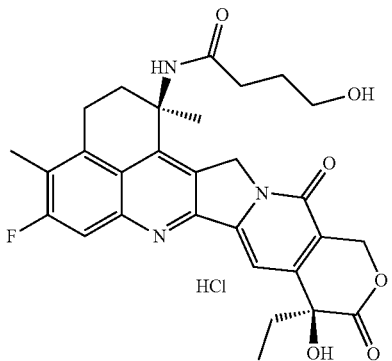

12-81

Example 12 (12-81) was made in a similar fashion to Example 11 using 8-72 instead of 8-71. $^1$H NMR (400 MHz, DMSO-D6) δ ppm 8.60 (s, 1H), 7.78 (d, J=10.8 Hz, 1H), 7.30 (s, 1H), 5.31-5.50 (m, 3H), 4.86 (d, J=18.8 Hz, 1H), 3.36 (t, J=6.4 Hz, 2H), 3.23-3.31 (m, 1H), 2.78-3.15 (m, 3H), 2.39 (s, 3H), 2.26-2.34 (m, 2H), 1.75-1.99 (m, 3H), 1.60 (quin, J=6.8 Hz, 2H), 1.50 (s, 3H), 0.86 (t, J=7.2 Hz, 3H). $^{19}$F NMR (376 MHz, DMSO-D6) δ ppm -111.95. LCMS (ESI+) m/z: [MH]$^+$ calcd for C29H31FN3O6+: 536.2, found: 536.1.

Example 13

Figure 22:
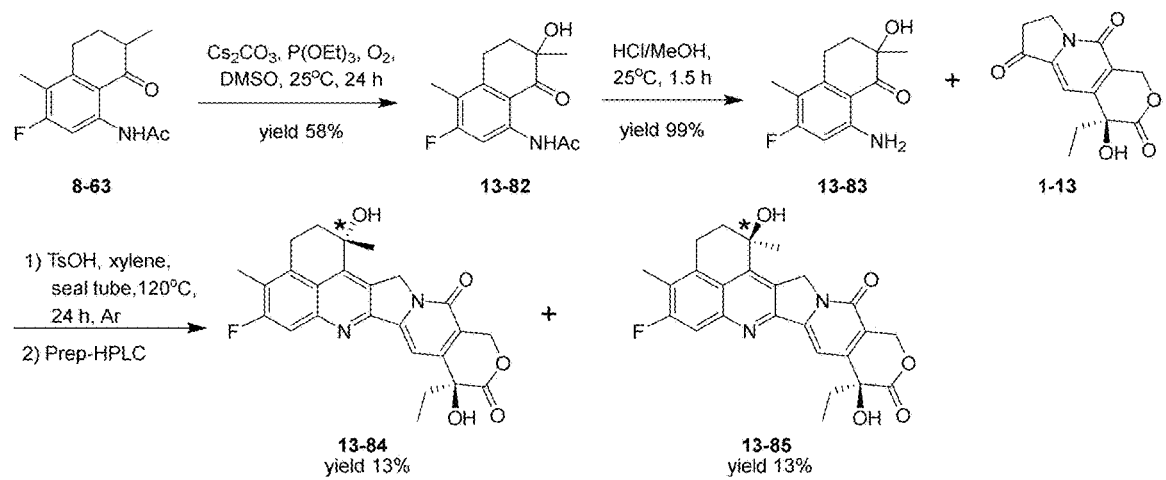
FIG. 22 illustrates a reaction scheme for making compounds 13-84 and 13-85.

(1S,9S)-9-ethyl-5-fluoro-1,9-dihydroxy-1,4-dimethyl-2,3,12,15-tetrahydrobenzo[de]pyrano[3', 4': 6, 7]indolizino[1,2-b]quinoline-10,13(1H,9H)-dione (13-84) and (1R, 9S)-9-ethyl-5-fluoro-1,9-dihydroxy-1,4-dimethyl-2,3,12,15-tetrahydrobenzo[de]pyrano[3', 4': 6, 7]indolizino[1,2-b]quinoline-10,13 (1H,9H)-dione (13-85) (FIG. 22)

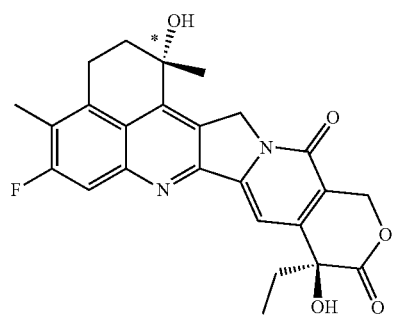

13-84

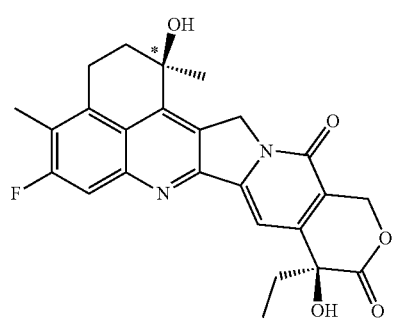

13-85

*Stereochemistry at this carbon is arbitrarily assigned.

N-(3-Fluoro-7-hydroxy-4,7-dimethyl-8-oxo-5,6,7,8-tetrahydronaphthalen-1-yl)acetamide (13-82)

To a mixture of N-(3-fluoro-4,7-dimethyl-8-oxo-5,6,7,8-tetrahydronaphthalen-1-yl)acetamide (8-63) (1.00 g, 4.01 mmol, 1.0 equiv) and cesium carbonate (261 mg, 0.802 mmol, 0.2 equiv) in dimethyl sulfoxide (16 mL) was added triethyl phosphite (1.33 g, 8.02 mmol, 1.38 mL, 2.0 equiv) at 25° C., the reaction mixture was vacuumed and filled with O$_2$ three times and stirred under O$_2$ (15 psi) at 25° C. for 24 h. After the oxygen atmosphere was replaced with nitrogen, the mixture was diluted with water (80 mL) and extracted with ethyl acetate (2×40 mL). The combined organic layers were washed with brine, dried over Na$_2$SO$_4$, filtered, concentrated under reduced pressure, and the residue purified by silica gel flash column chromatography eluting with 15% of ethyl acetate in petroleum ether to afford N-(3-fluoro-7-hydroxy-4,7-dimethyl-8-oxo-5,6,7,8-tetrahydronaphthalen-1-yl)acetamide (12-82) (620 mg, 58% yield). $^1$H NMR (400 MHz, DMSO-D$_6$) δ ppm 11.97 (s, 1H), 8.29 (d, J=13.08 Hz, 1H), 5.47 (s, 1H), 2.94-3.04 (m, 1H), 2.78-2.88 (m, 1H), 2.17 (s, 3H), 2.11 (d, J=1.59 Hz, 3H), 1.96-2.09 (m, 2H), 1.28 (s, 3H). $^{19}$F NMR (376 MHz, DMSO-D$_6$) δ ppm -104.38. LCMS (ESI+) m/z: [MH]$^+$ calcd for C$_{14}$H$_{17}$FNO$_3^+$: 266.1, found: 266.0.

8-Amino-6-fluoro-2-hydroxy-2, 5-dimethyl-3, 4-dihydronaphthalen-1(2H)-one (12-83)

To a mixture of N-(3-fluoro-7-hydroxy-4,7-dimethyl-8-oxo-5,6,7,8-tetrahydronaphthalen-1-yl)acetamide (12-82) (300 mg, 1.13 mmol, 1.0 equiv) in methanol (6 mL) was added HCl/MeOH (6 mL, 4 M) dropwise at 25° C., the mixture was stirred at 25° C. for 1.5 h, cooled to 0° C. and the pH adjusted to 7 by addition of saturated NaHCO$_3$ at 0° C. It was extracted with dichloromethane (3×10 mL), the combined organic layers dried over Na$_2$SO$_4$, filtered, concentrated under reduced pressure to give 8-amino-6-fluoro-2-hydroxy-2,5-dimethyl-3,4-dihydronaphthalen-1(2H)-one (13-83) (250 mg, 99% yield), which was used directly in the next step without further purification. $^1$H NMR (400 MHz, DMSO-D$_6$) δ ppm 7.41 (br s, 2H), 6.37 (d, J=12.59 Hz, 1H), 5.10 (s, 1H), 2.81-2.92 (m, 1H), 2.63-2.75 (m, 1H), 1.89-2.01 (m, 5H), 1.22 (s, 3H). $^{19}$F NMR (376 MHz, DMSO-D$_6$) δ ppm −108.05.

(1S, 9S)-9-Ethyl-5-fluoro-1,9-dihydroxy-1,4-dimethyl-2,3,12,15-tetrahydrobenzo[de]pyrano[3', 4': 6, 7]indolizino[1,2-b]quinoline-10,13(1H,9H)-dione (13-84) and (1R, 9S)-9-ethyl-5-fluoro-1,9-dihydroxy-1,4-dimethyl-2,3,12,15-tetrahydrobenzo[de]pyrano[3', 4': 6, 7]indolizino[1,2-b]quinoline-10,13 (1H,9H)-dione (13-85)

To a mixture of 8-amino-6-fluoro-2-hydroxy-2,5-dimethyl-3,4-dihydronaphthalen-1(2H)-one (13-83) (54.0 mg, 241 umol, 1.0 equiv) and (S)-4-ethyl-4-hydroxy-7,8-dihydro-1H-pyrano[3,4-f]indolizine-3,6,10(4H)-trione (1-13) (95.5 mg, 0.362 mmol, 1.5 equiv) in xylene (5.4 mL) was added 4-methylbenzenesulfonic acid (24.9 mg, 0.145 mmol, 0.6 equiv) at 120° C. under argon, the mixture was stirred at 120° C. for 24 h in a sealed tube. It was concentrated under reduced pressure, and the residue purified by silica gel flash column chromatography eluting with 60% of tetrahydrofuran in petroleum ether to give a residue, which was further separated by prep-HPLC and lyophilization to afford (1S, 9S)-9-ethyl-5-fluoro-1,9-dihydroxy-1,4-dimethyl-2,3,12,15-tetrahydrobenzo[de]pyrano[3',4':6,7]indolizino[1,2-b]quinoline-10,13(1H,9H)-dione (13-84) (70.1 mg, 13% yield) (compound 13-84 may be the opposite enantiomer of that depicted), and (1R,9S)-9-ethyl-5-fluoro-1,9-dihydroxy-1,4-dimethyl-2,3,12,15-tetrahydrobenzo[de]pyrano[3',4':6,7]indolizino[1,2-b]quinoline-10,13(1H,9H)-dione (13-85) (73.3 mg, 13% yield) (compound 13-85 may be the opposite enantiomer of that depicted). Note: the stereochemistry is arbitrarily assigned.

Prep-HPLC Method:
Instrument: Gilson 281 semi-preparative HPLC system
Mobile phase: A: H$_2$O; B: CH$_3$OH
Column: Phenomenex Luna 80*30 mm*3 um
Flow rate: 25 mL/min
Monitor wavelength: 220 & 254 nm

| Time | B % |
| --- | --- |
| 0.0 | 40 |
| 8.0 | 70 |
| 8.1 | 70 |
| 8.2 | 100 |
| 10.2 | 100 |
| 10.3 | 40 |
| 11.5 | 40 |

Spectra of 13-84: $^1$H NMR (400 MHz, DMSO-D$_6$) δ ppm 7.76 (d, J=10.88 Hz, 1H), 7.31 (s, 1H), 6.51 (s, 1H), 5.79 (br s, 1H), 5.43 (s, 4H), 3.25 (br d, J=2.57 Hz, 1H), 2.96-3.09 (m, 1H), 2.38 (s, 3H), 2.24 (br dd, J=13.08, 3.06 Hz, 1H), 2.11 (td, J=13.24, 5.69 Hz, 1H), 1.87 (m, 2H), 1.45 (s, 3H), 0.88 (t, J=7.34 Hz, 3H). $^{19}$F NMR (376 MHz, DMSO-D$_6$) δ ppm −112.10. LCMS (ESI+) m/z: [MH]$^+$ calcd for C$_{25}$H$_{24}$FN$_2$O$_5^+$: 451.1, found: 451.1. SFC: RT=1.338 min.

Spectra of 13-85: $^1$H NMR (400 MHz, DMSO-D$_6$) δ ppm 7.77 (d, J=11.00 Hz, 1H), 7.31 (s, 1H), 6.50 (s, 1H), 5.80 (br s, 1H), 5.44 (s, 4H), 3.25 (br s, 1H), 2.96-3.10 (m, 1H), 2.38 (s, 3H), 2.24 (br dd, J=12.65, 3.24 Hz, 1H), 2.12 (td, J=13.14, 5.38 Hz, 1H), 1.78-1.93 (m, 2H), 1.44 (s, 3H), 0.87 (t, J=7.27 Hz, 3H). $^{19}$F NMR (376 MHz, DMSO-D$_6$) δ ppm −112.07. LCMS (ESI+) m/z: [MH]$^+$ calcd for C$_{25}$H$_{24}$FN$_2$O$_5^+$: 451.1, found: 451.1. SFC: RT=1.453 min.

Example 14

Figure 23:
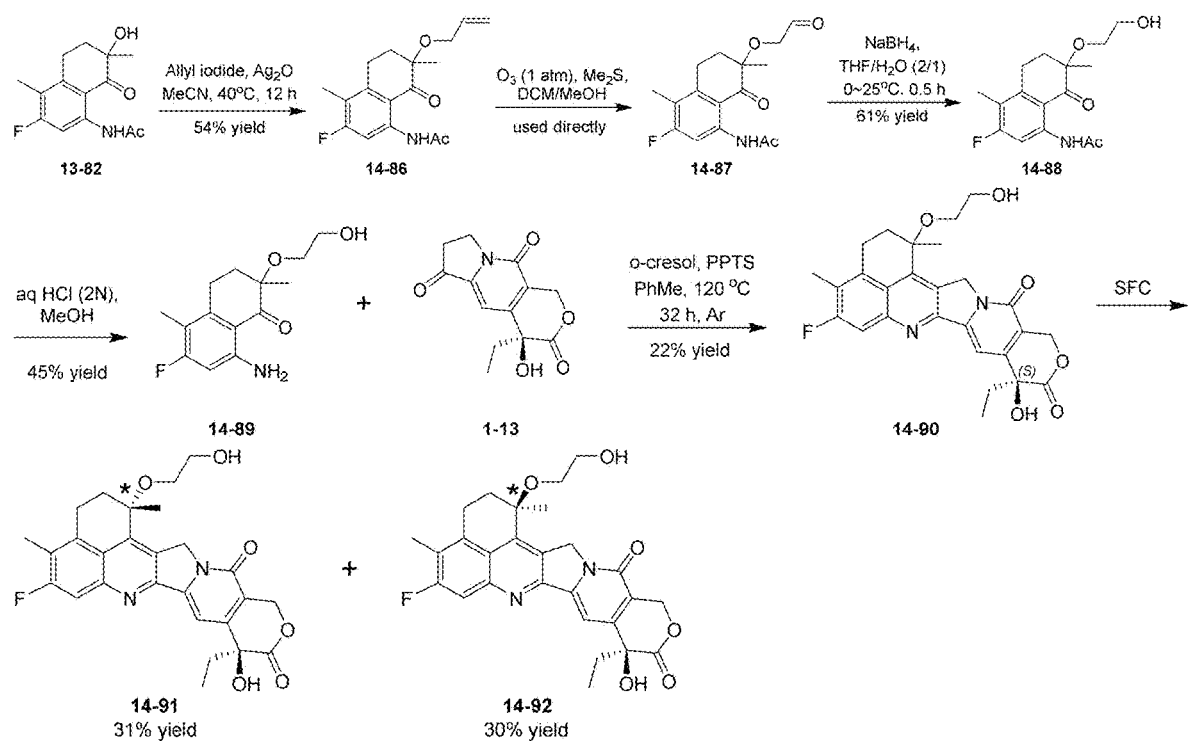
FIG. 23 illustrates a reaction scheme for making compounds 14-91 and 14-92.

(1S,9S)-9-ethyl-5-fluoro-9-hydroxy-1-(2-hydroxyethoxy)-1,4-dimethyl-2,3,12,15-tetrahydrobenzo[de]pyrano[3',4':6,7]indo-lizino[1,2-b]quinoline-10,13 (1H,9H)-dione (14-91) and (1R,9S)-9-ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H,9H)-dione (14-92) (FIG. 23)

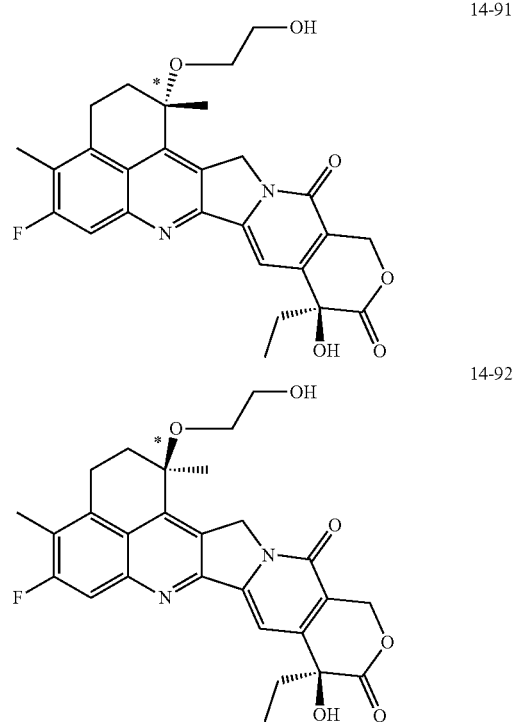

*Stereochemistry at this carbon is arbitrarily assigned.

N-(7-(Allyloxy)-3-fluoro-4,7-dimethyl-8-oxo-5,6,7,8-tetrahydronaphthalen-1-yl) acetamide (14-86)

To a mixture of N-(3-fluoro-7-hydroxy-4,7-dimethyl-8-oxo-5,6,7,8-tetrahydro-naphthalen-1-yl)acetamide (13-82)

(500 mg, 1.88 mmol, 1.0 equiv) and Ag$_2$O (4.37 g, 18.8 mmol, 10 equiv) in acetonitrile (10 mL) was added 3-iodoprop-1-ene (6.33 g, 3.44 mL, 37.7 mmol, 20 equiv) at 20° C. under argon, and the mixture was stirred at 40° C. for 12 h and cooled to 25° C. (Three additional reactions were set up as described above and four reaction mixtures were combined). The combined reaction mixtures were filtered through a pad of Celite, and the filter cake washed with dichloromethane (200 mL), combined filtrates concentrated, and the residue purified by silica gel flash column chromatography eluting with 5% ethyl acetate in petroleum ether to give N-(7-(allyloxy)-3-fluoro-4,7-dimethyl-8-oxo-5,6,7,8-tetrahydronaphthalen-1-yl)acetamide (14-86) (1.30 g, 54% yield). $^1$H NMR (400 MHz, DMSO-D$_6$) δ ppm 11.82 (s, 1H), 8.28 (d, J=13.13 Hz, 1H), 5.70-5.83 (m, 1H), 5.14 (m, 1H), 5.01 (m, 1H), 3.99 (m, 1H), 3.79 (m, 1H), 3.00 (m, 1H), 2.77-2.88 (m, 1H), 2.36 (dt, J=14.07, 5.22 Hz, 1H), 2.17 (s, 3H), 2.11 (d, J=1.63 Hz, 3H), 2.03 (m, 1H), 1.30-1.38 (m, 3H). $^{19}$F NMR (376 MHz, DMSO-D$_6$) δ ppm −104.04. LCMS (ESI+) m/z: [MH]$^+$ calcd for C$_{17}$H$_{21}$FNO$_3$$^+$: 306.1, found: 306.1.

N-(3-Fluoro-4,7-dimethyl-8-oxo-7-(2-oxoethoxy)-5,6,7,8-tetrahydronaphthalen-1-yl)acetamide (14-87)

To a stirred mixture of N-(7-(allyloxy)-3-fluoro-4,7-dimethyl-8-oxo-5,6,7,8-tetrahydro-naphthalen-1-yl)acetamide (14-86) (1.30 g, 4.17 mmol, 1.0 equiv) in dichloromethane (26 mL) and methanol (13 mL) at −78° C., was bubbled ozone over 5 min, followed by addition of dimethylsulfane (648 mg, 0.766 mL, 10.4 mmol, 2.5 equiv), the reaction mixture was warmed up to 25° C. and stirred at 25° C. for 1 h, quenched with water (40 mL) and extracted with dichloromethane (3×40 mL). The combined organic layers were washed with brine, dried over Na$_2$SO$_4$, filtered, concentrated under reduced pressure to give N-(3-fluoro-4,7-dimethyl-8-oxo-7-(2-oxoethoxy)-5,6,7,8-tetrahydronaphthalen-1-yl)acetamide (14-87) (1.20 g, crude), which was used directly in the next reaction without further purification.

N-(3-Fluoro-7-(2-hydroxyethoxy)-4,7-dimethyl-8-oxo-5,6,7,8-tetrahydronaphtha-len-1-yl)acetamide (14-88)

To a mixture of N-(3-fluoro-4,7-dimethyl-8-oxo-7-(2-oxoethoxy)-5,6,7,8-tetrahydro-naphthalen-1-yl)acetamide (14-87) (1.20 g, 2.73 mmol, 1.0 equiv) in tetrahydrofuran (30 mL) and H$_2$O (15 mL) at 0° C. was added sodium tetrahydroboride (51.7 mg, 1.37 mmol, 0.5 equiv) portion wise, the mixture was stirred at 0° C. for 10 min, warmed up to 25° C. and stirred at 25° C. for 20 min, quenched by water (30 mL) and extracted with dichloromethane (3×40 mL). The combined organic layers were washed with brine, dried over Na$_2$SO$_4$, filtered, concentrated under reduced pressure, and the residue purified by silica gel flash column chromatography eluting with 40% ethyl acetate in petroleum ether to give N-(3-fluoro-7-(2-hydroxyethoxy)-4,7-dimethyl-8-oxo-5,6,7,8-tetrahydronaphthalen-1-yl)acetamide (14-88) (800 mg, 61% yield). $^1$H NMR (400 MHz, CDCl$_3$) δ ppm 12.07 (br s, 1H), 8.46 (d, J=12.76 Hz, 1H), 3.63-3.76 (m, 2H), 3.53-3.61 (m, 1H), 3.44-3.52 (m, 1H), 3.03-3.23 (m, 1H), 2.74-2.92 (m, 1H), 2.35-2.46 (m, 1H), 2.22-2.26 (m, 3H), 2.12 (br s, 3H), 2.03-2.11 (m, 1H), 1.37-1.48 (m, 3H). $^{19}$F NMR (376 MHz, CDCl$_3$) δ ppm −101.12. LCMS (ESI+) m/z: [MH]$^+$ calcd for C$_{16}$H$_{21}$FNO$_4$$^+$: 310.1, found: 310.1.

8-Amino-6-fluoro-2-(2-hydroxyethoxy)-2,5-dimethyl-3,4-dihydronaphthalen-1(2H)-one (14-89)

To a solution of N-(3-fluoro-7-(2-hydroxyethoxy)-4,7-dimethyl-8-oxo-5,6,7,8-tetra-hydronaphthalen-1-yl)acetamide (14-88) (200 mg, 581 umol, 1.0 equiv) in methanol (8 mL) under argon was added 2 N hydrochloric acid (8 mL) at 20° C., and the mixture was stirred at 60° C. for 1 h, and cooled to 0° C. (Three additional reactions were set up as described above and four reaction mixtures were combined). The combined reaction mixtures were cooled to 0° C., pH adjusted to 8 by addition of saturated NaHCO$_3$, warmed up to 25° C., and extracted with dichloromethane (2×100 mL). The combined organic layers washed with brine, dried over Na$_2$SO$_4$, filtered, concentrated under reduced pressure, and the residue purified by silica gel flash column chromatography eluting with 40% ethyl acetate in petroleum ether to give 8-amino-6-fluoro-2-(2-hydroxyethoxy)-2,5-dimethyl-3,4-dihydronaphthalen-1(2H)-one (14-89) (310 mg, 45% yield). $^1$H NMR (400 MHz, CD$_3$OD) δ ppm 6.30 (d, J=12.26 Hz, 1H), 3.49-3.61 (m, 3H), 3.39 (m, 1H), 3.01-3.10 (m, 1H), 2.69-2.79 (m, 1H), 2.32 (m, 1H), 2.00 (d, J=2.25 Hz, 4H), 1.37 (s, 3H). $^{19}$F NMR (376 MHz, CD$_3$OD) δ ppm −108.91. LCMS (ESI+) m/z: [MH]$^+$ calcd for C$_{14}$H$_{19}$FNO$_3$$^+$: 268.1, found: 268.1.

(9S)-9-Ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H,9H)-dione (14-90)

To a mixture of 8-amino-6-fluoro-2-(2-hydroxyethoxy)-2,5-dimethyl-3,4-dihydro-naphthalen-1(2H)-one (14-89) (150 mg, 0.561 mmol, 1.0 equiv) and (S)-4-ethyl-4-hydroxy-7,8-dihydro-1H-pyrano[3,4-f]indolizine-3,6,10(4H)-trione (1-13) (162 mg, 0.617 mmol, 1.1 equiv) in toluene (7 mL) at 120° C. were added o-cresol (443 mg, 0.426 mL, 4.10 mmol, 7.3 equiv) and pyridine 4-methylbenzenesulfonate (21.1 mg, 0.084 mmol, 0.15 equiv) under argon, the mixture was stirred at 120° C. for 32 h in a seal tube and cooled to 25° C. (One additional reaction was set up as described above and two reaction mixtures were combined). The combined reaction mixtures were concentrated under reduced pressure, and the residue purified by silica gel flash column chromatography eluting with ethyl acetate to give (9S)-9-ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H, 9H)-dione (14-90) (210 mg, 22% yield). $^1$H NMR (400 MHz, DMSO-D$_6$) δ ppm 7.76 (dd, J=10.85, 3.46 Hz, 1H), 7.30 (s, 1H), 6.51 (d, J=2.15 Hz, 1H), 5.32-5.62 (m, 4H), 4.74 (q, J=5.21 Hz, 1H), 3.58-3.71 (m, 3H), 2.92-3.06 (m, 1H), 2.14-2.42 (m, 6H), 1.81-1.91 (m, 2H), 1.53 (br d, J=6.79 Hz, 3H), 0.81-0.94 (m, 3H). $^{19}$F NMR (376 MHz, DMSO-D$_6$) δ ppm −111.89. LCMS (ESI+) m/z: [MH]$^+$ calcd for C$_{27}$H$_{28}$FN$_2$O$_6$$^+$: 495.2, found: 495.2.

(1S,9S)-9-Ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H,9H)-dione (14-91) and (1R,9S)-9-ethyl-5-fluoro-9-hydroxy-1-(2-hydroxy-ethoxy)-1,4-dimethyl-2,3,12,15-tetrahydrobenzo[de]pyrano[3',4':6,7]indolizino[1,2-b]quinoline-10,13(1H,9H)-dione (14-92)

(9S)-9-ethyl-5-fluoro-9-hydroxy-1-(2-hydroxyethoxy)-1,4-dimethyl-2,3,12,15-tetra-hydrobenzo[de]pyrano[3',4':6,7]

indolizino[1,2-b]quinoline-10,13(1H,9H)-dione (14-90) (210 mg, 0.424 mmol) was dissolved in methanol and separated by chiral SFC (Instrument: Waters SFC150 preparative SFC. Column: DAICEL CHIRALPAK AD (250 mm*30 mm, 10 um); Mobile phase: A for $CO_2$ and B for ethanol; Gradient: B %=50% isocratic elution mode; Flow rate: 70 g/min; Wavelength: 220 nm; Column temperature: 40° C.; System back pressure: 120 bar) to afford (1S,9S)-9-ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H,9H)-dione (14-91) (65.1 mg, 31% yield) (compound 14-91 may be the opposite enantiomer of that depicted), and (1R,9S)-9-ethyl-5-fluoro-9-hydroxy-1-(2-hydroxyethoxy)-1,4-dimethyl-2,3,12,15-tetrahydrobenzo[de]pyrano[3',4':6,7]indolizino[1,2-b]quinoline-10,13(1H,9H)-dione (14-92) (62.5 mg, 30% yield) (compound 14-92 may be the opposite enantiomer of that depicted). Note: the stereochemistry is arbitrarily assigned.

Spectra of 14-91: $^1$H NMR (400 MHz, DMSO-$D_6$) δ ppm 7.77 (br d, J=10.88 Hz, 1H), 7.30 (s, 1H), 5.30-5.63 (m, 4H), 3.64 (br s, 3H), 3.28-3.31, (m, 2H), 2.99 (br s, 1H), 2.38 (br s, 3H), 2.33 (br s, 1H), 2.20 (br s, 1H), 1.76-1.93 (m, 2H), 1.53 (br s, 3H), 0.81-0.92 (m, 3H). $^{19}$F NMR (376 MHz, DMSO-$D_6$) δ ppm −111.87. LCMS (ESI+) m/z:
[MH]$^+$ calcd for $C_{27}H_{28}FN_2O_6^+$: 495.2, found: 495.1. Chiral SFC: RT=1.715 min.

Spectra of 14-92: $^1$H NMR (400 MHz, DMSO-$D_6$) δ ppm 7.77 (br d, J=10.88 Hz, 1H), 7.31 (s, 1H), 5.33-5.57 (m, 4H), 3.65 (br s, 3H), 3.28-3.30, (m, 2H), 2.95 (br s, 1H), 2.38 (br s, 3H), 2.33 (br s, 1H), 2.17 (br s, 1H), 1.76-1.93 (m, 2H), 1.53 (br s, 3 H), 0.84-0.92 (m, 3H). $^{19}$F NMR (376 MHz, DMSO-$D_6$) δ ppm −111.90. LCMS (ESI+) m/z: [MH]$^+$ calcd for $C_{27}H_{28}FN_2O_6^+$: 495.2, found: 495.3. Chiral SFC: RT=1.948 min.

Example 15

Figure 24:
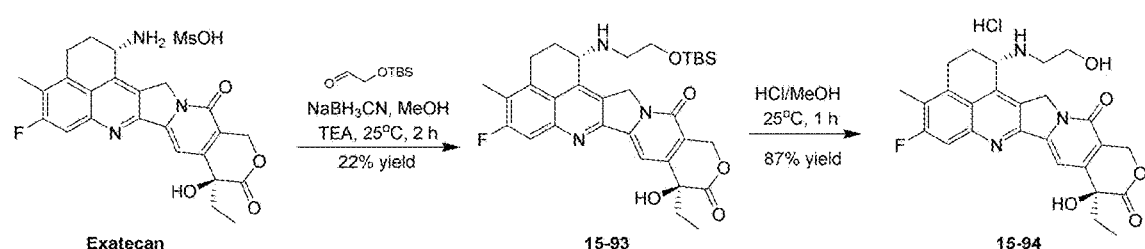
FIG. 24 illustrates a reaction scheme for making compound 15-94.

(1S,9S)-9-ethyl-5-fluoro-9-hydroxy-1-((2-hydroxyethyl)amino)-4-methyl-2,3,12,15-tetrahydrobenzo[de]pyrano[3',4':6,7]indolizino[1,2-b]quinoline-10,13(1H,9H)-dione hydrochloride (15-94) (FIG. 24)

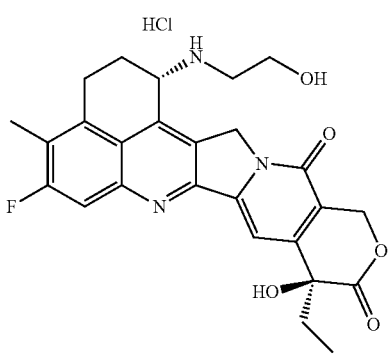

(1S,9S)-1-((2-((tert-Butyldimethylsilyl)oxy)ethyl)amino)-9-ethyl-5-fluoro-9-hydroxy-4-methyl-2,3,12,15-tetrahydrobenzo[de]pyrano[3',4':6,7]indolizino[1,2-b]quinoline-10,13(1H,9H)-dione (15-93)

A mixture of (1S,9S)-1-amino-9-ethyl-5-fluoro-9-hydroxy-4-methyl-2,3,12,15-tetrahydro-benzo[de]pyrano[3', 4':6,7]indolizino[1,2-b]quinoline-10,13(1H,9H)-dione methanesulfonate (Exatecan) (100 mg, 0.188 mmol, 1.0 equiv) and triethylamine (19.0 mg, 0.188 mmol, 1.0 equiv) in methanol (2 mL) was stirred at 25° C. for 0.5 h, followed by addition of 2-((tert-butyldimethylsilyl)oxy)acetaldehyde (32.8 mg, 0.188 mmol, 1.0 equiv). After the reaction mixture was stirred at 25° C. for 1 h, sodium cyanoborohydride (17.7 mg, 0.282 mmol, 1.5 equiv) added, and stirred at 25° C. for additional 2 h. It was quenched by addition of water (0.2 mL), diluted with dichloromethane (5 mL), dried over $Na_2SO_4$, filtered, concentrated under reduced pressure, and the residue purified by prep-HPLC to give (1S,9S)-1-((2-((tert-butyldimethyl-silyl)oxy)ethyl)amino)-9-ethyl-5-fluoro-9-hydroxy-4-methyl-2,3,12,15-tetrahydrobenzo[de]pyrano[3',4':6,7]indolizino[1,2-b]quinoline-10,13(1H,9H)-dione (15-93) (25.0 mg, 22% yield). $^1$H NMR (400 MHz, DMSO-$D_6$) δ ppm 7.74 (d, J=11.13 Hz, 1H), 7.30 (s, 1H), 6.51 (s, 1H), 5.34-5.47 (m, 4H), 4.30 (br s, 1H), 3.69 (t, J=5.93 Hz, 2H), 3.15-3.24 (m, 1H), 2.96-3.07 (m, 1H), 2.87 (br d, J=5.14 Hz, 1H), 2.73-2.82 (m, 1H), 2.37 (s, 3H), 2.22 (dd, J=13.57, 4.89 Hz, 1H), 1.99-2.14 (m, 2H), 1.87 (dt, J=17.36, 7.09 Hz, 2H), 0.87 (t, J=7.34 Hz, 3H), 0.82 (s, 9H), 0.03 (d, J=3.18 Hz, 6H). $^{19}$F NMR (400 MHz, DMSO-$D_6$) δ ppm −111.83. LCMS (ESI+) m/z: [MH]$^+$ calcd for $C_{32}H_{41}FN_3O_5Si^+$: 594.2, found: 594.2.

HPLC Method:
Instrument: Gilson 281 semi-preparative HPLC system
Mobile phase: A: 10 mM $NH_4HCO_3$ in $H_2O$; B: $CH_3CN$
Column: Waters Xbridge BEH C18 100*30 mm*10 um
Flow rate: 25 mL/min
Monitor wavelength: 220 & 254 nm

| Time | B % |
| --- | --- |
| 0.0 | 65 |
| 10.0 | 95 |
| 10.1 | 95 |
| 10.2 | 100 |
| 12.2 | 100 |
| 12.3 | 65 |
| 13.5 | 65 |

(1S,9S)-9-ethyl-5-fluoro-9-hydroxy-1-((2-hydroxyethyl)amino)-4-methyl-2,3,12,15-tetrahydrobenzo[de]pyrano[3',4':6,7]indolizino[1,2-b]quinoline-10,13(1H,9H)-dione hydrochloride (15-94)

To a mixture of (1S,9S)-1-((2-((tert-butyldimethylsilyl)oxy)ethyl)amino)-9-ethyl-5-fluoro-9-hydroxy-4-methyl-2,3,12,15-tetrahydrobenzo[de]pyrano[3',4':6,7]indolizino[1,2-b]quinoline-10,13(1H,9H)-dione (15-93) (25 mg, 0.042 mmol, 1.0 equiv) in methanol (0.5 mL) was added HCl/MeOH (2.5 mL, 4 M) dropwise at 25° C. under nitrogen, the mixture was stirred at 25° C. for 1 h, filtered, collected and dried under vacuum to give (1S,9S)-9-ethyl-5-fluoro-9-hydroxy-1-((2-hydroxyethyl)amino)-4-methyl-2,3,12,15-tetrahydrobenzo[de]pyrano[3',4':6,7]indolizino[1,2-b]quinoline-10,13(1H,9H)-dione hydrochloride (15-94) (18.0 mg, 87% yield). $^1$H NMR (400 MHz, DMSO-$D_6$) δ ppm 8.81-9.14 (m, 2H), 7.89 (d, J=10.85 Hz, 1H), 7.35 (s, 1H), 6.56 (s, 1H), 5.54-5.67 (m, 1H), 5.37-5.50 (m, 3H), 5.28 (br d, J=0.95 Hz, 1H), 5.10 (br s, 1H), 3.71 (br s, 2H), 3.09-3.26 (m, 3H), 2.79 (br d, J=13.95 Hz, 1H), 2.41 (s, 3H), 2.09-2.25 (m, 1H), 1.77-1.96 (m, 2H), 0.88 (t, J=7.33 Hz, 3H). $^{19}$F NMR (376

MHz, DMSO-D$_6$) δ ppm −110.92. LCMS (ESI+) m/z: [MH]$^+$ calcd for C$_{26}$H$_{27}$FN$_3$O$_5$$^+$: 480.2, found: 480.2.

Example 16

(1S,9S)-9-ethyl-5-fluoro-9-hydroxy-1-((2-hydroxyethyl)amino)-1,4-dimethyl-2,3,12,15-tetrahydrobenzo[de]pyrano[3',4':6,7]indolizino[1,2-b]quinoline-10,13(1H,9H)-dione hydrochloride (16-95)

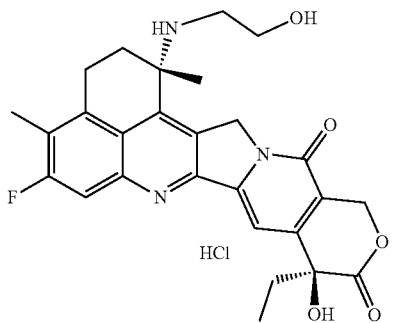

16-95

Example 16 (16-95) was made in a similar fashion to Example 15 using 8-71 instead of exatecan. $^1$H NMR (400 MHz, CD$_3$OD) δ ppm 7.82 (d, J=10.49 Hz, 1H), 7.68 (s, 1H), 5.71-5.78 (m, 1H), 5.57-5.65 (m, 2H), 5.41 (d, J=16.33 Hz, 1H), 3.74-3.84 (m, 2H), 3.35 (br s, 2H), 3.20-3.28 (m, 2H), 2.74 (dt, J=14.16, 5.80 Hz, 1H), 2.39-2.53 (m, 4H), 2.09 (s, 3H), 1.98 (qd, J=7.17, 3.99 Hz, 2H), 1.02 (t, J=7.33 Hz, 3H). $^{19}$F NMR (376 MHz, CD$_3$OD) δ ppm −111.87. LCMS (ESI+) m/z: [MH]$^+$ calcd for C$_{27}$H$_{29}$FN$_3$O$_5$$^+$: 494.2, found: 494.1.

Example 17

(1R,9S)-9-ethyl-5-fluoro-9-hydroxy-1-((2-hydroxyethyl)amino)-1,4-dimethyl-2,3,12,15-tetrahydrobenzo[de]pyrano[3',4':6,7]indolizino[1,2-b]quinoline-10,13(1H,9H)-dione hydrochloride (17-96)

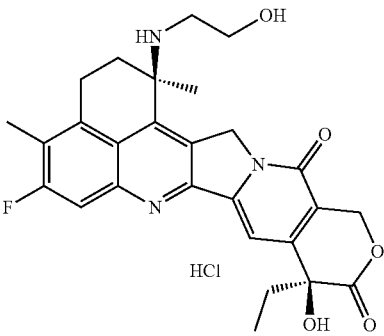

17-96

Example 17 (17-96) was made in a similar fashion to Example 15 using 8-72 instead of exatecan. $^1$H NMR (400 MHz, CD$_3$OD) δ ppm 7.82 (d, J=10.39 Hz, 1H), 7.68 (s, 1H), 5.73-5.81 (m, 1H), 5.63 (d, J=3.30 Hz, 1H), 5.58 (s, 1H), 5.42 (d, J=16.26 Hz, 1H), 3.74-3.87 (m, 2H), 3.34 (br s, 2H), 3.22-3.28 (m, 2H), 2.70-2.82 (m, 1H), 2.36-2.56 (m, 4H), 2.10 (s, 3H), 1.89-2.04 (m, 2H), 1.01 (t, J=7.34 Hz, 3H). $^{19}$F NMR (376 MHz, CD$_3$OD) δ ppm −111.90. LCMS (ESI+) m/z: [MH]$^+$ calcd for C$_{27}$H$_{29}$FN$_3$O$_5$$^+$: 494.2, found: 494.1.

Example 18

Figure 25:
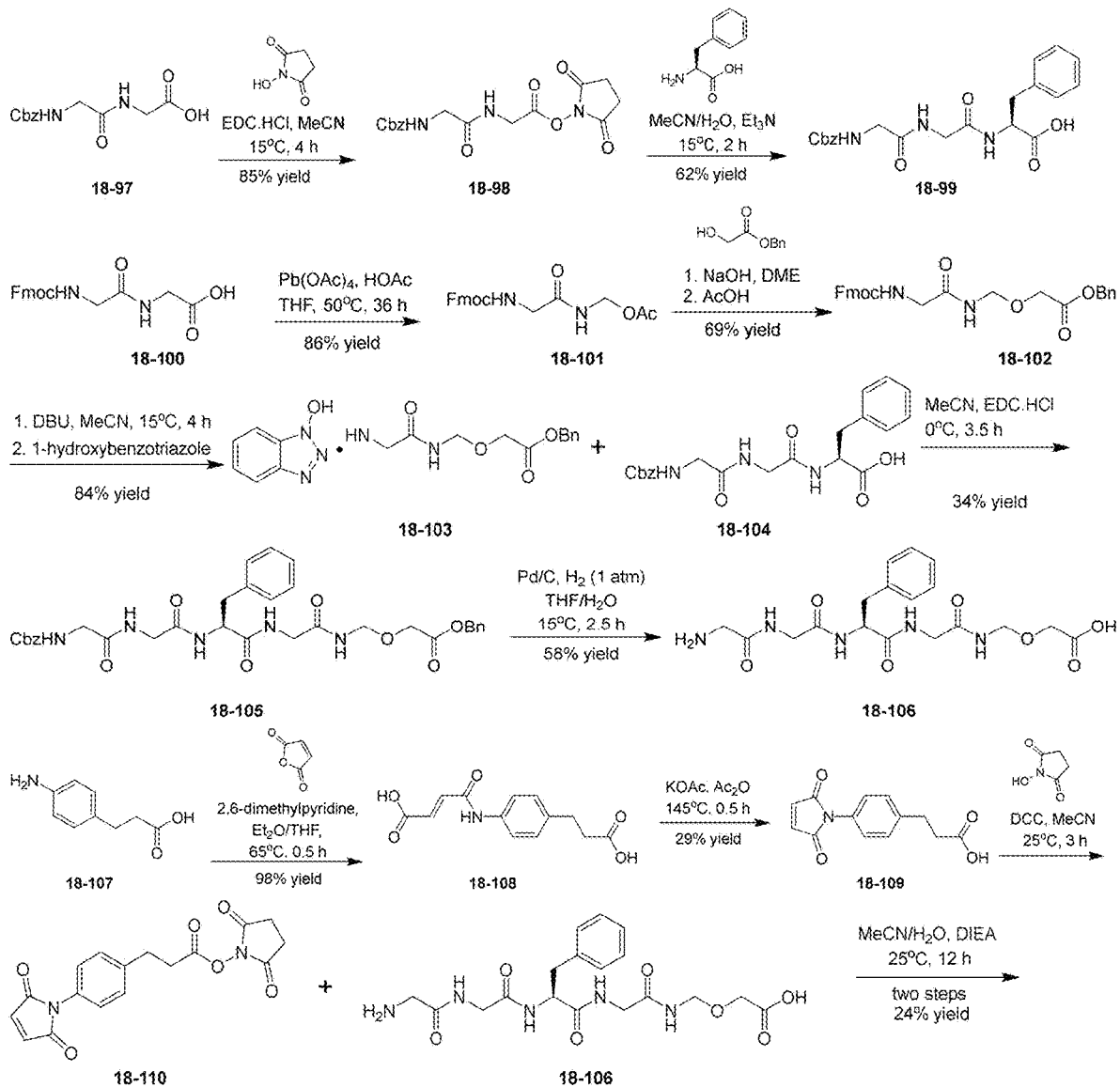
FIG. 25 illustrates a reaction scheme for making compound 18-112.
Figure 25:
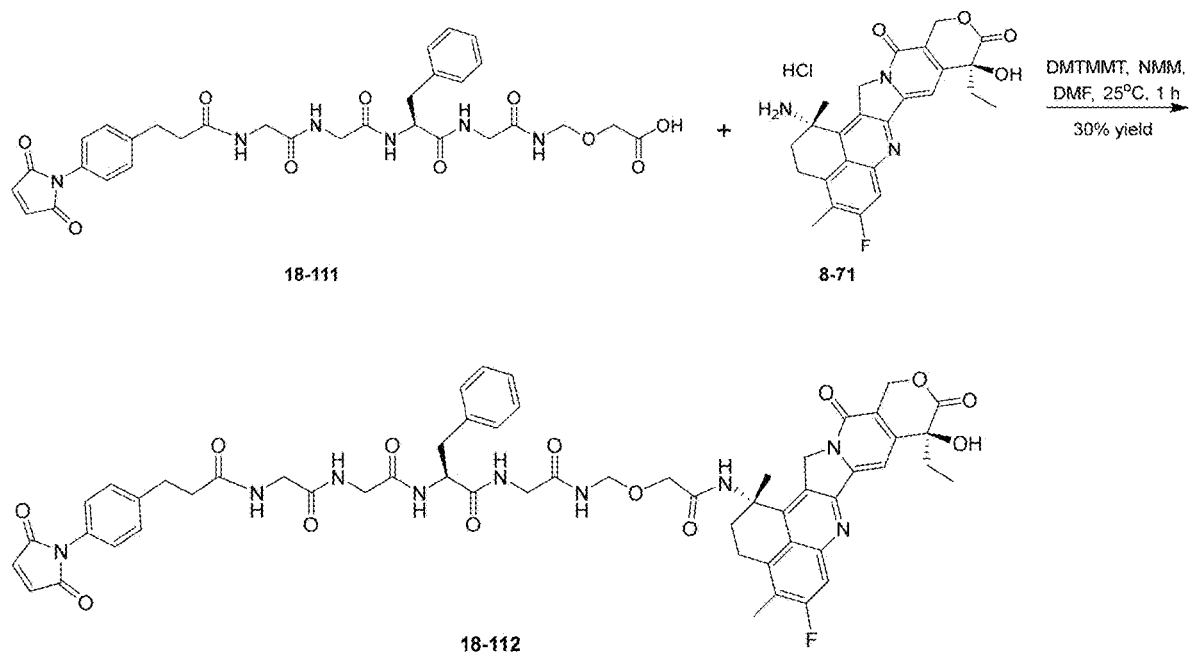

(S)-2-(2-(2-(3-(4-(2,5-dioxo-2,5-dihydro-1H-pyrrol-1-yl)phenyl)propanamido)acetamido)acetamido)-N-(2-(((2-(((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)amino)-2-oxoethoxy)methyl)amino)-2-oxoethyl)-3-phenylpropanamide (18-112) (FIG. 25)

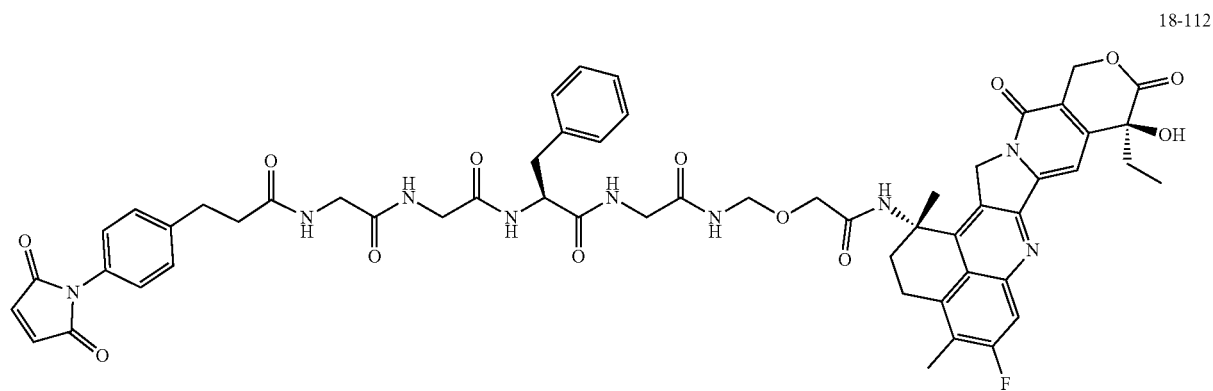 [SMILES: CC[C@@]1(O)C(=O)OCc2c1cc1n(c2=O)Cc2c-1nc1cc(F)c(C)c3c1c2[C@@](C)(NC(=O)COCNC(=O)CNC(=O)[C@H](Cc1ccccc1)NC(=O)CNC(=O)CNC(=O)CCc1ccc(N2C(=O)C=CC2=O)cc1)CC3]

18-112

2, 5-Dioxopyrrolidin-1-yl 2-(2-(((benzyloxy)carbonyl)amino)acetamido)acetate (18-98)

To a mixture of 2-[[2-(benzyloxycarbonylamino)acetyl]amino]acetic acid (18-97) (55.0 g, 206 mmol, 1.0 equiv) in acetonitrile (550 mL) were added 1-hydroxypyrrolidine-2,5-dione (26.1 g, 227 mmol, 1.1 equiv) and $N^1$-((ethylimino)methylene)-$N^3$,$N^3$-dimethylpropane-1,3-diamine hydrochloride (47.5 g, 247 mmol, 1.2 equiv), the mixture was stirred at 25° C. for 4 h, cooled to −10° C. and white material formed. The suspension was diluted with water (50 mL), stirred, filtered, and the filter cake dried under vacuum to give 2, 5-dioxopyrrolidin-1-yl 2-(2-(((benzyloxy)carbonyl)amino)acetamido)acetate (18-98) (85.0 g, 175 mmol, 85% yield), which was used directly in next step without purification. $^1$H NMR (400 MHz, DMSO-$d_6$) δ ppm 2.81 (s, 4H), 2.93-3.12 (m, 2H), 3.69 (d, J=6.11 Hz, 2H), 4.27 (d, J=5.87 Hz, 2H), 5.04 (s, 2H), 7.24-7.45 (m, 5H), 7.57 (t, J=6.11 Hz, 1H), 8.58 (t, J=5.87 Hz, 1H). LCMS (ESI+) m/z: [MH]$^+$ calcd for $C_{16}H_{18}N_3O_7^+$: 364.1, found: 364.1.

(S)-11-Benzyl-3,6,9-trioxo-1-phenyl-2-oxa-4,7,10-triazadodecan-12-oic acid (18-99)

To a mixture of 2, 5-dioxopyrrolidin-1-yl 2-(2-(((benzyloxy)carbonyl)amino)acetamido)acetate (18-98) (85.0 g, 175 mmol, 1.0 equiv) in acetonitrile (425 mL) and $H_2O$ (425 mL) were added (2S)-2-amino-3-phenyl-propanoic acid (34.7 g, 210 mmol, 1.2 equiv) and trimethylamine (26.8 mL, 193 mmol, 1.1 equiv), the mixture was stirred at 25° C. for 2 h, cooled to 0° C., hydrochloric acid (12 M, 16.2 mL, 1.1 equiv) added and stirred at 0° C. for 6 h. The resulting suspension was warmed up to 25° C., filtered and the filter cake dried under vacuum to give (S)-11-benzyl-3,6,9-trioxo-1-phenyl-2-oxa-4,7,10-triazadodecan-12-oic acid (18-99) (50.0 g, 108 mmol, 62% yield), which was used directly in next step without further purification. $^1$H NMR (400 MHz, DMSO-$d_6$) δ ppm 2.59 (s, 1H), 2.88 (dd, J=13.77, 9.00 Hz, 1H), 3.04-3.11 (m, 1H), 3.60-3.79 (m, 4H), 4.43 (td, J=8.43, 5.19 Hz, 1H), 5.03 (s, 2H), 7.15-7.40 (m, 10H), 7.50 (t, J=6.02 Hz, 1H), 8.04 (br t, J=5.60 Hz, 1H), 8.16 (d, J=8.11 Hz, 1H), 12.72 (br d, J=5.01 Hz, 1H). LCMS (ESI+) m/z: [MH]$^+$ calcd for $C_{21}H_{24}N_3O_6^+$: 414.2, found: 414.2.

(2-((((9H-fluoren-9-yl)methoxy)carbonyl)amino)acetamido)methyl acetate (18-101)

To a mixture of 2-[[2-(9H-fluoren-9-ylmethoxycarbonylamino)acetyl]amino]acetic acid (18-100) (100 g, 282 mmol, 1.0 equiv) in tetrahydrofuran (1.5 L) and acetic acid (300 mL) was added lead tetraacetate (150 g, 338 mmol, 1.2 equiv), the mixture was stirred at 50° C. for 36 h, cooled to 25° C., and filtered. The filtrate was washed with aqueous trisodium citrate dihydrate solution (2.5 L, 20% wt) twice, organic phase concentrated to about 2.0 L, water (2.5 L) added, and the mixture stirred at 5° C. for 2 h. The formed precipitates were filtered, washed with a mixture of cold (5° C.) tetrahydrofuran and water (3:10, 1.2 L), and dried under vacuum to give (2-((((9H-fluoren-9-yl)methoxy)carbonyl)amino)acetamido)methyl acetate (18-101) (100 g, 86% yield). $^1$H NMR (400 MHz, CDCl$_3$) δ ppm 2.09 (s, 3H), 3.90 (d, J=5.01 Hz, 2H), 4.19-4.28 (m, 1H), 4.41-4.52 (m, 2H), 5.25 (d, J=6.97 Hz, 2H), 5.41-5.60 (m, 1H), 7.17-7.27 (m, 1H), 7.29-7.36 (m, 2H), 7.41 (t, J=7.40 Hz, 2H), 7.55-7.64 (m, 2H), 7.77 (d, J=7.58 Hz, 2H). LCMS (ESI+) m/z: [MNa]$^+$ calcd for $C_{20}H_{20}N_2O_5Na^+$: 391.1, found: 391.1.

Benzyl 1-(9H-fluoren-9-yl)-3,6-dioxo-2,9-dioxa-4,7-diazaundecan-11-oate (18-102)

To a mixture of (2-((((9H-fluoren-9-yl)methoxy)carbonyl)amino)acetamido)methyl acetate (18-101) (80.0 g, 173 mmol, 1.0 equiv) in 1,2-dimethoxyethane (1.5 L) was added benzyl 2-hydroxyacetate (57.7 g, 49.3 mL, 347 mmol, 2.0 equiv), cooled to 0° C. acetic acid (5.22 g, 86.8 mmol, 4.97 mL, 0.5 equiv) added. The mixture was stirred at 0° C. for 1 h, sodium hydroxide (10 N, 17.3 mL, 1.0 equiv) added dropwise and stirred at 0° C. for 1 h, water (1.2 L) added and stirred at 0° C. for 2 h. The white precipitates formed was filtered, washed with cold (5° C.) 1,2-dimethoxyethane:water (1:2, 500 mL) and methyl tert-butyl ester (500 mL), and dried under vacuum at 40° C. to give benzyl 1-(9H-fluoren-9-yl)-3,6-dioxo-2,9-dioxa-4,7-diazaundecan-11-oate (18-102) (60.0 g, 69% yield). $^1$H NMR (400 MHz, CDCl$_3$) δ ppm 3.82 (d, J=5.26 Hz, 2H), 4.16-4.29 (m, 3H), 4.45 (d, J=6.80 Hz, 2H), 4.83 (d, J=7.02 Hz, 2H), 5.16 (s, 2H), 5.45 (t, J=5.59 Hz, 1H), 7.08 (s, 1H), 7.28-7.48 (m, 9H), 7.59 (d, J=7.23 Hz, 2H), 7.77 (d, J=7.45 Hz, 2H). LCMS (ESI+) m/z: [MNa]$^+$ calcd for $C_{27}H_{26}N_2O_6Na^+$: 497.2, found: 497.1.

Benzyl 2-((2-aminoacetamido)methoxy)acetate·HOBT salt (18-103)

To a mixture of benzyl 1-(9H-fluoren-9-yl)-3,6-dioxo-2,9-dioxa-4,7-diazaundecan-11-oate (18-102) (60.0 g, 126 mmol, 1.0 equiv) in acetonitrile (1.08 L) was added DBU (9.53 mL, 63.2 mmol, 0.5 equiv) at 0° C. The mixture was stirred at 25° C. for 4 h, cooled to 0° C., HOBt (34.1 g, 252 mmol, 2.0 equiv) added and stirred at 0° C. for 1.5 h. It was warmed up to 25° C., filtered, the filter cake washed with cold (5° C.) acetonitrile (200 mL), and dried under vacuum to give benzyl 2-((2-aminoacetamido)methoxy)acetate·HOBt (18-103) (46.0 g, 84% yield). $^1$H NMR (400 MHz, METHANOL-$d_4$) δ ppm 3.68 (s, 2H), 4.21 (s, 2H), 4.79 (s, 2H), 5.18 (s, 2H), 7.22-7.42 (m, 7H), 7.62-7.74 (m, 2H). LCMS (ESI−) m/z: [MH]$^-$ calcd for $C_{18}H_{33}N_5O_6^-$: 269.1, found: 269.0.

(S)-Benzyl 11-benzyl-3,6,9,12,15-pentaoxo-1-phenyl-2,18-dioxa-4,7,10,13,16-pentaazaicosan-20-oate (18-105)

To a mixture of benzyl 2-((2-aminoacetamido)methoxy)acetate·HOBt (18-103) (46.0 g, 118 mmol, 1.0 equiv) in acetonitrile (500 mL) were added (S)-11-benzyl-3,6,9-trioxo-1-phenyl-2-oxa-4,7,10-triazadodecan-12-oic acid (18-104) (45.0 g, 108 mmol, 0.9 equiv) and $N^1$-((ethylimino)methylene)-$N^3$,$N^3$-dimethylpropane-1,3-diamine hydrochloride (25.5 g, 133 mmol, 1.1 equiv) at 0° C. The mixture was stirred at 0° C. for 3.5 h, water (200 mL) added and stirred at 0° C. for 2 h. The precipitates formed were filtered, washed with cold (5° C.) acetonitrile:water (1:2, 201 mL) and dried under vacuum to give (S)-benzyl 11-benzyl-3,6,9,12,15-pentaoxo-1-phenyl-2,18-dioxa-4,7,10,13,16-pentaazaicosan-20-oate (18-105) (30.0 g, 34% yield). $^1$H NMR (400 MHz, DMSO-$d_6$) δ ppm 2.79 (dd, J=13.67, 9.92 Hz, 1H), 3.06 (dd, J=13.67, 4.41 Hz, 1H), 3.56-3.66 (m, 3H), 3.69-3.81 (m, 3H), 4.15 (s, 2H), 4.51 (td, J=8.76, 4.52 Hz, 1H), 4.63 (d, J=6.62 Hz, 2H), 5.03 (s, 2H) 5.13-5.17 (m, 2H), 7.03-7.46 (m, 15H), 7.49-7.55 (m, 1H), 8.00-8.10 (m, 1H), 8.18 (d, J=7.94 Hz, 1H), 8.36 (t, J=5.62 Hz, 1H), 8.62 (t, J=6.73 Hz, 1H).

(S)-16-Amino-10-benzyl-6,9,12,15-tetraoxo-3-oxa-5,8,11,14-tetraazahexadecan-1-oic acid (18-106)

To a mixture of (S)-benzyl 11-benzyl-3,6,9,12,15-pentaoxo-1-phenyl-2,18-dioxa-4,7,10,13,16-pentaazaicosan-20-oate (18-105) (10.0 g, 15.4 mmol, 1.0 equiv) in tetrahydrofuran (210 mL) and $H_2O$ (140 mL) was added Pd/C (10 wt %) (4.40 g, 1.2 equiv) at 25° C. under argon, the suspension was vacuumed and filled with $H_2$ three times, and stirred under $H_2$ (15 psi) at 25° C. for 2.5 h. Upon replacing $H_2$ atmosphere with argon, it was filtered through a pad of Celite, and the filter cake washed with water (80 mL) and ethanol (150 mL). The filtrate was concentrated to about 30 mL, ethanol (120 mL) was added, and the mixture stirred at 0° C. for 2 h. The precipitates formed was collected by filtration, washed with ethanol (30 mL), and dried under vacuum to give (S)-16-amino-10-benzyl-6,9,12,15-tetraoxo-3-oxa-5,8,11,14-tetraazahexadecan-1-oic acid (18-106) (4.00 g, 58% yield). $^1$H NMR (400 MHz, $D_2O$) δ ppm 2.88-3.26 (m, 2H), 3.64-4.16 (m, 8H), 4.55-4.71 (m, 3H), 7.11-7.50 (m, 5H). LCMS (ESI-) m/z: [MH]$^-$ calcd for $C_{18}H_{24}N_5O_7^-$: 422.2, found: 422.1.

(E)-4-((4-(2-Carboxyethyl)phenyl)amino)-4-oxobut-2-enoic acid (18-108)

To a mixture of furan-2,5-dione (4.16 g, 42.3 mmol, 1.0 equiv) in ether (42 mL) was added a solution of 3-(4-aminophenyl)propanoic acid (18-107) (7.00 g, 42.3 mmol, 1.0 equiv) and 2,6-dimethylpyridine (4.58 g, 4.98 mL, 42.3 mmol, 1.0 equiv) in tetrahydrofuran (70 mL) at 25° C. The reaction mixture was stirred at 65° C. for 0.5 h, cooled to 25° C., filtered, the filter cake washed with methyl tert-butyl ether (150 mL), and dried under vacuum to give (E)-4-((4-(2-carboxyethyl)phenyl)amino)-4-oxobut-2-enoic acid (18-108) (11.0 g, 98% yield). $^1$H NMR (400 MHz, DMSO-$d_6$) δ ppm 12.12-13.09 (m, 2H), 10.37 (s, 1H), 7.52 (d, J=8.4 Hz, 2H), 7.18 (d, J=8.4 Hz, 2H), 6.46 (d, J=12.0 Hz, 1H), 6.30 (d, J=12.0 Hz, 1H), 2.78 (t, J=7.6 Hz, 2H), 2.52 (s, 2H). LCMS (ESI-) m/z: [M-H]$^-$ calcd for $C_{13}H_{12}NO_5^-$: 262.0, found: 261.9.

3-(4-(2,5-Dioxo-2,5-dihydro-1H-pyrrol-1-yl)phenyl)propanoic acid (18-109)

To a mixture of (E)-4-((4-(2-carboxyethyl)phenyl)amino)-4-oxobut-2-enoic acid (18-108) (11.0 g, 41.7 mmol, 1.0 equiv) in acetic anhydride (100 mL) was added potassium;acetate (2.26 g, 22.9 mmol, 0.55 equiv) under nitrogen. The suspension was vacuumed and filled with nitrogen three times, stirred at 145° C. for 0.5 h, cooled to 20° C. and concentrated under reduced pressure. The residue was diluted with ethyl acetate (300 mL), washed with brine, dried over $Na_2SO_4$, filtered, concentrated, and the residue purified by silica gel flash column chromatography eluting with 33%-100% of ethyl acetate in petroleum ether containing 20% tetrahydrofuran to give 3-(4-(2,5-dioxo-2,5-dihydro-1H-pyrrol-1-yl)phenyl)propanoic acid (18-109) (3.60 g, 29% yield). $^1$H NMR (400 MHz, DMSO-$d_6$) δ ppm 12.16 (s, 1H), 7.33 (d, J=8.4 Hz, 2H), 7.20-7.24 (m, 2H), 7.16 (s, 2H), 2.86 (t, J=7.6 Hz, 2H), 2.57 (t, J=7.6 Hz, 2H). LCMS (ESI-) m/z: [M-H]-calcd for $C_{13}H_{10}NO_4^-$: 244.0, found: 243.9.

2,5-Dioxopyrrolidin-1-yl 3-(4-(2,5-dioxo-2,5-dihydro-1H-pyrrol-1-yl)phenyl)propanoate (18-110)

To a mixture of 3-(4-(2,5-dioxo-2,5-dihydro-1H-pyrrol-1-yl)phenyl)propanoic acid (18-109) (3.60 g, 14.6 mmol, 1.0 equiv) in acetonitrile (72 mL) were added 1-hydroxypyrrolidine-2,5-dione (1.77 g, 15.4 mmol, 1.05 equiv) and N,N'-methanediylidenedicyclohexanamine (3.18 g, 15.4 mmol, 1.05 equiv). The reaction mixture was stirred at 25° C. for 3 h, filtered, the filtrate containing 2,5-dioxopyrrolidin-1-yl 3-(4-(2,5-dioxo-2,5-dihydro-1H-pyrrol-1-yl)phenyl) propanoate (18-110) was used directly in the next step without work up and purification. LCMS (ESI+) m/z: [MH]$^+$ calcd for $C_{17}H_{15}N_2O_6^+$: 343.1, found: 343.1.

(S)-10-Benzyl-20-(4-(2,5-dioxo-2,5-dihydro-1H-pyrrol-1-yl)phenyl)-6,9,12,15,18-pentaoxo-3-oxa-5,8,11,14,17-pentaazaicosan-1-oic acid (18-111)

To a mixture of 2,5-dioxopyrrolidin-1-yl 3-(4-(2,5-dioxo-2,5-dihydro-1H-pyrrol-1-yl)phenyl)propanoate (18-110) (1.62 g, 4.72 mmol, 1.0 equiv) in acetonitrile (80 mL) was added a solution of (S)-16-amino-10-benzyl-6,9,12,15-tetraoxo-3-oxa-5,8,11,14-tetraazahexadecan-1-oic acid (18-106) (2.00 g, 4.72 mmol, 1.0 equiv) and N-ethyl-N-isopropylpropan-2-amine (0.658 mL, 3.78 mmol, 0.8 equiv) in $H_2O$ (20 mL) at 25° C. The reaction mixture was stirred at 25° C. for 12 h, filtered, concentrated and the residue purified by prep-HPLC to give (S)-10-benzyl-20-(4-(2,5-dioxo-2,5-dihydro-1H-pyrrol-1-yl)phenyl)-6,9,12,15,18-pentaoxo-3-oxa-5,8,11,14,17-pentaazaicosan-1-oic acid (18-111) (0.78 g, 24% yield). $^1$H NMR (400 MHz, DMSO-d$_6$) δ ppm 8.53-8.64 (m, 1H), 8.31 (t, J=5.6 Hz, 1H), 8.23 (t, J=5.6 Hz, 1H), 8.16 (d, J=8.0 Hz, 1H), 8.08 (t, J=5.2 Hz, 1H), 7.14-7.38 (m, 11H), 4.61 (d, J=6.8 Hz, 2H), 4.44-4.55 (m, 1H), 3.97 (s, 2H), 3.64-3.80 (m, 5H), 3.63 (d, J=5.6 Hz, 1H), 3.06 (dd, J=13.6, 4.4 Hz, 1H), 2.78-2.89 (m, 3H), 2.53-2.60 (m, 1H). LCMS (ESI−) m/z: [MH]$^-$ calcd for C$_{31}$H$_{33}$N$_6$O$_{10}$$^-$: 649.2, found: 649.3.

Prep-HPLC Condition:
Instrument: Gilson 281 semi-preparative HPLC system
Mobile phase: A: H$_2$O; B: ACN
Column: Agela DuraShell C18 250*70 mm*10 um
Flow rate: 130 mL/min
Monitor wavelength: 220 & 254 nm

| Time | B % |
| --- | --- |
| 0.0 | 10 |
| 20.0 | 40 |
| 20.1 | 40 |
| 20.2 | 100 |
| 26.2 | 100 |
| 26.3 | 10 |
| 27.5 | 10 |

(S)-2-(2-(2-(3-(4-(2,5-dioxo-2,5-dihydro-1H-pyrrol-1-yl)phenyl)propanamido)acetamido) acetamido)-N-(2-(((2-(((1S,9S)-9-ethyl-5-fluoro-9-hydroxy-1,4-dimethyl-10,13-dioxo-1,2,3,9, 10,12,13,15-octahydrobenzo[de]pyrano[3',4':6,7]indolizino[1,2-b]quinolin-1-yl)amino)-2-oxoethoxy)methyl)amino)-2-oxoethyl)-3-phenylpropanamide (18-112)

A mixture of (S)-10-benzyl-20-(4-(2,5-dioxo-2,5-dihydro-1H-pyrrol-1-yl)phenyl)-6,9,12,15,18-pentaoxo-3-oxa-5,8,11,14,17-pentaazaicosan-1-oic acid (18-111) (246 mg, 0.378 mmol, 1.0 equiv), (1S,9S)-1-amino-9-ethyl-5-fluoro-9-hydroxy-1,4-dimethyl-2,3,12,15-tetrahydrobenzo[de] pyrano[3',4':6,7]indolizino[1,2-b]quinoline-10,13(1H,9H)-dione hydrochloride (8-71) (170 mg, 0.378 mmol, 1.0 equiv), 4-(4,6-dimethoxy-1,3,5-triazin-2-yl)-4-methylmorpholin-4-ium tetrafluoroborate (124 mg, 0.378 mmol, 1.0 equiv) and 4-methylmorpholine (0.166 mL, 1.51 mmol, 4.0 equiv) in N,N-dimethylformamide (5 mL) was stirred at 25° C. for 1 h. The mixture was filtered and the filtrate purified by prep-HPLC to give (S)-2-(2-(2-(3-(4-(2,5-dioxo-2,5-dihydro-1H-pyrrol-1-yl)phenyl)propanamido)acetamido)acetamido)-N-(2-(((2-((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)amino)-2-oxoethoxy)methyl)amino)-2-oxoethyl)-3-phenylpropanamide (18-112) (130 mg, 30% yield). $^1$H NMR (400 MHz, DMSO-d$_6$) δ ppm 8.39 (s, 1H), 8.32-8.37 (m, 1H), 8.12-8.22 (m, 2H), 8.04 (t, J=5.6 Hz, 1H), 7.78 (d, J=10.8 Hz, 1H), 7.26-7.34 (m, 3H), 7.18-7.26 (m, 6H), 7.16 (s, 2H), 6.51 (s, 1H), 5.28-5.50 (m, 3H), 4.92 (d, J=18.8 Hz, 1H), 4.67 (d, J=6.8 Hz, 2H), 4.51 (d, J=4.0 Hz, 1H), 3.90-4.05 (m, 2H), 3.64-3.83 (m, 5H), 3.62 (d, J=5.6 Hz, 1H), 3.21-3.27 (m, 1H), 3.00-3.13 (m, 2H), 2.89-2.99 (m, 1H), 2.76-2.87 (m, 3H), 2.46 (s, 3H), 2.38 (s, 3H), 1.75-2.01 (m, 3H), 1.58 (s, 3H), 0.87 (t, J=7.2 Hz, 3H). $^{19}$F NMR (376 MHz, DMSO-d$_6$) δ ppm −111.87. LCMS (ESI+) m/z: [MH]$^+$ calcd for C$_{56}$H$_{57}$FN$_9$O$_{13}$$^+$: 1082.4, found: 1082.3.

Prep-HPLC Condition:
Instrument: Gilson 281 semi-preparative HPLC system
Mobile phase: A: H$_2$O; B: ACN
Column: Phenomenex C18 75*30 mm*3 um
Flow rate: 25 mL/min
Monitor wavelength: 220 & 254 nm

| Time | B % |
| --- | --- |
| 0.0 | 20 |
| 8.0 | 50 |
| 8.1 | 50 |
| 8.2 | 100 |
| 10.2 | 100 |
| 10.3 | 20 |
| 11.5 | 20 |

Example 19

N—((S)-10-benzyl-1-(((1S,9S)-9-ethyl-5-fluoro-9-hydroxy-1,4-dimethyl-10,13-dioxo-1,2,3,9,10,12,13,15-octahydrobenzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-3-(2,5-dioxo-2,5-dihydro-1H-pyrrol-1-yl)benzamide (19-113)

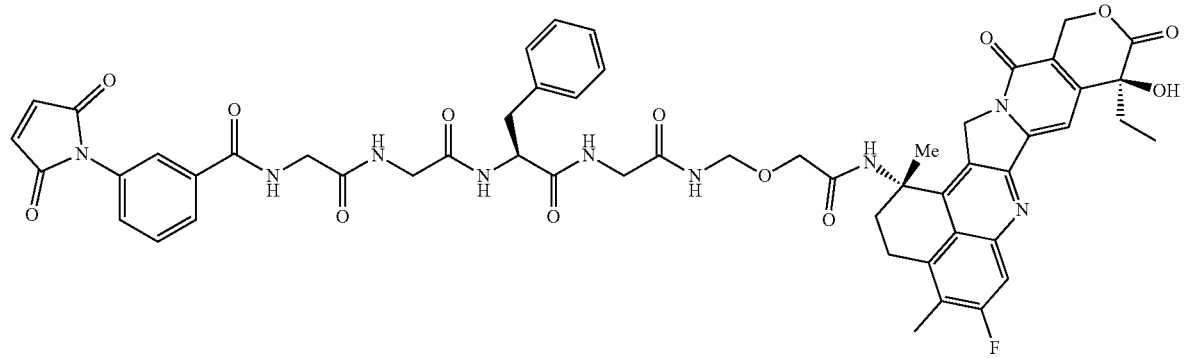

19-113

Example 19 (19-113) was made in a similar fashion to Example 18 (18-112). $^1$H NMR (400 MHz, DMSO-d$_6$) δ ppm 8.87 (t, J=5.6 Hz, 1H), 8.69 (t, J=6.4 Hz, 1H), 8.32-8.41 (m, 2H), 8.10-8.19 (m, 2H), 7.90 (d, J=7.6 Hz, 1H), 7.83-7.86 (m, 1H), 7.78 (d, J=10.8 Hz, 1H), 7.55-7.61 (m, 1H), 7.48-7.53 (m, 1H), 7.31 (s, 1H), 7.18-7.26 (m, 6H), 7.13-7.18 (m, 1H), 6.51 (s, 1H), 5.30-5.47 (m, 3H), 4.92 (d, J=18.8 Hz, 1H), 4.67 (d, J=7.2 Hz, 2H), 4.51 (dd, J=8.0, 4.4 Hz, 1H), 3.84-4.04 (m, 4H), 3.71-3.83 (m, 3H), 3.54-3.68 (m, 1H), 3.25 (s, 1H), 2.88-3.15 (m, 3H), 2.82 (dd, J=13.6, 9.6 Hz, 1H), 2.38 (s, 3H), 1.73-2.04 (m, 3H), 1.58 (s, 3H), 0.87 (t, J=7.2 Hz, 3H). $^{19}$F NMR (376 MHz, DMSO-d$_6$) δ ppm −111.87. LCMS (ESI+) m/z: [MH]$^+$ calcd for $C_{54}H_{53}FN_9O_{13}^+$: 1054.3, found: 1054.3.

Example 20

N—((S)-10-benzyl-1-(((1S,9S)-9-ethyl-5-fluoro-9-hydroxy-1,4-dimethyl-10,13-dioxo-1,2,3,9,10,12,13, 15-octahydrobenzo[de]pyrano[3',4':6,7]indolizino[1, 2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide (20-114)

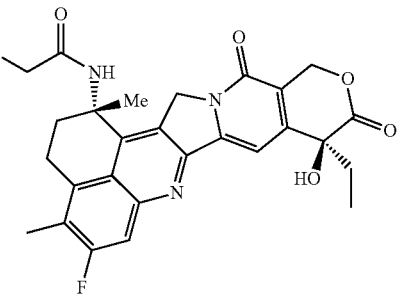

20-114

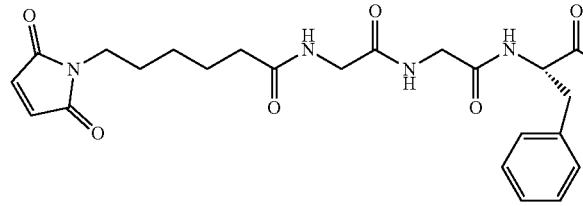

Example 20 (20-114) was made in a similar fashion to Example 18 (18-112). $^1$H NMR (400 MHz, DMSO-d$_6$) δ ppm 8.69 (t, J=6.4 Hz, 1H), 8.39 (s, 1H), 8.34 (J=5.6 Hz, 1H), 8.14 (d, J=8.0 Hz, 1H), 8.04 (t, J=5.6 Hz, 1H), 7.99 (t, J=5.6 Hz, 1H), 7.78 (d, J=10.8 Hz, 1H), 7.31 (s, 1H), 7.20-7.28 (m, 4H), 7.14-7.20 (m, 1H), 6.98 (s, 2H), 6.51 (s, 1H), 5.35-5.48 (m, 3H), 4.92 (d, J=18.8 Hz, 1H), 4.67 (d, J=6.8 Hz, 2H), 4.46-4.54 (m, 1H), 3.90-4.04 (m, 2H), 3.70-3.85 (m, 3H), 3.55-3.67 (m, 3H), 3.33-3.38 (m, 2H), 3.26 (d, J=2.0 Hz, 1H), 2.87-3.11 (m, 3H), 2.81 (dd, J=13.6, 9.6 Hz, 1H), 2.39 (s, 3H), 2.08 (t, J=7.6 Hz, 2H), 1.76-2.01 (m, 3H), 1.58 (s, 3H), 1.40-1.51 (m, 4H), 1.12-1.23 (m, 2H), 0.87 (t, J=7.2 Hz, 3H). $^{19}$F NMR (376 MHz, DMSO-d$_6$) δ ppm −111.88. LCMS (ESI+) m/z: [MH]$^+$ calcd for $C_{53}H_{59}FN_9O_{13}^+$: 1048.4, found: 1048.5.

Example 21

Figure 26:
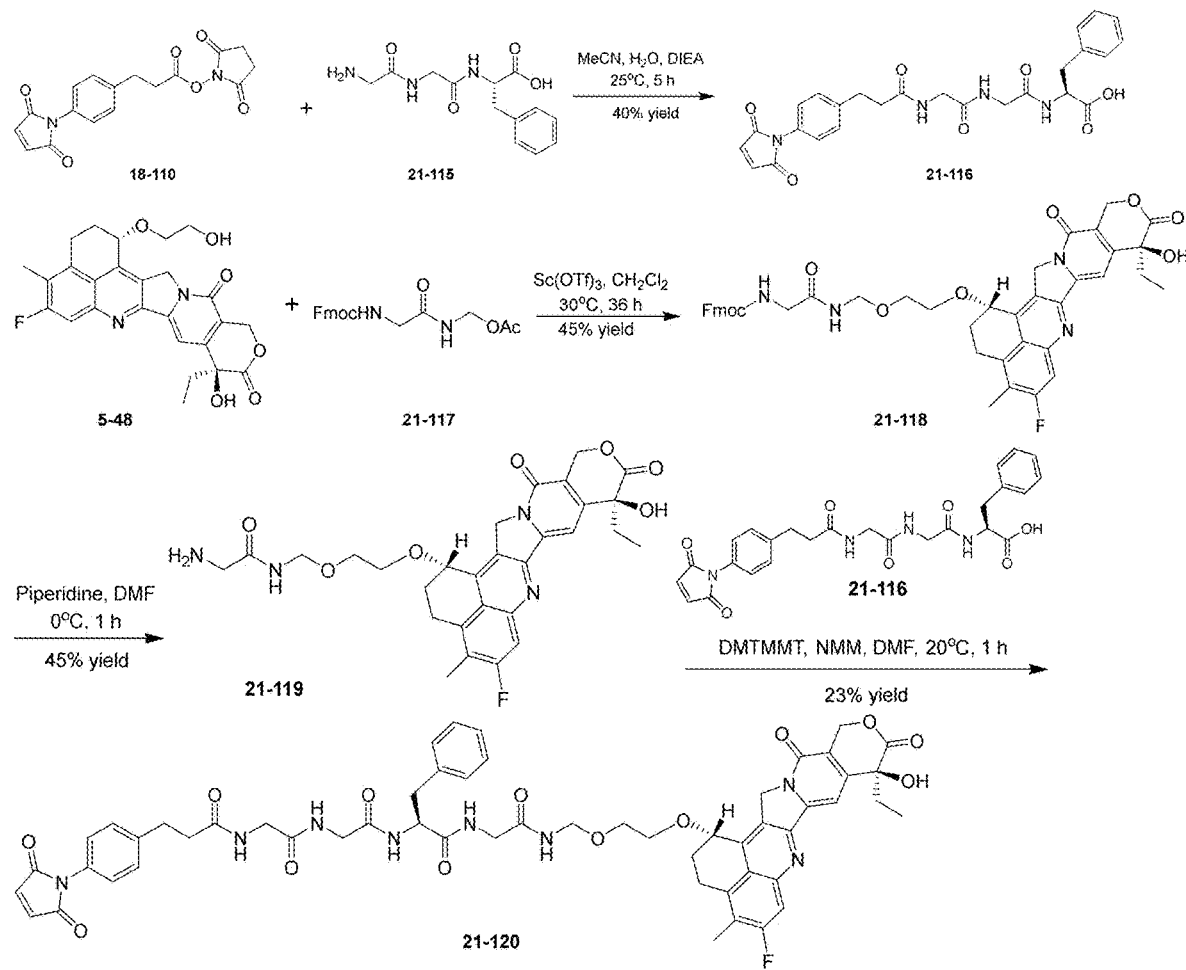
FIG. 26 illustrates a reaction scheme for making compound 21-120.

(S)-2-(2-(2-(3-(4-(2,5-dioxo-2,5-dihydro-1H-pyrrol-1-yl)phenyl)propanamido)acetamido)acetamido)-N-(2-(((2-(((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)oxy)ethoxy)methyl)amino)-2-oxoethyl)-3-phenylpropanamide (21-120) (FIG. 26)

21-120

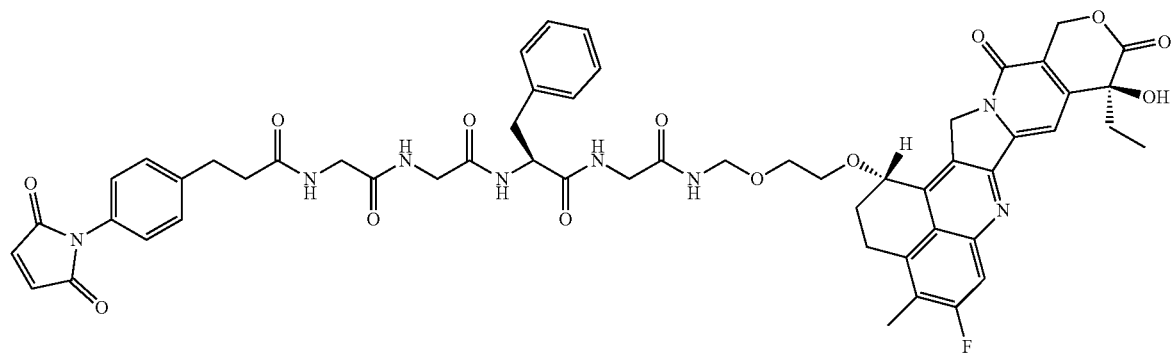

(2S)-2-[[2-[[2-[3-[4-(2,5-Dioxopyrrol-1 yl)phenyl]
propanoylamino]acetyl]amino]acetyl] amino]-3-
phenyl-propanoic acid (21-116)

A mixture of (S)-2-(2-(2-aminoacetamido)acetamido)-3-phenylpropanoic acid (21-115) (5.03 g, 14.6 mmol, 1.0 equiv) and N-ethyl-N,N-diisopropylamine (1.52 g, 11.7 mmol, 2.05 mL, 0.8 equiv) in H$_2$O (25 mL) was added dropwise to a mixture of 2,5-dioxopyrrolidin-1-yl 3-(4-(2,5-dioxo-2,5-dihydro-1H-pyrrol-1-yl)phenyl)propanoate (18-110) (4.10 g, 14.6 mmol, 1.0 equiv) in acetonitrile (75 mL). The reaction mixture was stirred at 25° C. for 5 h, filtered and the filtrate purified by prep-HPLC to give (2S)-2-[[2-[[2-[3-[4-(2,5-dioxopyrrol-1-yl)phenyl]propanoylamino] acetyl]amino]acetyl]amino]-3-phenyl-propanoic acid (21-116) (3.32 g, 40% yield). $^1$H NMR (400 MHz, DMSO-d$_6$) δ ppm 8.21 (t, J=5.6 Hz, 1H), 8.07 (t, J=5.6 Hz, 1H), 7.87 (d, J=7.6 Hz, 1H), 7.32 (d, J=8.4 Hz, 2H), 7.06-7.27 (m, 9H), 4.29 (d, J=5.2 Hz, 1H), 3.61-3.77 (m, 4H), 3.19 (s, 1H), 3.03 (d, J=4.8 Hz, 1H), 2.86 (t, J=8.0 Hz, 3H), 2.67 (s, 1H). LCMS (ESI−) m/z: [MH]$^+$ calcd for C$_{26}$H$_{25}$N$_4$O$_7^-$: 505.1, found: 505.2.

Prep-HPLC Condition:
Instrument: Gilson 281 semi-preparative HPLC system
Mobile phase: A: H2O; B: ACN
Column: Phenomenex C18 250*100 mm 10u
Flow rate: 260 mL/min
Monitor wavelength: 220 & 254 nm

| Time | B % |
| --- | --- |
| 0.0 | 1 |
| 20.0 | 40 |
| 20.1 | 40 |
| 20.2 | 100 |
| 25.2 | 100 |
| 25.3 | 1 |
| 26.5 | 1 |

(9H-Fluoren-9-yl)methyl (2-(((2-(((1S,9S)-9-ethyl-
5-fluoro-9-hydroxy-4-methyl-10,13-dioxo-1,2,3,9,
10,12,13,15-octahydrobenzo[de]pyrano[3',4':6,7]
indolizino[1,2-b]quinolin-1-yl)oxy)ethoxy)methyl)
amino)-2-oxoethyl)carbamate (21-118)

To a mixture of (1S,9S)-9-ethyl-5-fluoro-9-hydroxy-1-(2-hydroxyethoxy)-4-methyl-2,3,12,15-tetrahydrobenzo[de]pyrano[3',4':6,7]indolizino[1,2-b]quinoline-10,13(1H,9H)-dione (5-48) (1.25 g, 2.60 mmol, 1.0 equiv) in dichloromethane (37 mL) at 25° C. was added Scandium (III) trifluoromethanesulfonate (50.5 mg, 0.260 mmol, 0.1 equiv), and [[2-(9H-fluoren-9-ylmethoxycarbonylamino) acetyl]amino]methyl acetate (21-117) (1.44 g, 3.90 mmol, 1.5 equiv) in three portions over 1.5 h. The reaction mixture was stirred at 30° C. for 36 h, quenched with water (100 mL) and extracted with dichloromethane (3×100 mL). The combined organic phases were washed with brine, dried over Na$_2$SO$_4$, filtered, concentrated, and the residue purified by silica gel flash column chromatography eluting with 10%-100% of dichloromethane in ethyl acetate to give (9H-fluoren-9-yl)methyl (2-(((2-(((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl) oxy)ethoxy)methyl)amino)-2-oxoethyl) carbamate (21-118) (1.00 g, 45% yield). $^1$H NMR (400 MHz, DMSO-D$_6$) δ ppm 8.90 (br t, J=6.60 Hz, 1H), 7.80-7.91 (m, 2H), 7.73 (d, J=11.13 Hz, 1H), 7.56-7.63 (m, 2H), 7.23-7.44 (m, 6H), 6.53 (s, 1H), 5.32-5.53 (m, 3H), 4.96 (br dd, J=9.60, 4.10 Hz, 1H), 4.62-4.83 (m, 2H), 4.44-4.59 (m, 1H), 4.20-4.32 (m, 1H), 4.05-4.19 (m, 3H), 3.91-4.00 (m, 1H), 3.57-3.78 (m, 5H), 3.14-3.28 (m, 1H), 2.86-3.08 (m, 1H), 2.34 (s, 3H), 1.85 (br dd, J=7.03, 4.46 Hz, 3H), 0.78-0.94 (m, 3H). $^{19}$F NMR (376 MHz, DMSO-d$_6$) δ ppm −111.56. LCMS (ESI+) m/z: [MH]$^+$ calcd for C$_{44}$H$_{42}$FN$_4$O$_9^+$: 789.3, found: 789.3.

2-Amino-N-((2-(((1S,9S)-9-ethyl-5-fluoro-9-hy-
droxy-4-methyl-10,13-dioxo-1,2,3,9,10,12,13,
15-octahydrobenzo[de]pyrano[3',4':6,7]indolizino[1,
2-b]quinolin-1-yl)oxy)ethoxy)methyl) acetamide
(21-119)

To a mixture of (9H-fluoren-9-yl)methyl (2-(((2-(((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)oxy)ethoxy)methyl)amino)-2-oxoethyl)carbamate (21-118) (1.00 g, 1.27 mmol, 1.0 equiv) in N,N-dimethylformamide (20 mL) was added piperidine (0.125 mL, 1.27 mmol, 1.0 equiv). The reaction mixture was stirred at 0° C. for 1 h, filtered and the filtrate purified by prep-HPLC to give 2-amino-N-((2-(((1S,9S)-9-ethyl-5-fluoro-9-hydroxy-4-methyl-10,13-dioxo-1,2,3,9,10,12,13,15-octahydrobenzo[de]pyrano[3',4':6,7] indolizino[1,2-b]quinolin-1-yl)oxy)ethoxy)methyl)acetamide (21-119) (360 mg, 45% yield). $^1$H NMR (400 MHz, DMSO-d$_6$) δ ppm 8.78 (t, J=6.8 Hz, 1H), 7.66-7.81 (m, 1H), 7.32 (s, 1H), 6.52 (s, 1H), 5.35-5.46 (m, 3H), 5.01 (dd, J=9.2, 3.6 Hz, 1H), 4.59-4.83 (m, 2H), 3.92-4.03 (m, 1H), 3.77 (m, 1H), 3.59-3.71 (m, 2H), 3.20-3.29 (m, 2H), 3.16 (s, 2H), 2.92-3.05 (m, 1H), 2.59-2.84 (m, 1H), 2.29-2.41 (m, 3H), 1.72-2.09 (m, 3H), 0.78-0.97 (m, 3H). $^{19}$F NMR (376 MHz, DMSO-d$_6$) δ ppm −111.54. LCMS (ESI+) m/z: [MH]$^+$ calcd for C$_{29}$H$_{32}$FN$_4$O$_7^+$: 567.2, found: 567.3.

Prep-HPLC Conditions
Instrument: Gilson 281 semi-preparative HPLC system
Mobile phase: A: 10 mM NH$_4$HCO$_3$ in H$_2$O; B: ACN
Column: Phenomenex C18 75*30 mm*3 um
Flow rate: 25 mL/min
Monitor wavelength: 220 & 254 nm

| Time | B % |
| --- | --- |
| 0.0 | 10 |
| 8.0 | 40 |
| 8.1 | 40 |
| 8.2 | 100 |
| 10.2 | 100 |
| 10.3 | 10 |
| 11.5 | 10 |

(S)-2-(2-(2-(3-(4-(2,5-Dioxo-2,5-dihydro-1H-pyrrol-1-yl)phenyl)propanamido)acetamido) acetamido)-N-(2-(((2-(((1S,9S)-9-ethyl-5-fluoro-9-hydroxy-4-methyl-10,13-dioxo-1,2,3,9,10, 12,13,15-octahydrobenzo[de]pyrano[3',4':6,7]indolizino[1,2-b]quinolin-1-yl)oxy)ethoxy) methyl)amino)-2-oxoethyl)-3-phenylpropanamide (21-120)

A mixture of (2S)-2-[[2-[[2-[3-[4-(2,5-dioxopyrrol-1-yl)phenyl]propanoylamino]acetyl]amino] acetyl]amino]-3-phenyl-propanoic acid (21-116) (160 mg, 0.317 mmol, 1.0 equiv), 2-amino-N-((2-(((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)oxy)ethoxy)methyl)acetamide (21-119) (180 mg, 317 umol, 1.0 equiv), 4-(4,6-dimethoxy-1,3,5-triazin-2-yl)-4-methylmorpholin-4-ium tetrafluoroborate (104 mg, 0.317 mmol, 1.0 equiv) and 4-methylmorpholine (0.139 mL, 1.27 mmol, 4.0 equiv) in N,N-dimethylformamide (3.6 mL) was stirred at 25° C. for 1 h, filtered and the filtrate purified by prep-HPLC to give (S)-2-(2-(2-(3-(4-(2,5-dioxo-2,5-dihydro-1H-pyrrol-1-yl)phenyl)propanamido)acetamido)acetamido)-N-(2-(((2-(1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)oxy)ethoxy)methyl)amino)-2-oxoethyl)-3-phenyl-propanamide (21-120) (80.0 mg, 23% yield). $^1$H NMR (400 MHz, DMSO-$d_6$) δ ppm 8.69 (t, J=6.8 Hz, 1H), 8.28 (t, J=5.6 Hz, 1H), 8.19 (t, J=5.6 Hz, 1H), 8.10 (d, J=8.0 Hz, 1H), 8.03 (t, J=5.6 Hz, 1H), 7.76 (d, J=11.2 Hz, 1H), 7.26-7.35 (m, 3H), 7.13-7.25 (m, 8H), 6.52 (s, 1H), 5.34-5.53 (m, 4H), 5.03 (dd, J=8.8, 4.00 Hz, 1H), 4.63-4.81 (m, 2H), 4.41-4.57 (m, 1H), 3.90-4.03 (m, 1H), 3.74-3.84 (m, 3H), 3.54-3.74 (m, 6H), 3.16-3.30 (m, 2H), 2.93-3.07 (m, 2H), 2.73-2.88 (m, 3H), 2.42-2.48 (m, 3H), 2.37 (s, 3H), 1.80-2.03 (m, 3H), 0.87 (t, J=7.2 Hz, 3H). $^{19}$F NMR (376 MHz, DMSO-$d_6$) δ ppm −111.53. LCMS (ESI+) m/z: [MH]$^+$ calcd for $C_{55}H_{56}FN_8O_{13}{}^+$: 1055.4, found: 1055.3.

Prep-HPLC Conditions:
Instrument: Gilson 281 semi-preparative HPLC system
Mobile phase: A: $H_2O$; B: ACN
Column: Phenomenex C18 75*30 mm*3 um
Flow rate: 60 mL/min
Monitor wavelength: 220 & 254 nm

| Time | B % |
| --- | --- |
| 0.0 | 25 |
| 8.0 | 55 |
| 8.1 | 55 |
| 8.2 | 100 |
| 10.2 | 100 |
| 10.3 | 25 |
| 11.5 | 25 |

Example 22

N—((S)-10-benzyl-1-(((1S,9S)-9-ethyl-5-fluoro-9-hydroxy-4-methyl-10,13-dioxo-1,2,3,9,10,12,13,15-octahydrobenzo[de]pyrano[3',4':6,7] indolizino[1,2-b]quinolin-1-yl)oxy)-6,9,12,15-tetraoxo-3-oxa-5,8, 11,14-tetraazahexadecan-16-yl)-3-(2,5-dioxo-2,5-dihydro-1H-pyrrol-1-yl)benzamide (22-121)

22-121

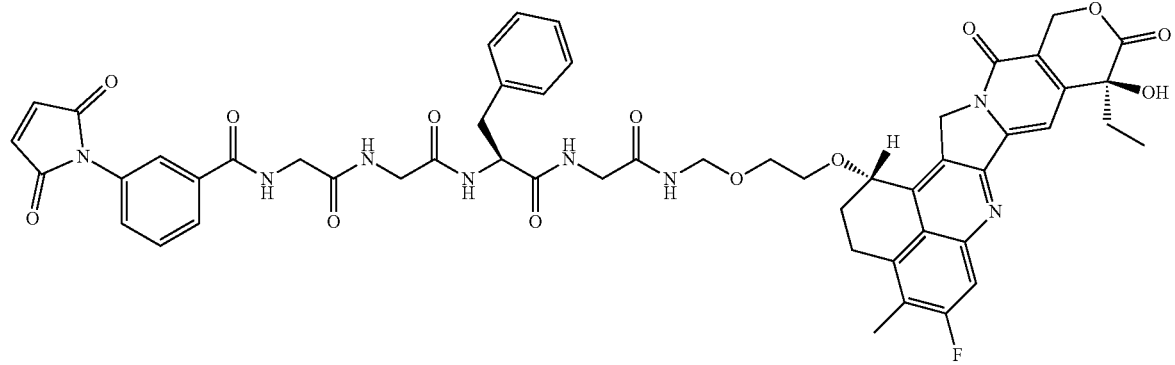

Example 22 (22-121) was made in a similar fashion to Example 21 (21-120). $^1$H NMR (400 MHz, DMSO-$d_6$) δ ppm 8.86 (t, J=5.60 Hz, 1H), 8.67 (br t, J=6.56 Hz, 1H), 8.29 (br t, J=5.66 Hz, 1H), 8.05-8.17 (m, 2H), 7.89 (d, J=7.99 Hz, 1H), 7.83 (s, 1H), 7.75 (d, J=10.97 Hz, 1H), 7.54-7.61 (m, 1H), 7.47-7.53 (m, 1H), 7.33 (s, 1H), 7.11-7.25 (m, 7H), 6.52 (s, 1H), 5.34-5.48 (m, 4H), 5.03 (br dd, J=8.82, 3.58 Hz, 1H), 4.63-4.79 (m, 2H), 4.44-4.54 (m, 1H), 3.96 (br dd, J=7.03, 4.17 Hz, 1H), 3.88 (br d, J=5.72 Hz, 2H), 3.57-3.81

(m, 7H), 3.19-3.27 (m, 1H), 2.93-3.08 (m, 2H), 2.78 (br dd, J=13.65, 9.83 Hz, 1H), 2.45 (br s, 1H), 2.36 (s, 3H), 1.81-2.02 (m, 3H), 0.83-0.91 (m, 3H). $^{19}$F NMR (376 MHz, DMSO-$d_6$) δ ppm −111.54. LCMS (ESI+) m/z: [MH]$^+$ calcd for $C_{53}H_{52}FN_8O_{13}{}^+$: 1027.3, found: 1027.3.

Example 23

N—((S)-10-benzyl-1-(((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)oxy)-6,9,12,15-tetraoxo-3-oxa-5,8,11,14-tetraazahexadecan-16-yl)-6-(2,5-dioxo-2,5-dihydro-1H-pyrrol-1-yl)hexanamide (23-122)

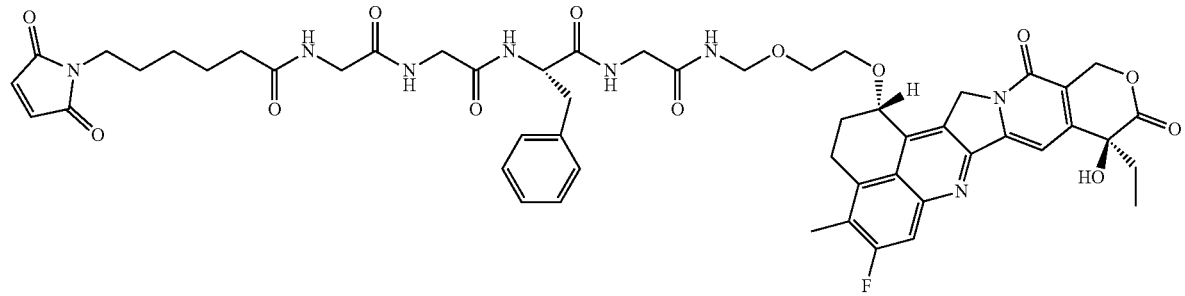

23-122

Example 23 (23-122) was made in a similar fashion to Example 21 (21-120). $^1$H NMR (400 MHz, DMSO-$D_6$) δ ppm 8.63-8.74 (m, 1H), 8.28 (t, J=5.63 Hz, 1H), 8.09 (d, J=8.13 Hz, 1H), 8.04 (t, J=5.63 Hz, 1H), 7.98 (t, J=5.63 Hz, 1H), 7.77 (d, J=11.01 Hz, 1H), 7.34 (s, 1H), 7.11-7.26 (m, 5H), 6.98 (s, 2H), 6.52 (s, 1H), 5.31-5.58 (m, 4H), 5.05 (br dd, J=9.13, 4.00 Hz, 1H), 4.61-4.82 (m, 2H), 4.40-4.55 (m, 1H), 3.90-4.04 (m, 1H), 3.73-3.84 (m, 3H), 3.60-3.73 (m, 5H), 3.53-3.60 (m, 1H), 3.33-3.37 (m, 2H), 3.21-3.27 (m, 1H), 2.94-3.08 (m, 2H), 2.77 (dd, J=13.70, 9.82 Hz, 1H), 2.46-2.48 (m, 1H), 2.38 (s, 3H), 2.05-2.12 (m, 2H), 1.82-2.01 (m, 3H), 1.45 (dq, J=14.13, 7.00 Hz, 4H), 1.10-1.22 (m, 2H), 0.87 (t, J=7.32 Hz, 3H). $^{19}$F NMR (376 MHz, DMSO-$d_6$) δ ppm −111.54. LCMS (ESI+) m/z: [MH]$^+$ calcd for $C_{52}H_{58}FN_8O_{13}{}^+$: 1021.4, found: 1021.4.

Example 24

CTG Assays (Jeko-1 and MDA-MB-468)

The CTG assay is a method of determining the number of viable cells in culture based on quantitation of the ATP present, an indicator of metabolically active cells. The cell assay requires the addition of a single reagent, Cell Titer Glo, in which cells are lysed and generation of a luminescent signal is produced. The luminescent signal is proportional to the amount of ATP present. The amount of ATP is directly proportional to the number of cells present in culture. For our assay, cells were ensured to be in log-phase for either Jeko-1 or MDA-MB-468. Cells were transferred to 96 wells and treated with compounds in three-fold serial dilution starting from 1 μM to 0.0000508 μM (10 points dilution), for 72 h. Cell viability was analyzed with CellTiter-Glo® Luminescent Cell Viability Assay (Promega) following manufactures' instruction. Percentage of viable cells in each compound concentration was determined by normalizing with the luminescence of vehicle control and plotted into percentage of viability versus dose response curve by nonlinear fit in GraphPad Prism software. Compound IC$_{50}$ was calculated as the concentration of compound killing 50% of cells. Representative assay results are summarized in Table 1.

Example 25

Human Hepatocyte Clearance (HHEP CL)

Suspensions of human hepatocytes (from 10 mixed gender human donors, final concentration 0.5×10$^6$ cell/mL) in Williams' E medium were incubated for 90 min with a test compound (0.90% acetonitrile and 0.10% DMSO, final concentration 1 mM) and positive controls (7-Ethoxycoumarin, 7-Hydroxycoumarin, 0.90% acetonitrile and 0.10% DMSO, final concentration 3 mM), with constant shaking at about 600 rpm at 37° C. in an incubator at 5% CO$_2$ and 95% humidity. The total volume of incubation was 200 μl. A sample (25 mL) was taken out at T0, 15, 30, 60 and 90 min, which was added intermediately to the ice-cold stop solution (acetonitrile with 200 ng/mL of tobutamide and labetalol as internal standard) (125 μl), and vortexed at 500 rpm for 10 min, centrifuged at 3220×g for 20 min at 4° C. Analytical plates are sealed and stored at 4° C. until LCMS analysis. Viability of hepatocytes at pre-incubation was determined to be 84.5%. Representative assay results are summarized in Table 1.

Example 26

Human Liver Microsome Clearance (HLM CL)

Working solution was prepared by adding 5 μL of compound and control stock solution (10 mM in dimethyl sulfoxide, DMSO) to 495 μL of acetonitrile (ACN) (intermediate solution concentration: 100 μM, 99% CAN and 1% DMSO. The appropriate concentrations of microsome working solutions were prepared in 100 mM potassium phosphate buffer. After reaction plates containing mixtures of compound and microsomes were pre-incubated at 37° C. for 10 min, 98 mL of 2 mM of NADPH and 2 mM of MgCl$_2$ solution was added to start the reaction. The final concentrations of incubation medium were as follows: microsome—0.5 mg protein/mL, test compound/control compound—1 mM, NADPH—1 mM, MgCl$_2$ —1 mM, acetonitrile 0.99%, DMSO 0.01%. Incubations were performed at 37° C. for 60 min. Samples were taken out at T0, T5, T15, T30, T45 and T60, which was added intermediately to the ice-cold stop solution (acetonitrile with 200 ng/mL of tobutamide and labetalol as internal standard) (125 μl), shaken for 10 min, centrifuged at 4000 rpm for 20 min at 4°

C. Analytical plates were analyzed by LCMS. Representative assay results are summarized in Table 1.

Human liver microsome clearance assay assess metabolism by the cytochrome P450 system (phase I enzymes). These enzymes oxidize substrates by incorporating oxygen atoms into hydrocarbons, thus causing the introduction of hydroxyl groups, or N- O- and S-dealkylation of substrates and forming more polar products easier to be cleared. Human hepatocyte clearance assay measures more broadly the overall cellular metabolism of the test compound (phase I and phase II enzyme pathways). Phase II enzymes catalyze the conjugation reaction of xenobiotic metabolites and charged species, such as glutathione, sulfate, glycine, or glucuronic acid to form even more polar compounds for easier clearance.

The payloads with higher intrinsic clearance may provide better therapeutic index due to their potential lower systemic plasma exposure. (Maderna, A.; Doroski, M; Subramanyam, C.; Porte, A.; Leverett, C. A.; Vetelino, B. C.; Chen, Z.; Risley, H.; Parris, K.; Pandit, J.; Varghese, A. H.; Shanker, S.; Song, C.; Sukuru, S. C. K.; Farley, K. A.; Wagenaar, M. M.; Shapiro, M. J.; Musto, S.; Lam, M-H.; Loganzo, F.; O'Donnell, C. J. "Discovery of cytotoxic dolastatin 10 analogues with N-terminal modifications" *Journal Medicinal Chemistry*, 2014, 57, 10527-10543). In Table 1, the payloads with higher intrinsic clearance likely have an improved safety profile because the payload, which is potentially toxic to healthy cells, is quickly removed from the plasma, decreasing its chance of interacting with healthy cells.

Example 27

PAMPA (Parallel Artificial Membrane Permeability Assay)

PAMPA is a method which determines the permeability of substances from a donor compartment, through a lipid-infused artificial membrane into an acceptor compartment. See Ottaviani, G.; Martel, S.; Carrupt, P-A. "Parallel Artificial Membrane Permeability Assay: A New Membrane for the Fast Prediction of Passive Human Skin Permeability", Journal of Medicinal Chemistry, 2006, 49 (13), 3948-3954). A multi-well microtitre plate is used for the donor and a membrane/acceptor compartment is placed on top; the whole assembly is commonly referred to as a "sandwich". At the beginning of the test, the drug is added to the donor compartment, and the acceptor compartment is drug-free. After an incubation period which may include stirring, the sandwich is separated, and the amount of drug is measured in each compartment. Mass balance allows calculation of drug that remains in the membrane.

The PAMPA was performed by Pion Inc using the GIT-0 lipid and 5 μM donor solution in pH 5.0 and pH 7.4 PRISMA buffer (containing 0.05% DMSO). The higher PAMPA data has been associated with better bystander killing. (Ogitani Y.; Hagihara K.; Oitate, M.; Naito, H.; Agatsuma T. "Bystander killing effect of DS-8201a, a novel anti-human epidermal growth factor receptor 2 antibody-drug conjugate, in tumors with human epidermal growth factor receptor 2 heterogeneity" *Cancer Science*, 2016, 107 (7), 1039-1046).

Representative assay results are summarized in Table 1. Higher permeability is important because it implies greater potential for "bystander killing". That is, once the payload has neutralized a tumor cell, a more permeable payload is more likely to escape the neutralized tumor cell, then imbed in a neighboring tumor cell. Once there, it can neutralize the tumor cell, escape, embed in another neighboring tumor cell, and repeat the process.

TABLE 1

| Compound | PAMPA Pe ($10^{-6}$ cm/s) pH 5.0/7.4 | HHEP Cl ($T_{1/2}$) | HLM Cl ($T_{1/2}$) | JeKo-1 $IC_{50}$ (nM) | MDA-MB-468 $IC_{50}$ (nM) |
|---|---|---|---|---|---|
| Dxd | 21.9/5.0 | 48.7 (79.0) | 8.6 (>145) | 1.42 | 11.6 |
| Exatecan | 37.2/5.7 | 59.3 (65.0) | 11.7 (106) | 0.59 | 6.2 |
| 3-34 | 78.3/8.2 | 79.2 (48.7) | 32.1 (38.8) | 0.59 | 6.0 |
| 3-35 | 66.1/11.1 | 50.4 (76.5) | 20.2 (61.8) | 0.46 | 4.7 |
| 5-47 | 76/.1/11.6 | 53.7 (71.7) | 17.3 (72.2) | 1.5 | 6.3 |
| 5-48 | 69.0/9.0 | 75.5 (51.1) | 17.4 (71.7) | 0.68 | 8.3 |
| 7-59 | ND | 69.4 (55.5) | 33.7 (37.0) | 2.9 | 14.8 |
| 7-60 | ND | 64.5 (59.7) | 40.8 (30.6) | 2.1 | 14.9 |
| 8-71 | 67.7/8.6 | 81.7 (47) | 41.9 (30) | 0.44 | 6.1 |
| 8-72 | 80.8/8.4 | 79.1 (49) | 35.9 (35) | 1.5 | 7.7 |
| 9-74 | 36.1/4.4 | 57.5 (67.0) | 22.7 (54.9) | 4.1 | 57.7 |
| 10-75 | 46.8/3.9 | 40.8 (94.4) | 27.2 (45.9) | 58.1 | 467 |
| 13-84 | 64.4/7.6 | 111.9 (34) | 58.9 (21) | 0.61 | 5.9 |
| 13-85 | 69.7/6.0 | 75.7 (51) | 58.3 (21) | 2.6 | 36.2 |
| 14-91 | 67.8/5.6 | 63.4 (60.8) | 46.5 (26.8) | 1.4 | 17.6 |
| 14-92 | 69.1/4.5 | 51.3 (75.1) | 19.2 (65.0) | 1.2 | 14.2 |
| 16-95 | 63.1/5.5 | 29.6 (130) | 25.4 (49.1) | 1.3 | 13.7 |
| 17-96 | 62.6/4.3 | 47.1 (82) | 71.3 (17.5) | 2.1 | 22 |

Dxd: deruxtecan;
HHEP Cl: human hepatocytes intrinsic clearance, mL/min/Kg;
HHEP $t_{1/2}$, min.
HLM: human liver microsome clearance, mL/min/Kg.
ND: Not determined.

Example 28

Novel and diversified anti-ROR-1 specific monoclonal antibodies were developed to bind to multiple regions of the ROR-1 extracellular domain (ECD) by employing an antibody development campaign using three strategies: (1) mice of cohort 1 were immunized using full length ROR-1 ECD; (2) mice of cohorts 2 and 3 were immunized with the ROR-1 IgG-like domain; and (3) mice of cohort 4 were immunized with a short region of the human IgG-like sequence of ROR-1. After immunization of the mice, monoclonal antibodies were generated using conventional approaches. Briefly, unique variable heavy and light chain pairs from hybridoma and phage display campaigns were cloned into vectors designed to express full length antibodies as IgGs in HEK293 cells under the control of a CMV promoter. Antibody expression vectors were complexed with polyethylenimine and transfected into HEK293 cultures. After 5 days of shaking at 37° C. in 293 cell culture media, antibodies were captured on agarose-based protein A resin. After several stringent washes, antibodies were eluted in glycine solution, pH 3, neutralized with Hepes, pH 9, and buffer exchanged into PBS.

Several monoclonal antibodies were developed using these approaches and the generated antibodies were subjected to additional screening to assess specific characteristics of the antibodies. To fully evaluate the characteristics of the novel antibodies several assays were performed. First, confirmation of antibody binding to the ROR-1 epitope was confirmed both biochemically, as well as, in ROR-1 positive cell lines. The specificity of binding was assessed biochemically by screening binding to human ROR-2 protein, rodent ROR-1 protein, as well as, in cell-based assays. Further screening parameters included analyses of antibody internalization, epitope binning against known anti-ROR-1 antibodies (UC961 and 4a5), binding to human ROR-1 Ig-like domain, thermal shift, and assessment for self-interaction with Affinity-Capture Self-Interaction Nanoparticle Spectroscopy (AC-SINS).

Example 29

Figure 27:
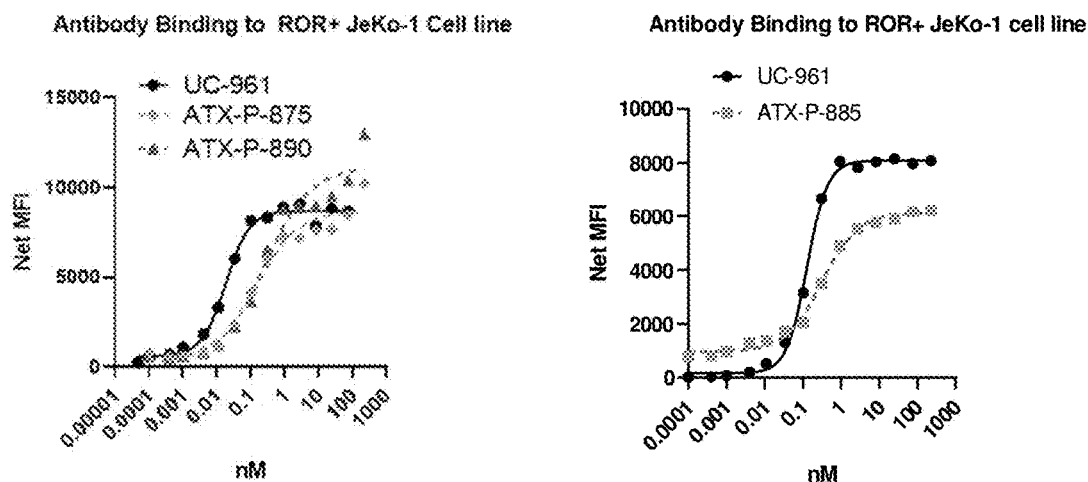
FIG. 27 illustrates a measurement of cell binding saturation data for the anti-ROR-1 antibodies generated by the methods described herein. A ROR-1 positive cell line JeKo-1 was incubated in a titration series with the anti-ROR-1 antibodies ATX-P-875, ATX-P-885, and ATX-P-890 in comparison to the positive control antibody UC961. Cells were washed, stained with secondary antibody and cell binding saturation was detected by flow cytometry and reported as mean fluorescent intensity (MFI).

A cell binding saturation assay was developed to evaluate how well the anti_ROR-1 antibodies developed in Example 28 bound to endogenously expressed extracellular ROR-1 protein on cell lines. More specifically, the anti-ROR-1 monoclonal antibodies developed in Example E, e.g., ATX-P-875, ATX-P-885, and ATX-P-890, were analyzed in a cellular binding assay. Briefly, two ROR-1 positive cell lines, JeKo-1 and MDA-MB-468, were incubated in a titration series concentration of each antibody construct. Cells were then washed and subjected to secondary antibody staining and detection by flow cytometry. Mean fluorescence (MFI) was determined by analysis on cytometer software. The binding of ATX-P-875, ATX-P-885, and ATX-P-890 was compared to cell binding saturation data for the monoclonal anti-ROR-1 antibody UC961. (See FIG. 27). As shown in FIG. 27, the cell binding saturation for antibodies ATX-P-875, ATX-P-885, and ATX-P-890 were comparable to the cell binding saturation for UC961 though a greater concentration of ATX-P-875 was needed to achieve saturation, as compared to UC961. ATX-P-890 and ATX-P-885 were as good or improved, respectively, compared to UC-961 in concentrations needed to achieve binding saturation. Comparable saturation to UC961 demonstrates that the anti-ROR-1 antibodies ATX-P-875, ATX-P-885, and ATX-P-890 have a similar affinity to the human ROR-1 target as a clinically approved antibody UC-961.

Example 30

Figure 28:
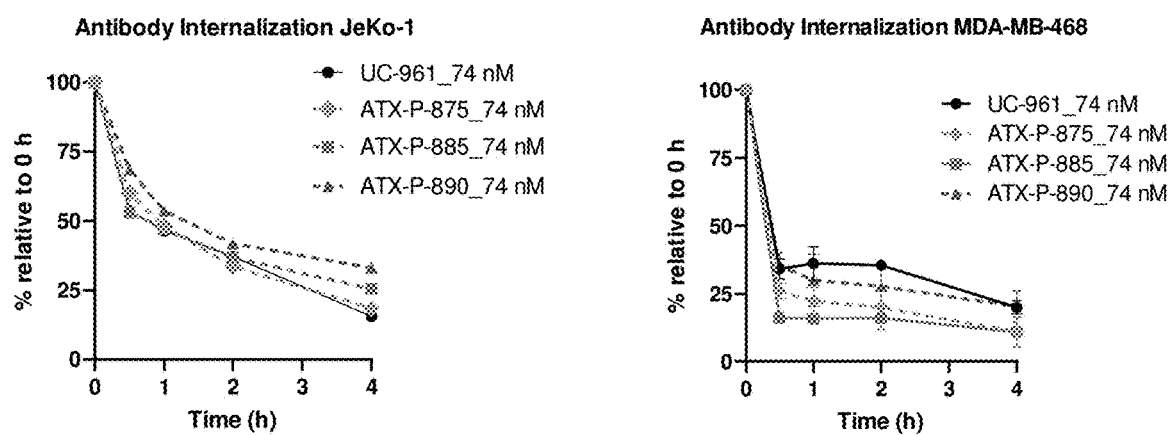
FIG. 28 illustrates ROR-1 receptor internalization data for the anti-ROR-1 antibodies ATX-875, ATX-P-885, ATX-P-890. ROR-1 positive cell lines JeKo-1 and MDA-MB-468 were incubated with the anti-ROR-1 antibodies ATX-P-875, ATX-P-885, and ATX-P-890 and positive control antibody UC961 at super saturating conditions so as to bind all available ROR-1 receptors. Cells were washed and incubated at 4 different timepoints (30 min, 1 hour, 2 hours and 4 hours) at 37° C. before internalization was halted by placing the cells in ice. Receptor internalization was determined by flow cytometry and reported as percent receptor internalization relative to zero hours.

After a saturating concentration (74 nM) was determined in the binding assay, the anti-ROR-1 antibodies developed herein (ATX-P-875, P-885, P-890) were evaluated for their capacity to internalize the ROR-1 receptor on human ROR-1 positive cells (JeKo-1 and MDA-MB-468). Briefly, the ROR positive cell lines were incubated with antibody at super saturating conditions so as to bind all available ROR-1 receptors. Excess antibody was washed off and the cells were incubated at 37° C. for a designated amount of time over a four-hour time course. At the end of each time point, internalization was stopped by placing an aliquot of cells on ice. The antibody remaining on the surface was detected using a labeled secondary antibody and flow cytometry. Percent internalization was calculated based on time zero, and time zero was assumed that 100% of available receptors are on the cell surface. The results in FIG. 28 demonstrate that all antibodies internalize ROR-1 receptor on JeKo-1 and MDA-MB-468 cells by a reduction of at least 75% over 4 hours. Unexpectedly, in MDA-MB-468, internalization of two of the anti-ROR-1 antibodies (ATX-P-875 and ATX-P-890) was improved over the clinically used UC961 anti-ROR-1 antibody providing evidence that the ATX-P-875 and ATX-P-890 antibodies have an improved ability to internalize the ROR-1 receptor from the surface of solid tumors.

Example 31

Figures 29A, 29B, 29C, 29D:
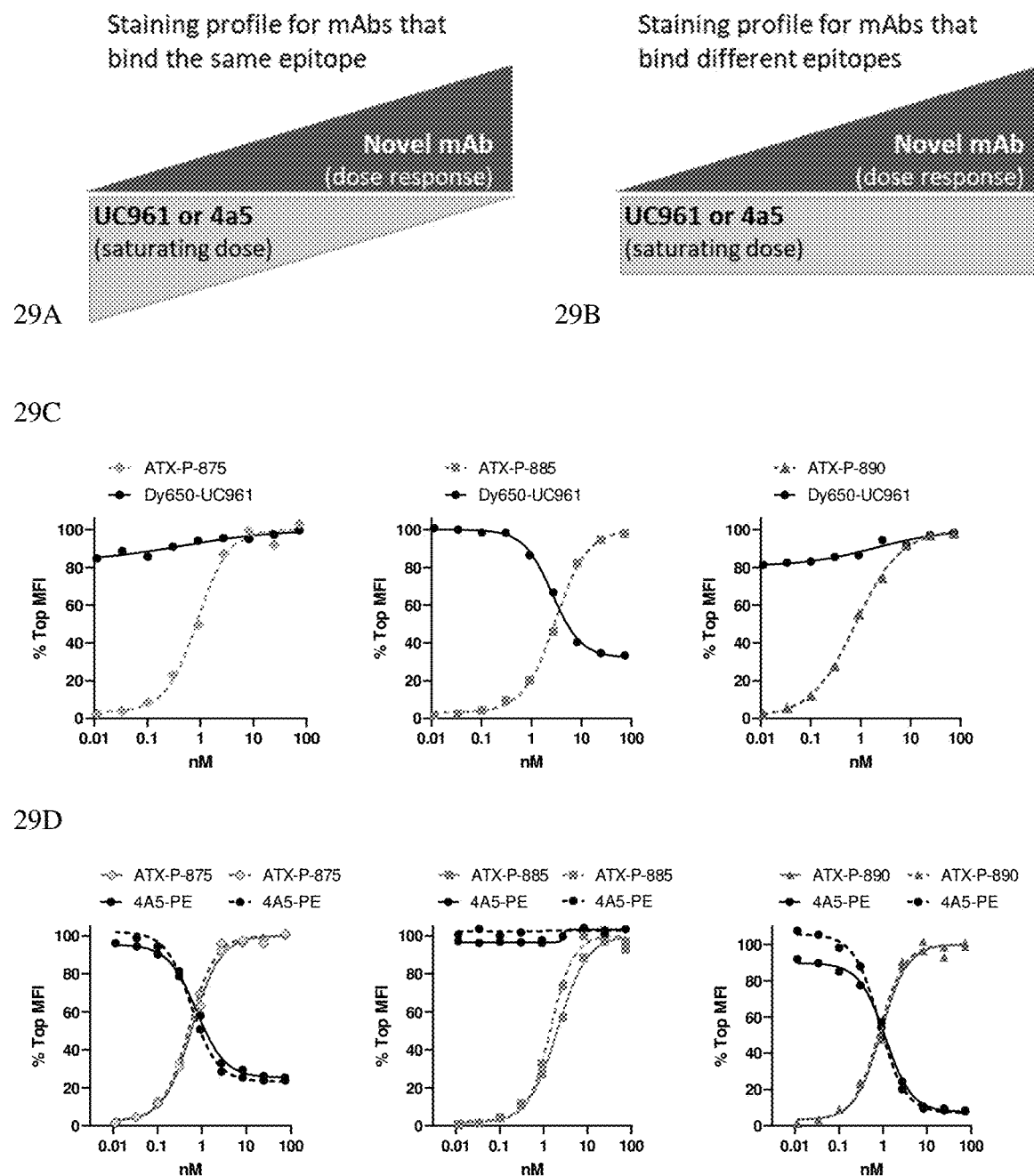
FIG. 29A-29D illustrates cellular binning data for the anti-ROR-1 antibodies ATX-P-875, ATX-P-885, and ATX-P-890. A cellular binning assay was performed to assess if ATX-P-875, ATX-P-885, and ATX-P-890 bound the same epitopes on the ROR-1 receptor as control antibodies UC961 and 4A5. (29A) depicts a staining profile for antibodies that bind the same epitope. (29B) depicts the staining profile for antibodies that bind different epitopes. ATX-P-875, ATX-P-885, and ATX-P-890 were separately incubated with ROR-1_+MDA-MB-468 at various amounts. Next, the anti-ROR-1 antibodies were fluorescently labeled with a secondary antibody. Finally, MDA-MB-468 cells coated with the anti-ROR-1 antibodies were incubated with a saturating dose of a fluorescently labeled UC961 (29C) or 4A5 (29D) and analyzed by flow cytometry and the ATX-P-875, ATX-P-885, and ATX-P-890 antibody signal were compared with the UC961 or 4A5 signal.

Cellular binning was also employed to determine if monoclonal antibodies ATX-P-875, ATX-P-885, and ATX-P-890 bound to the same epitopes as conventionally known anti-ROR-1 binding monoclonal antibodies UC961 and 4A5 (controls). In Step 1 of the cellular binning experiments, ATX-P-875, ATX-P-885, and ATX-P-890 monoclonal antibodies were separately incubated with ROR-1 expressing cells (MDA-MB-468) at various amounts. In Step 2, a fluorescently labeled secondary antibody recognizing the novel antibodies was incubated with the samples. And finally in Step 3, the ROR-1 expressing cells coated with ATX-P-875, ATX-P-885, and ATX-P-890 were incubated with a saturating dose of labeled UC961 (Dy650-UC 961) or 4A5 antibody (PE 4A5) and analyzed by flow cytometry. The UC961 and 4A5 staining signal was then compared to the novel antibody staining signal to determine if the ATX-P-875, ATX-P-885, and ATX-P-890 antibodies bound the same epitope as the known ROR-1 binding antibodies UC961 and 4A5. FIG. 29A below shows the staining profile expected if the ATX-P-875, ATX-P-885, and ATX-P-890 antibodies bound the same epitope as the UC961 and 4A5 antibodies. FIG. 29B, shows the expected profile if the ATX-P-875, ATX-P-885, and ATX-P-890 antibodies bound to a separate epitope on ROR-1 than the UC961 or 4A5 antibodies. Briefly, if binding the same epitope, increased novel antibody concentration would block the binding of prelabeled competitor antibody, thereby reducing the signal of the competitor at higher concentrations. In the case antibodies bound separate epitopes, each antibody, novel and competitor, would have increased staining with increased dose as there would be no competition for binding to the receptor. The cellular binning data obtained in MDA-MB-468 cells indicated that ATX-P-885 appreciably bound the same epitope as UC961 and both ATX-P-875 and ATX-P-890 appreciably bound the same epitope as 4A5. (See FIG. 29C, 29D and FIG. 30). The ability of the antibodies developed herein to bind distinct ROR-1 epitopes provides the opportunity to regulate the target in a variety of ways.

Example 32

Biochemical binning by SPR was also evaluated for the anti-ROR1 antibodies (ATX-P-875, P-885, P-890) as compared against control anti-ROR-1 antibodies UC961 and 4a5. In these experiments 10 ug/ml of purified clonal protein of Hu/Cy/Rh ROR1-His was covalently coupled to the HC30M chip. Individual dilutions of each antibody at 10 μg/mL were injected over the chip and binding was evaluated by Carterra SPR. Unexpectedly the data demonstrate that there are 3 distinct binding epitopes between ATX-P-875, ATX-P-885, and ATX-P-890 with ATX-885 being the only antibody to impart partial blocking to the UC961 antibody (See FIG. 31). Cellular binning only evaluated the antibodies ability to block either UC961 or 4a5, two clinically used ROR-1 antibodies. Biochemical SPR evaluation also tested the antibodies' ability to block each other and found that ATX-P-875 was able to block the binding of 4a5 as well as ATX-P-885, while still not being able to block UC961.

Example 33

Figures 30, 31:
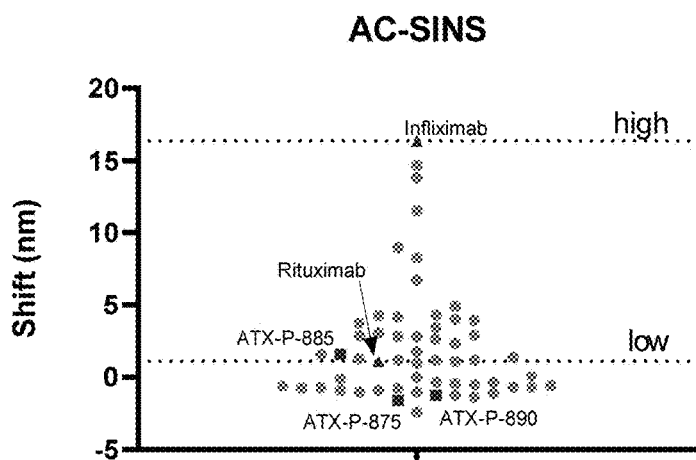
FIG. 30 illustrates AC-SINS data for the anti-ROR-1 antibodies ATX-P-875, ATX-P-885, and ATX-P-890. Antibody developability was assessed by performing an AC-SINS assay and evaluating the potential for self-interaction. Rituximab and Infliximab were used as controls to demonstrate a low and high shift, respectively. Assay results for ATX-P-875, ATX-P-885, and ATX-P-890 fell within the range determined by the control antibodies.
FIG. 31 illustrates biochemical binning data by SPR for the anti-ROR1 antibodies ATX-P-875, ATX-P-885, ATX-P-890 as compared against control anti-ROR-1 antibodies UC961 (ATX-P-453) and 4a5.

Antibody characterization of ATX-P-875, ATX-P-885, and ATX-P-890, as compared to UC961, are summarized in FIG. 30 and TABLES 2-7. An initial assessment of antibody developability was performed by AC-SINS to evaluate the potential for self-interaction (FIG. 30). Control antibodies Adalimumab and Rituximab show expected low shift and Infliximab shows an expected high shift. The anti-ROR-1 antibodies developed herein, ATX-P-875, ATX-P-885, and ATX-P-890, are in line with control antibodies that do not show significant self-interaction and are not likely to pose a significant developability risk. Additionally, the binding characteristics of monoclonal antibodies ATX-P-875, ATX-P-885, and ATX-P-890 were compared to the binding characteristics for UC961 in additional experiments. TABLES 2-5 provide this antibody characterization data in comparison to the known ROR-1 binding antibody UC961 including tabled results for biochemical binding to purified proteins and measured by SPR (TABLES 2-5), cellular binding to ROR-1 positive cell lines JeKo-1 and MDA-MB-468 (EC50) (TABLE 6), and cellular internalization (% internalized) (TABLE 7). Of particular note, it is believed that the reduced affinity of ATX-P-885 (KD: 1.09E-08) compared to UC961 and other anti-ROR-1 antibodies (ATX-P-875 and ATX-P-890) can provide an unexpected therapeutic benefit. It is contemplated that by binding less tightly to the ROR-1 epitope, the ATX-P-885 antibody can penetrate further into the tumor to reach more distant cells expressing ROR-1 target.

TABLE 2

HUMAN/CYNO/RHESUS ROR-1 BINDING
Hu/Cy/Rh ROR1 - His

| Name | $k_a$ (M-1 s-1) | $k_d$ (s-1) | $K_D$ (M) | Rmax (RU) | Res SD | % Rmax |
|---|---|---|---|---|---|---|
| ATX-P-453 (UC961) | 1.26E+06 | 5.91E-03 | 4.69E-09 | 529.0 | 25.6 | 4.85% |
| ATX-P-875 | 4.93E+05 | 3.16E-03 | 6.45E-09 | 593.6 | 22.3 | 3.76% |
| ATX-P-885 | 2.70E+05 | 2.95E-03 | 1.09E-08 | 341.6 | 10.2 | 2.99% |
| ATX-P-890 | 3.92E+05 | 3.14E-03 | 8.40E-09 | 504.2 | 15.0 | 2.97% |

TABLE 3

MOUSE ROR-1 BINDING
Mouse ROR1 - His

| Name | $k_a$ (M-1 s-1) | $k_d$ (s-1) | $K_D$ (M) | Rmax (RU) | Res SD | % Rmax |
|---|---|---|---|---|---|---|
| ATX-P-453 (UC961) | N/A | N/A | N/A | N/A | N/A | N/A |
| ATX-P-875 | N/A | N/A | N/A | N/A | N/A | N/A |
| ATX-P-885 | 2.92E+04 | 1.32E-03 | 4.53E-08 | 73.5 | 8.9 | 12.14% |
| ATX-P-890 | N/A | N/A | N/A | N/A | N/A | N/A |

TABLE 4

RAT ROR-1 BINDING
Rat ROR1 - His

| $k_a$ (M-1 s-1) | $k_a$ (M-1 s-1) | $k_d$ (s-1) | $K_D$ (M) | Rmax (RU) | Res SD | % Rmax |
|---|---|---|---|---|---|---|
| N/A | N/A | N/A | N/A | N/A | N/A | N/A |
| N/A | N/A | N/A | N/A | N/A | N/A | N/A |
| N/A | N/A | N/A | N/A | N/A | N/A | N/A |
| N/A | N/A | N/A | N/A | N/A | N/A | N/A |

TABLE 5

HUMAN ROR-2 BINDING
Human ROR2/NTRKR2-His

| Name | $k_a$ (M-1 s-1) | $k_d$ (s-1) | $K_D$ (M) | Rmax(RU) | Res SD | % Rmax |
|---|---|---|---|---|---|---|
| ATX-P-453 (UC961) | N/A | N/A | N/A | N/A | N/A | N/A |
| ATX-P-875 | N/A | N/A | N/A | N/A | N/A | N/A |
| ATX-P-885 | N/A | N/A | N/A | N/A | N/A | N/A |
| ATX-P-890 | N/A | N/A | N/A | N/A | N/A | N/A |

TABLE 6

CELLULAR BINDING SUMMARY
Cellular Binding Summary

| Name | JeKo-1 (Avg EC50) | MDA-MB-468 (Avg EC50) |
|---|---|---|
| ATX-P-453 (UC961) | 0.073 | 0.176 |
| ATX-P-875 | 0.145 | 0.708 |
| ATX-P-885 | 1.075 | 2.508 |
| ATX-P-890 | 0.174 | 1.016 |

TABLE 7

CELLULAR BINDING SUMMARY
Cellular Internalization Summary

| Name | JeKo-1 (Avg EC50) | MDA-MB-468 (Avg EC50) |
|---|---|---|
| ATX-P-453 (UC961) | 0.073 | 0.176 |
| ATX-P-875 | 0.145 | 0.708 |
| ATX-P-885 | 1.075 | 2.508 |
| ATX-P-890 | 0.174 | 1.016 |

Example 34

The synthesis of the immunoconjugates was accomplished as set forth in this example. The antibodies were produced as described in Example 28 and were suspended in PBS pH 7.2 with protein concentrations as follows: mAb A at 12.44 mg/ml, mAb B at 13.29 mg/ml, mAb C at 14.90 mg/ml. For the reduction and conjugation calculations, a molecular weight of 150000 Da for all antibodies was used.

Each antibody was prepared for reduction by the addition of 5% v/v of 500 mM Tris, 25 mM EDTA, pH 8.5, followed by the addition of TCEP (6 equivilant, 10 mM stock of TCEP in water) and the mixture was maintained at 20° C. for 2 h.

After DMA was added and gently mixed with the above reduced protein solution to achieve a final 10% v/v during conjugation, a toxin-linker stock solution (12 equivalent, 50 mM in DMA) was added and gently mixed. The bioconjugation was allowed to proceed for approximately 16-20 h overnight at 20° C.; it was complete within 2 h with the extended time allowed for maleimide ring opening.

The crude conjugate was buffer exchanged to PBS pH 7.4 using a gravity fed NAP 25 (small scale) or a flow HiPrep G25 (large scale) with the columns prepared and operated according to manufacturer's (Cytivia) instructions. To remove residual toxin, a 100 mg/ml slurry of activated carbon (Sigma/C9157) in PBS pH 7.4 was prepared and added to achieve 1 mg carbon to 1 mg starting antibody mass. It was mixed gently for 2 h, sufficiently to maintain the carbon in suspension. Then, the carbon was removed by centrifugation at 4000 g. Polysorbate 20 (PS20) was added from a 10% w/v stock solution in PBS pH7.4 to achieve a final 0.02% PS20 w/v in the product. The ADC was terminally filtered through a suitably sized 0.2 μm PES filter (chromatography direct/FIL-S-PES-022-13-100-S) under grade A laminar flow. The final product was analysed as follows: monomer and [ADC] mg/ml by SEC HPLC, average DAR by PLRP, residual toxin by RP-HPLC, and endotoxin by Endosafe kinetic chromogenic.

Analytical processes were carried out on HPLC instruments Agilent 1100 or 1260 using the protocol set forth below and in Tables 8 and 9.

SEC-HPLC—Monomer Contents and ADC Concentration (Mg/mL)

Column: TOSOH TSKgel G3000SWXL 7.8 mm×30 cm 5 μm particle (MERCK808541) combined with a security guard column (MERCK 822858) with a GFC3000 4×3 mm cartridge (Phenomenex)

Buffer: 0.2M Phosphate 0.25M KCl 10% IPA pH 6.95±0.1

Gradient: Isocratic @0.5 ml/min at 25° C.

Sample load was approximately 10 μg with monomer and concentration determined from 214 nm signal. Monomer reported based on peak integration and [ADC] mg/mL based on a calibration curve of antibody.

PLRP-HPLC—DAR Determination

Column: PLRP-S 2.1 mm×5 cm, 5 μm (Agilent PL912-1502)

mobile phase A: 0.1% v/v TFA in water mobile phase B: 0.1% v/v TFA in ACN.

Gradient: 50° C. at 1 ml/min sample load was 2 μg and analyzed at 214 nm.

TABLE 8

| TIME | % B |
|---|---|
| 0.00 | 30 |
| 2.00 | 30 |
| 10.00 | 41 |
| 11.50 | 90 |
| 15.50 | 90 |
| 16.50 | 30 |
| 20.00 | 30 |

Residual Toxin

Column Kinetex® 2.6 μm C8 100 Å, LC Column 50×4.6 mm, (Phenomex 00B-4497-E0)

Mobile Phase A 0.05% TFA in water

Mobile Phase B 0.05% TFA in CAN

Gradient: 60° C. at 2 ml/min

TABLE 9

| TIME | % B |
|---|---|
| 0.00 | 5 |
| 8.00 | 95 |
| 8.10 | 100 |
| 9.00 | 100 |
| 9.10 | 5 |
| 10.00 | 5 |

Analytical sample preparation: A sample (50 μl, ADC or PBS/PS20 matrix) was diluted with 2 μl 5M NaCl, 150 μl cold MeOH (from −20° C. freezer), incubated at −20° C. for 30 min, and centrifuged at 21,000 g at 4° C. for 30 min. Then, the supernatant (125 μl) was extracted and mixed with 125 μl WFI, 100 μl of this was injected onto the Kinetex column. Data was analyzed at 214 nm and the residual toxin in the sample estimated from an external calibration curve of the relevant toxin linker. The result is expressed as the percentage free relative to free and bound using the ADC concentration and calculated DAR to determine the amount of bound toxin.

Example 35

Figure 32:
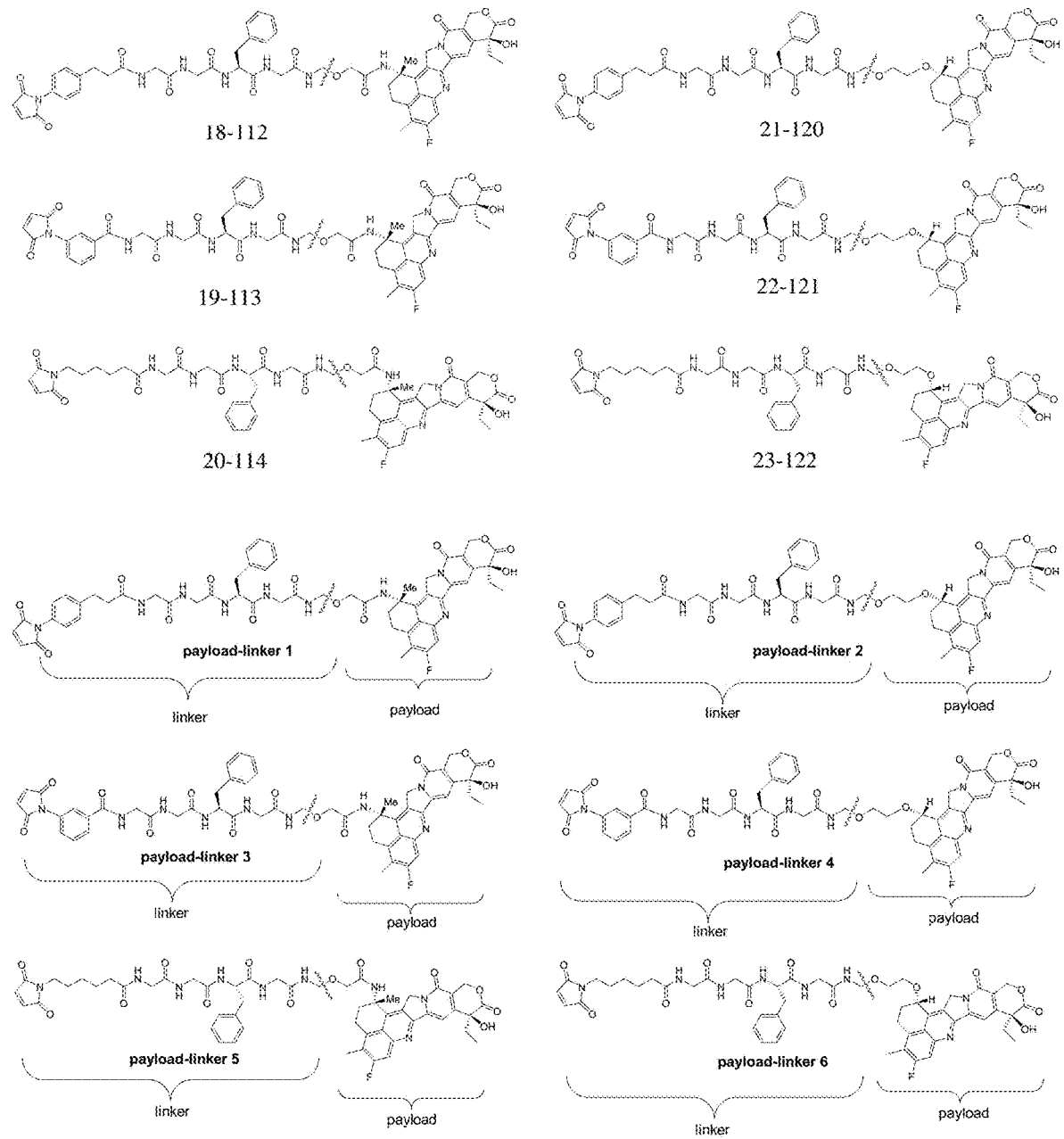
FIG. 32 illustrates linker and payload combinations that were conjugated to the 3 unique antibodies (mAb A=ATX-P-875, mAb B=ATX-P-885, mAb C=ATX-P-890). The antibodies, mAb A (ATX-P-875), mAb B (ATX-P-885), and mAb C (ATX-P-890) were conjugated to 6 separate novel linker/payloads (18-112, 19-113, 20-114, 21-120, 22-121, 23-122) to establish antibody-drug conjugates (ADCs).
Figure 33:
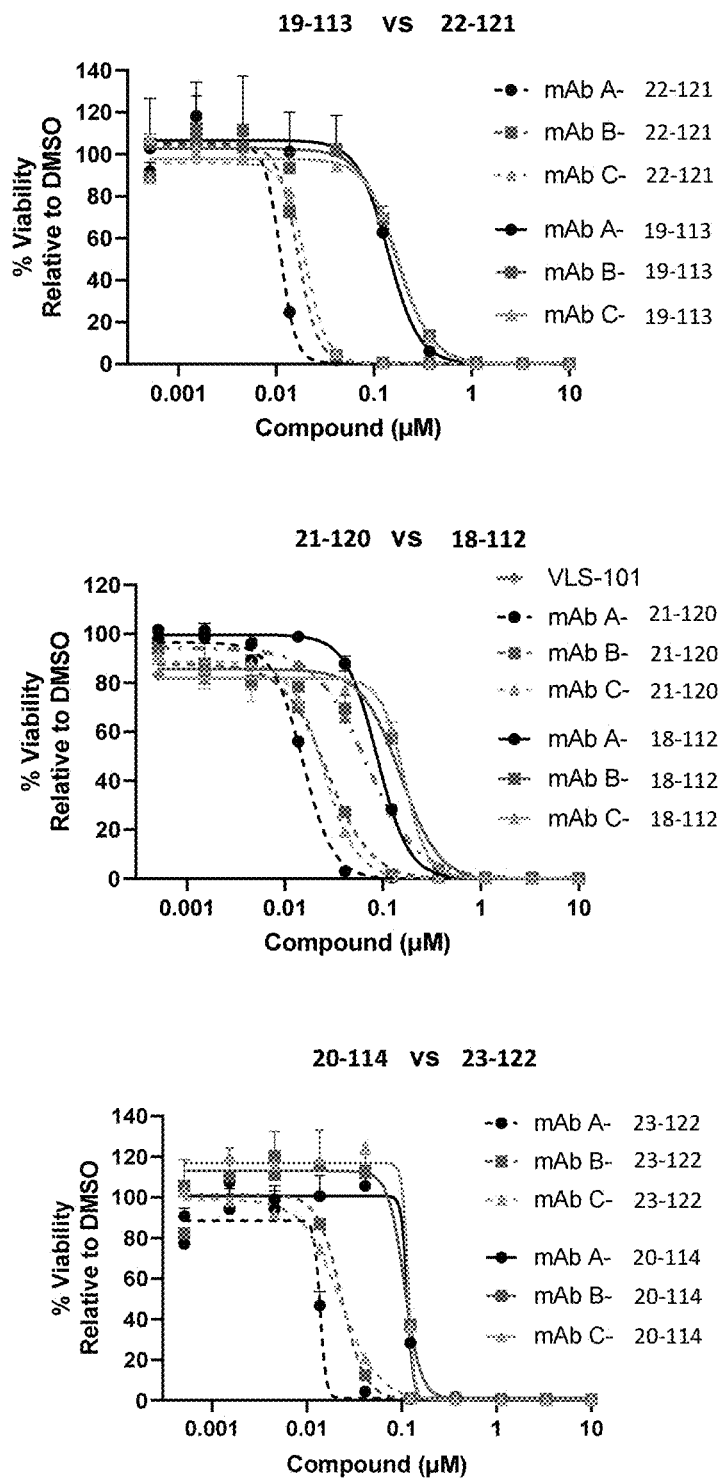
FIG. 33 illustrates a CTG assay wherein ROR+(JeKo-1) cells were incubated with the ADCs generated as described in FIG. 32 in serial three-fold dilutions and cell viability was assessed after 72 hours.

Novel ROR-1 antibody-drug conjugates (ADCs) were evaluated by CTG Assay in a similar manner as was described in Example 24 for screening of payloads. A total of 3 unique antibodies (mAb A=875, mAb B=885, mAb C=890) were conjugated to 6 separate novel linker/payloads (18-112, 19-113, 20-114, 21-120, 22-121 and 23-122) (FIG. 32). Briefly ROR+(JeKo-1/MDA-MB-468) or ROR− (Ramos) cells were transferred to 96 wells and treated with the ADCs in three-fold serial dilution starting from 1 mM to 0.0000508 mM (10 points dilution), for 72 h. Cell viability was analyzed with CellTiter-Glo® Luminescent Cell Viability Assay (Promega) following the manufactures' instructions (FIG. 33). The percentage of viable cells at each ADC concentration was determined by normalizing with the luminescence of vehicle control and plotted into percentage of viability versus dose response curve by nonlinear fit in GraphPad Prism software. The IC50 for each ADC was calculated as the concentration of compound killing 50% of cells. Representative assay results are summarized in TABLE 10. Approximately a 4-fold increase in potency was achieved with ADCs containing 22-121, 21-120 and 23-122 compared to VLS-101, in ROR+ cells lines. Also in vitro data evidence that mAb A (ATX-P-875) is slightly more potent than the other 2 ROR-1 targeted antibodies B and C (ATX-P-885 and ATX-P-895 respectively).

TABLE 10

| ADC #/ Toxin | mAb | Toxin- linker | Jeko-1 P3 (RUN1) IC50 nM | Jeko-1 P4 (RUN2) IC50 nM | Avg. IC50 nM |
|---|---|---|---|---|---|
| 1 | A | 18-122 | 87.1 | 113.2 | 100.1 |
| 2 | A | 21-120 | 14.8 | 19.0 | 16.9 |
| 3 | B | 18-122 | 128.0 | 183.9 | 156.0 |
| 4 | B | 21-120 | 23.4 | 37.3 | 30.3 |
| 5 | C | 18-112 | 146.1 | 197.3 | 171.7 |
| 6 | C | 21-120 | 22.6 | 29.4 | 26.0 |
| 7 | UC-961 | 18-112 | 181.2 | 218.2 | 199.7 |

TABLE 10-continued

| ADC #/ Toxin | mAb | Toxin-linker | | Jeko-1 P3 (RUN1) IC50 nM | Jeko-1 P4 (RUN2) IC50 nM | Avg. IC50 nM |
|---|---|---|---|---|---|---|
| 8 | UC-961 | | | 21-120 | 28.3 | 40.5 | 34.4 |
| 9 | A | | | 19-113 | 146.3 | 164.4 | 155.4 |
| 10 | A | | | 22-121 | 11.2 | 12.7 | 11.9 |
| 11 | B | | | 19-113 | 172.1 | 197.2 | 184.7 |
| 12 | B | | | 22-121 | 17.1 | 18.3 | 17.7 |
| 13 | C | | | 19-113 | 177.0 | 212.4 | 194.7 |
| 14 | C | | | 22-121 | 19.7 | 19.1 | 19.4 |
| 15 | A | | | 20-114 | 115.4 | 120.8 | 118.1 |
| 16 | A | | | 23-122 | 13.6 | 16.3 | 14.9 |
| 17 | B | | | 20-114 | 112.2 | 106.2 | 109.2 |
| 18 | B | | | 23-122 | 23.4 | 24.9 | 24.1 |
| 19 | C | | | 20-114 | 119.1 | 126.5 | 122.8 |
| 20 | C | | | 23-122 | 22.2 | 29.8 | 26.0 |
| 21 | UC-691 | | | 23-122 | 25.1 | 31.0 | 28.1 |
| VLS-101 | | mc-vc-PAB | MMAE | | 63.4 | 56.8 | 60.1 |
| MMAE | | | | | 0.2 | 0.2 | 0.2 |
| Dxd | | | | | 0.9 | | 0.9 |
| 5-48 | | | | | 0.5 | 0.5 | 0.5 |
| 9-74 | | | | | 2.4 | 3.7 | 3.1 |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

SEQUENCE LISTING

SEQ ID NO: 1
ATX-P-875 VH CDR1 (Kabat)
GFTFSNAW

SEQ ID NO: 2
ATX-P-875 VH CDR2 (Kabat)
IKSKTDGGTT

SEQ ID NO: 3
ATX-P-875 VH CDR3 (Kabat)
TTGPDDLDY

SEQ ID NO: 4
ATX-P-875 VH nt
GAGGTGCAGCTGGTGGAGTCCGGGGGAGGCCTGGTCAAGCCTGGGGGGTCCCTGAGACTCTC
CTGTGCAGCCTCTGGATTCACTTTCAGTAACGCCTGGATGAGCTGGGTCCGCCAGGCTCCAG
GGAAGGGGCTGGAGTGGGTTGGCCGTATTAAAAGCAAAACTGATGGTGGGACAACAGACTAC
GCTGCACCCGTGAAAGGCAGATTCACCATCTCAAGAGATGATTCAAAAAACACGCTCTATCT
GCAAATGAACAGCCTGAAAACCGAGGACACAGCCGTGTATTACTGTACCACAGGCCCTGACG
ATCTTGACTACTGGGGCCAGGGAACCCCGGTCACCGTCTCCTCA

SEQ ID NO: 5
ATX-P-875 VH AA
EVQLVESGGGLVKPGGSLRLSCAASGFTFSNAWMSWVRQAPGKGLEWVGRIKSKTDGGTTDY
AAPVKGRFTISRDDSKNTLYLQMNSLKTEDTAVYYCTTGPDDLDYWGQGTPVTSS

SEQ ID NO: 6
ATX-P-875 HC IgG1-Fc nt
GAGGTGCAGCTGGTGGAGTCCGGGGGAGGCCTGGTCAAGCCTGGGGGGTCCCTGAGACTCTC
CTGTGCAGCCTCTGGATTCACTTTCAGTAACGCCTGGATGAGCTGGGTCCGCCAGGCTCCAG
GGAAGGGGCTGGAGTGGGTTGGCCGTATTAAAAGCAAAACTGATGGTGGGACAACAGACTAC
GCTGCACCCGTGAAAGGCAGATTCACCATCTCAAGAGATGATTCAAAAAACACGCTCTATCT
GCAAATGAACAGCCTGAAAACCGAGGACACAGCCGTGTATTACTGTACCACAGGCCCTGACG
ATCTTGACTACTGGGGCCAGGGAACCCCGGTCACCGTCTCCTCAGCTAGCACTAAAGGGCCT
TCTGTATTTCCCTTGGCCCCGTCCAGCAAATCGACCTCGGGAGGGACAGCCGCCCTGGGTTG
CCTTGTGAAAGATTATTTCCCTGAGCCAGTTACCGTAAGTTGGAACAGTGGGGCGCTGACAA
GTGGTGTGCACACGTTTCCTGCCGTCCTGCAATCATCGGGCTTGTATAGCCTCAGCTCTGTG
GTCACTGTCCCAAGTTCATCGCTGGGCACTCAGACGTATATTTGCAATGTGAACCACAAACC

| SEQUENCE LISTING |
|---|
| TTCAAATACAAAAGTGGATAAACGCGTAGAACCGAAATCGTGTGATAAAACTCACACATGCC<br>CGCCATGCCCGGCACCTGAACTGCTTGGTGGTCCCAGCGTGTTCCTGTTCCCGCCGAAGCCT<br>AAAGATACTCTAATGATCAGCCGTACGCCAGAGGTGACATGTGTCGTGGTTGACGTGTCCCA<br>CGAAGATCCCGAAGTTAAGTTCAATTGGTATGTTGATGGTGTAGAGGTACACAATGCTAAGA<br>CTAAACCTCGCGAGGAGCAGTACAATTCGACCTATCGTGTCGTGAGCGTTCTGACCGTCCTT<br>CACCAAGATTGGCTTAACGGCAAAGAATATAAGTGCAAGGTAAGCAATAAAGCACTTCCGGC<br>CCCAATCGAGAAAACCATTTCCAAGGCCAAAGGTCAACCAAGAGAACCCCAGGTGTATACTC<br>TTCCGCCTTCTCGTGAGGAAATGACTAAAAATCAAGTATCCCTTACGTGTCTGGTTAAAGGT<br>TTTTATCCTAGCGATATTGCTGTTGAATGGGAATCGAACGGTCAGCCGGAGAATAATTATAA<br>AACAACGCCACCCGTCCTGGATAGCGACGGCTCATTTTTTCTGTATAGCAAACTGACTGTAG<br>ATAAATCACGGTGGCAGCAGGGCAATGTATTCAGTTGCTCCGTTATGCATGAAGCGTTACAT<br>AATCACTACACGCAGAAATCTCTTAGTCTTTCACCCGGT |

```
                                                         SEQ ID NO: 7
ATX-P-875 HC IgG1-Fc AA
EVQLVESGGGLVKPGGSLRLSCAASGFTFSNAWMSWVRQAPGKGLEWVGRIKSKTDGGTTDY
AAPVKGRFTISRDDSKNTLYLQMNSLKTEDTAVYYCTTGPDDLDYWGQGTPVTVSSASTKGP
SVFPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCSVMHEALH
NHYTQKSLSLSPG

SEQ ID NO: 8
ATX-P-875 VL CDR1 (Kabat)
QSISSY

ATX-P-875 VL CDR2 (Kabat)
AAS

SEQ ID NO: 10
ATX-P-875 VL CDR3 (Kabat)
QQYDNLPIT

SEQ ID NO: 11
ATX-P-875 VL nt
GACATCCAGATGACCCAGTCTCCATCCTCCCTGTCTGCATCTGTAGGAGACAGAGTCACCAT
CACTTGCCGGGCAAGTCAGAGCATTAGCAGCTATTTAAATTGGTATCAGCAGAAACCAGGGA
AAGCCCCTAAGCTCCTGATCTATGCTGCATCCAGTTTGCAAAGTGGGGTCCCATCAAGGTTC
AGCGGCAGTGGATCTGGGACAGATTTCACTCTCACCATCAGCAGCCTGCAACCTGAAGATTT
TGCAACTTACTACTGTCAACAGTATGATAATCTCCCGATCACCTTCGGCCAAGGGACACGAC
TGGAGATTAAA

SEQ ID NO: 12
ATX-P-875 VL AA
DIQMTQSPSSLSASVGDRVTITCRASQSISSYLNWYQQKPGKAPKLLIYAASSLQSGVPSRF
SGSGSGTDFTLTISSLQPEDFATYYCQQYDNLPITFGQGTRLEIK

SEQ ID NO: 13
ATX-P-875 Kappa LC nt
GACATCCAGATGACCCAGTCTCCATCCTCCCTGTCTGCATCTGTAGGAGACAGAGTCACCAT
CACTTGCCGGGCAAGTCAGAGCATTAGCAGCTATTTAAATTGGTATCAGCAGAAACCAGGGA
AAGCCCCTAAGCTCCTGATCTATGCTGCATCCAGTTTGCAAAGTGGGGTCCCATCAAGGTTC
AGCGGCAGTGGATCTGGGACAGATTTCACTCTCACCATCAGCAGCCTGCAACCTGAAGATTT
TGCAACTTACTACTGTCAACAGTATGATAATCTCCCGATCACCTTCGGCCAAGGGACACGAC
TGGAGATTAAACGTACGGTAGCGCCCCTTCAGTTTTTATCTTTCCGCCGTCTGACGAGCAG
TTAAAATCCGGGACCGCTTCTGTAGTTTGCCTGCTGAATAATTTTTATCCGCGTGAGGCTAA
AGTACAATGGAAAGTCGACAATGCTTTGCAGTCGGGAAATTCACAGGAAAGTGTTACGGAGC
AGGATTCTAAAGATTCCACATATTCACTCAGCTCCACCCTTACACTGAGCAAAGCCGACTAT
GAAAAACATAAAGTTTACGCATGTGAGGTGACGCACCAAGGATTATCCAGTCCGGTCACAAA
ATCGTTTAACCGCGGTGAGTGT SEQ ID NO: 14
ATX-P-875 Kappa LC AA
DIQMTQSPSSLSASVGDRVTITCRASQSISSYLNWYQQKPGKAPKLLIYAASSLQSGVPSRF
SGSGSGTDFTLTISSLQPEDFATYYCQQYDNLPITFGQGTRLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC SEQ ID NO: 15
ATX-P-885 VH CDR1 (Kabat)
GGSFSGYY SEQ ID NO: 16
ATX-P-885 VH CDR2 (Kabat)
INHSGST
```

SEQUENCE LISTING

SEQ ID NO: 17
ATX-P-885 VH CDR3 (Kabat)
AREGVYEDY

SEQ ID NO: 18
ATX-P-885 VH nt
CAGGTGCAGCTACAGCAGTGGGGCGCAGGACTGTTGAAGCCTTCGGAGACCCTGTCCCTCAC
CTGCGCTGTCTATGGTGGGTCCTTCAGTGGTTACTACTGGAGCTGGATCCGCCAGCCCCAG
GGAAGGGGCTGGAGTGGATTGGGGAAATCAATCATAGTGGAAGCACCAACTACAACCCGTCC
CTCAAGAGTCGAGTCACCATATCAGTAGACACGTCCAAGAACCAGTTCTCCCTGAAGCTGAG
CTCTGTGACCGCCGCGGACACGGCTGTATATTACTGTGCGAGAGAGGGTGTCTACGAGGACT
ACTGGGGCCAGGGAACCCTGGTCACCGTCTCCTCA

SEQ ID NO: 19
ATX-P-885 VH AA
QVQLQQWGAGLLKPSETLSLTCAVYGGSFSGYYWSWIRQPPGKGLEWIGEINHSGSTNYNPS
LKSRVTISVDTSKNQFSLKLSSVTAADTAVYYCAREGVYEDYWGQGTLVTVSS

SEQ ID NO: 20
ATX-P-885 HC IgG1-Fc nt
CAGGTGCAGCTACAGCAGTGGGGCGCAGGACTGTTGAAGCCTTCGGAGACCCTGTCCCTCAC
CTGCGCTGTCTATGGTGGGTCCTTCAGTGGTTACTACTGGAGCTGGATCCGCCAGCCCCAG
GGAAGGGGCTGGAGTGGATTGGGGAAATCAATCATAGTGGAAGCACCAACTACAACCCGTCC
CTCAAGAGTCGAGTCACCATATCAGTAGACACGTCCAAGAACCAGTTCTCCCTGAAGCTGAG
CTCTGTGACCGCCGCGGACACGGCTGTATATTACTGTGCGAGAGAGGGTGTCTACGAGGACT
ACTGGGGCCAGGGAACCCTGGTCACCGTCTCCTCAGCTAGCACTAAAGGGCCTTCTGTATTT
CCCTTGGCCCCGTCCAGCAAATCGACCTCGGGAGGGACAGCCGCCCTGGGTTGCCTTGTGA
AGATTATTTCCCTGAGCCAGTTACCGTAAGTTGGAACAGTGGGGCGCTGACAAGTGGTGTGC
ACACGTTTCCTGCCGTCCTGCAATCATCGGGCTTGTATAGCCTCAGCTCTGTGGTCACTGTC
CCAAGTTCATCGCTGGGCACTCAGACGTATATTTGCAATGTGAACCACAAACCTTCAAATAC
AAAAGTGGATAAACGCGTAGAACCGAAATCGTGTGATAAAACTCACACATGCCCGCCATGCC
CGGCACCTGAACTGCTTGGTGGTCCCAGCGTGTTCCTGTTCCCGCCGAAGCCTAAAGATACT
CTAATGATCAGCCGTACGCCAGAGGTGACATGTGTCGTGTTGACGTGTCCCACGAAGATCC
CGAAGTTAAGTTCAATTGGTATGTTGATGGTGTAGAGGTACACAATGCTAAGACTAAACCTC
GCGAGGAGCAGTACAATTCGACCTATCGTGTCGTGAGCGTTCTGACCGTCCTTCACCAAGAT
TGGCTTAACGGCAAGAATATAAGTGCAAGGTAAGCAATAAAGCACTTCCGGCCCCAATCGA
GAAAACCATTTCCAAGGCCAAAGGTCAACCAAGAGAACCCCAGGTGTATACTCTTCCGCCTT
CTCGTGAGGAAATGACTAAAAATCAAGTATCCCTTACGTGTCTGGTTAAAGGTTTTTATCCT
AGCGATATTGCTGTTGAATGGGAATCGAACGGTCAGCCGGAGAATAATTATAAAACAACGCC
ACCCGTCCTGGATAGCGACGGCTCATTTTTCT

SEQ ID NO: 21
ATX-P-885 HC IgG1-Fc AA
QVQLQQWGAGLLKPSETLSLTCAVYGGSFSGYYWSWIRQPPGKGLEWIGEINHSGSTNYNPS
LKSRVTISVDTSKNQFSLKLSSVTAADTAVYYCAREGVYEDYWGQGTLVTVSSASTKGPSVF
PLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGEYP
SDIAVEWESNGQPENNYKTTPPVLDSDGSFFLYSKLTVDKSRWQQGNVFSCSVMHEALHNHY
TQKSLSLSPG

SEQ ID NO: 22
ATX-P-885 VL CDR1 (Kabat)
QSVSNY

ATX-P-885 VL CDR2 (Kabat)
DAY

SEQ ID NO: 24
ATX-P-885 VL CDR3 (Kabat)
QQRSNWPLT

SEQ ID NO: 25
ATX-P-885 VL nt
GAAATTGTGTTGACACAGTCTCCAGCCACCCTGTCTTTGTCTCCAGGGGAAAGAGCCACCCT
CTCCTGCAGGGCCAGTCAGAGTGTTAGCAACTACTTAGCCTGGTACCAACAGAAACCTGGCC
AGGCTCCCAGGCTCCTCATCTATGATGCCTACAACAGGGCCACTGGCATCCCAGCCAGGTTC
AGTGGCAGTGGGTCTGGGACAGACTTCACTCTCACCATCAGCAGCCTAGAGCCTGAAGATTT
TGCAGTTTATTACTGTCAGCAGCGTAGCAACTGGCCTCTCACCTTCGGCCAAGGGACACGAC
TGGAGATTAAA

SEQ ID NO: 26
ATX-P-885 VL AA
EIVLTQSPATLSLSPGERATLSCRASQSVSNYLAWYQQKPGQAPRLLIYDAYNRATGIPARF
SGSGSGTDFTLTISSLEPEDFAVYYCQQRSNWPLTFGQGTRLEIK

-continued

SEQUENCE LISTING

SEQ ID NO: 27
ATX-P-885 Kappa LC nt
GAAATTGTGTTGACACAGTCTCCAGCCACCCTGTCTTTGTCTCCAGGGGAAAGAGCCACCCT
CTCCTGCAGGGCCAGTCAGAGTGTTAGCAACTACTTAGCCTGGTACCAACAGAAACCTGGCC
AGGCTCCCAGGCTCCTCATCTATGATGCCTACAACAGGGCCACTGGCATCCCAGCCAGGTTC
AGTGGCAGTGGGTCTGGGACAGACTTCACTCTCACCATCAGCAGCCTAGAGCCTGAAGATTT
TGCAGTTTATTACTGTCAGCAGCGTAGCAACTGGCCTCTCACCTTCGGCCAAGGGACACGAC
TGGAGATTAAACGTACGGTAGCTGCCCCTTCAGTTTTTATCTTTCCGCCGTCTGACGAGCAG
TTAAAATCCGGGACCGCTTCTGTAGTTTGCCTGCTGAATAATTTTTATCCGCGTGAGGCTAA
AGTACAATGGAAAGTCGACAATGCTTTGCAGTCGGGAAATTCACAGGAAAGTGTTACGGAGC
AGGATTCTAAAGATTCCACATATTCACTCAGCTCCACCCTTACACTGAGCAAAGCCGACTAT
GAAAAACATAAAGTTTACGCATGTGAGGTGACGCACCAAGGATTATCCAGTCCGGTCACAAA
ATCGTTTAACCGCGGTGAGTGT SEQ ID NO: 28
ATX-P-885 Kappa LC AA
EIVLTQSPATLSLSPGERATLSCRASQSVSNYLAWYQQKPGQAPRLLIYDAYNRATGIPARF
SGSGSGTDFTLTISSLEPEDFAVYYCQQRSNWPLTFGQGTRLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC SEQ ID NO: 29
ATX-P-890 VH CDR1 (Kabat)
GYTFTGYY SEQ ID NO: 30
ATX-P-890 VH CDR2 (Kabat)
INPNSGGT SEQ ID NO: 31
ATX-P-890 VH CDR3 (Kabat)
VRDQVQLERFDS SEQ ID NO: 32
ATX-P-890 VH nt
CAGGTGCAGCTGGTGCAGTCTGGGGCTGAGGTGAAGAAGCCTGGGGCCTCAGTGAAGGTCTC
CTGCAAGGCTTCTGGATACACCTTCACCGGCTACTATATGCACTGGGTGCGACAGGCCCCTG
GACAAGGGCTTGAGTGGATGGGATGGATCAACCCTAACAGTGGTGGCACAAACTATGCACAG
AAGTTTCAGGGCAGGGTCACCATGACCAGGGACACGTCCATCAGCACAGCCTACATGGAGCT
GAGCAGGCTGAGATCTGACGACACGGCCGTGTATTACTGTGTGAGAGATCAGGTACAACTGG
AACGGTTCGACTCCTGGGGCCAGGGAACCCTGGTCACCGTCTCCTCA SEQ ID NO: 33
ATX-P-890 VH AA
QVQLVQSGAEVKKPGASVKVSCKASGYTFTGYYMHWVRQAPGQGLEWMGWINPNSGGTNYAQ
KFQGRVTMTRDTSISTAYMELSRLRSDDTAVYYCVRDQVQLERFDSWGQGTLVTVSS SEQ ID NO: 34
ATX-P-890 HC IgG1-Fc nt
CAGGTGCAGCTGGTGCAGTCTGGGGCTGAGGTGAAGAAGCCTGGGGCCTCAGTGAAGGTCTC
CTGCAAGGCTTCTGGATACACCTTCACCGGCTACTATATGCACTGGGTGCGACAGGCCCCTG
GACAAGGGCTTGAGTGGATGGGATGGATCAACCCTAACAGTGGTGGCACAAACTATGCACAG
AAGTTTCAGGGCAGGGTCACCATGACCAGGGACACGTCCATCAGCACAGCCTACATGGAGCT
GAGCAGGCTGAGATCTGACGACACGGCCGTGTATTACTGTGTGAGAGATCAGGTACAACTGG
AACGGTTCGACTCCTGGGGCCAGGGAACCCTGGTCACCGTCTCCTCAGCTAGCACTAAAGGG
CCTTCTGTATTTCCCTTGGCCCCGTCCAGCAAATCGACCTCGGGAGGGACAGCCGCCCTGGG
TTGCCTTGTGAAAGATTATTTCCCTGAGCCAGTTACCGTAAGTTGGAACAGTGGGGCGCTGA
CAAGTGGTGTGCACACGTTTCCTGCCGTCCTGCAATCATCGGGCTTGTATAGCCTCAGCTCT
GTGGTCACTGTCCCAAGTTCATCGCTGGGCACTCAGACGTATATTTGCAATGTGAACCACAA
ACCTTCAAATACAAAAGTGGATAAACGCGTAGAACCGAAATCGTGTGATAAAACTCACACAT
GCCCGCCATGCCCGGCACCTGAACTGCTTGGTGGTCCCAGCGTGTTCCTGTTCCCGCCGAAG
CCTAAAGATACTCTAATGATCAGCCGTACGCCAGAGGTGACATGTGTCGTGGTTGACGTGTC
CCACGAAGATCCCGAAGTTAAGTTCAATTGGTATGTTGATGGTGTAGAGGTACACAATGCTA
AGACTAAACCTCGCGAGGAGCAGTACAATTCGACCTATCGTGTCGTGAGCGTTCTGACCGTC
CTTCACCAAGATTGGCTTAACGGCAAAGAATATAAGTGCAAGGTAAGCAATAAAGCACTTCC
GGCCCCAATCGAGAAAACCATTTCCAAGGCCAAAGGTCAACCAAGAGAACCCCAGGTGTATA
CTCTTCCGCCTTCTCGTGAGGAAATGACTAAAAATCAAGTATCCCTTACGTGTCTGGTTAAA
GGTTTTTATCCTAGCGATATTGCTGTTGAATGGGAATCGAACGGTCAGCCGGAGAATAATTA
TAAAACAACGCCACCCGTCCTGGATAGCGACGGCTCATTTTTTCTGTATAGCAAACTGACTG
TAGATAAATCACGGTGGCAGCAGGGCAATGTATTCAGTTGCTCCGTTATGCATGAAGCGTTA
CATAATCACTACACGCAGAAATCTCTTAGTCTTTCACCCGGT SEQ ID NO: 35
ATX-P-890 HC IgG1-Fc AA
QVQLVQSGAEVKKPGASVKVSCKASGYTFTGYYMHWVRQAPGQGLEWMGWINPNSGGTNYAQ
KFQGRVTMTRDTSISTAYMELSRLRSDDTAVYYCVRDQVQLERFDSWGQGTLVTVSSASTKG PSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSCSVMHEAL
HNHYTQKSLSLSPG SEQ ID NO: 36
ATX-P-890 VL CDR1 (Kabat)
QDISNY ATX-P-890 VL CDR2 (Kabat)
DAS SEQ ID NO: 38
ATX-P-890 VL CDR3 (Kabat)
QQYDNLPPT SEQ ID NO: 39
ATX-P-890 VL nt
GACATCCAGATGACCCAGTCTCCATCCTCCCTGTCTGCATCTGTAGGAGACAGAGTCACCAT
CACTTGCCAGGCGAGTCAGGACATTAGCAACTATTTAAATTGGTATCAGCAGAAACCAGGGA
AAGCCCCTAAGCTCCTGATCTACGATGCATCCAATTTGGAAACAGGGGTCCCATCAAGGTTC
AGTGGAAGTGGATCTGGGACAGATTTTACTTTCACCATCAGCAGCCTGCAGCCTGAAGATAT
TGCAACATATTACTGTCAACAGTATGATAATCTCCCTCCCACTTTCGGCCCTGGGACCAAGG
TGGAAATCAAA SEQ ID NO: 40
ATX-P-890 VL AA
DIQMTQSPSSLSASVGDRVTITCQASQDISNYLNWYQQKPGKAPKLLIYDASNLETGVPSRF
SGSGSGTDFTFTISSLQPEDIATYYCQQYDNLPPTFGPGTKVEIK SEQ ID NO: 41
ATX-P-890 Kappa LC nt
GACATCCAGATGACCCAGTCTCCATCCTCCCTGTCTGCATCTGTAGGAGACAGAGTCACCAT
CACTTGCCAGGCGAGTCAGGACATTAGCAACTATTTAAATTGGTATCAGCAGAAACCAGGGA
AAGCCCCTAAGCTCCTGATCTACGATGCATCCAATTTGGAAACAGGGGTCCCATCAAGGTTC
AGTGGAAGTGGATCTGGGACAGATTTTACTTTCACCATCAGCAGCCTGCAGCCTGAAGATAT
TGCAACATATTACTGTCAACAGTATGATAATCTCCCTCCCACTTTCGGCCCTGGGACCAAGG
TGGAAATCAAACGTACGGTAGCTGCCCCTTCAGTTTTTATCTTTCCGCCGTCTGACGAGCAG
TTAAAATCCGGGACCGCTTCTGTAGTTTGCCTGCTGAATAATTTTTATCCGCGTGAGGCTAA
AGTACAATGGAAAGTCGACAATGCTTTGCAGTCGGGAAATTCACAGGAAAGTGTTACGGAGC
AGGATTCTAAAGATTCCACATATTCACTCAGCTCCACCCTTACACTGAGCAAAGCCGACTAT
GAAAAACATAAAGTTTACGCATGTGAGGTGACGCACCAAGGATTATCCAGTCCGGTCACAAA
ATCGTTTAACCGCGGTGAGTGT SEQ ID NO: 42
ATX-P-890 Kappa LC AA
DIQMTQSPSSLSASVGDRVTITCQASQDISNYLNWYQQKPGKAPKLLIYDASNLETGVPSRF
SGSGSGTDFTFTISSLQPEDIATYYCQQYDNLPPTFGPGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC

SEQUENCE LISTING

```
Sequence total quantity: 46
SEQ ID NO: 1            moltype = AA   length = 8
FEATURE                 Location/Qualifiers
source                  1..8
                        mol_type = protein
                        organism = synthetic construct
SEQUENCE: 1
GFTFSNAW                                                                    8

SEQ ID NO: 2            moltype = AA   length = 10
FEATURE                 Location/Qualifiers
source                  1..10
                        mol_type = protein
                        organism = synthetic construct
SEQUENCE: 2
IKSKTDGGTT                                                                 10
```

```
SEQ ID NO: 3              moltype = AA   length = 9
FEATURE                   Location/Qualifiers
source                    1..9
                          mol_type = protein
                          organism = synthetic construct
SEQUENCE: 3
TTGPDDLDY                                                                9

SEQ ID NO: 4              moltype = AA   length = 354
FEATURE                   Location/Qualifiers
source                    1..354
                          mol_type = protein
                          organism = synthetic construct
SEQUENCE: 4
GAGGTGCAGC TGGTGGAGTC CGGGGGAGGC CTGGTCAAGC CTGGGGGGTC CCTGAGACTC    60
TCCTGTGCAG CCTCTGGATT CACTTTCAGT AACGCCTGGA TGAGCTGGGT CCGCCAGGCT   120
CCAGGGAAGG GGCTGGAGTG GGTTGGCCGT ATTAAAAGCA AAACTGATGG TGGGACAACA   180
GACTACGCTG CACCCGTGAA AGGCAGATTC ACCATCTCAA GAGATGATTC AAAAAACACG   240
CTCTATCTGC AAATGAACAG CCTGAAAACC GAGGACACAG CCGTGTATTA CTGTACCACA   300
GGCCCTGACG ATCTTGACTA CTGGGGCCAG GGAACCCCGG TCACCGTCTC CTCA         354

SEQ ID NO: 5              moltype = AA   length = 118
FEATURE                   Location/Qualifiers
source                    1..118
                          mol_type = protein
                          organism = synthetic construct
SEQUENCE: 5
EVQLVESGGG LVKPGGSLRL SCAASGFTFS NAWMSWVRQA PGKGLEWVGR IKSKTDGGTT    60
DYAAPVKGRF TISRDDSKNT LYLQMNSLKT EDTAVYYCTT GPDDLDYWGQ GTPVTVSS    118

SEQ ID NO: 6              moltype = AA   length = 1341
FEATURE                   Location/Qualifiers
source                    1..1341
                          mol_type = protein
                          organism = synthetic construct
SEQUENCE: 6
GAGGTGCAGC TGGTGGAGTC CGGGGGAGGC CTGGTCAAGC CTGGGGGGTC CCTGAGACTC    60
TCCTGTGCAG CCTCTGGATT CACTTTCAGT AACGCCTGGA TGAGCTGGGT CCGCCAGGCT   120
CCAGGGAAGG GGCTGGAGTG GGTTGGCCGT ATTAAAAGCA AAACTGATGG TGGGACAACA   180
GACTACGCTG CACCCGTGAA AGGCAGATTC ACCATCTCAA GAGATGATTC AAAAAACACG   240
CTCTATCTGC AAATGAACAG CCTGAAAACC GAGGACACAG CCGTGTATTA CTGTACCACA   300
GGCCCTGACG ATCTTGACTA CTGGGGCCAG GGAACCCCGG TCACCGTCTC CTCAGCTAGC   360
ACTAAAGGGC CTTCTGTATT TCCCTTGGCC CCGTCCAGCA AATCGACCTC GGGAGGGACA   420
GCCGCCCTGG GTTGCCTTGT GAAAGATTAT TTCCCTGAGC CAGTTACCGT AAGTTGGAAC   480
AGTGGGGCGC TGACAAGTGG TGTGCACACG TTTCCTGCCG TCCTGCAATC ATCGGGCTTG   540
TATAGCCTCA GCTCTGTGGT CACTGTCCCA AGTTCATCGC TGGGCACTCA GACGTATATT   600
TGCAATGTGA ACCACAAACC TTCAAATACA AAAGTGGATA AACGCGTAGA ACCGAAATCG   660
TGTGATAAAA CTCACACATG CCCGCCATGC CCGGCACCTG AACTGCTTGG TGGTCCCAGC   720
GTGTTCCTGT TCCCGCCGAA GCCTAAAGAT ACTCTAATGA TCAGCCGTAC GCCAGAGGTG   780
ACATGTGTCG TGGTTGACGT GTCCCACGAA GATCCCGAAG TTAAGTTCAA TTGGTATGTT   840
GATGGTGTAG AGGTACACAA TGCTAAGACT AAACCTCGCG AGGAGCAGTA CAATTCGACC   900
TATCGTGTCG TGAGCGTTCT GACCGTCCTT CACCAAGATT GGCTTAACGG CAAAGAATAT   960
AAGTGCAAGG TAAGCAATAA AGCACTTCCG GCCCCAATCG AGAAACCAT TTCCAAGGCC   1020
AAAGGTCAAC CAAGAGAACC CCAGGTGTAT ACTCTTCCGC CTTCCGTGA GGAAATGACT   1080
AAAAATCAAG TATCCCTTAC GTGTCTGGTT AAAGGTTTTT ATCCTAGCGA TATTGCTGTT   1140
GAATGGGAAT CGAACGGTCA GCCGGAGAAT AATTATAAAA CAACGCCACC CGTCCTGGAT   1200
AGCGACGGCT CATTTTTTCT GTATAGCAAA CTGACTGTAG ATAAATCACG GTGGCAGCAG   1260
GGCAATGTAT TCAGTTGCTC CGTTATGCAT GAAGCGTTAC ATAATCACTA CACGCAGAAA   1320
TCTCTTAGTC TTTCACCCGG T                                           1341

SEQ ID NO: 7              moltype = AA   length = 447
FEATURE                   Location/Qualifiers
source                    1..447
                          mol_type = protein
                          organism = synthetic construct
SEQUENCE: 7
EVQLVESGGG LVKPGGSLRL SCAASGFTFS NAWMSWVRQA PGKGLEWVGR IKSKTDGGTT    60
DYAAPVKGRF TISRDDSKNT LYLQMNSLKT EDTAVYYCTT GPDDLDYWGQ GTPVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                      447

SEQ ID NO: 8              moltype = AA   length = 6
FEATURE                   Location/Qualifiers
source                    1..6
```

```
                        mol_type = protein
                        organism = synthetic construct
SEQUENCE: 8
QSISSY                                                                      6

SEQ ID NO: 9            moltype =   length =
SEQUENCE: 9
000

SEQ ID NO: 10           moltype = AA   length = 9
FEATURE                 Location/Qualifiers
source                  1..9
                        mol_type = protein
                        organism = synthetic construct
SEQUENCE: 10
QQYDNLPIT                                                                   9

SEQ ID NO: 11           moltype = AA   length = 321
FEATURE                 Location/Qualifiers
source                  1..321
                        mol_type = protein
                        organism = synthetic construct
SEQUENCE: 11
GACATCCAGA TGACCCAGTC TCCATCCTCC CTGTCTGCAT CTGTAGGAGA CAGAGTCACC          60
ATCACTTGCC GGGCAAGTCA GAGCATTAGC AGCTATTTAA ATTGGTATCA GCAGAAACCA         120
GGGAAAGCCC CTAAGCTCCT GATCTATGCT GCATCCAGTT TGCAAAGTGG GGTCCCATCA         180
AGGTTCAGCG GCAGTGGATC TGGGACAGAT TTCACTCTCA CCATCAGCAG CCTGCAACCT         240
GAAGATTTTG CAACTTACTA CTGTCAACAG TATGATAATC TCCCGATCAC CTTCGGCCAA         300
GGGACACGAC TGGAGATTAA A                                                   321

SEQ ID NO: 12           moltype = AA   length = 107
FEATURE                 Location/Qualifiers
source                  1..107
                        mol_type = protein
                        organism = synthetic construct
SEQUENCE: 12
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ YDNLPITFGQ GTRLEIK                        107

SEQ ID NO: 13           moltype = AA   length = 642
FEATURE                 Location/Qualifiers
source                  1..642
                        mol_type = protein
                        organism = synthetic construct
SEQUENCE: 13
GACATCCAGA TGACCCAGTC TCCATCCTCC CTGTCTGCAT CTGTAGGAGA CAGAGTCACC          60
ATCACTTGCC GGGCAAGTCA GAGCATTAGC AGCTATTTAA ATTGGTATCA GCAGAAACCA         120
GGGAAAGCCC CTAAGCTCCT GATCTATGCT GCATCCAGTT TGCAAAGTGG GGTCCCATCA         180
AGGTTCAGCG GCAGTGGATC TGGGACAGAT TTCACTCTCA CCATCAGCAG CCTGCAACCT         240
GAAGATTTTG CAACTTACTA CTGTCAACAG TATGATAATC TCCCGATCAC CTTCGGCCAA         300
GGGACACGAC TGGAGATTAA ACGTACGGTA GCTGCCCCTT CAGTTTTTAT CTTTCCGCCG         360
TCTGACGAGC AGTTAAAATC CGGGACCGCT TCTGTAGTTT GCCTGCTGAA TAATTTTTAT         420
CCGCGTGAGG CTAAAGTACA ATGGAAAGTC GACAATGCTT TGCAGTCGGG AAATTCACAG         480
GAAAGTGTTA CGGAGCAGGA TTCTAAAGAT TCCACATATT CACTCAGCTC CACCCTTACA         540
CTGAGCAAAG CCGACTATGA AAAACATAAA GTTTACGCAT GTGAGGTGAC GCACCAAGGA         600
TTATCCAGTC CGGTCACAAA ATCGTTTAAC CGCGGTGAGT GT                            642

SEQ ID NO: 14           moltype = AA   length = 214
FEATURE                 Location/Qualifiers
source                  1..214
                        mol_type = protein
                        organism = synthetic construct
SEQUENCE: 14
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ YDNLPITFGQ GTRLEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                     214

SEQ ID NO: 15           moltype = AA   length = 8
FEATURE                 Location/Qualifiers
source                  1..8
                        mol_type = protein
                        organism = synthetic construct
SEQUENCE: 15
GGSFSGYY                                                                    8

SEQ ID NO: 16           moltype = AA   length = 7
FEATURE                 Location/Qualifiers
source                  1..7
```

```
                        mol_type = protein
                        organism = synthetic construct
SEQUENCE: 16
INHSGST                                                                 7

SEQ ID NO: 17           moltype = AA   length = 9
FEATURE                 Location/Qualifiers
source                  1..9
                        mol_type = protein
                        organism = synthetic construct
SEQUENCE: 17
AREGVYEDY                                                               9

SEQ ID NO: 18           moltype = AA   length = 345
FEATURE                 Location/Qualifiers
source                  1..345
                        mol_type = protein
                        organism = synthetic construct
SEQUENCE: 18
CAGGTGCAGC TACAGCAGTG GGGCGCAGGA CTGTTGAAGC CTTCGGAGAC CCTGTCCCTC        60
ACCTGCGCTG TCTATGGTGG GTCCTTCAGT GGTTACTACT GGAGCTGGAT CCGCCAGCCC       120
CCAGGGAAGG GGCTGGAGTG GATTGGGGAA ATCAATCATA GTGGAAGCAC CAACTACAAC       180
CCGTCCCTCA AGAGTCGAGT CACCATATCA GTAGACACGT CCAAGAACCA GTTCTCCCTG       240
AAGCTGAGCT CTGTGACCGC CGCGGACACG GCTGTATATT ACTGTGCGAG AGAGGGTGTC       300
TACGAGGACT ACTGGGGCCA GGGAACCCTG GTCACCGTCT CCTCA                       345

SEQ ID NO: 19           moltype = AA   length = 115
FEATURE                 Location/Qualifiers
source                  1..115
                        mol_type = protein
                        organism = synthetic construct
SEQUENCE: 19
QVQLQQWGAG LLKPSETLSL TCAVYGGSFS GYYWSWIRQP PGKGLEWIGE INHSGSTNYN        60
PSLKSRVTIS VDTSKNQFSL KLSSVTAADT AVYYCAREGV YEDYWGQGTL VTVSS            115

SEQ ID NO: 20           moltype = AA   length = 1332
FEATURE                 Location/Qualifiers
source                  1..1332
                        mol_type = protein
                        organism = synthetic construct
SEQUENCE: 20
CAGGTGCAGC TACAGCAGTG GGGCGCAGGA CTGTTGAAGC CTTCGGAGAC CCTGTCCCTC        60
ACCTGCGCTG TCTATGGTGG GTCCTTCAGT GGTTACTACT GGAGCTGGAT CCGCCAGCCC       120
CCAGGGAAGG GGCTGGAGTG GATTGGGGAA ATCAATCATA GTGGAAGCAC CAACTACAAC       180
CCGTCCCTCA AGAGTCGAGT CACCATATCA GTAGACACGT CCAAGAACCA GTTCTCCCTG       240
AAGCTGAGCT CTGTGACCGC CGCGGACACG GCTGTATATT ACTGTGCGAG AGAGGGTGTC       300
TACGAGGACT ACTGGGGCCA GGGAACCCTG GTCACCGTCT CCTCAGCTAG CACTAAAGGG       360
CCTTCTGTAT TTCCCTTGGC CCCGTCCAGC AAATCGACCT CGGGAGGGAC AGCCGCCCTG       420
GGTTGCCTTG TGAAAGATTA TTTCCCTGAG CCAGTTACCG TAAGTTGGAA CAGTGGGGCG       480
CTGACAAGTG GTGTGCACAC GTTTCCTGCC GTCCTGCAAT CATCGGGCTT GTATAGCCTC       540
AGCTCTGTGG TCACTGTCCC AAGTTCATCG CTGGGCATCC AGACGTATAT TTGCAATGTG       600
AACCACAAAC CTTCAAATAC AAAAGTGGAT AAACGCGTAG AACCGAAATC GTGTGATAAA       660
ACTCACACAT GCCCGCCATG CCCGGCACCT GAACTGCTTG GTGGTCCCAG CGTGTTCCTG       720
TTCCCGCCGA AGCCTAAAGA TACTCTAATG ATCAGCCGTA CGCCAGAGGT GACATGTGTC       780
GTGGTTGACG TGTCCCACGA AGATCCCGAA GTTAAGTTCA ATTGGTATGT TGATGGTGTA       840
GAGGTACACA ATGCTAAGAC TAAACCTCGC GAGGAGCAGT ACAATTCGAC CTATCGTGTC       900
GTGAGCGTTC TGACCGTCCT TCACCAAGAT TGGCTTAACG GCAAAGAATA TAAGTGCAAG       960
GTAAGCAATA AAGCACTTCC GGCCCCAATC GAGAAAACCA TTTCCAAGGC CAAAGGTCAA      1020
CCAAGAGAAC CCCAGGTGTA TACTCTTCCG CCTTCTCGTG AGGAAATGAC TAAAAATCAA      1080
GTATCCCTTA CGTGTCTGGT TAAAGGTTTT TATCCTAGCG ATATTGCTGT TGAATGGGAA      1140
TCGAACGGTC AGCCGGAGAA TAATTATAAA ACAACGCCAC CCGTCCTGGA TAGCGACGGC      1200
TCATTTTTTC TGTATAGCAA ACTGACTGTA GATAAATCAC GGTGGCAGCA GGGCAATGTA      1260
TTCAGTTGCT CCGTTATGCA TGAAGCGTTA CATAATCACT ACACGCAGAA ATCTCTTAGT      1320
CTTTCACCCG GT                                                         1332

SEQ ID NO: 21           moltype = AA   length = 444
FEATURE                 Location/Qualifiers
source                  1..444
                        mol_type = protein
                        organism = synthetic construct
SEQUENCE: 21
QVQLQQWGAG LLKPSETLSL TCAVYGGSFS GYYWSWIRQP PGKGLEWIGE INHSGSTNYN        60
PSLKSRVTIS VDTSKNQFSL KLSSVTAADT AVYYCAREGV YEDYWGQGTL VTVSSASTKG       120
PSVFPLAPSS KSTSGGTAAL GCLVKDYFPE PVTVSWNSGA LTSGVHTFPA VLQSSGLYSL       180
SSVVTVPSSS LGTQTYICNV NHKPSNTKVD KRVEPKSCDK THTCPPCPAP ELLGGPSVFL       240
FPPKPKDTLM ISRTPEVTCV VVDVSHEDPE VKFNWYVDGV EVHNAKTKPR EEQYNSTYRV       300
VSVLTVLHQD WLNGKEYKCK VSNKALPAPI EKTISKAKGQ PREPQVYTLP PSREEMTKNQ       360
VSLTCLVKGF YPSDIAVEWE SNGQPENNYK TTPPVLDSDG SFFLYSKLTV DKSRWQQGNV       420
FSCSVMHEAL HNHYTQKSLS LSPG                                             444
```

```
SEQ ID NO: 22           moltype = AA  length = 6
FEATURE                 Location/Qualifiers
source                  1..6
                        mol_type = protein
                        organism = synthetic construct
SEQUENCE: 22
QSVSNY                                                                    6

SEQ ID NO: 23           moltype =     length =
SEQUENCE: 23
000

SEQ ID NO: 24           moltype = AA  length = 9
FEATURE                 Location/Qualifiers
source                  1..9
                        mol_type = protein
                        organism = synthetic construct
SEQUENCE: 24
QQRSNWPLT                                                                 9

SEQ ID NO: 25           moltype = AA  length = 321
FEATURE                 Location/Qualifiers
source                  1..321
                        mol_type = protein
                        organism = synthetic construct
SEQUENCE: 25
GAAATTGTGT TGACACAGTC TCCAGCCACC CTGTCTTTGT CTCCAGGGGA AAGAGCCACC    60
CTCTCCTGCA GGGCCAGTCA GAGTGTTAGC AACTACTTAG CCTGGTACCA ACAGAAACCT   120
GGCCAGGCTC CCAGGCTCCT CATCTATGAT GCCTACAACA GGGCCACTGG CATCCCAGCC   180
AGGTTCAGTG GCAGTGGGTC TGGGACAGAC TTCACTCTCA CCATCAGCAG CCTAGAGCCT   240
GAAGATTTTG CAGTTTATTA CTGTCAGCAG CGTAGCAACT GGCCTCTCAC CTTCGGCCAA   300
GGGACACGAC TGGAGATTAA A                                              321

SEQ ID NO: 26           moltype = AA  length = 107
FEATURE                 Location/Qualifiers
source                  1..107
                        mol_type = protein
                        organism = synthetic construct
SEQUENCE: 26
EIVLTQSPAT LSLSPGERAT LSCRASQSVS NYLAWYQQKP GQAPRLLIYD AYNRATGIPA    60
RFSGSGSGTD FTLTISSLEP EDFAVYYCQQ RSNWPLTFGQ GTRLEIK                  107

SEQ ID NO: 27           moltype = AA  length = 642
FEATURE                 Location/Qualifiers
source                  1..642
                        mol_type = protein
                        organism = synthetic construct
SEQUENCE: 27
GAAATTGTGT TGACACAGTC TCCAGCCACC CTGTCTTTGT CTCCAGGGGA AAGAGCCACC    60
CTCTCCTGCA GGGCCAGTCA GAGTGTTAGC AACTACTTAG CCTGGTACCA ACAGAAACCT   120
GGCCAGGCTC CCAGGCTCCT CATCTATGAT GCCTACAACA GGGCCACTGG CATCCCAGCC   180
AGGTTCAGTG GCAGTGGGTC TGGGACAGAC TTCACTCTCA CCATCAGCAG CCTAGAGCCT   240
GAAGATTTTG CAGTTTATTA CTGTCAGCAG CGTAGCAACT GGCCTCTCAC CTTCGGCCAA   300
GGGACACGAC TGGAGATTAA ACGTACGGTA GCTGCCCCTT CAGTTTTTAT CTTTCCGCCG   360
TCTGACGAGC AGTTAAAATC CGGGACCGCT TCTGTAGTTT GCCTGCTGAA TAATTTTTAT   420
CCGCGTGAGG CTAAAGTACA ATGGAAAGTC GACAATGCTT TGCAGTCGGG AAATTCACAG   480
GAAAGTGTTA CGGAGCAGGA TTCTAAAGAT TCCACATATT CACTCAGCTC CACCCTTACA   540
CTGAGCAAAG CCGACTATGA AAAACATAAA GTTTACGCAT GTGAGGTGAC GCACCAAGGA   600
TTATCCAGTC CGGTCACAAA ATCGTTTAAC CGCGGTGAGT GT                      642

SEQ ID NO: 28           moltype = AA  length = 214
FEATURE                 Location/Qualifiers
source                  1..214
                        mol_type = protein
                        organism = synthetic construct
SEQUENCE: 28
EIVLTQSPAT LSLSPGERAT LSCRASQSVS NYLAWYQQKP GQAPRLLIYD AYNRATGIPA    60
RFSGSGSGTD FTLTISSLEP EDFAVYYCQQ RSNWPLTFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 29           moltype = AA  length = 8
FEATURE                 Location/Qualifiers
source                  1..8
                        mol_type = protein
                        organism = synthetic construct
SEQUENCE: 29
GYTFTGYY                                                                  8
```

```
SEQ ID NO: 30           moltype = AA  length = 8
FEATURE                 Location/Qualifiers
source                  1..8
                        mol_type = protein
                        organism = synthetic construct
SEQUENCE: 30
INPNSGGT                                                                 8

SEQ ID NO: 31           moltype = AA  length = 12
FEATURE                 Location/Qualifiers
source                  1..12
                        mol_type = protein
                        organism = synthetic construct
SEQUENCE: 31
VRDQVQLERF DS                                                           12

SEQ ID NO: 32           moltype = AA  length = 357
FEATURE                 Location/Qualifiers
source                  1..357
                        mol_type = protein
                        organism = synthetic construct
SEQUENCE: 32
CAGGTGCAGC TGGTGCAGTC TGGGGCTGAG GTGAAGAAGC CTGGGGCCTC AGTGAAGGTC        60
TCCTGCAAGG CTTCTGGATA CACCTTCACC GGCTACTATA TGCACTGGGT GCGACAGGCC       120
CCTGGACAAG GGCTTGAGTG GATGGGATGG ATCAACCCTA ACAGTGGTGG CACAAACTAT       180
GCACAGAAGT TCAGGGCAG GGTCACCATG ACCAGGGACA CGTCCATCAG CACAGCCTAC        240
ATGGAGCTGA GCAGGCTGAG ATCTGACGAC ACGGCCGTGT ATTACTGTGT GAGAGATCAG       300
GTACAACTGG AACGGTTCGA CTCCTGGGGC CAGGGAACCC TGGTCACCGT CTCCTCA         357

SEQ ID NO: 33           moltype = AA  length = 119
FEATURE                 Location/Qualifiers
source                  1..119
                        mol_type = protein
                        organism = synthetic construct
SEQUENCE: 33
QVQLVQSGAE VKKPGASVKV SCKASGYTFT GYYMHWVRQA PGQGLEWMGW INPNSGGTNY        60
AQKFQGRVTM TRDTSISTAY MELSRLRSDD TAVYYCVRDQ VQLERFDSWG QGTLVTVSS       119

SEQ ID NO: 34           moltype = AA  length = 1344
FEATURE                 Location/Qualifiers
source                  1..1344
                        mol_type = protein
                        organism = synthetic construct
SEQUENCE: 34
CAGGTGCAGC TGGTGCAGTC TGGGGCTGAG GTGAAGAAGC CTGGGGCCTC AGTGAAGGTC        60
TCCTGCAAGG CTTCTGGATA CACCTTCACC GGCTACTATA TGCACTGGGT GCGACAGGCC       120
CCTGGACAAG GGCTTGAGTG GATGGGATGG ATCAACCCTA ACAGTGGTGG CACAAACTAT       180
GCACAGAAGT TCAGGGCAG GGTCACCATG ACCAGGGACA CGTCCATCAG CACAGCCTAC        240
ATGGAGCTGA GCAGGCTGAG ATCTGACGAC ACGGCCGTGT ATTACTGTGT GAGAGATCAG       300
GTACAACTGG AACGGTTCGA CTCCTGGGGC CAGGGAACCC TGGTCACCGT CTCCTCAGCT       360
AGCACTAAAG GCCTTCTGT ATTTCCCTTG GCCCCGTCCA GCAAATCGAC CTCGGGAGGG        420
ACAGCCGCCC TGGGTTGCCT TGTGAAAGAT TATTTCCCTG AGCCAGTTAC CGTAAGTTGG       480
AACAGTGGGG CGCTGACAAG TGGTGTGCAC ACGTTTCCTG CCGTCCTGCA ATCATCGGGC       540
TTGTATAGCC TCAGCTCTGT GGTCACTGTC CCAAGTTCAT CGCTGGGCAC TCAGACGTAT       600
ATTTGCAATG TGAACCACAA ACCTTCAAAT ACAAAAGTGG ATAAACGCGT AGAACCGAAA       660
TCGTGTGATA AAACTCACAC ATGCCCGCCA TGCCCGGCAC CTGAACTGCT TGGTGGTCCC       720
AGCGTGTTCC TGTTCCCGCC GAAGCCTAAA GATACTCTAA TGATCAGCCG TACGCCAGAG       780
GTGACATGTG TCGTGGTTGA CGTGTCCCAC GAAGATCCCG AAGTTAAGTT CAATTGGTAT       840
GTTGATGGTG TAGAGGTACA CAATGCTAAG ACTAAACCTC GCGAGGAGCA GTACAATTCG       900
ACCTATCGTG TCGTGAGCGT TCTGACCGTC CTTCACCAAG ATTGGCTTAA CGGCAAAGAA       960
TATAAGTGCA AGGTAAGCAA TAAAGCACTT CCGGCCCCAA TCGAGAAAAC CATTTCCAAG      1020
GCCAAAGGTC AACCAAGAGA ACCCCAGGTG TATACTCTTC CGCCTTCTCG TGAGGAAATG      1080
ACTAAAAATC AAGTATCCCT TACGTGTCTG GTTAAAGGTT TTTATCCTAG CGATATTGCT      1140
GTTGAATGGG AATCGAACGG TCAGCCGGAG AATAATTATA AACAACGCC ACCCGTCCTG       1200
GATAGCGACG GCTCATTTTT TCTGTATAGC AAACTGACTG TAGATAAATC ACGGTGGCAG      1260
CAGGGCAATG TATTCAGTTG CTCCGTTATG CATGAAGCGT TACATAATCA CTACACGCAG      1320
AAATCTCTTA GTCTTTCACC CGGT                                            1344

SEQ ID NO: 35           moltype = AA  length = 448
FEATURE                 Location/Qualifiers
source                  1..448
                        mol_type = protein
                        organism = synthetic construct
SEQUENCE: 35
QVQLVQSGAE VKKPGASVKV SCKASGYTFT GYYMHWVRQA PGQGLEWMGW INPNSGGTNY        60
AQKFQGRVTM TRDTSISTAY MELSRLRSDD TAVYYCVRDQ VQLERFDSWG QGTLVTVSSA       120
STKGPSVFPL APSSKSTSGG TAALGCLVKD YFPEPVTVSW NSGALTSGVH TPAVLQSSG        180
LYSLSSVVTV PSSSLGTQTY ICNVNHKPSN TKVDKRVEPK SCDKTHTCPP CPAPELLGGP       240
```

```
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 36           moltype = AA   length = 6
FEATURE                 Location/Qualifiers
source                  1..6
                        mol_type = protein
                        organism = synthetic construct
SEQUENCE: 36
QDISNY                                                                6

SEQ ID NO: 37           moltype =     length =
SEQUENCE: 37
000

SEQ ID NO: 38           moltype = AA   length = 9
FEATURE                 Location/Qualifiers
source                  1..9
                        mol_type = protein
                        organism = synthetic construct
SEQUENCE: 38
QQYDNLPPT                                                             9

SEQ ID NO: 39           moltype = AA   length = 321
FEATURE                 Location/Qualifiers
source                  1..321
                        mol_type = protein
                        organism = synthetic construct
SEQUENCE: 39
GACATCCAGA TGACCCAGTC TCCATCCTCC CTGTCTGCAT CTGTAGGAGA CAGAGTCACC    60
ATCACTTGCC AGGCGAGTCA GGACATTAGC AACTATTTAA ATTGGTATCA GCAGAAACCA    120
GGGAAAGCCC CTAAGCTCCT GATCTACGAT GCATCCAATT TGGAAACAGG GGTCCCATCA    180
AGGTTCAGTG GAAGTGGATC TGGGACAGAT TTTACTTTCA CCATCAGCAG CCTGCAGCCT    240
GAAGATATTG CAACATATTA CTGTCAACAG TATGATAATC TCCCTCCCAC TTTCGGCCCT    300
GGGACCAAGG TGGAAATCAA A                                              321

SEQ ID NO: 40           moltype = AA   length = 107
FEATURE                 Location/Qualifiers
source                  1..107
                        mol_type = protein
                        organism = synthetic construct
SEQUENCE: 40
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDNLPPTFGP GTKVEIK                  107

SEQ ID NO: 41           moltype = AA   length = 642
FEATURE                 Location/Qualifiers
source                  1..642
                        mol_type = protein
                        organism = synthetic construct
SEQUENCE: 41
GACATCCAGA TGACCCAGTC TCCATCCTCC CTGTCTGCAT CTGTAGGAGA CAGAGTCACC    60
ATCACTTGCC AGGCGAGTCA GGACATTAGC AACTATTTAA ATTGGTATCA GCAGAAACCA    120
GGGAAAGCCC CTAAGCTCCT GATCTACGAT GCATCCAATT TGGAAACAGG GGTCCCATCA    180
AGGTTCAGTG GAAGTGGATC TGGGACAGAT TTTACTTTCA CCATCAGCAG CCTGCAGCCT    240
GAAGATATTG CAACATATTA CTGTCAACAG TATGATAATC TCCCTCCCAC TTTCGGCCCT    300
GGGACCAAGG TGGAAATCAA ACGTACGGTA GCTGCCCCTT CAGTTTTTAT CTTTCCGCCG    360
TCTGACGAGC AGTTAAAATC CGGGACCGCT TCTGTAGTTT GCCTGCTGAA TAATTTTTAT    420
CCGCGTGAGG CTAAAGTACA ATGGAAAGTC GACAATGCTT TGCAGTCGGG AAATTCACAG    480
GAAAGTGTTA CGGAGCAGGA TTCTAAAGAT TCCACATATT CACTCAGCTC CACCCTTACA    540
CTGAGCAAAG CCGACTATGA AAAACATAAA GTTTACGCAT GTGAGGTGAC GCACCAAGGA    600
TTATCCAGTC CGGTCACAAA ATCGTTTAAC CGCGGTGAGT GT                       642

SEQ ID NO: 42           moltype = AA   length = 214
FEATURE                 Location/Qualifiers
source                  1..214
                        mol_type = protein
                        organism = synthetic construct
SEQUENCE: 42
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDNLPPTFGP GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 43           moltype = AA   length = 4
FEATURE                 Location/Qualifiers
source                  1..4
```

```
                        mol_type = protein
                        organism = synthetic construct
SEQUENCE: 43
GGFG                                                                    4

SEQ ID NO: 44           moltype = AA  length = 4
FEATURE                 Location/Qualifiers
source                  1..4
                        mol_type = protein
                        organism = synthetic construct
SEQUENCE: 44
EGGF                                                                    4

SEQ ID NO: 45           moltype = AA  length = 4
FEATURE                 Location/Qualifiers
source                  1..4
                        mol_type = protein
                        organism = synthetic construct
SEQUENCE: 45
SGGF                                                                    4

SEQ ID NO: 46           moltype = AA  length = 4
FEATURE                 Location/Qualifiers
source                  1..4
                        mol_type = protein
                        organism = synthetic construct
SEQUENCE: 46
KGGF                                                                    4
```

What is claimed is:

1. An antibody or antigen-binding fragment thereof that specifically binds human receptor tyrosine kinase like orphan receptor 1 (ROR1), comprising:
   a) a variable heavy chain region (VH) comprising: (i) a VHCDR1 comprising the amino acid sequence of SEQ ID NO: 1; (ii) VHCDR2 comprising the amino acid sequence of SEQ ID NO: 2; and (iii) a VHCDR3 comprising the amino acid sequence of SEQ ID NO: 3; and
   b) a variable light chain region (VL) comprising: (i) a VLCDR1 comprising the amino acid sequence of SEQ ID NO: 8; ii) a VLCDR2 comprising the amino acid sequence AAS; and iii) a VLCDR3 comprising the amino acid sequence of SEQ ID NO: 10.

2. An antibody or antigen-binding fragment thereof that specifically binds human receptor tyrosine kinase like orphan receptor 1 (ROR1), comprising:
   a) a variable heavy chain region (VH) comprising: (i) a VHCDR1 comprising the amino acid sequence of SEQ ID NO: 15; (ii) VHCDR2 comprising the amino acid sequence of SEQ ID NO: 16; and (iii) a VHCDR3 comprising the amino acid sequence of SEQ ID NO: 17; and
   b) a variable light chain region (VL) comprising: (i) a VLCDR1 comprising the amino acid sequence of SEQ ID NO: 22; ii) a VLCDR2 comprising the amino acid sequence DAY; and iii) a VLCDR3 comprising the amino acid sequence of SEQ ID NO: 24.

3. An antibody or antigen-binding fragment thereof that specifically binds human receptor tyrosine kinase like orphan receptor 1 (ROR1), comprising:
   a) a variable heavy chain region (VH) comprising: (i) a VHCDR1 comprising the amino acid sequence of SEQ ID NO: 29; (ii) VHCDR2 comprising the amino acid sequence of SEQ ID NO: 30; and (iii) a VHCDR3 comprising the amino acid sequence of SEQ ID NO: 31; and a variable light chain region (VL) comprising: (i) a VLCDR1 comprising the amino acid sequence of SEQ ID NO: 36; ii) a VLCDR2 comprising the amino acid sequence DAS; and iii) a VLCDR3 comprising the amino acid sequence of SEQ ID NO: 38.

* * * * *